(12) United States Patent
Lindsley et al.

(10) Patent No.: US 9,783,510 B2
(45) Date of Patent: Oct. 10, 2017

(54) SMALL MOLECULE MEDIATED TRANSCRIPTIONAL INDUCTION OF E-CADHERIN

(71) Applicant: Vanderbilt University, Nashville, TN (US)

(72) Inventors: Craig W. Lindsley, Brentwood, TN (US); Alex G. Waterson, Murfreesboro, TN (US); R. Daniel Beauchamp, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/828,230

(22) Filed: Aug. 17, 2015

(65) Prior Publication Data
US 2016/0052895 A1 Feb. 25, 2016

Related U.S. Application Data

(60) Provisional application No. 62/040,972, filed on Aug. 22, 2014.

(51) Int. Cl.
| | | |
|---|---|---|
| *C07D 261/18* | (2006.01) | |
| *C07D 401/12* | (2006.01) | |
| *C07D 413/12* | (2006.01) | |
| *C07D 417/12* | (2006.01) | |
| *C07D 471/04* | (2006.01) | |
| *C07D 487/04* | (2006.01) | |
| *C07D 495/04* | (2006.01) | |
| *C07D 413/14* | (2006.01) | |

(52) U.S. Cl.
CPC ......... *C07D 261/18* (2013.01); *C07D 401/12* (2013.01); *C07D 413/12* (2013.01); *C07D 413/14* (2013.01); *C07D 417/12* (2013.01); *C07D 471/04* (2013.01); *C07D 487/04* (2013.01); *C07D 495/04* (2013.01)

(58) Field of Classification Search
CPC combination set(s) only.
See application file for complete search history.

(56) References Cited

U.S. PATENT DOCUMENTS 8,193,225 B2 * 6/2012 Schneider .............. C07C 311/49
514/378

FOREIGN PATENT DOCUMENTS

| WO | WO-2007/078113 A1 | 7/2007 | |
|---|---|---|---|
| WO | WO 2008046072 A2 * | 4/2008 | ........... C07D 231/12 |

OTHER PUBLICATIONS

Response to Requirement for Restriction/ Election was mailed on Sep. 9, 2016 to the U.S. Patent and Trademark Office for U.S. Appl. No. 14/828,286, which was filed Aug. 17, 2015 and published as US 2016-0052896 A1 on Feb. 25, 2016 (Inventor—Lindsley et al; Applicant—Vanderbilt Univ.) (12 pages).
Notice of Allowance was issued on Oct. 5, 2016 to the U.S. Patent and Trademark Office for U.S. Appl. No. 14/828,286, which was filed Aug. 17, 2015 and published as US 2016-0052896 A1 on Feb. 25, 2016 (Inventor—Lindsley et al; Applicant—Vanderbilt Univ.) (12 pages).
Al-Greene, N. T., et al. (2013) Four jointed box 1 promotes angiogenesis and is associated with poor patient survival in colorectal carcinoma. *PLoS One* 8: 369660.
An, H., et al. (2015) Small molecule/ML327 mediated transcriptional de-repression of E-cadherin and inhibition of epithelial-to-mesenchymal transition. *Oncotarget.* 6(26): 22934-22948.
Diehl, J. A., et al. (1998) Glycogen synthase kinase-3beta regulates cyclin D1 poteolysis and subcellular localization. *Genes & Development* 12: 3499-3511.
Freeman, T. J. et al. (2012) Smad4-Mediated Signaling Inhibits Intestinal Neoplasia by Inhibiting Expression of β-Catenin. *Gastroenterology* 142: 562-572.
GI Cancer SPORE grant No. P50CA095103. (Abstract).
Grant No. U54MH084659 awarded by the National Institute of Health (NIH).
Gupta, G. P. and Massague, J. (2006) Cancer metastasis: building a framework. *Cell* 127: 679-695.
Heldin, C. H., et al. (2012) Regulation of EMT by TGFβ in cancer. *FEBS Lett.* 586: 1959-1970.
Iwatsuki, M., et al. (2010) Epithelial-mesenchymal transition in cancer development and its clinical significance. *Cancer Sci.* 101: 293-299.
Jemal, A., et al. (2007). Cancer statistics, 2007. *CA: A Cancer Journal for Clinicians* 57: 43-66.
Kain, K. H., et al. (2014) The chick embryo as an expanding experimental model for cancer and cardiovascular research. *Dev. Dyn.* 243(2): 216-228.
Kakihana, M., et al. (2009) Induction of E-cadherin in lung cancer and interaction with growth suppression by histone deacetylase inhibition. *Journal of Thoracic Oncology* 4: 1455-1465.
Katsuno, Y., et al. (2013) TGF-β signaling and epithelial-mesenchymal transition in cancer progression. *Current Opinion in Oncology* 25: 76-84.
Lim, J., et al. (2012) Epithelial-mesenchymal transitions: insights from development. *Development* 139: 3471-3486.
Liu, Y.N. et al. (2005) Regulatory mechanisms controlling human E-cadherin gene expression. *Oncogene* 24: 8277-8290.
Miettinen, P. J., et al. (1994) TGF-beta induced transdifferentiation of mammary epithelial cells to mesenchymal cells: involvement of type I receptors. *J. Cell Biol.* 127: 2021-2036.
Stevens, T., et al. (2000) Mechanisms regulating endothelial cell barrier function. *American Journal of Physiology Lung Cellular and Molecular Physiology* 279: L419-422.
Stoops, S. L., et al. (2011) Identification and optimization of small molecules that restore E-cadherin expression and reduce invasion in colorectal carcinoma cells. *ACS Chemical Biology* 6: 452-465.

(Continued)

*Primary Examiner* — Nyeemah A Grazier
(74) *Attorney, Agent, or Firm* — Ballard Spahr LLP

(57) ABSTRACT

In one aspect, the invention relates to N-acetamidoalkyl-5-arylisoxazole-3-carboxamide analogs, derivatives thereof, and related compounds, which are useful as mediators of transcriptional induction of E-cadherin; synthesis methods for making the compounds; pharmaceutical compositions comprising the compounds; and methods of treating disorders associated with E-cadherin activity using the compounds and compositions. This abstract is intended as a scanning tool for purposes of searching in the particular art and is not intended to be limiting of the present invention.

21 Claims, 30 Drawing Sheets

(56) References Cited

OTHER PUBLICATIONS

Suzuki, H., et al. (2002) A genomic screen for genes upregulated by demethylation and histone deacetylase inhibition in human colorectal cancer. *Nat. Genet.* 31: 141-149.

Unger, R. E., et al. (2002) In vitro expression of the endothelial phenotype: comparative study of primary isolated cells and cell lines, including the novel cell line HPMEC-ST1.6R. *Microvascular Research* 64: 384-397.

Valastyan, S., et al. (2011) Activation of miR-31 function in already-established metastases elicits metastatic regression. *Genes Dev.* 25: 646-659.

Vestweber, D. (2008) VE-cadherin: the major endothelial adhesion molecule controlling cellular junctions and blood vessel formation. *Arteriosclerosis, Thrombosis, and Vascular Biology* 28: 223-232.

Wang, Y. and Shang, Y. (2013) Epigenetic control of epithelial-to-mesenchymal transition and cancer metastasis. *Experimental Cell Research* 319: 160-169.

Zijlstra, A., et al. (2008) The inhibition of tumor cell intravasation and subsequent metastasis via regulation of in vivo tumor cell motility by the tetraspanin CD151. *Cancer Cell* 13(3): 221-234.

Project 2 of GI Cancer SPORE grant No. P50CA095103.

Requirement for Restriction/ Election was issued on May 10, 2016 by the U.S. Patent and Trademark Office for U.S. Appl. No. 14/828,286, which was filed Aug. 17, 2015 and published as US 2016-0052896 A1 on Feb. 25, 2016 (Inventor—Lindsley et al; Applicant—Vanderbilt Univ.) (8 pages).

\* cited by examiner

SMALL MOLECULE MEDIATED TRANSCRIPTIONAL INDUCTION OF E-CADHERIN

CROSS-REFERENCE TO RELATED APPLICATIONS

This application claims the benefit of U.S. Provisional Application No. 62/040,972, filed on Aug. 22, 2014, which is incorporated herein by reference in its entirety.

STATEMENT REGARDING FEDERALLY SPONSORED RESEARCH

This invention was made with U.S. government support under grant number U54MH084659, awarded by the National Institute of Health (NIH) and the GI Cancer SPORE grant P50CA095103. The U.S. government has certain rights in the invention.

REFERENCE TO SEQUENCE LISTINGS

The Sequence Listing submitted Sep. 30, 2015 as a text file named "22000_0289U2_ST25.txt," created on Sep. 30, 2015, and having a size of 2,421 bytes is hereby incorporated by reference pursuant to 37 C.F.R. §1.52(e)(5).

BACKGROUND

Cancer is a leading cause of death in the United States (~25% of the population), and the vast majority of these cancers are of epithelial cell origin (Jemal, A., et al. (2007) *CA: A Cancer Journal for Clinicians* 57, 43-66). Over 90% of cancer deaths related to solid malignancies are due to metastatic dissemination of cancer to secondary organs (Gupta, G. P. and Massague, J. (2006) *Cell* 127, 679-695; Valastyan, S., et al. (2011) *Genes Dev.* 25, 646-659). A hallmark of tumor malignancy, and a requirement for metastasis, is the acquired ability of cells to detach from the primary tumor mass and invade into surrounding stromal tissues. This capacity is highly associated with the loss of expression of epithelial cadherin (E-cadherin), since most solid tumors are carcinomas that are derived from epithelial cells/tissues. E-cadherin is a key adhesion molecule that plays a pivotal role in maintaining cell polarity, epithelial architecture, and cell differentiation. The epithelial-mesenchymal transition (EMT) is a reversible process whereby epithelial cells undergo coordinated reprogramming of their gene expression and lose the epithelial characteristics of tight cell-cell adhesiveness and apical-basal polarity, while gaining mesenchymal properties, including increased motility and capacity for invasion through the basement membrane (Valastyan, S., et al. (2011) *Genes Dev.* 25, 646-659; Katsuno, Y., et al. (2013) *Current Opinion in Oncology* 25, 76-84; Lim, J., et a. (2012) *Development* 139, 3471-3486). Gene expression profiling has indicated that de-differentiated cancer cells combine the EMT properties with a stem-cell like phenotype.

As a feature of the reprogramming of gene expression during EMT, an invariable hallmark of EMT is the marked decrease of E-cadherin expression and function. Alterations in E-cadherin expression have a major impact on cell-cell interactions, resulting in disturbed epithelial tissue homeostasis. Indeed, upon loss of functional E-cadherin, cells become more prone to acquire a motile and invasive phenotype, accounting for the metastatic potential of many epithelial cancer cells. The expression of E-cadherin is frequently lost in human cancers, and, while this can be due to mutational inactivation (as in familial gastric cancer syndrome), more frequently the loss of expression is due to transcriptional inhibition or silencing (as occurs in EMT). Several developmentally important transcriptional regulatory proteins, such as ZEB1, ZEB2, Snail, Snai2/SLUG, TWIST 1, and E47/TCF3, induce EMT and are directly involved in repression of E-cadherin expression (Wang, Y. and Shang, Y. (2013) *Experimental Cell Research* 319, 160-169).

Despite knowledge that the acquisition of EMT features is associated with chemoresistance, often leading to recurrence and metastasis after standard chemotherapeutic treatment (Iwatsuki, M., et al. (2010) *Cancer Sci.* 101, 293-299), very few experimental therapeutic agents are known to inhibit the EMT phenotype. These needs and other needs are addressed by the present invention.

SUMMARY

In accordance with the purpose(s) of the invention, as embodied and broadly described herein, the invention, in one aspect, relates to N-acetamidoalkyl-5-arylisoxazole-3-carboxamide analogs useful as mediators of transcriptional induction of E-cadherin (E-cad), methods of making same, pharmaceutical compositions comprising same, and methods of treating cancers associated with functional loss of E-cadherin using same.

Disclosed are compound having a structure represented by a formula:

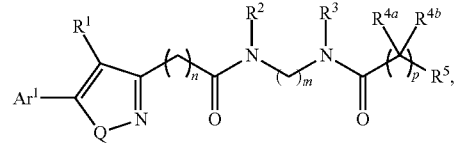

wherein m is an integer selected from 2, 3, and 4; wherein n is an integer selected from 0 and 1; wherein p is an integer selected 0, 1, and 2; wherein Q is selected from $NR^6$, O, and S; wherein $R^6$ is selected from hydrogen and C1-4 alkyl; wherein $R^1$ is selected from hydrogen and C1-C4 alkyl; wherein each of $R^2$ and $R^3$ is independently selected from hydrogen and C1-C4 alkyl; wherein each occurrence of $R^{4a}$ and $R^{4b}$ is independently selected from hydrogen, halogen, —OH, —CN, —$N_3$, —$NH_2$, and C1-C4 alkyl, or wherein each of $R^{4a}$ and $R^{4b}$ are optionally covalently bonded and, together with the intermediate atoms, comprise a 3- to 5-membered cycle; wherein $R^5$ is selected from $Cy^2$ and $Ar^2$; wherein $Cy^2$, when present, is selected from cycloalkyl and heterocycloalkyl, and $Cy^2$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, provided that when m is 2 then $Cy^2$ is not cycloalkyl; wherein $Ar^2$, when present, is selected from aryl and heteroaryl, and $Ar^2$ is substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, C1-C4 dialkylamino, $Cy^3$, $Ar^3$, and —NH(C=O)(C1-C4 alkyl)$Cy^3$, provided that when m is 2 then $Ar^2$ is not substituted or unsubstituted phenyl, substituted or unsubstituted furanyl, or substituted or unsubstituted pyridinyl; wherein $Cy^3$, when present, is selected from cycloalkyl and heterocycloalkyl, and Cy³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; wherein Ar³, when present, is selected from aryl and heteroaryl, and Ar³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; provided that when m is 3, n is 0, and p is 0, that Ar², when present, is not a structure represented by a formula:

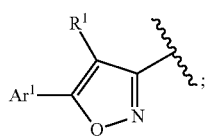

and wherein Ar¹, is selected from aryl and heteroaryl, and Ar¹ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

Also disclosed are pharmaceutical compositions comprising an effective amount of at least one disclosed compound, or a pharmaceutically acceptable salt thereof, and a pharmaceutically acceptable carrier.

Also disclosed are methods for manufacturing a medicament comprising combining at least one disclosed compound with a pharmaceutically acceptable carrier or diluent.

Also disclosed are methods for modulating the expression of E-cadherin in at least one cell, the method comprising the step of contacting the at least one cell with at least one compound having a structure represented by a formula:

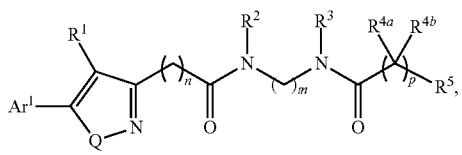

wherein m is an integer selected from 2, 3, and 4; wherein n is an integer selected from 0 and 1; wherein p is an integer selected 0, 1, and 2; wherein Q is selected from NR⁶, O, and S; wherein R⁶ is selected from hydrogen and C1-C4 alkyl; wherein R¹ is selected from hydrogen and C1-C4 alkyl; wherein each of R² and R³ is independently selected from hydrogen and C1-C4 alkyl; wherein each occurrence of R⁴ᵃ and R⁴ᵇ is independently selected from hydrogen, halogen, —OH, —CN, —N₃, —NH₂, and C1-C4 alkyl, or wherein each of R⁴ᵃ and R⁴ᵇ are optionally covalently bonded and, together with the intermediate atoms, comprise a 3- to 5-membered cycle; wherein R⁵ is selected from Cy² and Ar²; wherein Cy², when present, is selected from cycloalkyl and heterocycloalkyl, and Cy² is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, and C1-C4 dialkylamino; wherein Ar², when present, is selected from aryl and heteroaryl, and Ar² is substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³; wherein Cy³, when present, is selected from cycloalkyl and heterocycloalkyl, and Cy³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; wherein Ar³, when present, is selected from aryl and heteroaryl, and Ar³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; and wherein Ar¹, when present, is selected from aryl and heteroaryl, and Ar¹ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

Also disclosed are methods for treating a disorder associated with E-cadherin activity in a subject, the method comprising administering to the subject an effective amount of at least one compound having a structure represented by a formula:

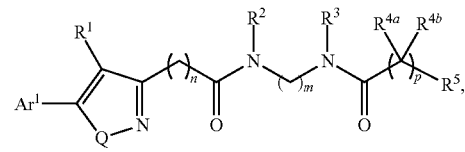

wherein m is an integer selected from 2, 3, and 4; wherein n is an integer selected from 0 and 1; wherein p is an integer selected 0, 1, and 2; wherein Q is selected from NR⁶, O, and S; wherein R⁶ is selected from hydrogen and C1-C4 alkyl; wherein R¹ is selected from hydrogen and C1-C4 alkyl; wherein each of R² and R³ is independently selected from hydrogen and C1-C4 alkyl; wherein each occurrence of R⁴ᵃ and R⁴ᵇ is independently selected from hydrogen, halogen, —OH, —CN, —N₃, —NH₂, and C1-C4 alkyl, or wherein each of R⁴ᵃ and R⁴ᵇ are optionally covalently bonded and, together with the intermediate atoms, comprise a 3- to 5-membered cycle; wherein R⁵ is selected from Cy² and Ar²; wherein Cy², when present, is selected from cycloalkyl and heterocycloalkyl, and Cy² is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; wherein Ar², when present, is selected from aryl and heteroaryl, and Ar² is substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³; wherein Cy³, when present, is selected from cycloalkyl and heterocycloalkyl, and Cy³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; wherein Ar³, when present, is selected from aryl and heteroaryl, and Ar³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; and wherein Ar¹, when present, is selected from aryl and heteroaryl, and Ar¹ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof, thereby treating the disorder in the subject.

Also disclosed are kits comprising at least one compound having a structure represented by a formula:

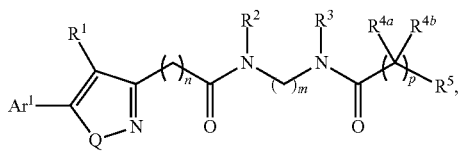

wherein m is an integer selected from 2, 3, and 4; wherein n is an integer selected from 0 and 1; wherein p is an integer selected 0, 1, and 2; wherein Q is selected from NR⁶, O, and S; wherein R⁶ is selected from hydrogen and C1-C4 alkyl; wherein R¹ is selected from hydrogen and C1-C4 alkyl; wherein each of R² and R³ is independently selected from hydrogen and C1-C4 alkyl; wherein each occurrence of $R^{4a}$ and $R^{4b}$ is independently selected from hydrogen, halogen, —OH, —CN, —N₃, —NH₂, and C1-C4 alkyl, or wherein each of $R^{4a}$ and $R^{4b}$ are optionally covalently bonded and, together with the intermediate atoms, comprise a 3- to 5-membered cycle; wherein R⁵ is selected from Cy² and Ar²; wherein Cy², when present, is selected from cycloalkyl and heterocycloalkyl, and Cy² is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; wherein Ar², when present, is selected from aryl and heteroaryl, and Ar² is substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³; wherein Cy³, when present, is selected from cycloalkyl and heterocycloalkyl, and Cy³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; wherein Ar³, when present, is selected from aryl and heteroaryl, and Ar³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; and wherein Ar¹, when present, is selected from aryl and heteroaryl, and Ar¹ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof, and one or more of: (a) at least one agent known to increase E-cadherin expression; (b) at least one agent known to decrease E-cadherin expression; (c) at least one agent known to treat a disorder of uncontrolled cellular proliferation; or (d) instructions for treating a disorder of uncontrolled cellular proliferation.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying figures, which are incorporated in and constitute a part of this specification, illustrate several aspects and together with the description serve to explain the principles of the invention.

Figure 1A:
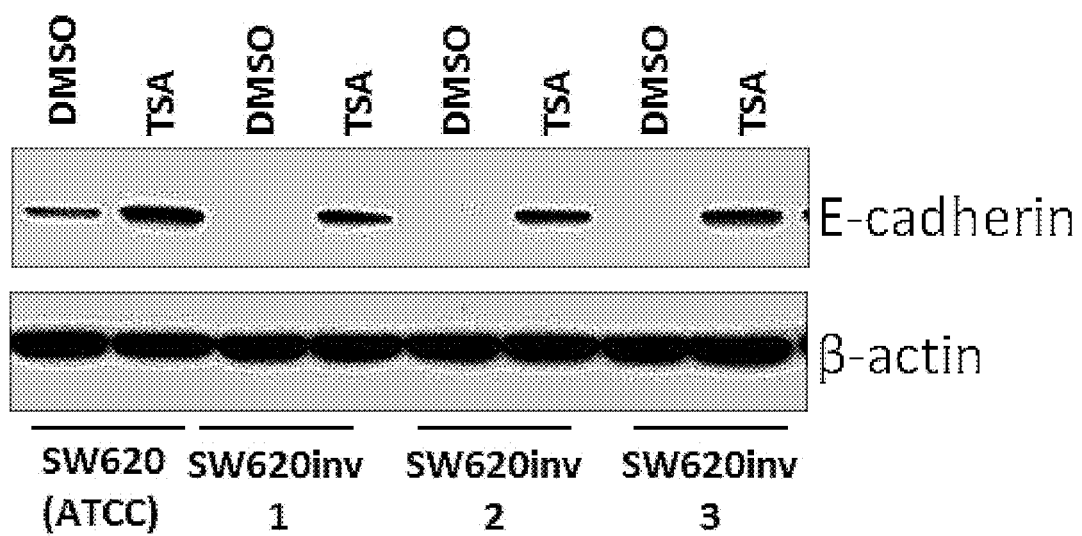
FIG. 1A-C show representative data pertaining to the characterization of highly invasive "SW620inv" cells via Western blot (1A), immunofluorescence (1B), and matrigel transwell invasion assay (1C).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal A patient refers to a subject afflicted with a disease or disorder. The term "patient" includes human and veterinary subjects. In some aspects of the disclosed methods, the subject has been diagnosed with a need for treatment of a cancer prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a cancer treatable by restoration of E-cadherin expression" means having been subjected to a physical examination by a person of skill, for example, a physician, and found to have a condition that can be diagnosed or treated by a compound or composition that can restore E-cadherin expression. As a further example, "diagnosed with a need for restoration of E-cadherin expression" refers to having been subjected to a physical examination by a person of skill, for example, a physician, and found to have a condition characterized by loss of E-cadherin expression. Such a diagnosis can be in reference to a disease, such as a cancer, and the like, as discussed herein.

As used herein, the phrase "identified to be in need of treatment for a disease," or the like, refers to selection of a subject based upon need for treatment of the disease. For example, a subject can be identified as having a need for treatment of a disease (e.g., a disease related to E-cadherin expression) based upon an earlier diagnosis by a person of skill and thereafter subjected to treatment for the disease. It is contemplated that the identification can, in one aspect, be performed by a person different from the person making the diagnosis. It is also contemplated, in a further aspect, that the administration can be performed by one who subsequently performed the identification.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "EC$_{50}$," is intended to refer to the concentration of a substance (e.g., a compound or a drug) that is required for 50% potentiation of a biological process, or component of a process, including a protein, subunit, organelle, ribonucleoprotein, etc. In a further aspect, EC$_{50}$ refers to the concentration of agonist that provokes a response halfway between the baseline and maximum response. In a yet further aspect, the response is in vitro.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A_3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide", as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further nonlimiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group.

The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. It is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group is independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $(CH_2)_{0-4}N(R^\circ)C(O)NR^\circ)_2$; $-N(R^\circ)C(S)NR^\circ)_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ)_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ{}_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ)_2$; $-C(S)NR^\circ)_2$; $-C(S)SR^\circ$; $-SC(S)SR^\circ$, $-(CH_2)_{0-4}OC(O)NR^\circ)_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ)_2$; $-(CH_2)_{0-4}S(O)R^\circ$; $-N(R^\circ)S(O)_2NR^\circ)_2$; $-N(R^\circ)S(O)_2R^\circ$; $-N(OR^\circ)R^\circ$; $-C(NH)NR^\circ)_2$; $-P(O)_2R^\circ$; $-P(O)R^\circ)_2$; $-OP(O)R^\circ)_2$; $-OP(O)(OR^\circ)_2$; $SiR^\circ{}_3$; $-(C_{1-4}$ straight or branched)alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), is independently halogen, $-(CH_2)_{0-2}R^\bullet$, -(halo$R^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet{}_2$, $-NO_2$, $-SiR^\bullet{}_3$, $-OSiR^\bullet{}_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R^*{}_2))_{2-3}O-$, or $-S(C(R^*{}_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*{}_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, -(halo$R^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet{}_2$, or $-NO_2$, wherein each $R^\bullet$ is unsubstituted or where preceded by "halo" is substituted only with one or more halogens, and is independently $C_1$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger{}_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger{}_2$, $-C(S)NR^\dagger{}_2$, $-C(NH)NR^\dagger{}_2$, or $-N(R^\dagger)S(O)_2R^\dagger$; wherein each $R^\dagger$ is independently hydrogen, $C_1$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ is independently halogen, $-R^\bullet$, -(halo$R^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet{}_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups (PG's) known in the art (see, for example, "Protective Groups in Organic Synthesis," T. W. Greene, P. G. M. Wuts, Wiley-Interscience, 1999).

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

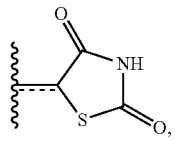

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkyl-carboxamide, dialkylcarboxamide, substituted dialkylcar-boxamide, alkylsulfonyl, alkylsulfinyl, thioalkyl, thioha-loalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g., "Crystal Engineering of the Composition of Pharmaceutical Phases. Do Pharmaceutical Co-crystals Represent a New Path to Improved Medicines?" Almarasson, O. et al. (2004) The Royal Society of Chemistry, 1889-1896. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

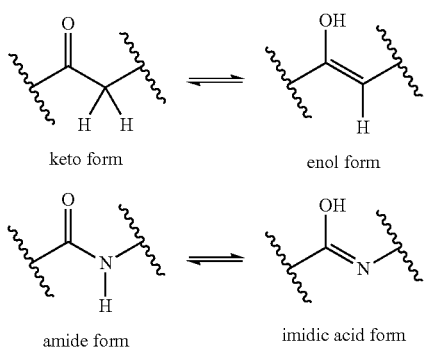

keto form          enol form amide form         imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

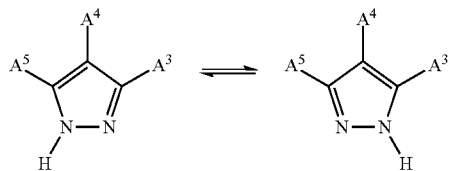

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

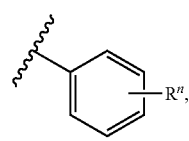

which is understood to be equivalent to a formula:

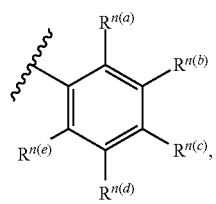

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful as mediators of transcriptional induction of E-cadherin. More specifically, in one aspect, the present invention relates to compounds that promote E-cadherin expression.

In one aspect, the disclosed compounds exhibit an increase in E-cadherin mRNA levels as an increase in E-cadherin mRNA expression in SW620 colon cancer cells in the presence of the compound, compared to E-cadherin mRNA expression in the absence of the compound. In a further aspect, the disclosed compounds exhibit an increase in E-cadherin protein levels as an increase in E-cadherin protein levels in SW620 colon cancer cells in the presence of the compound, compared to E-cadherin protein levels in the absence of the compound.

In one aspect, the compounds of the invention are useful in the treatment of cancers and other diseases associated with loss of E-cadherin expression, as described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, a compound can have a structure represented by a formula:

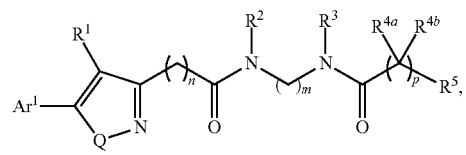

wherein m is an integer selected from 2, 3, and 4; wherein n is an integer selected from 0 and 1; wherein p is an integer selected 0, 1, 2, 3, and 4; wherein Q is selected from $NR^6$, O, and S; wherein $R^6$ is selected from hydrogen and C1-4 alkyl; wherein $R^1$ is selected from hydrogen and C1-C4 alkyl; wherein each of $R^2$ and $R^3$ is independently selected from hydrogen and C1-C4 alkyl; wherein each occurrence of $R^{4a}$ and $R^{4b}$ is independently selected from hydrogen, halogen, —OH, —CN, —$N_3$, —$NH_2$, C1-C4 alkyl, and C1-C4 cycloalkyl; wherein R⁵ is selected from Cy² and Ar²; wherein Cy², when present, is selected from cycloalkyl and heterocycloalkyl, and Cy² is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, provided that when m is 2 then Cy² is not cycloalkyl; wherein Ar², when present, is selected from aryl and heteroaryl, and Ar² is substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³, provided that when m is 2 then Ar² is not substituted or unsubstituted phenyl, substituted or unsubstituted furanyl, or substituted or unsubstituted pyridinyl; wherein Cy³, when present, is selected from cycloalkyl and heterocycloalkyl, and Cy³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; wherein Ar³, when present, is selected from aryl and heteroaryl, and Ar³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; provided that when m is 3, n is 0, and p is 0, that Ar², when present, is not a structure represented by a formula:

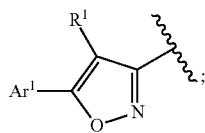

and
wherein Ar¹ is selected from aryl and heteroaryl, and Ar¹ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

In a further aspect, a compound can have a structure listed herein. In a further aspect, the compounds can be selected from two or more of the structures listed herein.

In a further aspect, the invention relates to a compound having a structure represented by a formula:

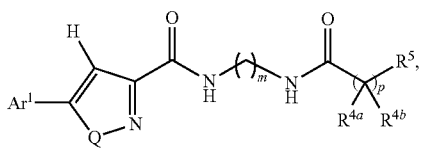

wherein all other variables are as defined herein; or a pharmaceutically acceptable salt thereof.

In a further aspect, the invention relates to a compound having a structure represented by a formula:

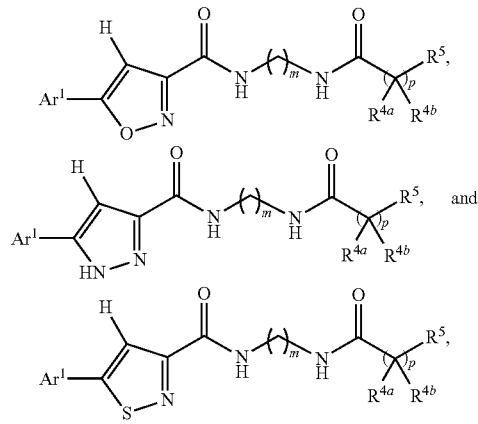

wherein all other variables are as defined herein; or a pharmaceutically acceptable salt thereof.

In a further aspect, the invention relates to a compound having a structure represented by a formula:

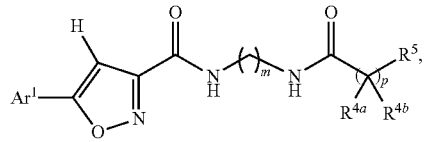

wherein all other variables are as defined herein; or a pharmaceutically acceptable salt thereof.

In a further aspect, the invention relates to a compound having a structure represented by a formula:

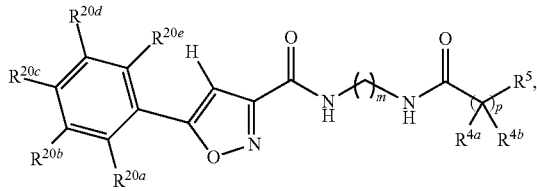

wherein each of $R^{20a}$, $R^{20b}$, $R^{20c}$, $R^{20d}$, and $R^{20e}$ are independently selected from hydrogen, halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, provided that at least two of $R^{20a}$, $R^{20b}$, $R^{20c}$, $R^{20d}$, and $R^{20e}$ are hydrogen, and wherein all other variables are as defined herein; or a pharmaceutically acceptable salt thereof.

In a further aspect, the invention relates to a compound having a structure represented by a formula:

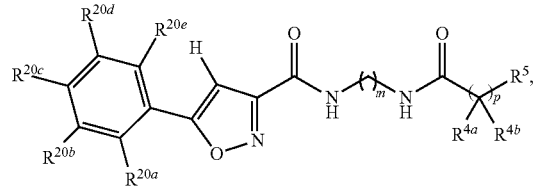

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least three $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

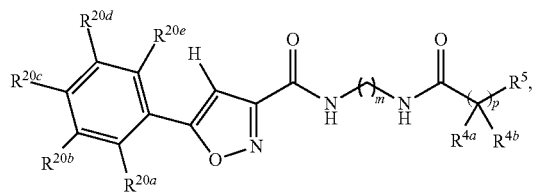

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least four of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

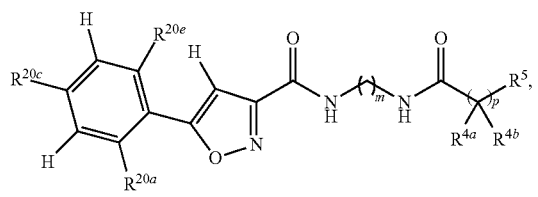

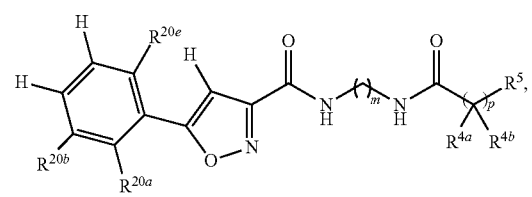

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

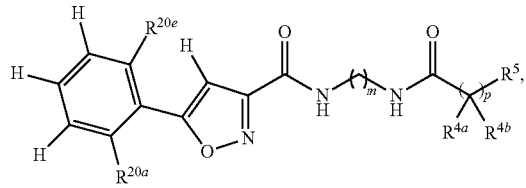

wherein each of $R^{20a}$ and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

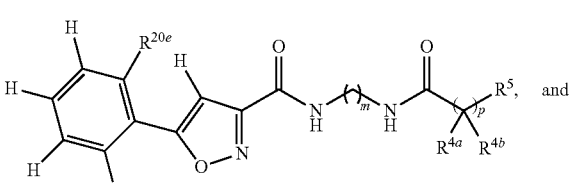

and

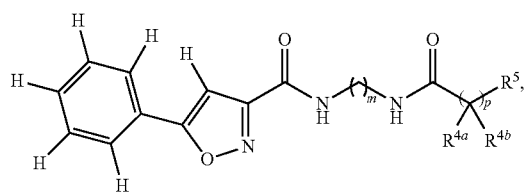

wherein each of $R^{20a}$ and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

wherein all other variables are as defined herein; or a pharmaceutically acceptable salt thereof.

In a further aspect, the invention relates to a compound having a structure represented by a formula:

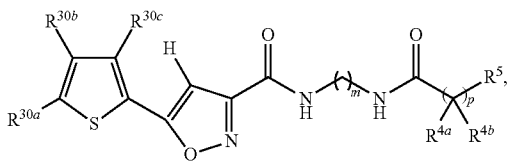

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

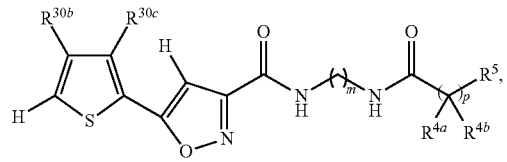

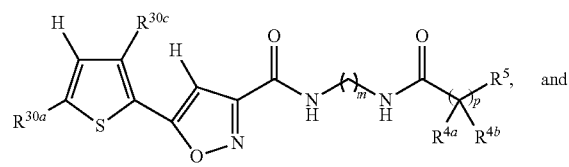

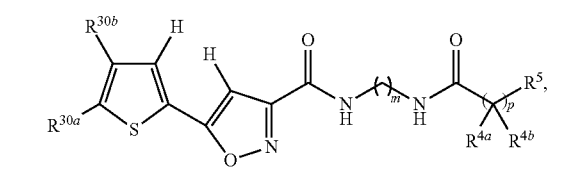

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

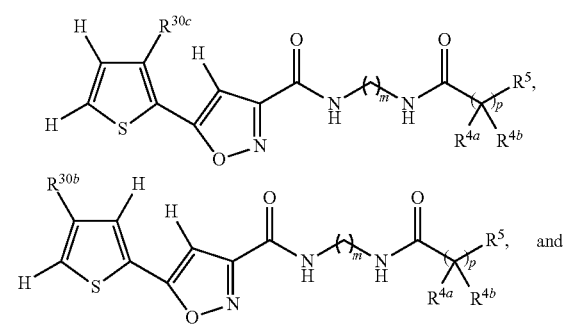

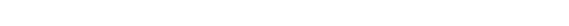

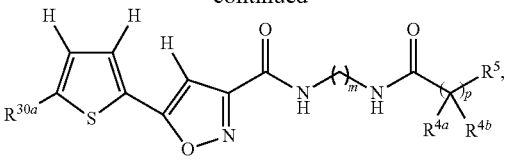

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

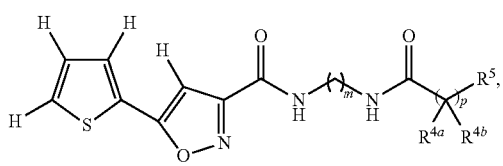

wherein all other variables are as defined herein; or a pharmaceutically acceptable salt thereof.

In a further aspect, the invention relates to a compound having a structure represented by a formula:

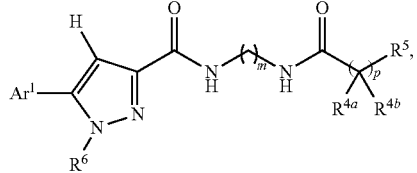

wherein all other variables are as defined herein; or a pharmaceutically acceptable salt thereof.

In a further aspect, the invention relates to a compound having a structure represented by a formula:

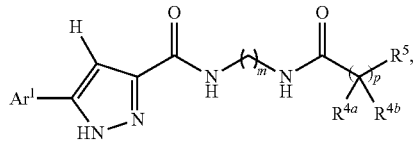

wherein all other variables are as defined herein; or a pharmaceutically acceptable salt thereof.

In a further aspect, the invention relates to a compound having a structure represented by a formula:

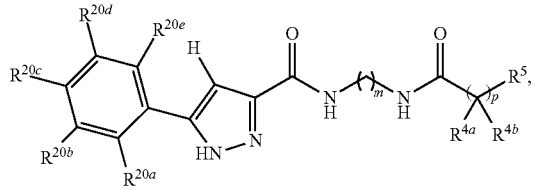

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least two of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

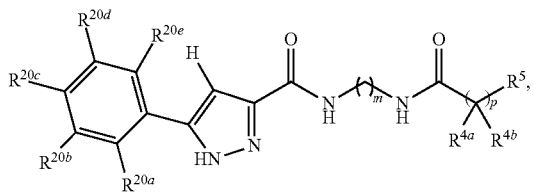

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least three $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

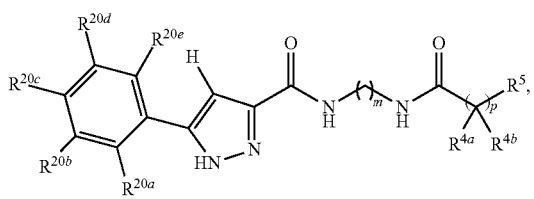

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least four of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

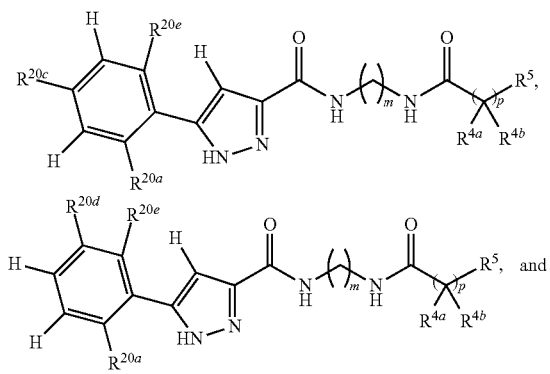

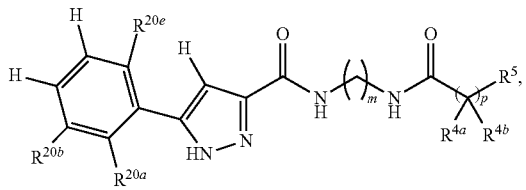

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

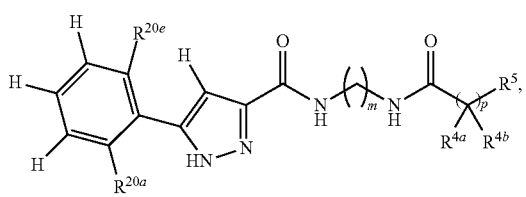

wherein each of $R^{20a}$ and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

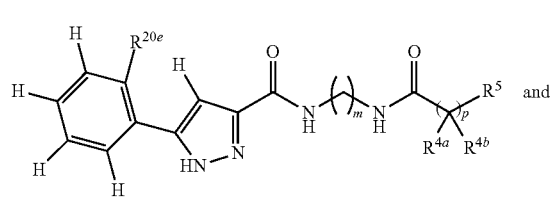

wherein each of $R^{20a}$ and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

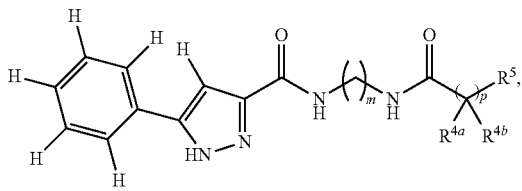

wherein all other variables are as defined herein; or a pharmaceutically acceptable salt thereof.

In a further aspect, the invention relates to a compound having a structure represented by a formula:

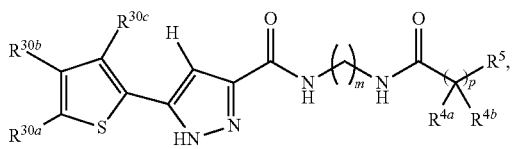

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

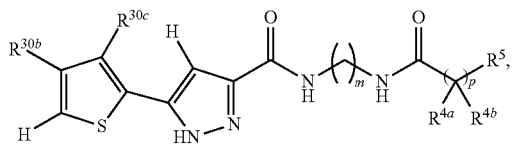

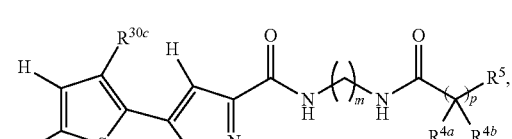

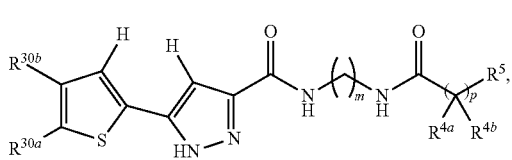

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

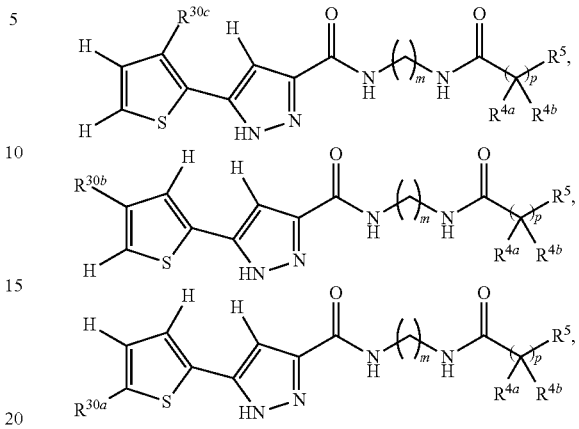

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

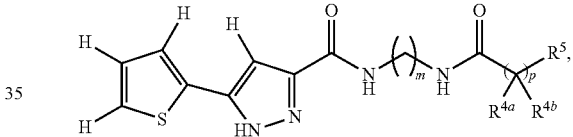

wherein all other variables are as defined herein; or a pharmaceutically acceptable salt thereof.

In a further aspect, the invention relates to a compound having a structure represented by a formula:

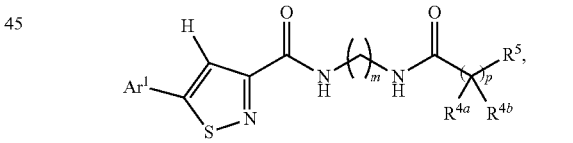

wherein all other variables are as defined herein; or a pharmaceutically acceptable salt thereof.

In a further aspect, the invention relates to a compound having a structure represented by a formula:

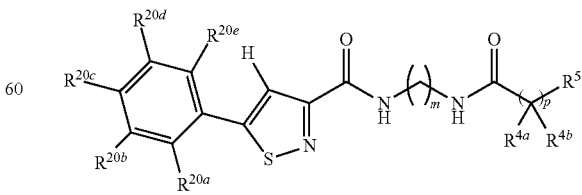

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least two of R$^{20a}$, R$^{20b}$, R$^{20c}$, R$^{20d}$, and R$^{20e}$ are hydrogen; and wherein all other variables are as defined herein; or a pharmaceutically acceptable salt thereof.

In a further aspect, the invention relates to a compound having a structure represented by a formula:

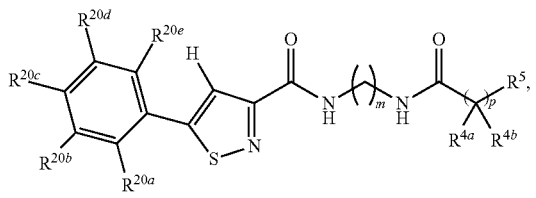

wherein each of R$^{20a}$, R$^{20b}$, R$^{20c}$, R$^{20d}$, and R$^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least three of R$^{20a}$, R$^{20b}$, R$^{20c}$, R$^{20d}$, and R$^{20e}$ are hydrogen; and wherein all other variables are as defined herein; or a pharmaceutically acceptable salt thereof.

In a further aspect, the invention relates to a compound having a structure represented by a formula:

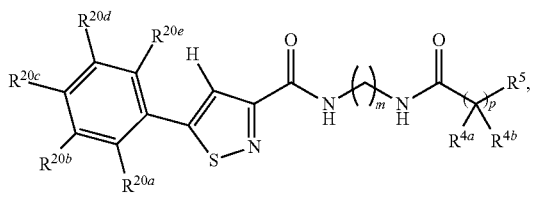

wherein each of R$^{20a}$, R$^{20b}$, R$^{20c}$, R$^{20d}$, and R$^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least four of R$^{20a}$, R$^{20b}$, R$^{20c}$, R$^{20d}$, and R$^{20e}$ are hydrogen; and wherein all other variables are as defined herein; or a pharmaceutically acceptable salt thereof.

In a further aspect, the invention relates to a compound having a structure represented by a formula:

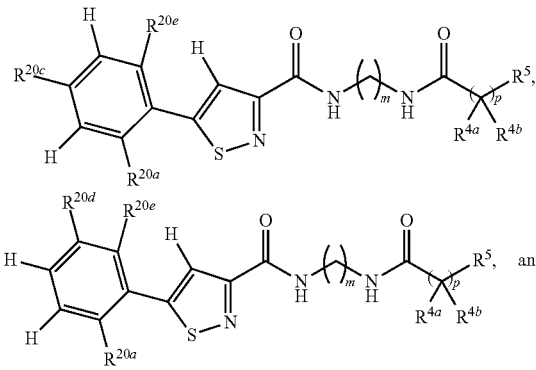

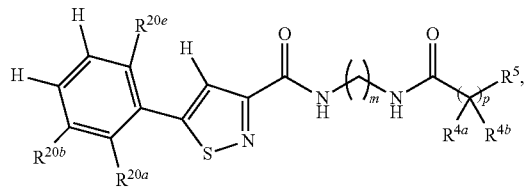

wherein each of R$^{20a}$, R$^{20b}$, R$^{20c}$, R$^{20d}$, and R$^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

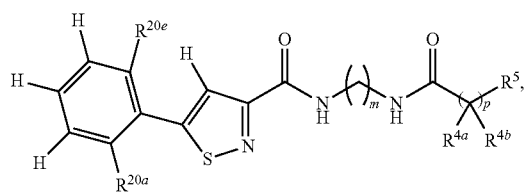

wherein each of R$^{20a}$ and R$^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

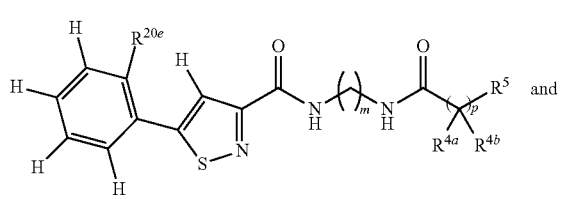

wherein each of R$^{20a}$ and R$^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

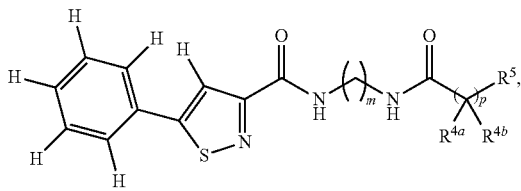

wherein all other variables are as defined herein; or a pharmaceutically acceptable salt thereof.

In a further aspect, the invention relates to a compound having a structure represented by a formula:

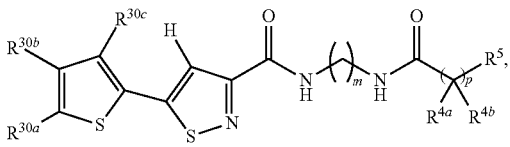

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

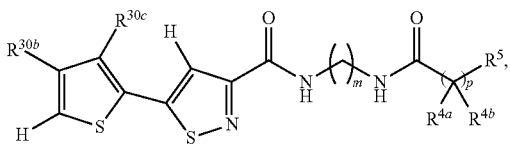

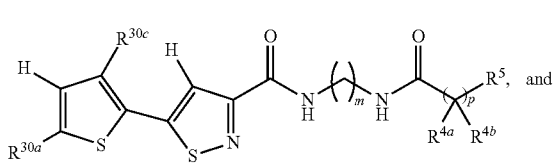

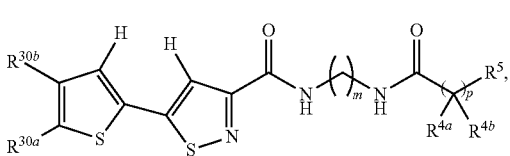

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

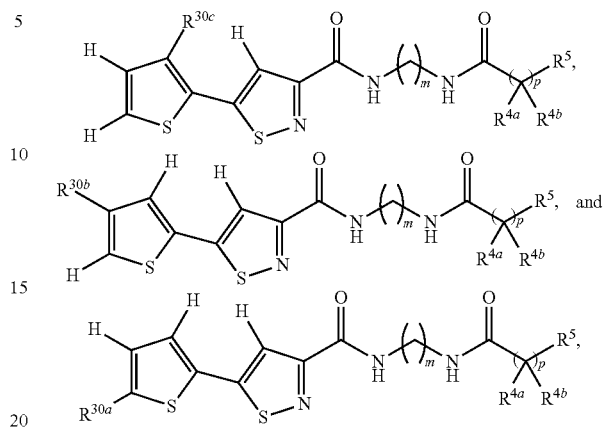

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

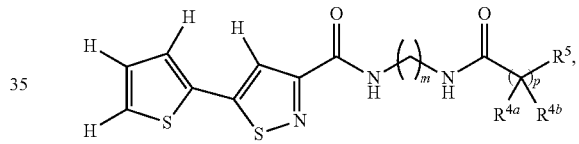

wherein all other variables are as defined herein; or a pharmaceutically acceptable salt thereof.

In a further aspect, the compound does not have a structure represented by a formula:

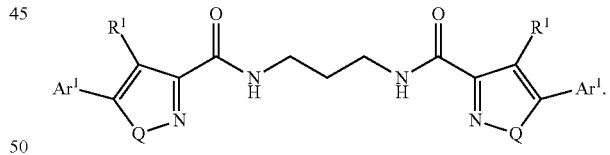

In one aspect, m is an integer selected from 2, 3, and 4. In a further aspect, m is an integer selected from 2 and 3. In a still further aspect, m is 4. In yet a further aspect, m is 3. In an even further aspect, m is 2.

In one aspect, n is an integer selected from 0 and 1. In a further aspect, n is 1. In a still further aspect, n is 0.

In one aspect, p is an integer selected from 0, 1, 2, 3, and 4. In a further aspect, p is an integer selected from 0, 1, 2, and 3. In a still further aspect, p is an integer selected from 0, 1, and 2. In yet a further aspect, p is an integer selected from 0 and 1. In an even further aspect, p is 4. In a still further aspect, p is 3. In yet a further aspect, p is 2. In an even further aspect, p is 1. In a still further aspect, p is 0.

A. Q Groups

In one aspect, Q is selected from NR$^6$, O, and S. In a further aspect, Q is selected from NR$^6$ and O. In a still further aspect, Q is selected from O and S. In yet a further aspect, Q is NR$^6$. In an even further aspect, Q is O. In a still further aspect, Q is S.

b. R$^1$ Groups

In one aspect, R$^1$ is selected from hydrogen and C1-C4 alkyl. In a further aspect, R$^1$ is C1-C4 alkyl. In a still further aspect, R$^1$ is ethyl. In yet a further aspect, R$^1$ is methyl. In an even further aspect, R$^1$ is hydrogen.

In a further aspect, R$^1$ is selected from hydrogen, methyl, ethyl, propyl, isopropyl, tert-butyl, sec-butyl, and isobutyl. In a still further aspect, R$^1$ is selected from hydrogen, methyl, ethyl, propyl, and isopropyl. In yet a further aspect, R$^1$ is selected from hydrogen, methyl, and ethyl. In an even further aspect, R$^1$ is selected from hydrogen and ethyl. In a still further aspect, R$^1$ is selected from hydrogen and methyl.

C. R$^2$ Groups

In one aspect, R$^2$ is selected from hydrogen and C1-C4 alkyl. In a further aspect, R$^2$ is C1-C4 alkyl. In a still further aspect, R$^2$ is ethyl. In yet a further aspect, R$^2$ is methyl. In an even further aspect, R$^2$ hydrogen.

In a further aspect, R$^2$ is selected from hydrogen, methyl, ethyl, propyl, isopropyl, tert-butyl, sec-butyl, and isobutyl. In a still further aspect, R$^2$ is selected from hydrogen, methyl, ethyl, propyl, and isopropyl. In yet a further aspect, R$^2$ is selected from hydrogen, methyl, and ethyl. In an even further aspect, R$^2$ is selected from hydrogen and ethyl. In a still further aspect, R$^2$ is selected from hydrogen and methyl.

D. R$^3$ Groups

In one aspect, R$^3$ is selected from hydrogen and C1-C4 alkyl. In a further aspect, R$^3$ is C1-C4 alkyl. In a still further aspect, R$^3$ is ethyl. In yet a further aspect, R$^3$ is methyl. In an even further aspect, R$^3$ hydrogen.

In a further aspect, R$^3$ is selected from hydrogen, methyl, ethyl, propyl, isopropyl, tert-butyl, sec-butyl, and isobutyl. In a still further aspect, R$^3$ is selected from hydrogen, methyl, ethyl, propyl, and isopropyl. In yet a further aspect, R$^3$ is selected from hydrogen, methyl, and ethyl. In an even further aspect, R$^3$ is selected from hydrogen and ethyl. In a still further aspect, R$^3$ is selected from hydrogen and methyl.

E. R$^{4a}$ and R$^{4b}$ Groups

In one aspect, each occurrence of R$^{4a}$ and R$^{4b}$ is independently selected from hydrogen, halogen, —OH, —CN, —N$_3$, —NH$_2$, and C1-C4 alkyl, or each of R$^{4a}$ and R$^{4b}$ are optionally covalently bonded and, together with the intermediate atoms, comprise a 3- to 5-membered cycle.

In a further aspect, each occurrence of R$^{4a}$ and R$^{4b}$ is independently selected from hydrogen, halogen, —OH, —CN, —N$_3$, —NH$_2$, and C1-C4 alkyl. In a still further aspect, each occurrence of R$^{4a}$ and R$^{4b}$ is independently selected from hydrogen, halogen, —OH, —CN, —N$_3$, —NH$_2$, and C1-C4 alkyl. In yet a further aspect, each occurrence of R$^{4a}$ and R$^{4b}$ is hydrogen.

In a further aspect, each of R$^{4a}$ and R$^{4b}$ are optionally covalently bonded and, together with the intermediate atoms, comprise a 3- to 5-membered cycle. In a still further aspect, each of R$^{4a}$ and R$^{4b}$ are optionally covalently bonded and, together with the intermediate atoms, comprise a 3- to 5-membered cycle selected from cyclopropyl, cyclobutyl, and cyclopentyl. In yet a further aspect, each of R$^{4a}$ and R$^{4b}$ are optionally covalently bonded and, together with the intermediate atoms, comprise a 3- to 5-membered cycle selected from cyclopropyl and cyclobutyl. In an even further aspect, each of R$^{4a}$ and R$^{4b}$ are optionally covalently bonded and, together with the intermediate atoms, comprise a cyclopropyl.

In a further aspect, p is 0 and R$^{4a}$ and R$^{4b}$ are not present. In a still further aspect, p is 1 and each occurrence of R$^{4a}$ and R$^{4b}$ is hydrogen. In a yet further aspect, p is 2 and each occurrence of R$^{4a}$ and R$^{4b}$ is hydrogen. In an even further aspect, p is 3 and each occurrence of R$^{4a}$ and R$^{4b}$ is hydrogen. In a still further aspect, p is 4 and each occurrence of R$^{4a}$ and R$^{4b}$ is hydrogen.

In various further aspects, it is understood that multiple uses of the substituents labeled as R$^{4a}$ and R$^{4b}$ can involve multiple occurrences of the various selected substituents, each such substituent independently selected. For example, in such instances, the invention relates to a structure represented by a formula:

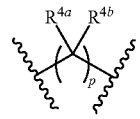

wherein p is 0-4 (i.e., p=0, p=1, p=2, or p=3); wherein each R$^{4a}$, when present, is selected from hydrogen, methyl, and ethyl; and wherein each R$^{4b}$, when present, is selected from hydrogen, —F, —Cl, —OH, —CN, —N$_3$, —NH$_2$, methyl, ethyl, propyl, isopropyl, tert-butyl, sec-butyl, and isobutyl. This is understood to include and disclose a moiety wherein, e.g., for moiety p=1, substituted with R$^{4a1}$ and R$^{4b1}$, each such substituent is independently hydrogen, —F, —Cl, —OH, —CN, —N$_3$, —NH$_2$, methyl, ethyl, propyl, isopropyl, tert-butyl, sec-butyl, and isobutyl. This also includes and discloses a moiety wherein, for moiety p=2, substituted with R$^{4a2}$ and R$^{4b2}$, each such substituent is independently hydrogen, —F, —Cl, —OH, —CN, —N$_3$, —NH$_2$, methyl, ethyl, propyl, isopropyl, tert-butyl, sec-butyl, or isobutyl, irrespective of the selection for R$^{4a1}$ and R$^{4b1}$.

Such structures (e.g., wherein p=2) are also understood to refer to a moiety having a structure alternatively represented by a formula:

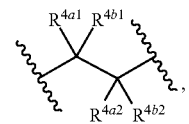

wherein each of R$^{4a1}$, R$^{4b1}$, R$^{4a2}$, and R$^{4b2}$ is independently selected from hydrogen, —F, —Cl, —OH, —CN, —N$_3$, —NH$_2$, methyl, ethyl, propyl, isopropyl, tert-butyl, sec-butyl, and isobutyl (again, irrespective of the other selections).

F. R$^5$ Groups

In one aspect, R$^5$ is selected from Cy$^2$ and Ar$^2$. In a further aspect, R$^5$ is Cy$^2$. In a still further aspect, R$^5$ is Ar$^2$.

G. R$^6$ Groups

In one aspect, R$^6$, when present, is selected from hydrogen and C1-C4 alkyl. In a further aspect, R$^6$, when present, is C1-C4 alkyl. In a still further aspect, R$^6$, when present, is ethyl. In yet a further aspect, R$^6$, when present, is methyl. In an even further aspect, R$^6$, when present, is hydrogen.

In a further aspect, R$^6$, when present, is selected from hydrogen, methyl, ethyl, propyl, isopropyl, tert-butyl, sec-butyl, and isobutyl. In a still further aspect, R$^6$, when present, is selected from hydrogen, methyl, ethyl, propyl, and isopropyl. In yet a further aspect, R$^6$, when present, is selected from hydrogen, methyl, and ethyl. In an even further aspect, $R^6$, when present, is selected from hydrogen and ethyl. In a still further aspect, $R^6$, when present, is selected from hydrogen and methyl.

h. $R^{20a}$, $R^{20b}$, $R^{20c}$, $R^{20d}$, and $R^{20e}$ Groups

In one aspect, each of $R^{20a}$, $R^{20b}$, $R^{20c}$, $R^{20d}$, and $R^{20e}$, when present, are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least two of $R^{20a}$, $R^{20b}$, $R^{20c}$, $R^{20d}$, and $R^{20e}$ are hydrogen. In a further aspect, each of $R^{20a}$, $R^{20b}$, $R^{20c}$, $R^{20d}$, and $R^{20e}$, when present, are independently selected from hydrogen, —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$, provided that at least two of $R^{20a}$, $R^{20b}$, $R^{20c}$, $R^{20d}$, and $R^{20e}$ are hydrogen. In a still further aspect, each of $R^{20a}$, $R^{20b}$, $R^{20c}$, $R^{20d}$, and $R^{20e}$, when present, are independently selected from hydrogen, —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$, provided that at least two of $R^{20a}$, $R^{20b}$, $R^{20c}$, $R^{20d}$, and $R^{20e}$ are hydrogen. In yet a further aspect, each of $R^{20a}$, $R^{20b}$, $R^{20c}$, $R^{20d}$, and $R^{20e}$, when present, are independently selected from hydrogen, —F, —Cl, —OH, —CN, —N$_3$, —NH$_2$, methyl, —CF$_3$, —OCH$_3$, —OCF$_3$, —NHCH$_3$, and —N(CH$_3$)$_2$, provided that at least two of $R^{20a}$, $R^{20b}$, $R^{20c}$, $R^{20d}$, and $R^{20e}$ are hydrogen. In an even further aspect, each of $R^{20a}$, $R^{20b}$, $R^{20c}$, $R^{20d}$, and $R^{20e}$, when present, are independently selected from hydrogen, —F, —Cl, —N$_3$, and methyl, provided that at least two of $R^{20a}$, $R^{20b}$, $R^{20c}$, $R^{20d}$, and $R^{20e}$ are hydrogen.

In a further aspect, each of $R^{20a}$, $R^{20b}$, and $R^{20c}$, when present, is hydrogen, and each of $R^{20d}$ and $R^{20e}$, when present, are independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20b}$, and $R^{20c}$, when present, is hydrogen, and each of $R^{20d}$ and $R^{20e}$, when present, are independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20b}$, and $R^{20c}$, when present, is hydrogen, and each of $R^{20d}$ and $R^{20e}$, when present, are independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20b}$, and $R^{20c}$, when present, is hydrogen, and each of $R^{20d}$ and $R^{20e}$, when present, are independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20b}$, and $R^{20c}$, when present, is hydrogen, and each of $R^{20d}$ and $R^{20e}$, when present, are independently selected from —F, —Cl, —N$_3$, and methyl.

In a further aspect, each of $R^{20a}$, $R^{20b}$, and $R^{20d}$, when present, is hydrogen, and each of $R^{20c}$ and $R^{20e}$, when present, are independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20b}$, and $R^{20d}$, when present, is hydrogen, and each of $R^{20c}$ and $R^{20e}$, when present, are independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20b}$ and $R^{20d}$, when present, is hydrogen, and each of $R^{20c}$ and $R^{20e}$, when present, are independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20b}$, and $R^{20d}$, when present, is hydrogen, and each of $R^{20c}$ and $R^{20e}$, when present, are independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20b}$, and $R^{20d}$, when present, is hydrogen, and each of $R^{20c}$ and $R^{20e}$, when present, are independently selected from —F, —Cl, —N$_3$, and methyl.

In a further aspect, each of $R^{20a}$, $R^{20b}$, and $R^{20e}$, when present, is hydrogen, and each of $R^{20c}$ and $R^{20d}$, when present, are independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20b}$, and $R^{20e}$, when present, is hydrogen, and each of $R^{20c}$ and $R^{20d}$, when present, are independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20b}$, and $R^{20e}$, when present, is hydrogen, and each of $R^{20c}$ and $R^{20d}$, when present, are independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20b}$, and $R^{20e}$, when present, is hydrogen, and each of $R^{20c}$ and $R^{20d}$, when present, are independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20b}$, and $R^{20e}$, when present, is hydrogen, and each of $R^{20c}$ and $R^{20d}$, when present, are independently selected from —F, —Cl, —N$_3$, and methyl.

In a further aspect, each of $R^{20a}$, $R^{20c}$, and $R^{20d}$, when present, is hydrogen, and each of $R^{20b}$ and $R^{20e}$, when present, are independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20c}$, and $R^{20d}$, when present, is hydrogen, and each of $R^{20b}$ and $R^{20e}$, when present, are independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20c}$, and $R^{20d}$, when present, is hydrogen, and each of $R^{20b}$ and $R^{20e}$, when present, are independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20c}$, and $R^{20d}$, when present, is hydrogen, and each of $R^{20b}$ and $R^{20e}$, when present, are independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20a}$, R$^{20c}$, and R$^{20d}$, when present, is hydrogen, and each of R$^{20b}$ and R$^{20e}$, when present, are independently selected from —F, —Cl, —N$_3$, and methyl.

In a further aspect, each of R$^{20a}$, R$^{20c}$, and R$^{20e}$, when present, is hydrogen, and each of R$^{20b}$ and R$^{20d}$, when present, are independently selected from halogen, —OH, —CN, —N$_3$, —NH$_2$, C1-C4 alkyl, C1-C4 alkoxy, C1-C4 monohaloalkyl, C1-C4 polyhaloalkyl, C1-when present, is hydrogen, and each of R$^{20b}$ and R$^{20d}$, when present, are independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{20a}$, R$^{20c}$ and R$^{20e}$, when present, is hydrogen, and each of R$^{20b}$ and R$^{20d}$, when present, are independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{20a}$, R$^{20c}$, and R$^{20e}$, when present, is hydrogen, and each of R$^{20b}$ and R$^{20d}$, when present, are independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20a}$, R$^{20c}$, and R$^{20e}$, when present, is hydrogen, and each of R$^{20b}$ and R$^{20d}$, when present, are independently selected from —F, —Cl, —N$_3$, and methyl.

In a further aspect, each of R$^{20a}$, R$^{20d}$, and R$^{20e}$, when present, is hydrogen, and each of R$^{20b}$ and R$^{20c}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{20a}$, R$^{20d}$, and R$^{20e}$, when present, is hydrogen, and each of R$^{20b}$ and R$^{20c}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{20a}$, R$^{20d}$, and R$^{20e}$, when present, is hydrogen, and each of R$^{20b}$ and R$^{20c}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{20a}$, R$^{20d}$, and R$^{20e}$, when present, is hydrogen, and each of R$^{20b}$ and R$^{20c}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20a}$, R$^{20d}$, and R$^{20e}$, when present, is hydrogen, and each of R$^{20b}$ and R$^{20c}$, when present, is independently selected from —F, —Cl, —N$_3$, and methyl.

In a further aspect, each of R$^{20b}$, R$^{20c}$, and R$^{20d}$, when present, is hydrogen, and each of R$^{20a}$ and R$^{20e}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{20b}$, R$^{20c}$ and R$^{20d}$, when present, is hydrogen, and each of R$^{20a}$ and R$^{20e}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{20b}$, R$^{20c}$, and R$^{20d}$, when present, is hydrogen, and each of R$^{20a}$ and R$^{20e}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{20b}$, R$^{20c}$, and R$^{20d}$, when present, is hydrogen, and each of R$^{20a}$ and R$^{20e}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20b}$, R$^{20c}$, and R$^{20d}$, when present, is hydrogen, and each of R$^{20a}$ and R$^{20e}$, when present, is independently selected from —F, —Cl, —N$_3$, and methyl.

In a further aspect, each of R$^{20b}$, R$^{20d}$, and R$^{20e}$, when present, is hydrogen, and each of R$^{20a}$ and R$^{20c}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{20b}$, R$^{20d}$, and R$^{20e}$, when present, is hydrogen, and each of R$^{20a}$ and R$^{20c}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20b}$, R$^{20d}$, and R$^{20e}$, when present, is hydrogen, and each of R$^{20a}$ and R$^{20c}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{20b}$, R$^{20d}$, and R$^{20e}$, when present, is hydrogen, and each of R$^{20a}$ and R$^{20c}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{20b}$, R$^{20d}$, and R$^{20e}$, when present, is hydrogen, and each of R$^{20a}$ and R$^{20c}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20b}$, R$^{20d}$, and R$^{20e}$, when present, is hydrogen, and each of R$^{20a}$ and R$^{20c}$, when present, is independently selected from —F, —Cl, —N$_3$, and methyl.

In a further aspect, each of R$^{20b}$, R$^{20c}$, and R$^{20e}$, when present, is hydrogen, and each of R$^{20a}$ and R$^{20d}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{20b}$, R$^{20c}$, and R$^{20e}$, when present, is hydrogen, and each of R$^{20a}$ and R$^{20d}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{20b}$, R$^{20c}$, and R$^{20e}$, when present, is hydrogen, and each of R$^{20a}$ and R$^{20d}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{20b}$, R$^{20c}$, and R$^{20e}$, when present, is hydrogen, and each of R$^{20a}$ and R$^{20d}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20b}$, R$^{20c}$, and R$^{20e}$, when present, is hydrogen, and each of R$^{20a}$ and R$^{20d}$, when present, is independently selected from —F, —Cl, —N$_3$, and methyl.

In a further aspect, each of R$^{20c}$, R$^{20d}$, and R$^{20e}$, when present, is hydrogen, and each of R$^{20a}$ and R$^{20b}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{20c}$, R$^{20d}$, and R$^{20e}$, when present, is hydrogen, and each of R$^{20a}$ and R$^{20b}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{20c}$, R$^{20d}$, and R$^{20e}$, when present, is hydrogen, and each of R$^{20a}$ and R$^{20b}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{20c}$, R$^{20d}$, and R$^{20e}$, when present, is hydrogen, and each of R$^{20a}$ and R$^{20b}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20c}$, R$^{20d}$, and R$^{20e}$, when present, is hydrogen, and each of R$^{20a}$ and R$^{20b}$, when present, is independently selected from —F, —Cl, —N$_3$, and methyl.

In a further aspect, each of R$^{20a}$, R$^{20b}$, R$^{20c}$, and R$^{20d}$, when present, is hydrogen, and R$^{20e}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{20a}$, R$^{20b}$, R$^{20c}$, and R$^{20d}$, when present, is hydrogen, and R$^{20e}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{20a}$, R$^{20b}$, R$^{20c}$, and R$^{20d}$, when present, is hydrogen, and R$^{20e}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{20a}$, R$^{20b}$, R$^{20c}$, and R$^{20d}$, when present, is hydrogen, and R$^{20e}$, when present, is selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20a}$, R$^{20b}$, R$^{20c}$, and R$^{20d}$, when present, is hydrogen, and R$^{20e}$, when present, is selected from —F, —Cl, —N$_3$, and methyl.

In a further aspect, each of R$^{20a}$, R$^{20b}$, R$^{20c}$, and R$^{20e}$, when present, is hydrogen, and R$^{20d}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{20a}$, R$^{20b}$, R$^{20c}$, and R$^{20e}$, when present, is hydrogen, and R$^{20d}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{20a}$, R$^{20b}$, R$^{20c}$, and R$^{20e}$, when present, is hydrogen, and R$^{20d}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{20a}$, R$^{20b}$, R$^{20c}$, and R$^{20e}$, when present, is hydrogen, and R$^{20d}$, when present, is selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20a}$, R$^{20b}$, R$^{20c}$, and R$^{20e}$, when present, is hydrogen, and R$^{20d}$, when present, is selected from —F, —Cl, —N$_3$, and methyl.

In a further aspect, each of R$^{20a}$, R$^{20b}$, R$^{20d}$, and R$^{20e}$, when present, is hydrogen, and R$^{20c}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{20a}$, R$^{20b}$, R$^{20d}$, and R$^{20e}$, when present, is hydrogen, and R$^{20c}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{20a}$, R$^{20b}$, R$^{20d}$, and R$^{20e}$, when present, is hydrogen, and R$^{20c}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{20a}$, R$^{20b}$, R$^{20d}$, and R$^{20e}$, when present, is hydrogen, and R$^{20c}$, when present, is selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of R$^{20a}$, R$^{20b}$, R$^{20d}$, and R$^{20e}$, when present, is hydrogen, and R$^{20c}$, when present, is selected from —F, —Cl, —N$_3$, and methyl.

In a further aspect, each of R$^{20a}$, R$^{20b}$, R$^{20d}$, and R$^{20e}$, when present, is hydrogen, and R$^{20b}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{20a}$, R$^{20c}$, R$^{20d}$, and R$^{20e}$, when present, is hydrogen, and R$^{20b}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{20a}$, R$^{20c}$, R$^{20d}$, and R$^{20e}$, when present, is hydrogen, and $R^{20b}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20c}$, $R^{20d}$, and $R^{20e}$, when present, is hydrogen, and $R^{20b}$, when present, is selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20c}$, $R^{20d}$, and $R^{20e}$, when present, is hydrogen, and $R^{20b}$, when present, is selected from —F, —Cl, —N$_3$, and methyl.

In a further aspect, each of $R^{20b}$, $R^{20c}$, $R^{20d}$, and $R^{20e}$, when present, is hydrogen, and $R^{20a}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20b}$, $R^{20c}$, $R^{20d}$, and $R^{20e}$, when present, is hydrogen, and $R^{20a}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20b}$, $R^{20c}$, $R^{20d}$, and $R^{20e}$, when present, is hydrogen, and $R^{20a}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20b}$, $R^{20c}$, $R^{20d}$, and $R^{20e}$, when present, is hydrogen, and $R^{20a}$, when present, is selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20b}$, $R^{20c}$, $R^{20d}$, and $R^{20e}$, when present, is hydrogen, and $R^{20a}$, when present, is selected from —F, —Cl, —N$_3$, and methyl.

In a further aspect, each of $R^{20a}$, $R^{20b}$, $R^{20c}$, $R^{20d}$, and $R^{20e}$, when present, is hydrogen.

i. $R^{30a}$, $R^{30b}$, and $R^{30c}$ Groups

In one aspect, each of $R^{30a}$, $R^{30b}$, and $R^{30c}$, when present, are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a further aspect, each of $R^{30a}$, $R^{30b}$, and $R^{30c}$, when present, are independently selected from hydrogen, —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In a still further aspect, each of $R^{30a}$, $R^{30b}$, and $R^{30c}$, when present, are independently selected from hydrogen, —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In yet a further aspect, each of $R^{30a}$, $R^{30b}$, and $R^{30c}$, when present, are independently selected from hydrogen, —F, —Cl, —OH, —CN, —N$_3$, —NH$_2$, methyl, —CF$_3$, —OCH$_3$, —OCF$_3$, —NHCH$_3$, and —N(CH$_3$)$_2$. In an even further aspect, each of $R^{30a}$, $R^{30b}$, and $R^{30c}$, when present, are independently selected from hydrogen, —F, —Cl, —N$_3$, and methyl.

In a further aspect, $R^{30a}$, when present, is hydrogen and each of $R^{30b}$ and $R^{30c}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, $R^{30a}$, when present, is hydrogen and each of $R^{30b}$ and $R^{30c}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, $R^{30a}$, when present, is hydrogen and each of $R^{30b}$ and $R^{30c}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, $R^{30a}$, when present, is hydrogen and each of $R^{30b}$ and $R^{30c}$, when present, is independently selected from —F, —Cl, —N$_3$, and methyl.

In a further aspect, $R^{30b}$, when present, is hydrogen and each of $R^{30a}$ and $R^{30c}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, $R^{30b}$, when present, is hydrogen and each of $R^{30a}$ and $R^{30c}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, $R^{30b}$, when present, is hydrogen and each of $R^{30a}$ and $R^{30c}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, $R^{30b}$, when present, is hydrogen and each of $R^{30a}$ and $R^{30c}$, when present, is independently selected from —F, —Cl, —N$_3$, and methyl.

In a further aspect, $R^{30c}$, when present, is hydrogen and each of $R^{30a}$ and $R^{30b}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, $R^{30c}$, when present, is hydrogen and each of $R^{30a}$ and $R^{30b}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, $R^{30c}$, when present, is hydrogen and each of $R^{30a}$ and $R^{30b}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, $R^{30c}$, when present, is hydrogen and each of $R^{30a}$ and $R^{30b}$, when present, is independently selected from —F, —Cl, —N$_3$, and methyl.

In a further aspect, each of $R^{30a}$ and $R^{30b}$, when present, are hydrogen and $R^{30c}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{30a}$ and $R^{30b}$, when present, are hydrogen and $R^{30c}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{30a}$ and $R^{30b}$, when present, are hydrogen and $R^{30c}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{30a}$ and R$^{30b}$, when present, are hydrogen and R$^{30c}$, when present, is selected from —F, —Cl, —N$_3$, and methyl.

In a further aspect, each of R$^{30a}$ and R$^{30c}$, when present, are hydrogen and R$^{30b}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{30a}$ and R$^{30c}$, when present, are hydrogen and R$^{30b}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{30a}$ and R$^{30c}$, when present, are hydrogen and R$^{30b}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{30a}$ and R$^{30c}$, when present, are hydrogen and R$^{30b}$, when present, is selected from —F, —Cl, —N$_3$, and methyl.

In a further aspect, each of R$^{30b}$ and R$^{30c}$, when present, are hydrogen and R$^{30a}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of R$^{30b}$ and R$^{30c}$, when present, are hydrogen and R$^{30a}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of R$^{30b}$ and R$^{30c}$, when present, are hydrogen and R$^{30a}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of R$^{30b}$ and R$^{30c}$, when present, are hydrogen and R$^{30a}$, when present, is selected —F, —Cl, —N$_3$, and methyl.

In a further aspect, each of R$^{30a}$, R$^{30b}$, and R$^{30c}$, when present, is hydrogen.

J. Ar$^1$ Groups

In one aspect, Ar$^1$ is selected from aryl and heteroaryl, and Ar$^1$ is substituted with 0, 1, 2, or 3 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a further aspect, Ar$^1$ is selected from aryl and heteroaryl, and Ar$^1$ is substituted with 0, 1, 2, or 3 substituents independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar$^1$ is selected from aryl and heteroaryl, and Ar$^1$ is unsubstituted.

In a further aspect, Ar$^1$ is selected from aryl and heteroaryl, and Ar$^1$ is substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^1$ is aryl, and substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^1$ is heteroaryl, and substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^1$ is phenyl, and substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^1$ is thiophenyl, and substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^1$ is selected from aryl and heteroaryl, and Ar$^1$ is substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is selected from aryl and heteroaryl, and Ar$^1$ is substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^1$ is selected from aryl and heteroaryl, and Ar$^1$ is substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Ar$^1$ is aryl, and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is aryl, and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^1$ is aryl, and substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Ar$^1$ is heteroaryl, and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is heteroaryl, and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^1$ is heteroaryl, and substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Ar$^1$ is phenyl, and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is phenyl, and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^1$ is phenyl, and substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Ar$^1$ is thiophenyl, and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is thiophenyl, and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^1$ is thiophenyl, and substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Ar$^1$ is selected from aryl and heteroaryl, and Ar$^1$ is substituted with 0, 1, or 2 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^1$ is selected from aryl and heteroaryl, and Ar$^1$ is substituted with 0 or 1 substituent selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In yet a further aspect, Ar$^1$ is selected from aryl and heteroaryl, and Ar$^1$ is monosubstituted with a substituent selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino.

In a further aspect, Ar$^1$ is selected from aryl and heteroaryl, and Ar$^1$ is substituted with 0, 1, or 2 substituents independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar$^1$ is selected from aryl and heteroaryl, and Ar$^1$ is substituted with 0 or 1 substituent selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^1$ is selected from aryl and heteroaryl, and Ar$^1$ is monosubstituted with a substituent selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino.

In a further aspect, Ar$^1$ is aryl and substituted with 0, 1, 2, or 3 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^1$ is aryl and substituted with 0, 1, 2, or 3 substituents independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^1$ is unsubstituted aryl.

In a further aspect, Ar¹ is heteroaryl and substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar¹ is heteroaryl and substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar¹ is unsubstituted heteroaryl.

In a further aspect, Ar¹ is phenyl and substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar¹ is phenyl and substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar¹ is unsubstituted phenyl.

In a further aspect, Ar¹ is thiophenyl and substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar¹ is thiophenyl and substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar¹ is unsubstituted thiophenyl.

K. Ar² Groups

In one aspect, wherein Ar², when present, is selected from aryl and heteroaryl, and Ar² is substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³, provided that when m is 2 then Ar² is not substituted or unsubstituted phenyl, substituted or unsubstituted furanyl, or substituted or unsubstituted pyridinyl, and provided that when m is 3, n is 0, and p is 0, that Ar², when present, is not a structure represented by a formula:

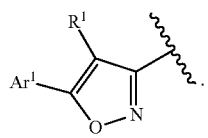

In a further aspect, Ar², when present, is selected from aryl and heteroaryl, and Ar² is substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, C1-C2 dialkylamino, Cy³, Ar³, and —NH(C=O)(C1-C2 alkyl)Cy³. In a still further aspect, Ar², when present, is selected from aryl and heteroaryl, and Ar² is unsubstituted.

In a further aspect, m is 2 and Ar² is not phenyl. In a still further aspect, the phenyl is substituted. In yet a further aspect, the phenyl is unsubstituted.

In a further aspect, m is 2 and Ar² is not furanyl. In a still further aspect, the furanyl is substituted. In yet a further aspect, the furanyl is unsubstituted.

In a further aspect, m is 2 and Ar² is not pyridinyl. In a still further aspect, the pyridinyl is substituted. In yet a further aspect, the pyridinyl is unsubstituted.

In a further aspect, m is 3, n is 0, and p is 0, that Ar², when present, is not a structure represented by a formula:

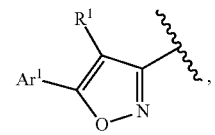

wherein each Ar¹, when present, is selected from aryl and heteroaryl, and Ar¹ is substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, and wherein each R¹, when present, is selected from hydrogen and C1-C4 alkyl. In a still further aspect, each Ar¹, when present, is not independently selected. In yet a further aspect, each R¹, when present, is not independently selected.

In a further aspect, Ar², when present, is selected from aryl and heteroaryl, and Ar² is substituted with 0, 1, 2, or 3 substituents independently selected from —F, —Cl, —Br, —I, hydroxyl, cyano, —N₃, —NH₂, methyl, ethyl, propyl, isopropyl, tert-butyl, sec-butyl, isobutyl, tert-butyl, —OCH₃, —OCH₂CH₃, —O(CH₂)₂CH₃, —OCH(CH₃)₂, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, Cy³, Ar³, and —NH(C=O)(CH₂)₄Cy³.

In a further aspect, Ar², when present, is aryl and substituted with 0, 1, 2, or 3 substituents independently selected from —F, —Cl, —Br, —I, hydroxyl, cyano, —N₃, —NH₂, methyl, ethyl, propyl, isopropyl, tert-butyl, sec-butyl, isobutyl, tert-butyl, —OCH₃, —OCH₂CH₃, —O(CH₂)₂CH₃, —OCH(CH₃)₂, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂CHI₂, —(CH₂)₂CI₃, —NHCH₃, —NHCH₂CH₃, —NH(CH₂)₂CH₃, —NHCH(CH₃)₂, —NH(CH₂)₃CH₃, —NH(CH₂)₄CH₃, —N(CH₃)₂, —N(CH₃)CH₂CH₃, —N(CH₃)(CH₂)₂CH₃, —N(CH₃)CH(CH₃)₂, —N(CH₂CH₃)₂, Cy³, Ar³, and —NH(C=O)(CH₂)₄Cy³.

In a further aspect, Ar², when present, is heteroaryl and substituted with 0, 1, 2, or 3 substituents independently selected from —F, —Cl, —Br, —I, hydroxyl, cyano, —N₃, —NH₂, methyl, ethyl, propyl, isopropyl, tert-butyl, sec-butyl, isobutyl, tert-butyl, —OCH₃, —OCH₂CH₃, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, Cy$^3$, Ar$^3$, and —NH(C=O)(CH$_2$)$_4$Cy$^3$.

In a further aspect, Ar$^2$, when present, is selected from phenyl, furanyl, thiophenyl, pyrrolyl, oxazolyl, isoxazolyl, thiazolyl, isothiazolyl, imidazolyl, pyrazolyl, oxadiazolyl, triazolyl, pyridinyl, pyrimidinyl, pyrazinyl, indolyl, benzofuranyl, imidazo[1,2-a]pyridinyl, [1,2,4]triazolo[1,5-a]pyridinyl, quinolinyl, and isoquinolinyl, and Ar$^2$ is substituted with 0, 1, 2, or 3 substituents independently selected from —F, —Cl, —Br, —I, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, —N(CH$_2$CH$_3$)$_2$, Cy$^3$, Ar$^3$, and —NH(C=O)(CH$_2$)$_4$Cy$^3$.

In a further aspect, Ar$^2$, when present, is selected from aryl and heteroaryl, and Ar$^2$ is substituted with 0, 1, 2, or 3 substituents independently selected from —F, —Cl, —Br, —I, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^2$, when present, is selected from aryl and heteroaryl, and Ar$^2$ is substituted with 0, 1, 2, or 3 substituents independently selected from —F, —Cl, —Br, —I, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^2$, when present, is selected from aryl and heteroaryl, and Ar$^2$ is substituted with 0, 1, 2, or 3 substituents independently selected from —F, —Cl, —Br, —I, —N$_3$, hydroxyl, methyl, —OCH$_3$, —CF$_3$, —CCl$_3$, —NHCH$_3$, and —N(CH$_3$)$_2$.

In a further aspect, Ar$^2$, when present, is aryl and substituted with 0, 1, 2, or 3 substituents independently selected from —F, —Cl, —Br, —I, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^2$, when present, is aryl and substituted with 0, 1, 2, or 3 substituents independently selected from —F, —Cl, —Br, —I, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^2$, when present, is aryl and substituted with 0, 1, 2, or 3 substituents independently selected from —F, —Cl, —Br, —I, —N$_3$, hydroxyl, methyl, —OCH$_3$, —CF$_3$, —CCl$_3$, —NHCH$_3$, and —N(CH$_3$)$_2$.

In a further aspect, Ar$^2$, when present, is heteroaryl and substituted with 0, 1, 2, or 3 substituents independently selected from —F, —Cl, —Br, —I, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^2$, when present, is heteroaryl and substituted with 0, 1, 2, or 3 substituents independently selected from —F, —Cl, —Br, —I, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^2$, when present, is heteroaryl and substituted with 0, 1, 2, or 3 substituents independently selected from —F, —Cl, —Br, —I, —N$_3$, hydroxyl, methyl, —OCH$_3$, —CF$_3$, —CCl$_3$, —NHCH$_3$, and —N(CH$_3$)$_2$.

In a further aspect, Ar$^2$, when present, is selected from phenyl, furanyl, thiophenyl, pyrrolyl, oxazolyl, isoxazolyl, thiazolyl, isothiazolyl, imidazolyl, pyrazolyl, oxadiazolyl, triazolyl, pyridinyl, pyrimidinyl, pyrazinyl, indolyl, benzofuranyl, imidazo[1,2-a]pyridinyl, [1,2,4]triazolo[1,5-a]pyridinyl, quinolinyl, and isoquinolinyl, and Ar$^2$ is substituted with 0, 1, 2, or 3 substituents independently selected from —F, —Cl, —Br, —I, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^2$, when present, is selected from phenyl, furanyl, thiophenyl, pyrrolyl, oxazolyl, isoxazolyl, thiazolyl, isothiazolyl, imidazolyl, pyrazolyl, oxadiazolyl, triazolyl, pyridinyl, pyrimidinyl, pyrazinyl, indolyl, benzofuranyl, imidazo[1,2-a]pyridinyl, [1,2,4]triazolo[1,5-a]pyridinyl, quinolinyl, and isoquinolinyl, and Ar$^2$ is substituted with 0, 1, 2, or 3 substituents independently selected from —F, —Cl, —Br, —I, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^2$, when present, is selected from phenyl, furanyl, thiophenyl, pyrrolyl, oxazolyl, isoxazolyl, thiazolyl, isothiazolyl, imidazolyl, pyrazolyl, oxadiazolyl, triazolyl, pyridinyl, pyrimidinyl, pyrazinyl, indolyl, benzofuranyl, imidazo[1,2-a]pyridinyl, [1,2,4]triazolo[1,5-a]pyridinyl, quinolinyl, and isoquinolinyl, and Ar$^2$ is substituted with 0, 1, 2, or 3 substituents independently selected from —F, —Cl, —Br, —I, —N$_3$, hydroxyl, methyl, —OCH$_3$, —CF$_3$, —CCl$_3$, —NHCH$_3$, and —N(CH$_3$)$_2$.

In a further aspect, Ar$^2$, when present, is selected from aryl and heteroaryl, and Ar$^2$ is substituted with 0, 1, or 2 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, C1-C4 dialkylamino, Cy$^3$, Ar$^3$, and —NH(C=O)(C1-C4 alkyl)Cy³. In a still further aspect, Ar², when present, is selected from aryl and heteroaryl, and Ar² is substituted with 0 or 1 substituent selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino Cy³, Ar³, and —NH(C=O)(C1-C4 alkyl)Cy³. In yet a further aspect, Ar², when present, is selected from aryl and heteroaryl, and Ar² is monosubstituted with a substituent selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³.

In a further aspect, Ar², when present, is selected from aryl and heteroaryl, and Ar² is substituted with 0, 1, or 2 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, C1-C2 dialkylamino, Cy³, Ar³, and —NH(C=O)(C1-C2 alkyl)Cy³. In a still further aspect, Ar², when present, is selected from aryl and heteroaryl, and Ar² is substituted with 0 or 1 substituent selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, C1-C2 dialkylamino, Cy³, Ar³, and —NH(C=O)(C1-C2 alkyl) Cy³. In yet a further aspect, Ar², when present, is selected from aryl and heteroaryl, and Ar² is monosubstituted with a substituent selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, C1-C2 dialkylamino, Cy³, Ar³, and —NH(C=O)(C1-C2 alkyl)Cy³.

In a further aspect, Ar², when present, is aryl and substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³. In a still further aspect, Ar², when present, is aryl and substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, C1-C2 dialkylamino, Cy³, Ar³, and —NH(C=O)(C1-C2 alkyl)Cy³. In yet a further aspect, Ar², when present, is unsubstituted aryl.

In a further aspect, Ar², when present, is heteroaryl and substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³. In a still further aspect, Ar², when present, is heteroaryl and substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, C1-C2 dialkylamino, Cy³, Ar³, and —NH(C=O) (C1-C4 alkyl)Cy³. In yet a further aspect, Ar², when present, is unsubstituted heteroaryl.

In a further aspect, Ar², when present, is selected from phenyl, furanyl, thiophenyl, pyrrolyl, oxazolyl, isoxazolyl, thiazolyl, isothiazolyl, imidazolyl, pyrazolyl, oxadiazolyl, triazolyl, pyridinyl, pyrimidinyl, pyrazinyl, indolyl, benzofuranyl, imidazo[1,2-a]pyridinyl, [1,2,4]triazolo[1,5-a]pyridinyl, quinolinyl, and isoquinolinyl, and Ar² is substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³. In a still further aspect, Ar², when present, is selected from phenyl, furanyl, thiophenyl, pyrrolyl, oxazolyl, isoxazolyl, thiazolyl, isothiazolyl, imidazolyl, pyrazolyl, oxadiazolyl, triazolyl, pyridinyl, pyrimidinyl, pyrazinyl, indolyl, benzofuranyl, imidazo[1,2-a]pyridinyl, [1,2,4]triazolo[1,5-a]pyridinyl, quinolinyl, and isoquinolinyl, and Ar² is substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, C1-C2 dialkylamino, Cy³, Ar³, and —NH(C=O)(C1-C2 alkyl)Cy³. In yet a further aspect, Ar², when present, is selected from phenyl, furanyl, thiophenyl, pyrrolyl, oxazolyl, isoxazolyl, thiazolyl, isothiazolyl, imidazolyl, pyrazolyl, oxadiazolyl, triazolyl, pyridinyl, pyrimidinyl, pyrazinyl, indolyl, benzofuranyl, imidazo[1,2-a]pyridinyl, [1,2,4]triazolo[1,5-a]pyridinyl, quinolinyl, and isoquinolinyl, and Ar² is unsubstituted.

In a further aspect, Ar², when present, is phenyl and substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³. In a still further aspect, Ar², when present, is phenyl and substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, C1-C2 dialkylamino, Cy³, Ar³, and —NH(C=O)(C1-C2 alkyl)Cy³. In yet a further aspect, Ar², when present, is unsubstituted phenyl.

In a further aspect, Ar², when present, is pyridinyl and substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³. In a still further aspect, Ar², when present, is pyridinyl and substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, C1-C2 dialkylamino, Cy³, Ar³, and —NH(C=O)(C1-C4 alkyl)Cy³. In yet a further aspect, Ar², when present, is unsubstituted pyridinyl.

In a further aspect, Ar², when present, is indolyl and substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, Cy³, Ar³, and —NH(C=O)(C1-C4 alkyl)Cy³. In a still further aspect, Ar², when present, is indolyl and substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, C1-C2 dialkylamino, Cy³, Ar³, and —NH(C=O)(C1-C2 alkyl)Cy³. In yet a further aspect, Ar², when present, is unsubstituted indolyl.

1. Ar³ Groups

In one aspect, Ar³, when present, is selected from aryl and heteroaryl, and Ar³ is substituted with 0, 1, 2, or 3 substituents independently selected from halogen, —OH, —CN, —N₃, —NH₂, C1-C3 alkyl, C1-C4 alkyl, C1-C4 alkoxy, C1-C4 monohaloalkyl, C1-C4 polyhaloalkyl, C1-C4 alkylamino, and C1-C4 dialkylamino. In a further aspect, Ar³, when present, is selected from aryl and heteroaryl, and Ar³ is substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, and C1-C2 dialkylamino. In a still further aspect, $Ar^3$, when present, is selected from aryl and heteroaryl, and $Ar^3$ is unsubstituted.

In a further aspect, $Ar^3$, when present, is selected from aryl and heteroaryl, and $Ar^3$ is substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, $Ar^3$, when present, is aryl and substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, $Ar^3$, when present, is heteroaryl and substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, $Ar^3$, when present, is phenyl and substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, $Ar^3$, when present, is selected from aryl and heteroaryl, and $Ar^3$ is substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, $Ar^3$, when present, is selected from aryl and heteroaryl, and $Ar^3$ is substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, $Ar^3$, when present, is selected from aryl and heteroaryl, and $Ar^3$ is substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, $Ar^3$, when present, is aryl and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, $Ar^3$, when present, is aryl and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, $Ar^3$, when present, is aryl and substituted with 0, 1, 2, or 3 substituents independently selected from —F, —Cl, —N$_3$, hydroxyl, methyl, —OCH$_3$, —CF$_3$, —CCl$_3$, —NHCH$_3$, and —N(CH$_3$)$_2$.

In a further aspect, $Ar^3$, when present, is heteroaryl and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, $Ar^3$, when present, is heteroaryl and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, $Ar^3$, when present, is heteroaryl and substituted with 0, 1, 2, or 3 substituents independently selected from —F, —Cl, —N$_3$, hydroxyl, methyl, —OCH$_3$, —CF$_3$, —CCl$_3$, —NHCH$_3$, and —N(CH$_3$)$_2$.

In a further aspect, $Ar^3$, when present, is phenyl and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^3$, when present, is phenyl and Ar$^3$ is substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^3$, when present, is phenyl and Ar$^3$ is substituted with 0, 1, 2, or 3 substituents independently selected from —F, —Cl, —N$_3$, hydroxyl, methyl, —OCH$_3$, —CF$_3$, —CCl$_3$, —NHCH$_3$, and —N(CH$_3$)$_2$.

In a further aspect, Ar$^3$, when present, is selected from aryl and heteroaryl, and Ar$^3$ is substituted with 0, 1, or 2 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is selected from aryl and heteroaryl, and Ar$^3$ is substituted with 0 or 1 substituent selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In yet a further aspect, Ar$^3$, when present, is selected from aryl and heteroaryl, and Ar$^3$ is monosubstituted with a substituent selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino.

In a further aspect, Ar$^3$, when present, is selected from aryl and heteroaryl, and Ar$^3$ is substituted with 0, 1, or 2 substituents independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar$^3$, when present, is selected from aryl and heteroaryl, and Ar$^3$ is substituted with 0 or 1 substituent selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is selected from aryl and heteroaryl, and Ar$^3$ is monosubstituted with a substituent selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino.

In a further aspect, Ar$^3$, when present, is aryl and substituted with 0, 1, 2, or 3 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is aryl and substituted with 0, 1, 2, or 3 substituents independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is unsubstituted aryl.

In a further aspect, Ar$^3$, when present, is heteroaryl and substituted with 0, 1, 2, or 3 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is heteroaryl and substituted with 0, 1, 2, or 3 substituents independently selected from halogen, —OH, —CN, —N$_3$, —NH$_2$, C1-C2 alkyl, C1-C2 alkoxy, C1-C2 monohaloalkyl, C1-C2 polyha-loalkyl, C1-C2 alkylamino, and C1-C2 dialkylamino. In yet a further aspect, Ar$^3$, when present, is unsubstituted heteroaryl.

In a further aspect, Ar$^3$, when present, is phenyl and substituted with 0, 1, 2, or 3 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is phenyl and substituted with 0, 1, 2, or 3 substituents independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is unsubstituted phenyl.

M. Cy$^2$ Groups

In one aspect, Cy$^2$, when present, is selected from cycloalkyl and heterocycloalkyl, and Cy$^2$ is substituted with 0, 1, 2, or 3 groups independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that when m is 2 then Cy$^2$ is not cycloalkyl. In a further aspect, Cy$^2$, when present, is selected from cycloalkyl and heterocycloalkyl, and Cy$^2$ is substituted with 0, 1, 2, or 3 substituents independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In a still further aspect, Cy$^2$, when present, is selected from cycloalkyl and heterocycloalkyl, and Cy$^2$ is unsubstituted.

In a further aspect, m is 2 and Cy$^2$, when present, is heterocycloalkyl and substituted with 0, 1, 2, or 3 groups independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a further aspect, Cy$^2$, when present, is heterocycloalkyl and substituted with 0, 1, 2, or 3 substituents independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In a still further aspect, Cy$^2$, when present, is unsubstituted heterocycloalkyl.

In a further aspect, Cy$^2$, when present, is selected from cycloalkyl and heterocycloalkyl, and Cy$^2$ is substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Cy$^2$, when present, is cycloalkyl, and substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Cy$^2$, when present, is heterocycloalkyl, and substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Cy$^2$, when present, is tetrahydro-2H-pyranyl and substituted with 0, 1, 2, or 3 substituents independently selected from —F, —Cl, hydroxyl, cyano, —N$_3$, —NH$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Cy$^2$, when present, is selected from cycloalkyl and heterocycloalkyl, and Cy$^2$ is substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Cy$^2$, when present, is selected from cycloalkyl and heterocycloalkyl, and Cy$^2$ is substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Cy$^2$, when present, is selected from cycloalkyl and heterocycloalkyl, and Cy$^2$ is substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Cy$^2$, when present, is cycloalkyl and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Cy$^2$, when present, is cycloalkyl and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Cy$^2$, when present, is cycloalkyl and substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Cy$^2$, when present, is heterocycloalkyl and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Cy$^2$, when present, is heterocycloalkyl and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Cy$^2$, when present, is heterocycloalkyl and substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Cy$^2$, when present, is tetrahydro-2H-pyranyl and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Cy$^2$, when present, is tetrahydro-2H-pyranyl and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Cy$^2$, when present, is tetrahydro-2H-pyranyl and substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Cy$^2$, when present, is selected from cycloalkyl and heterocycloalkyl, and Cy$^2$ is substituted with 0, 1, or 2 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Cy$^2$, when present, is selected from cycloalkyl and heterocycloalkyl, and Cy$^2$ is substituted with 0 or 1 substituent selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In yet a further aspect, Cy$^2$, when present, is selected from cycloalkyl and heterocycloalkyl, and $Cy^2$ is monosubstituted with a substituent selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino.

In a further aspect, $Cy^2$, when present, is selected from cycloalkyl and heterocycloalkyl, and $Cy^2$ is substituted with 0, 1, or 2 substituents independently selected from halogen, —OH, —CN, —$N_3$, —$NH_2$, C1-C2 alkyl, C1-C2 alkoxy, C1-C2 monohaloalkyl, C1-C2 polyhaloalkyl, C1-C2 alkylamino, and C1-C2 dialkylamino. In a still further aspect, $Cy^2$, when present, is selected from cycloalkyl and heterocycloalkyl, and $Cy^2$ is substituted with 0 or 1 substituent selected from halogen, —OH, —CN, —$N_3$, —$NH_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, $Cy^2$, when present, is selected from cycloalkyl and heterocycloalkyl, and $Cy^2$ is monosubstituted with a substituent selected from halogen, —OH, —CN, —$N_3$, —$NH_2$, C1-C2 alkyl, C1-C2 alkoxy, C1-C2 monohaloalkyl, C1-C2 polyhaloalkyl, C1-C2 alkylamino, and C1-C2 dialkylamino.

In a further aspect, $Cy^2$, when present, is cycloalkyl and substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, $Cy^2$, when present, is cycloalkyl and substituted with 0, 1, 2, or 3 substituents independently selected from halogen, —OH, —CN, —$N_3$, —$NH_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, $Cy^2$, when present, is unsubstituted cycloalkyl.

In a further aspect, $Cy^2$, when present, is heterocycloalkyl and substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, $Cy^2$, when present, is heterocycloalkyl and substituted with 0, 1, 2, or 3 substituents independently selected from halogen, —OH, —CN, —$N_3$, —$NH_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, $Cy^2$, when present, is unsubstituted heterocycloalkyl.

In a further aspect, $Cy^2$, when present, is tetrahydro-2H-pyranyl and substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, $Cy^2$, when present, is tetrahydro-2H-pyranyl and substituted with 0, 1, 2, or 3 substituents independently selected from halogen, —OH, —CN, —$N_3$, —$NH_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, $Cy^2$, when present, is unsubstituted tetrahydro-2H-pyranyl.

N. $Cy^3$ Groups

In one aspect, $Cy^3$, when present, is selected from cycloalkyl and heterocycloalkyl, and $Cy^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino. In a further aspect, $Cy^3$, when present, is selected from cycloalkyl and heterocycloalkyl, and $Cy^3$ is substituted with 0, 1, 2, or 3 substituents independently selected from halogen, —OH, —CN, —$N_3$, —$NH_2$, C1-C2 alkyl, C1-C2 alkoxy, C1-C2 monohaloalkyl, C1-C2 polyhaloalkyl, C1-C2 alkylamino, and C1-C2 dialkylamino. In a still further aspect, $Cy^3$, when present, is selected from cycloalkyl and heterocycloalkyl, and $Cy^3$ is unsubstituted.

In a further aspect, $Cy^3$, when present, is selected from cycloalkyl and heterocycloalkyl, and $Cy^3$ is substituted with 0, 1, 2, or 3 substituents independently selected from —F, —Cl, hydroxyl, cyano, —$N_3$, —$NH_2$, methyl, ethyl, propyl, isopropyl, tert-butyl, sec-butyl, isobutyl, tert-butyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$.

In a further aspect, $Cy^3$, when present, is cycloalkyl, and substituted with 0, 1, 2, or 3 substituents independently selected from —F, —Cl, hydroxyl, cyano, —$N_3$, —$NH_2$, methyl, ethyl, propyl, isopropyl, tert-butyl, sec-butyl, isobutyl, tert-butyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$.

In a further aspect, $Cy^3$, when present, is heterocycloalkyl, and substituted with 0, 1, 2, or 3 substituents independently selected from —F, —Cl, hydroxyl, cyano, —$N_3$, —$NH_2$, methyl, ethyl, propyl, isopropyl, tert-butyl, sec-butyl, isobutyl, tert-butyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$.

In a further aspect, $Cy^3$, when present, is tetrahydro-1H-thieno[3,4-d]imidazol-2(3H)-onyl and substituted with 0, 1, 2, or 3 substituents independently selected from —F, —Cl, hydroxyl, cyano, —$N_3$, —$NH_2$, methyl, ethyl, propyl, isopropyl, tert-butyl, sec-butyl, isobutyl, tert-butyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2I$, —$CH_2CH_2F$, —$CH_2CH_2Cl$, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Cy$^3$, when present, is selected from cycloalkyl and heterocycloalkyl, and Cy$^3$ is substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Cy$^3$, when present, is selected from cycloalkyl and heterocycloalkyl, and Cy$^3$ is substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Cy$^3$, when present, is selected from cycloalkyl and heterocycloalkyl, and Cy$^3$ is substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Cy$^3$, when present, is cycloalkyl and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Cy$^3$, when present, is cycloalkyl and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Cy$^3$, when present, is cycloalkyl and substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Cy$^3$, when present, is heterocycloalkyl and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Cy$^3$, when present, is heterocycloalkyl and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Cy$^3$, when present, is heterocycloalkyl and substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Cy$^3$, when present, is tetrahydro-1H-thieno[3,4-d]imidazol-2(3H)-onyl and substituted with 0, 1, 2, or 3 substituents independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Cy$^3$, when present, is tetrahydro-1H-thieno[3,4-d]imidazol-2(3H)-onyl and substituted with 0, 1, 2, or 3 substituents independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Cy$^3$, when present, is tetrahydro-1H-thieno[3,4-d]imidazol-2(3H)-onyl and substituted with 0, 1, 2, or 3 substituents independently selected from —F, —Cl, —N$_3$, methyl, —OCH$_3$, —CF$_3$, —CCl$_3$, —NHCH$_3$, and —N(CH$_3$)$_2$.

In a further aspect, Cy$^3$, when present, is selected from cycloalkyl and heterocycloalkyl, and Cy$^3$ is substituted with 0, 1, or 2 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Cy$^3$, when present, is selected from cycloalkyl and heterocycloalkyl, and Cy$^3$ is substituted with 0 or 1 substituent selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In yet a further aspect, Cy$^3$, when present, is selected from cycloalkyl and heterocycloalkyl, and Cy$^3$ is monosubstituted with a substituent selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino.

In a further aspect, Cy$^3$, when present, is selected from cycloalkyl and heterocycloalkyl, and Cy$^3$ is substituted with 0, 1, or 2 substituents independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In a still further aspect, Cy$^3$, when present, is selected from cycloalkyl and heterocycloalkyl, and Cy$^3$ is substituted with 0 or 1 substituent selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Cy$^3$, when present, is selected from cycloalkyl and heterocycloalkyl, and Cy$^3$ is monosubstituted with a substituent selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino.

In a further aspect, Cy$^3$, when present, is cycloalkyl and substituted with 0, 1, 2, or 3 substituents independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Cy$^3$, when present, is cycloalkyl and substituted with 0, 1, 2, or 3 substituents independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Cy$^3$, when present, is unsubstituted cycloalkyl.

In a further aspect, Cy$^3$, when present, is heterocycloalkyl and substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Cy³, when present, is heterocycloalkyl and substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Cy³, when present, is unsubstituted heterocycloalkyl.

In a further aspect, Cy³, when present, is tetrahydro-1H-thieno[3,4-d]imidazol-2(3H)-onyl and substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Cy³, when present, is tetrahydro-1H-thieno[3,4-d]imidazol-2(3H)-onyl and substituted with 0, 1, 2, or 3 substituents independently selected from halogen, —OH, —CN, —N₃, —NH₂, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Cy³, when present, is unsubstituted tetrahydro-1H-thieno[3,4-d]imidazol-2(3H)-onyl.

2. Compound Examples

In one aspect, a compound is selected from:

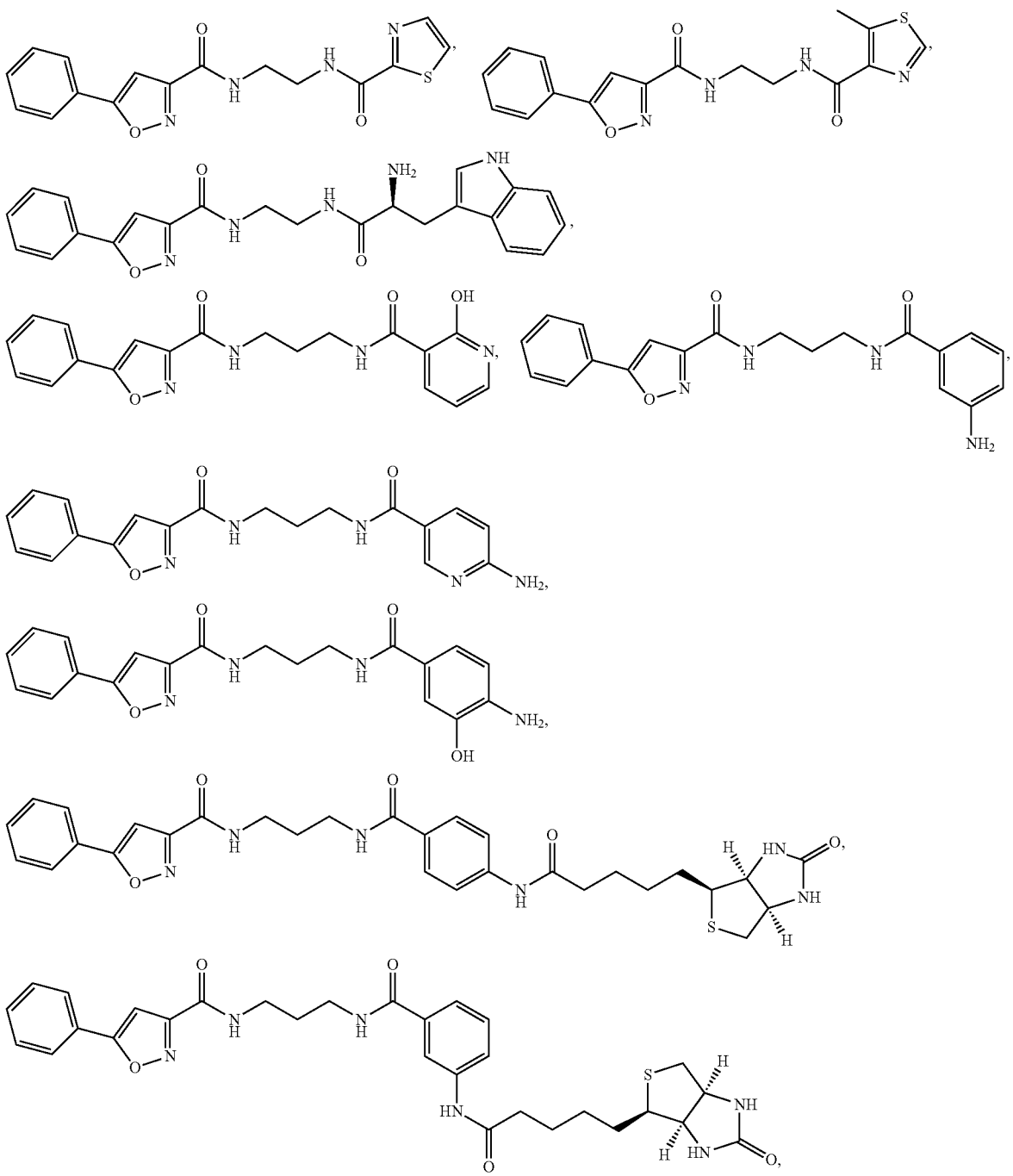

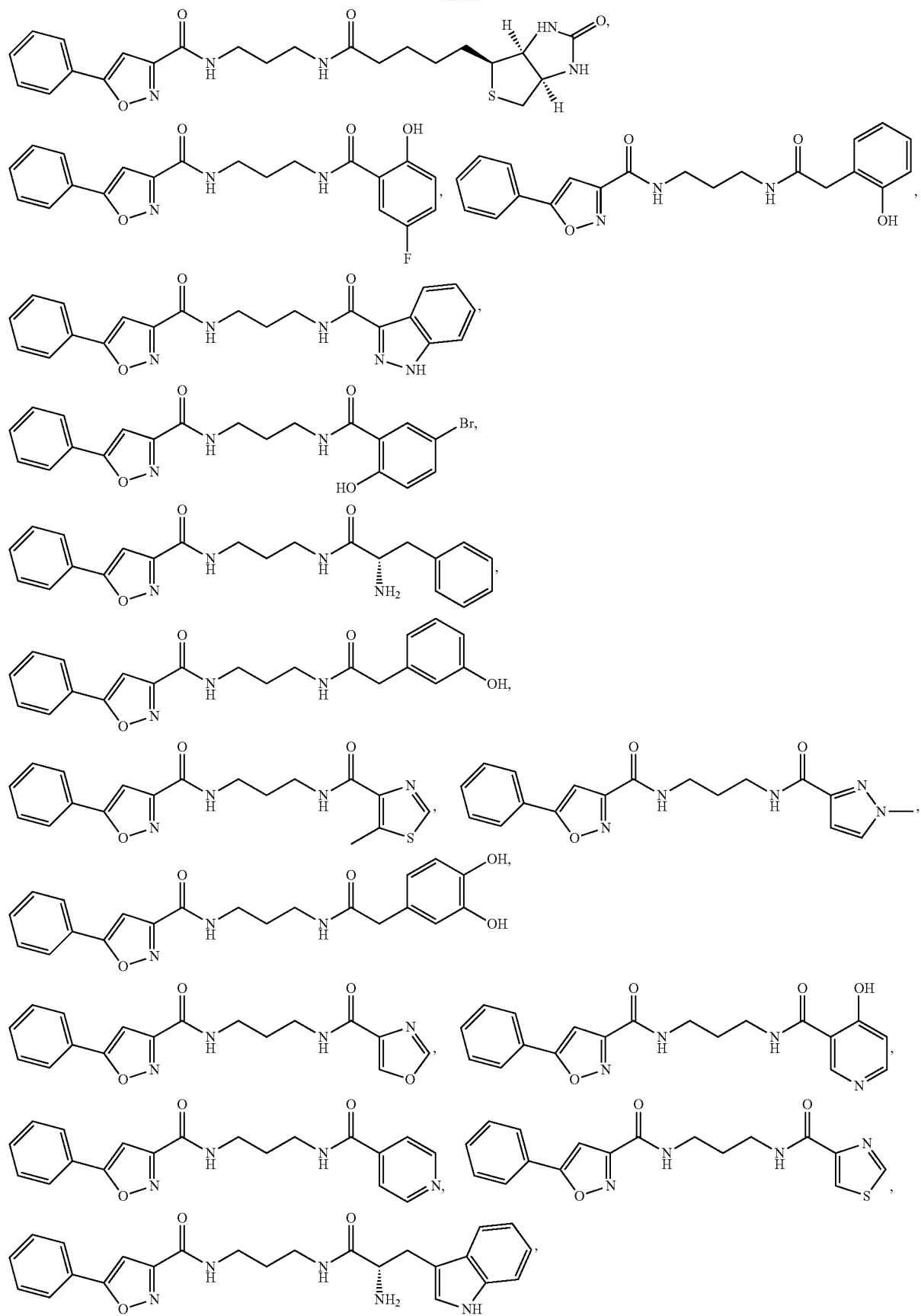

75 76
-continued
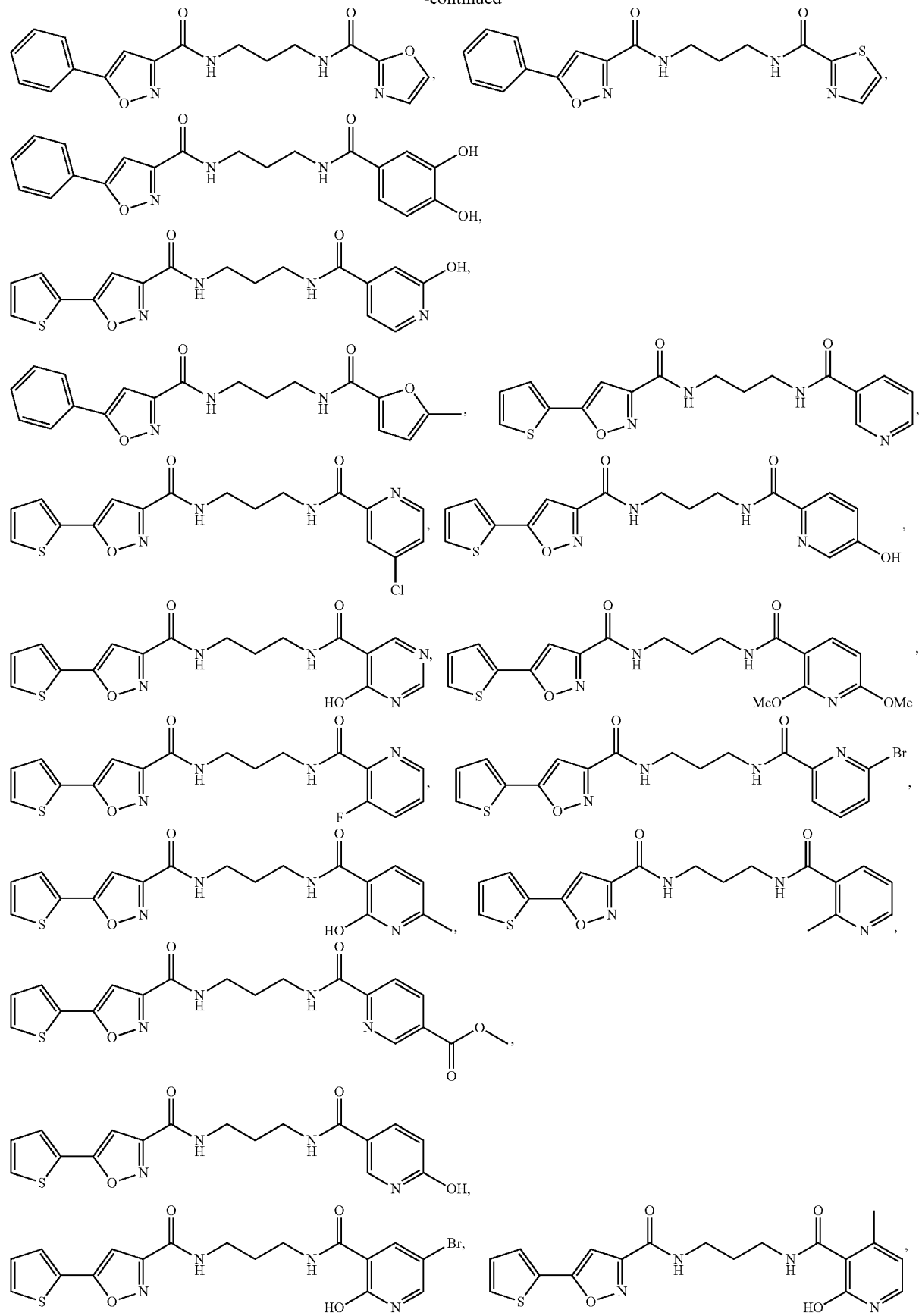

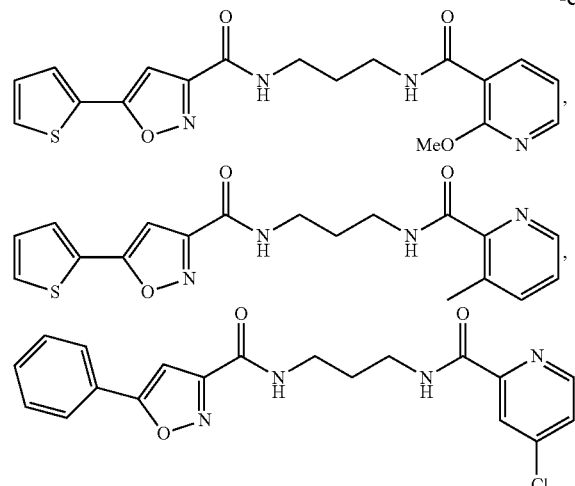
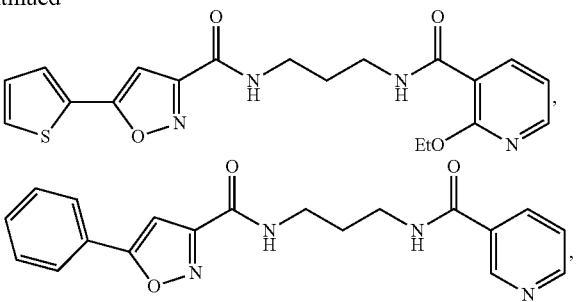
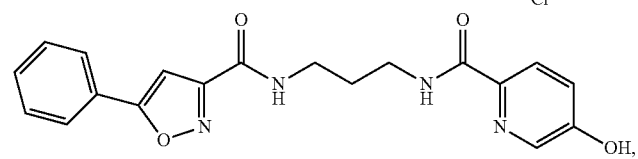
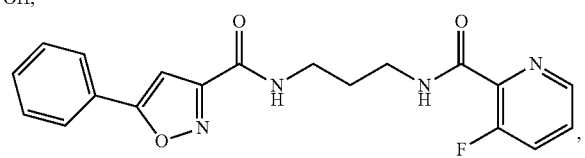
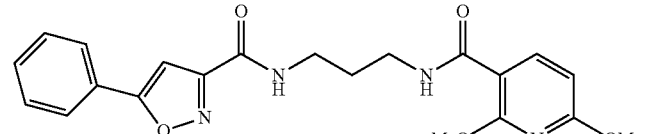
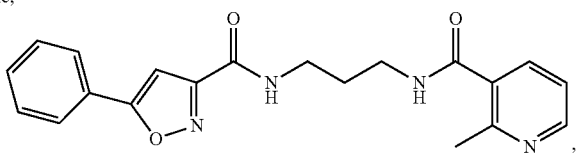
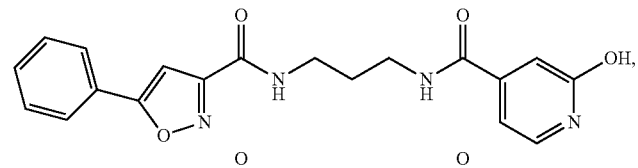
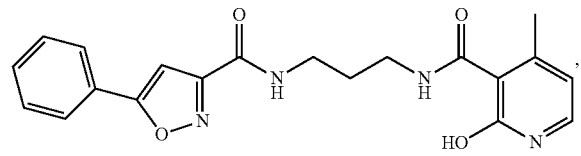
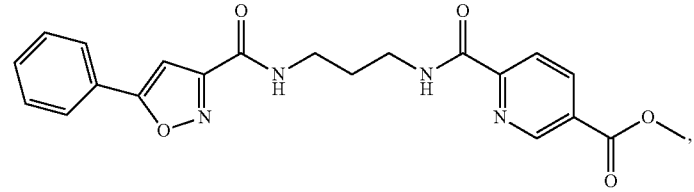
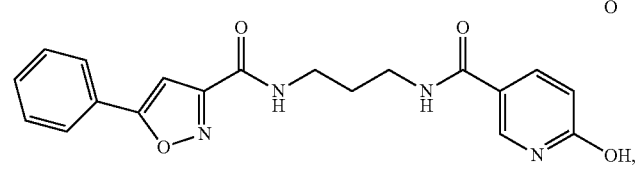

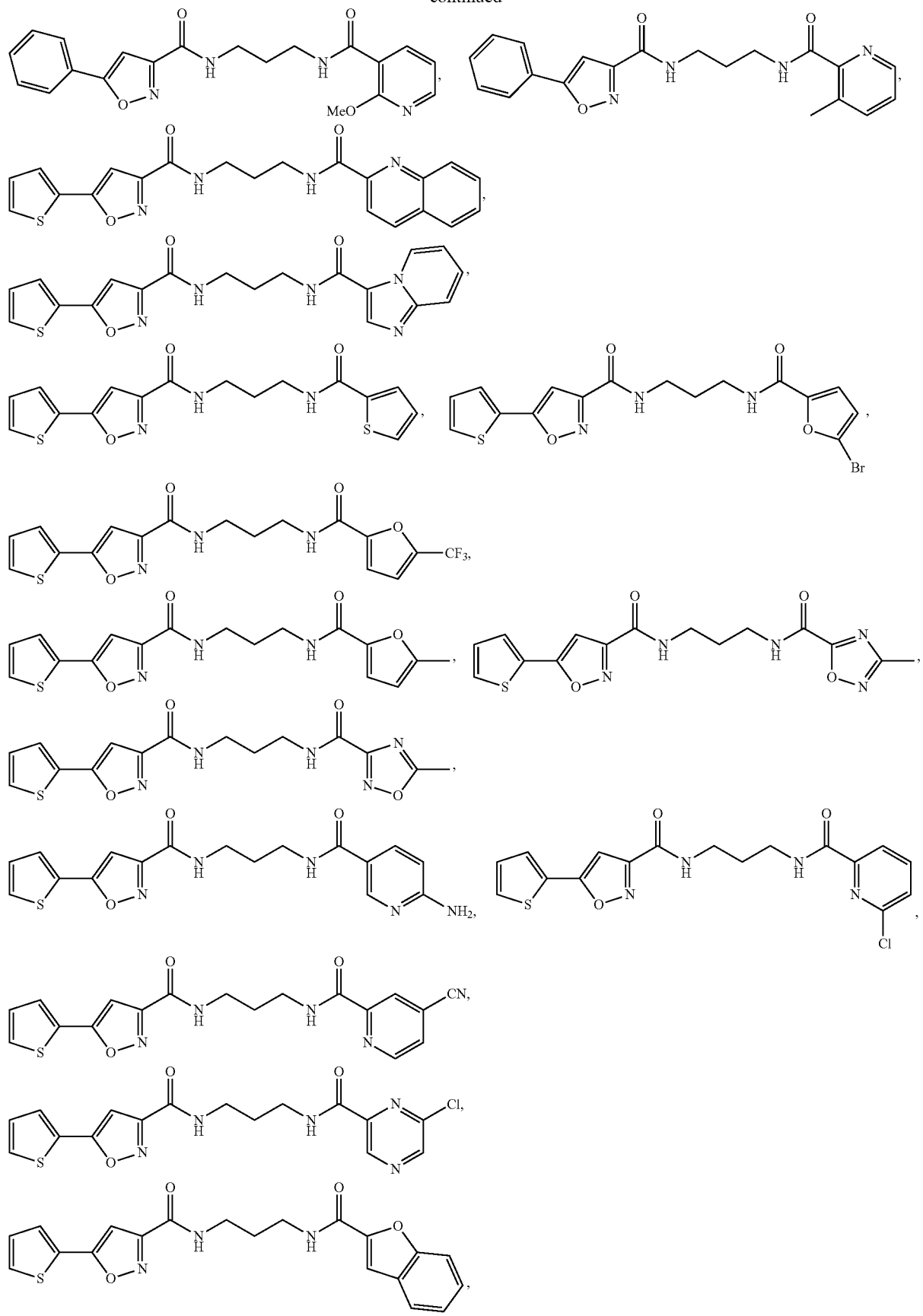

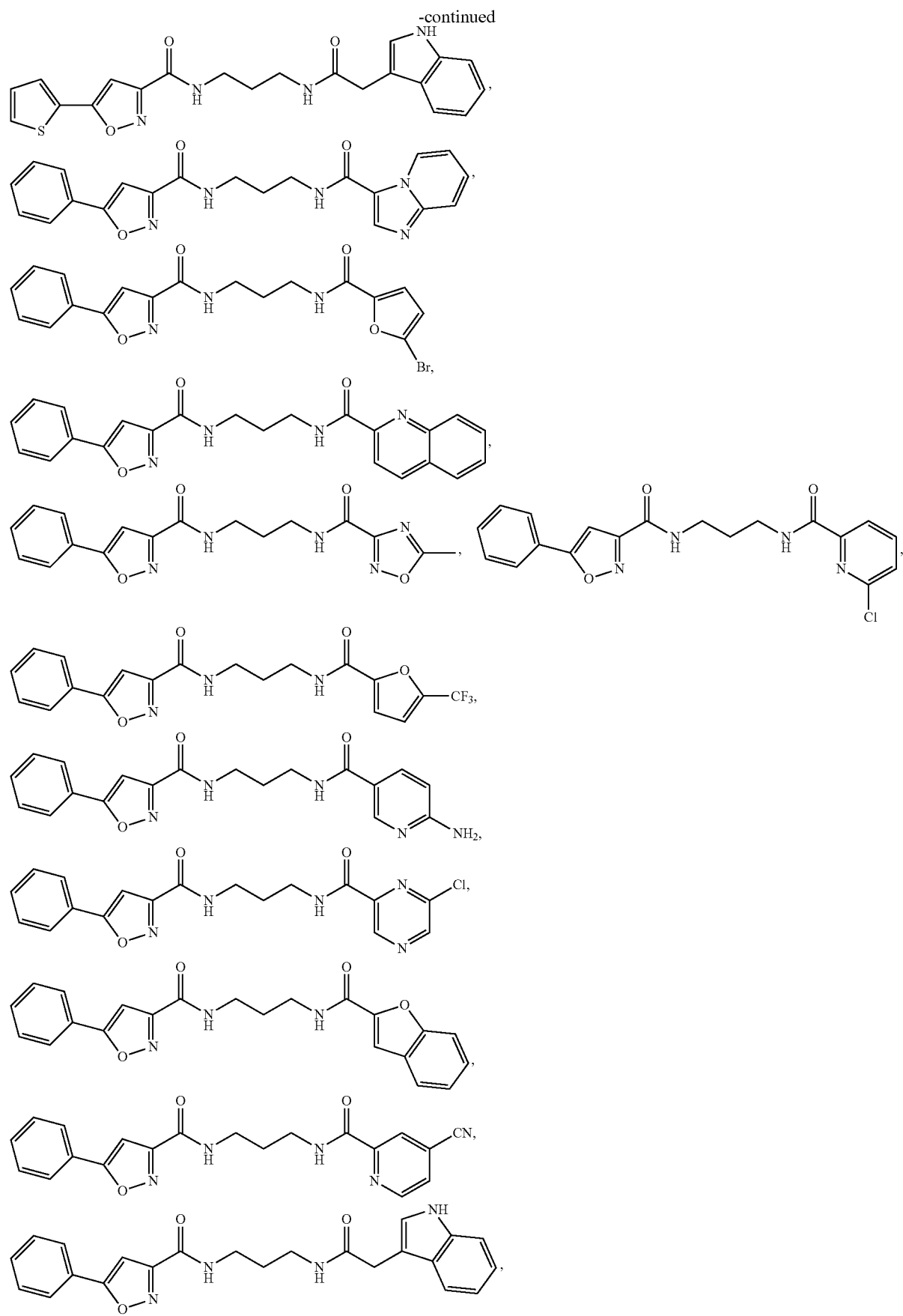

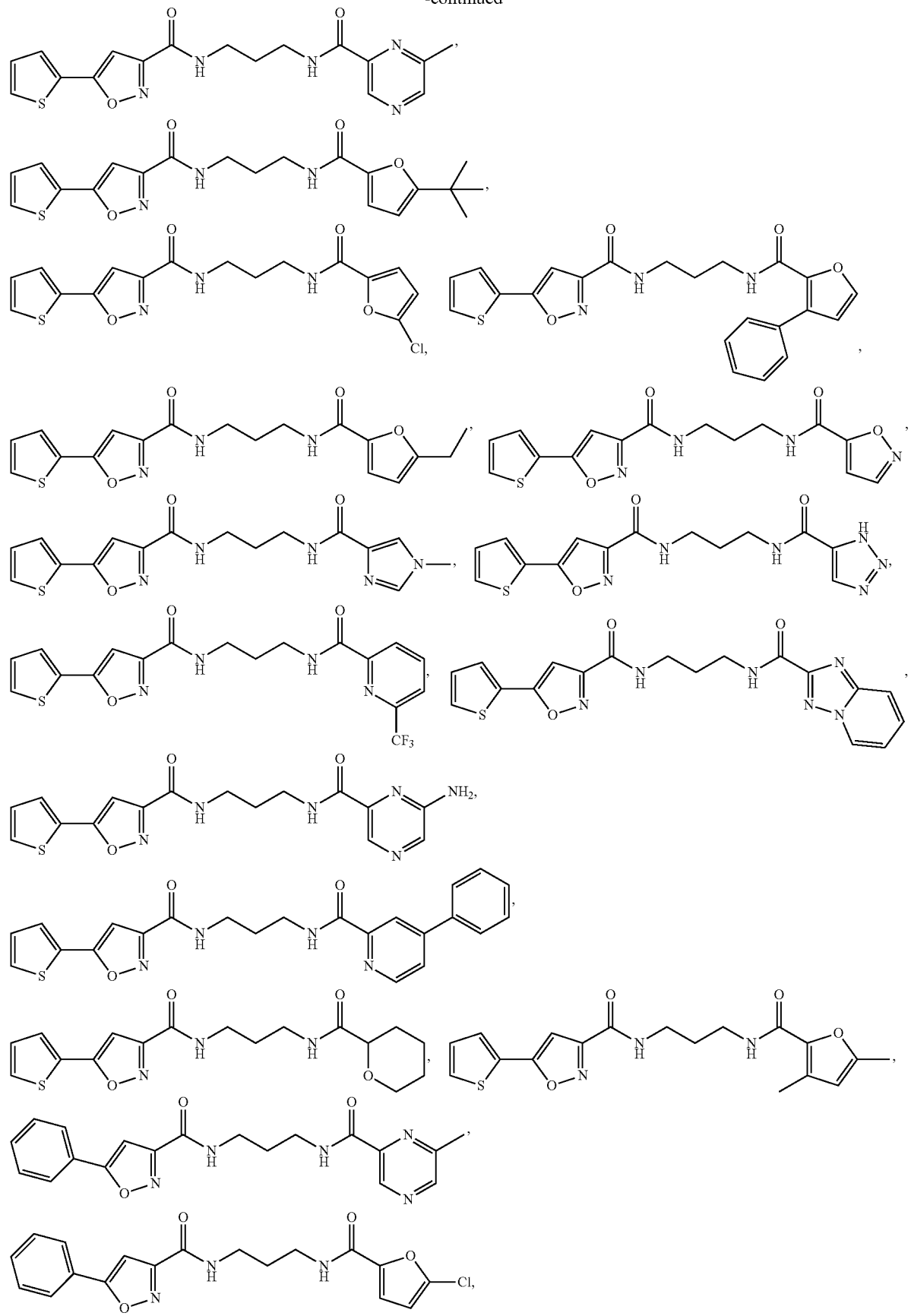

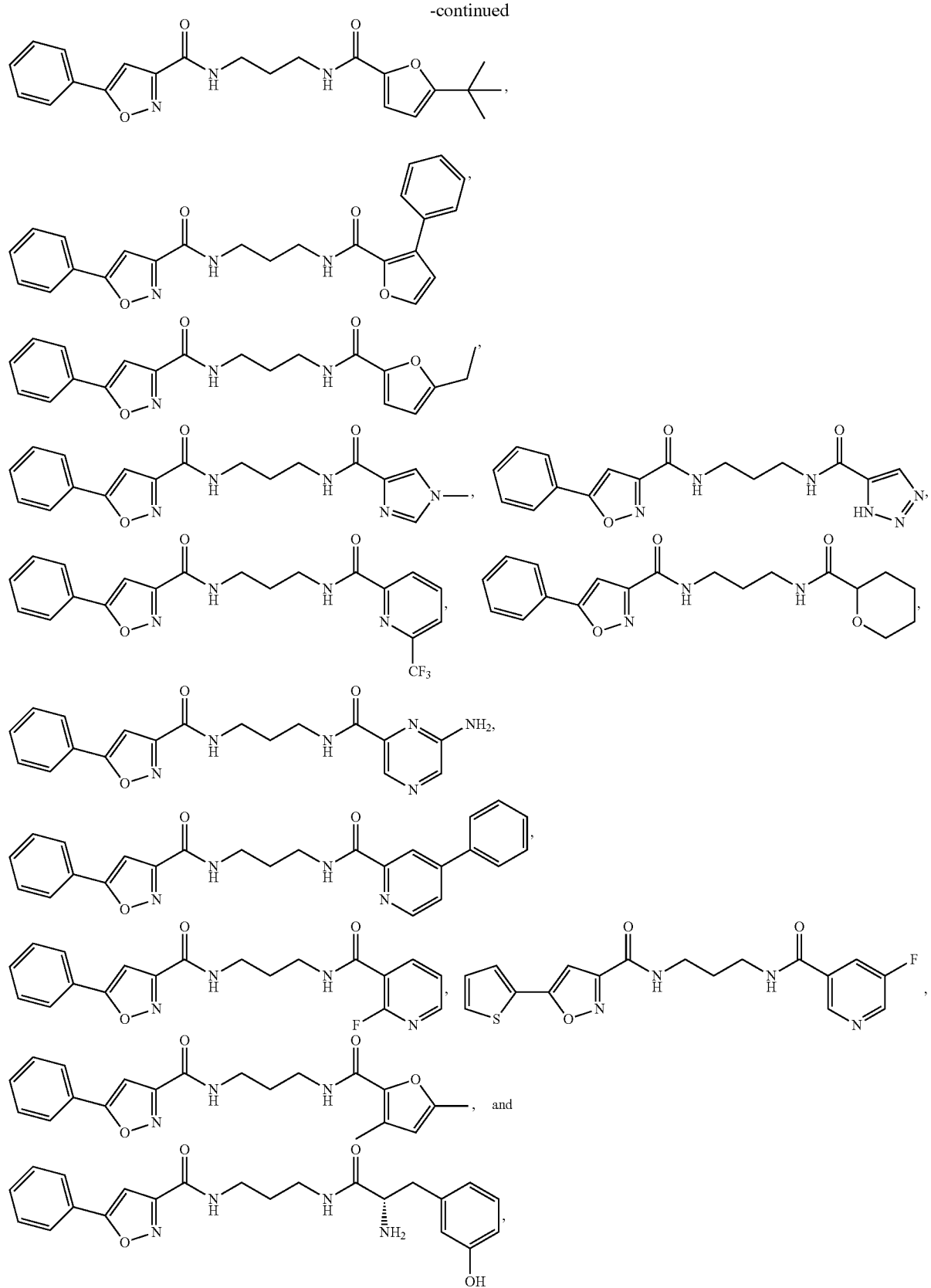
or a pharmaceutically acceptable salt thereof.

In a further aspect, a compound is selected from:
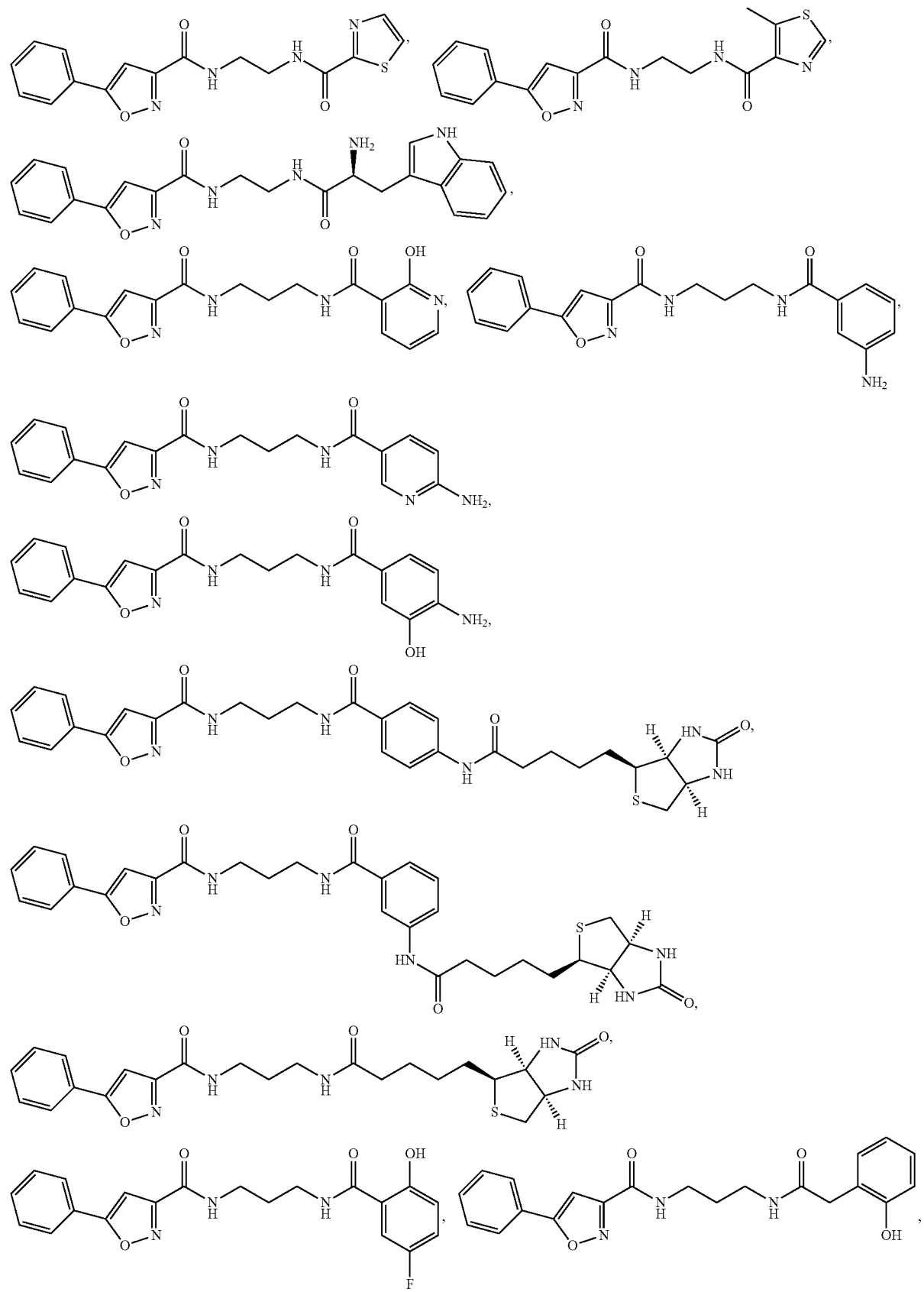

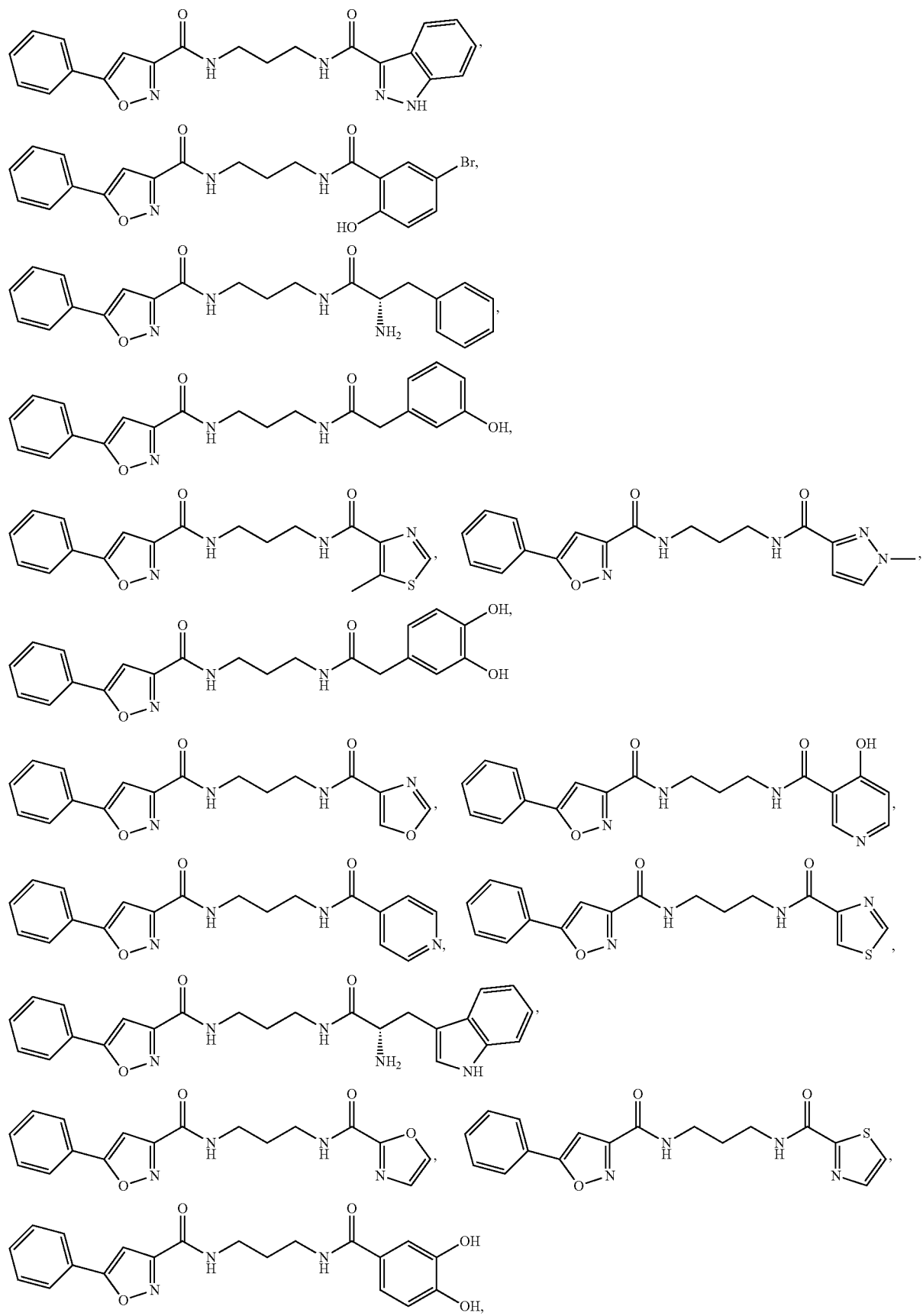

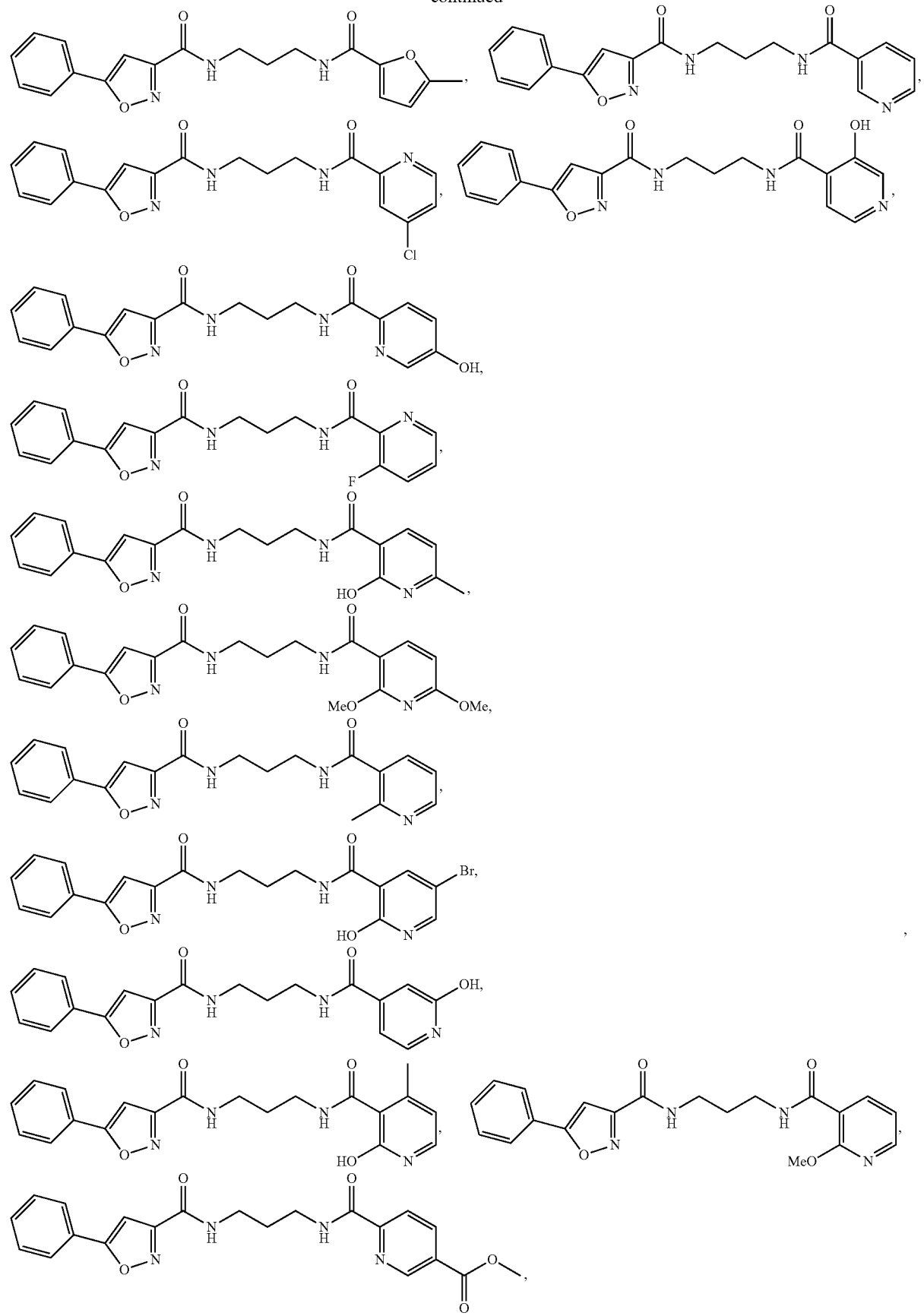

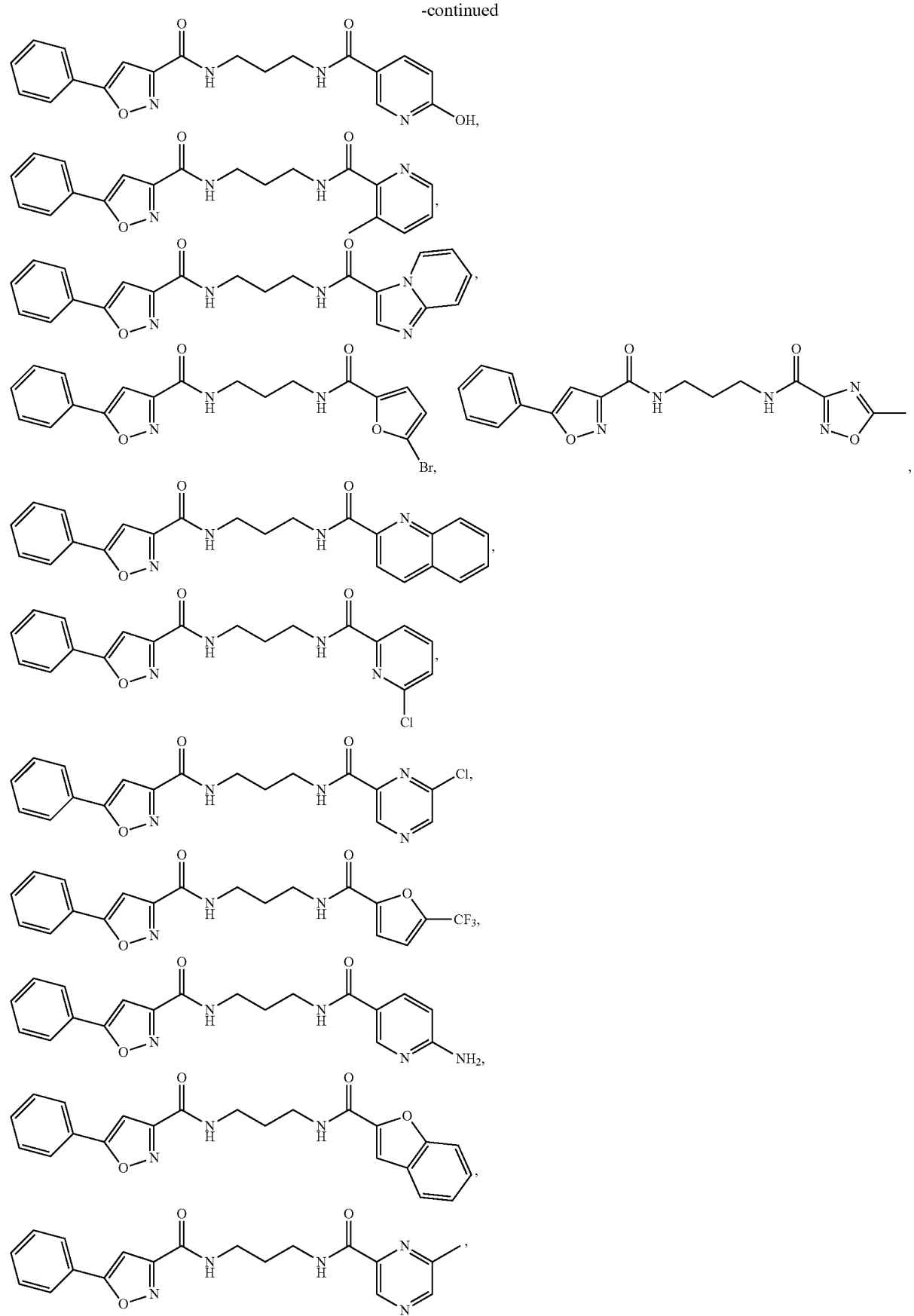

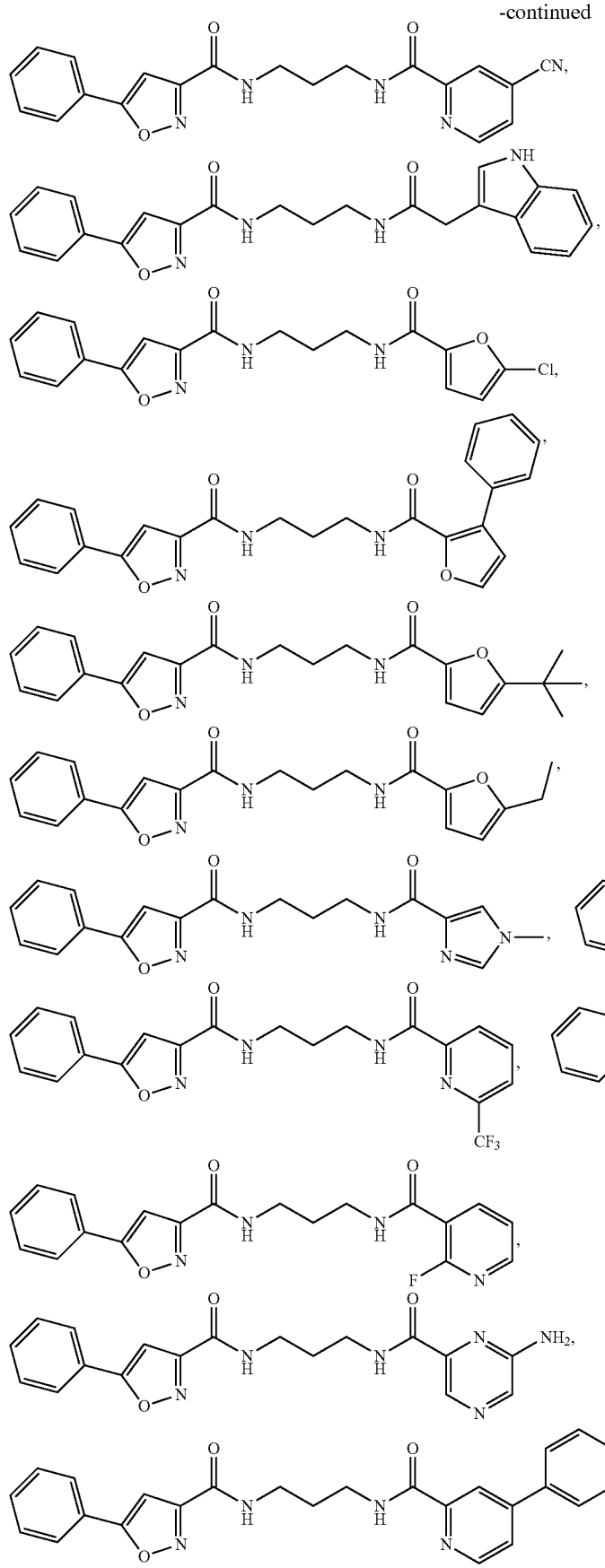

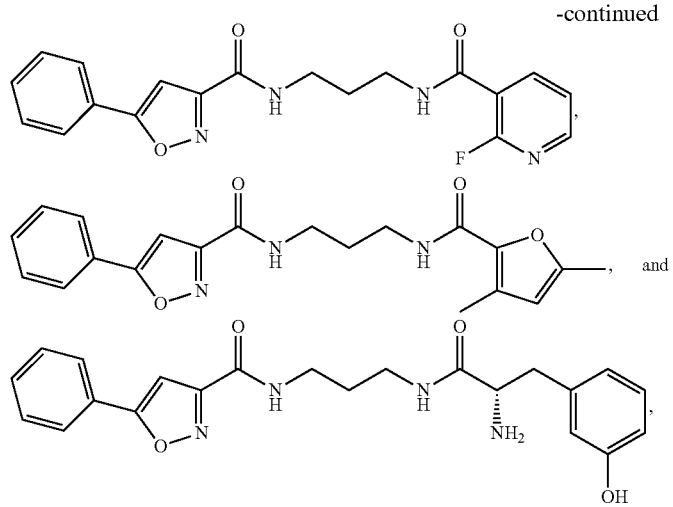
or a pharmaceutically acceptable salt thereof.
In a still further aspect, a compound is selected from:
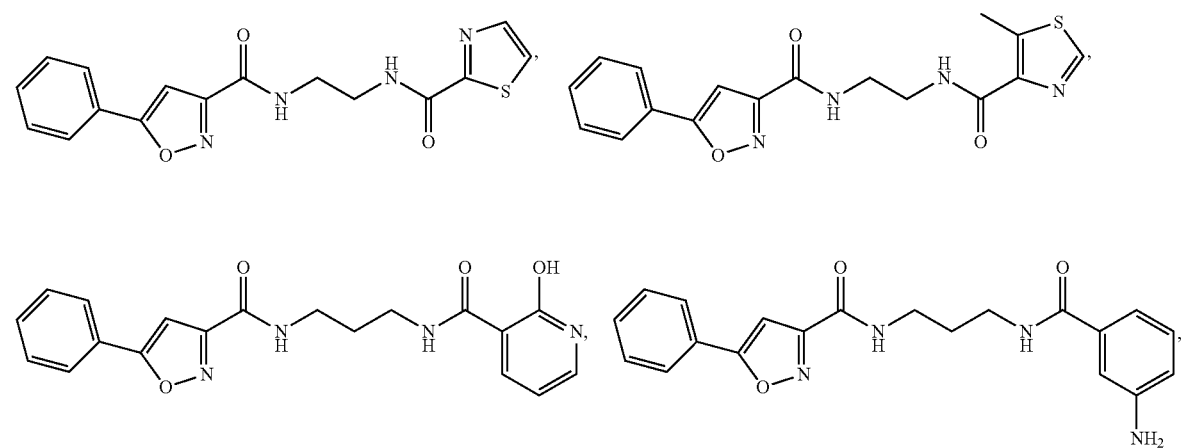
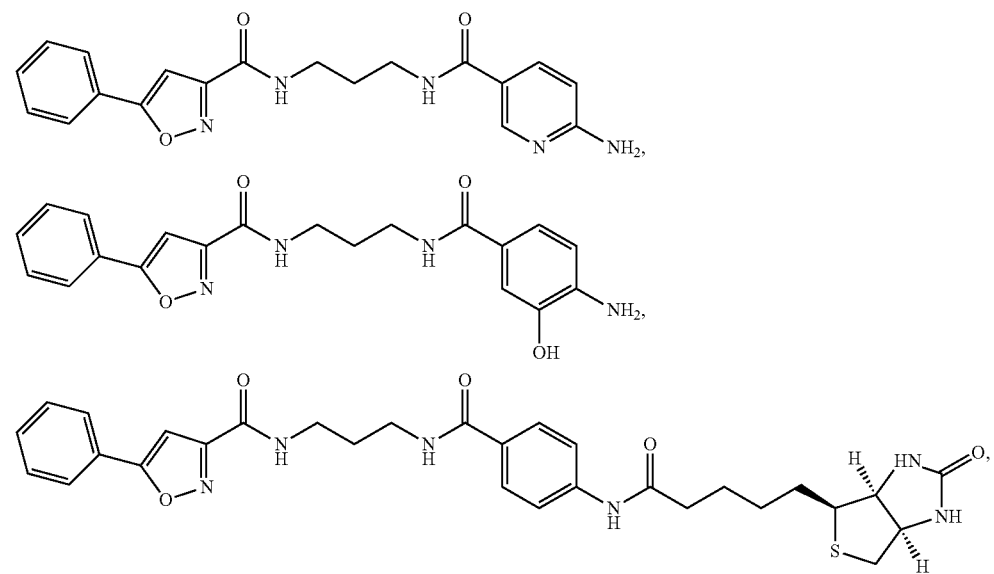

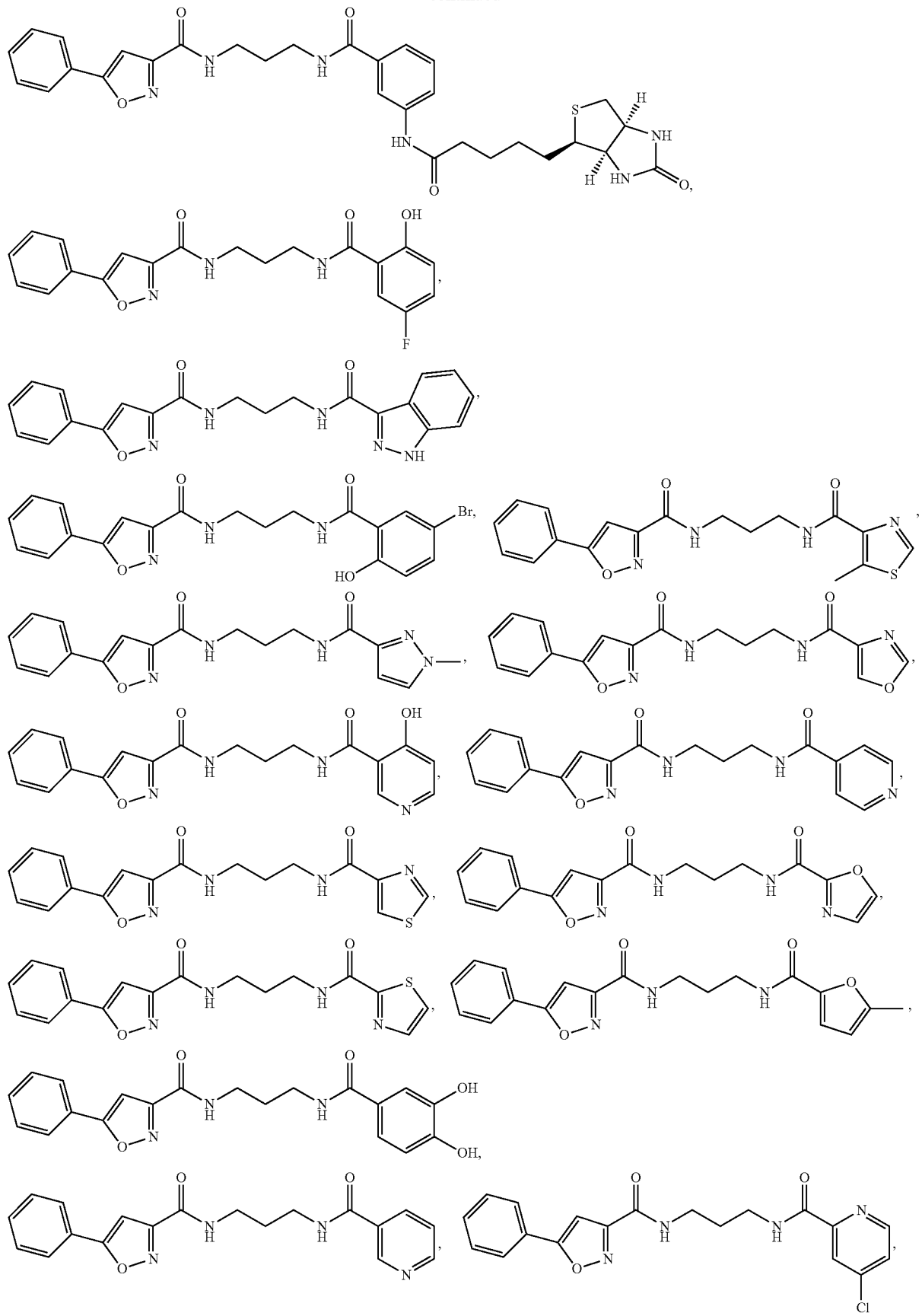

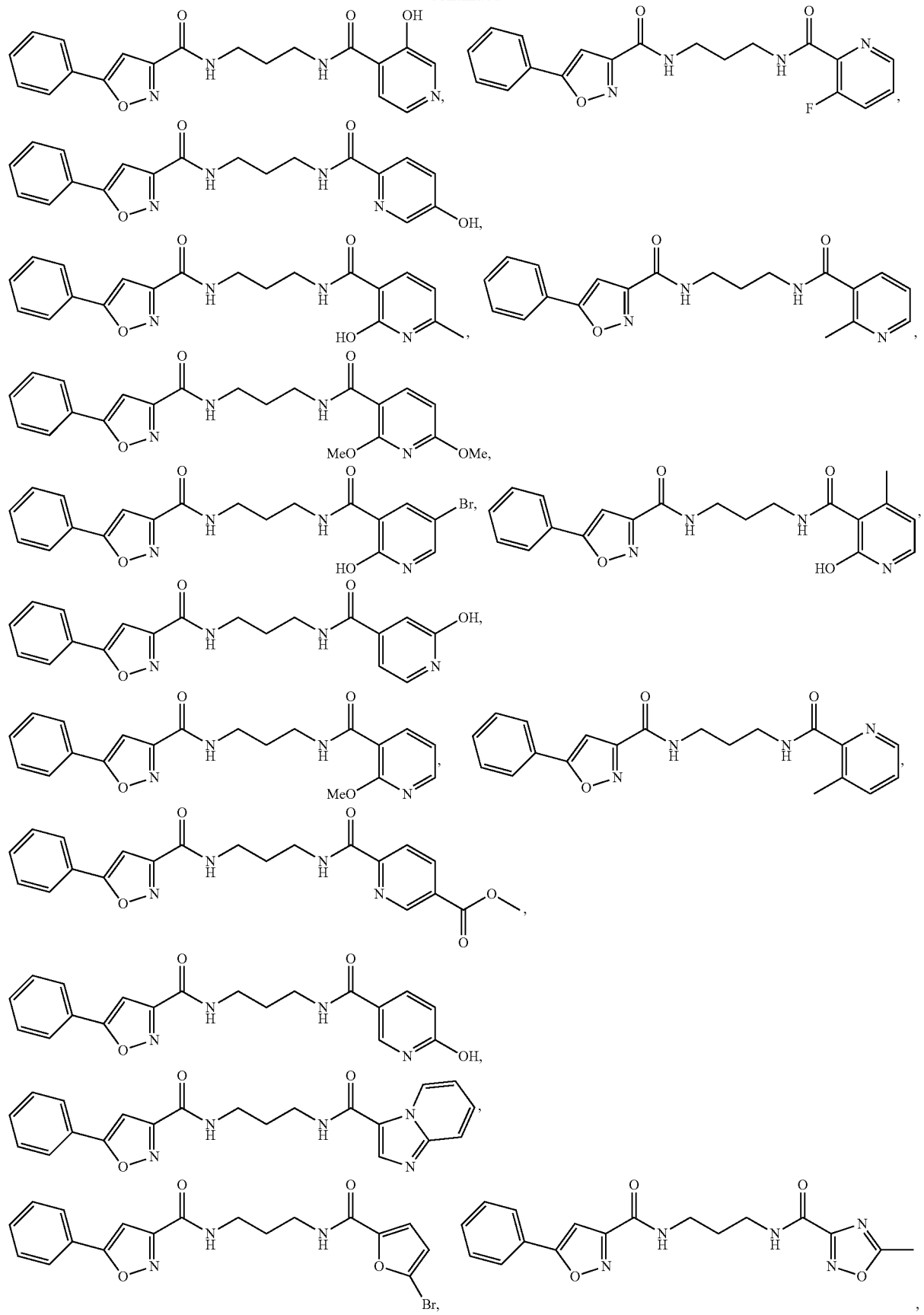

-continued
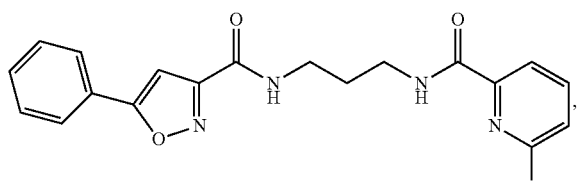
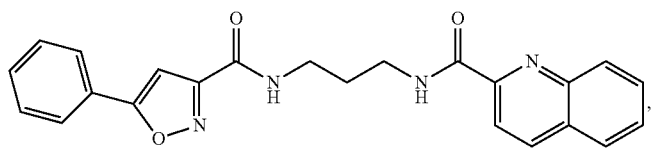
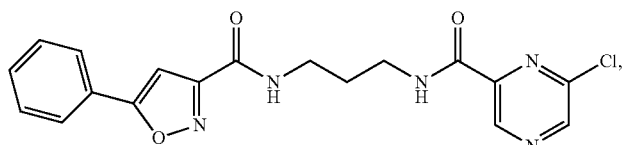
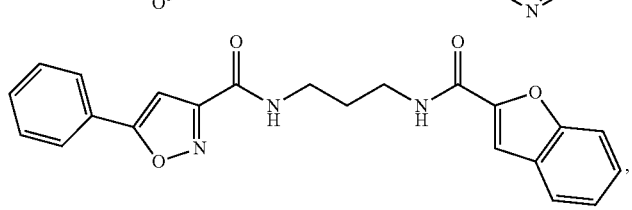
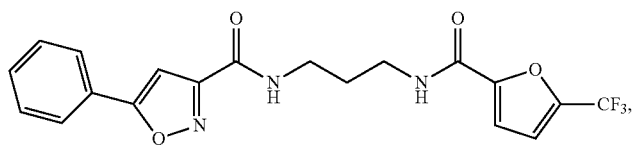
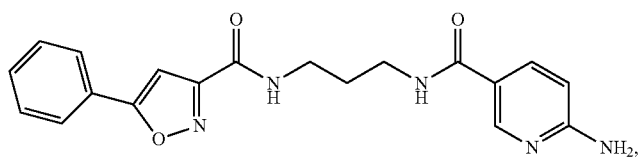
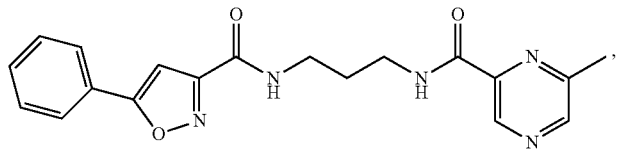
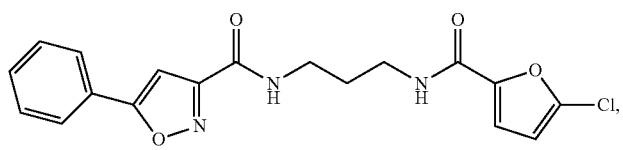
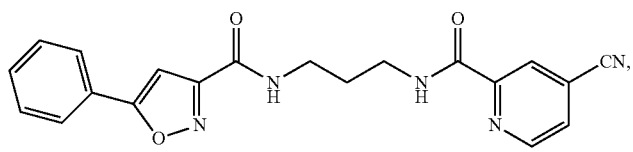
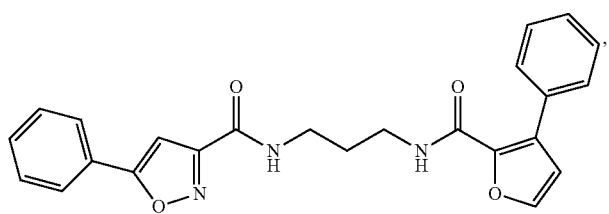

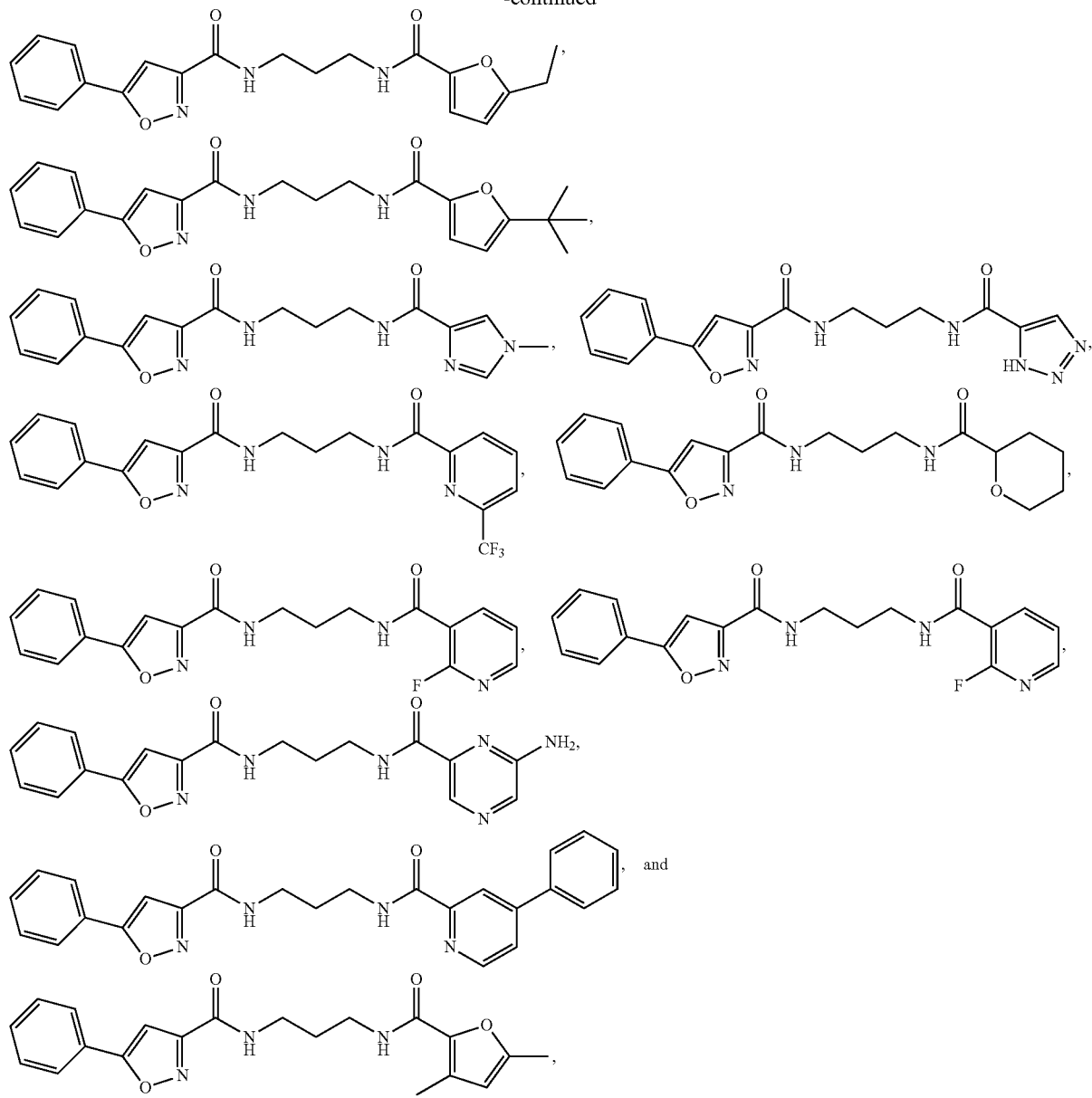
or a pharmaceutically acceptable salt thereof.
In yet a further aspect, a compound is selected from:
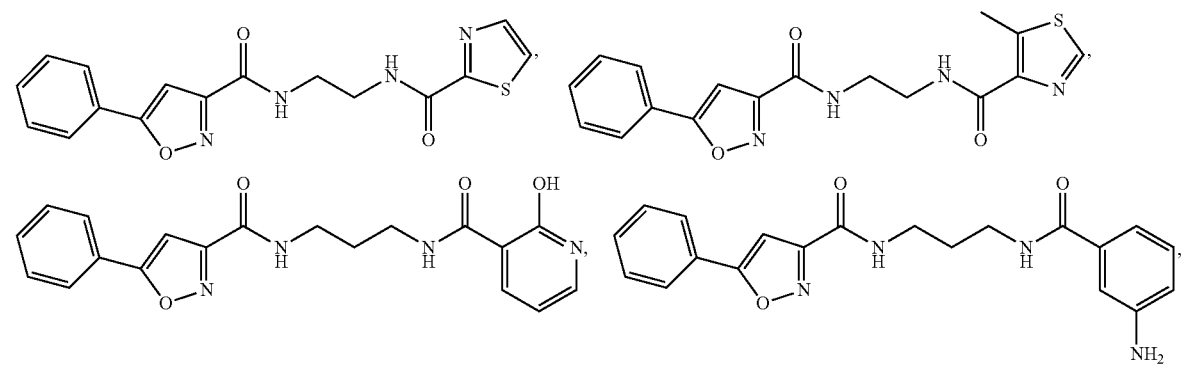

-continued
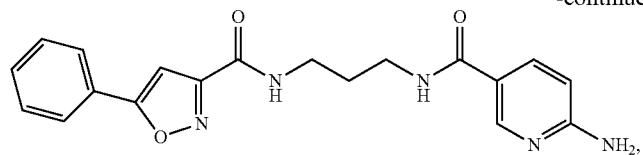
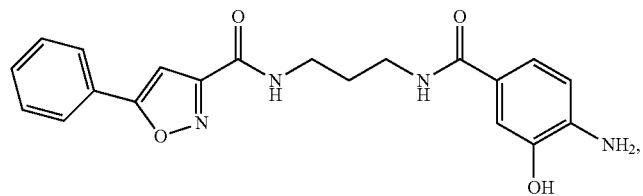
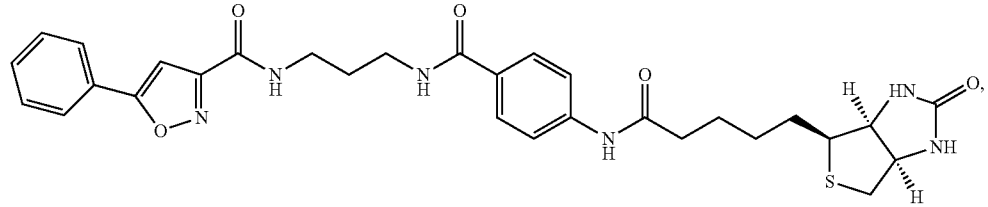
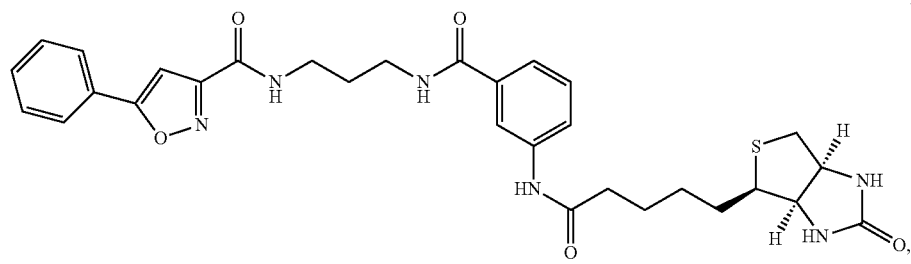
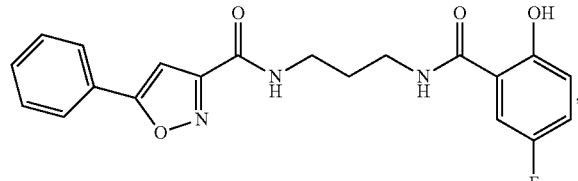
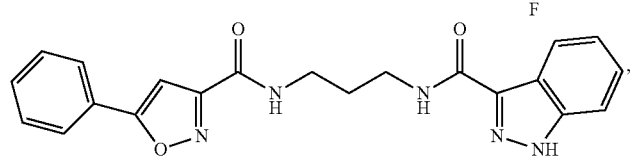
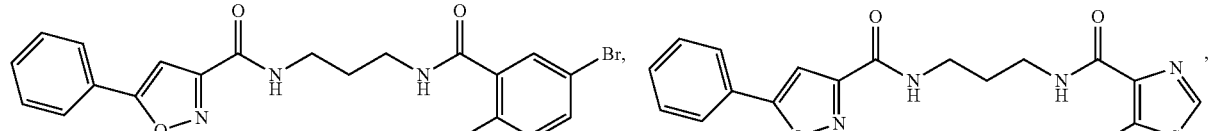
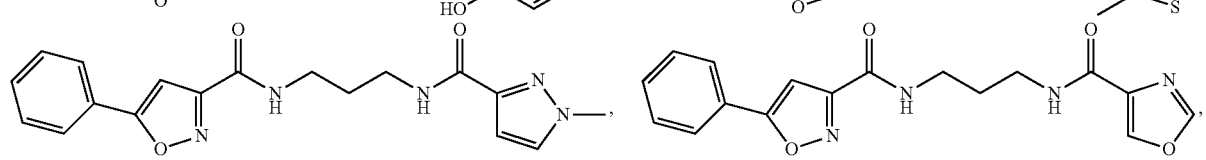
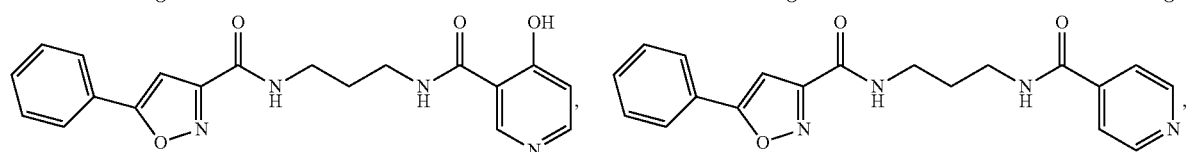
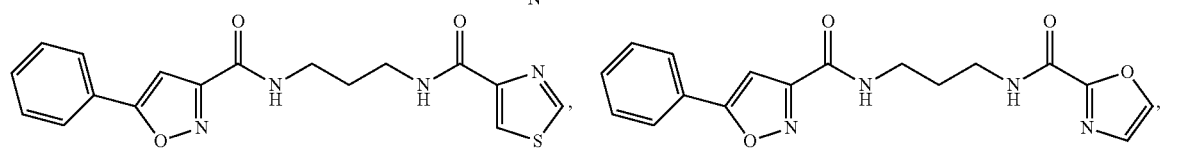

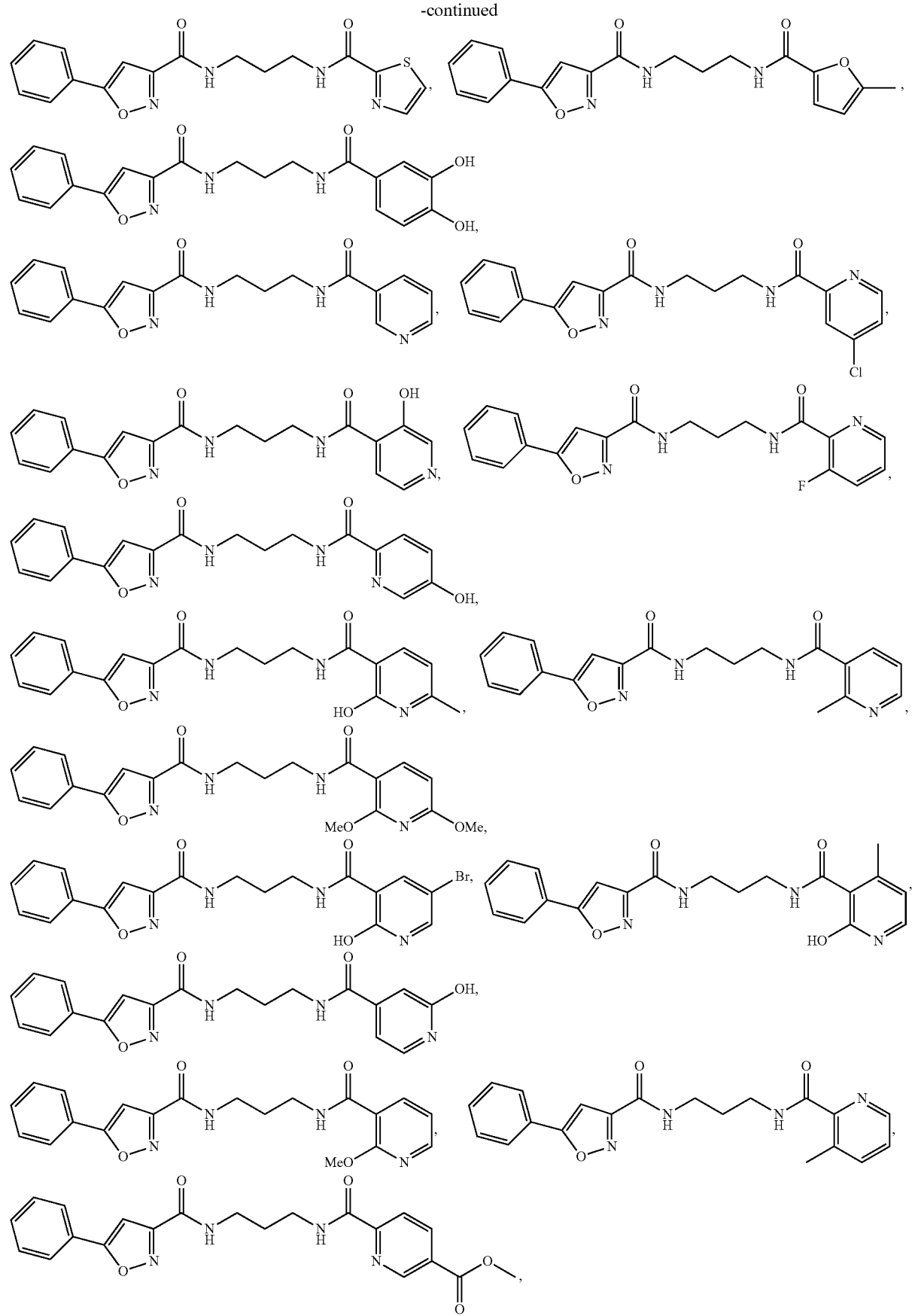

-continued
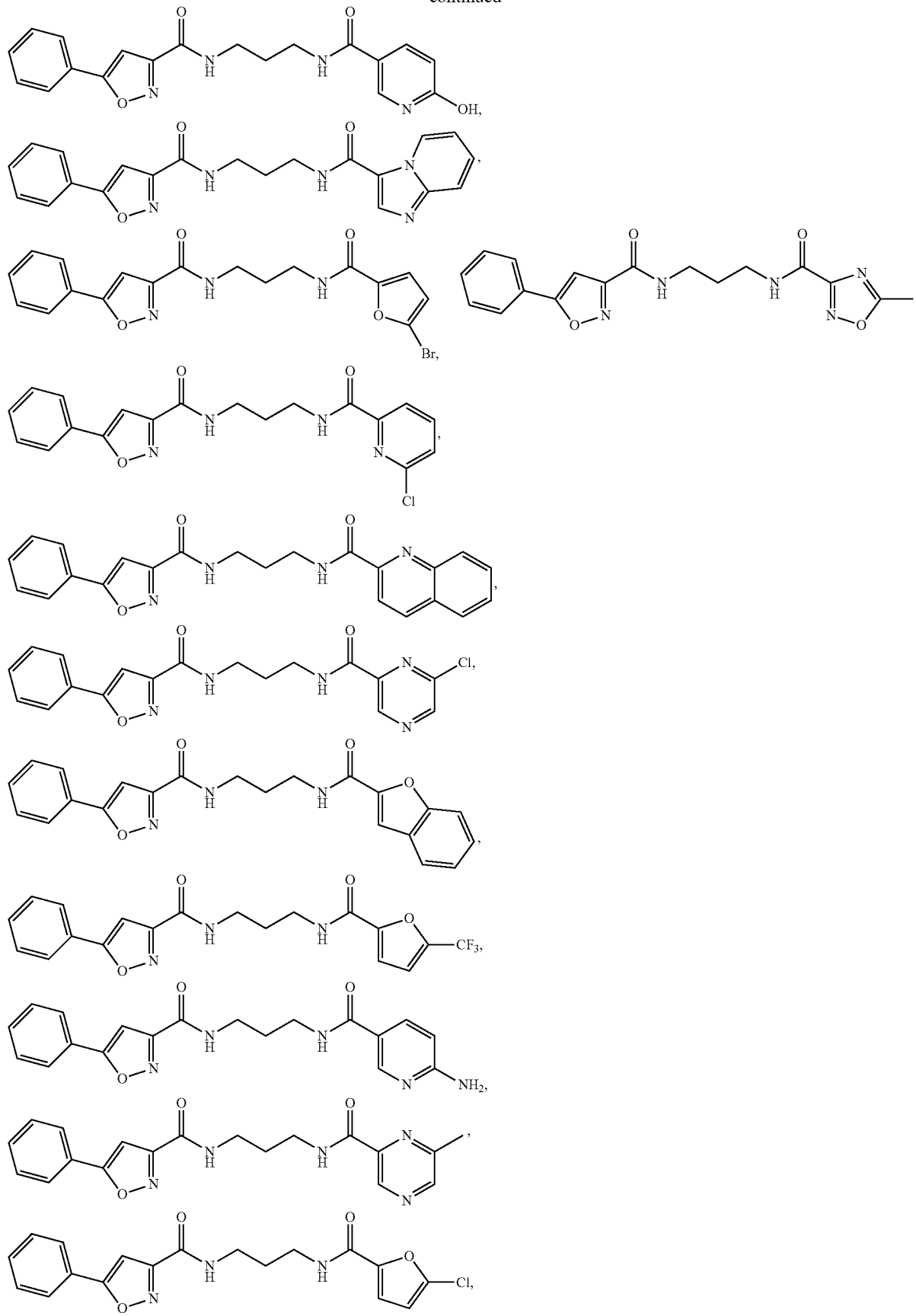

-continued
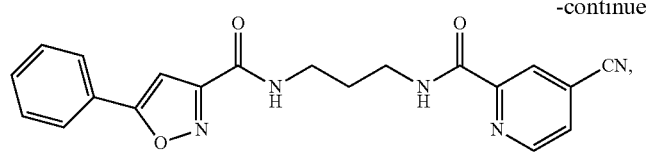
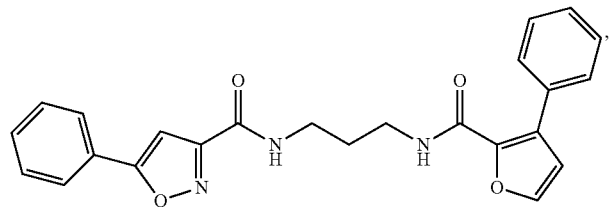
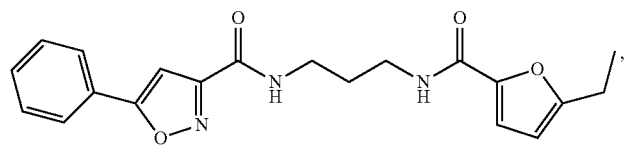
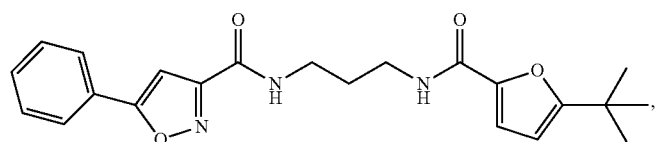
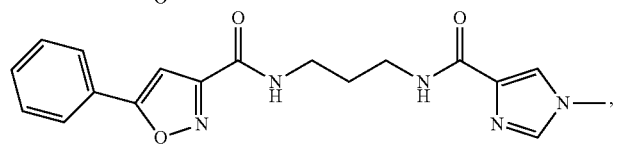
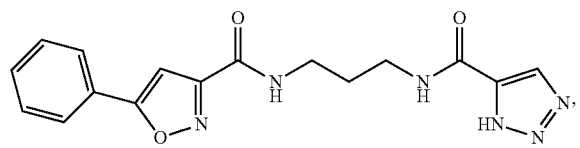
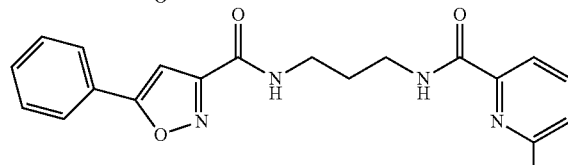
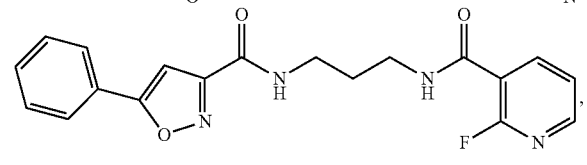
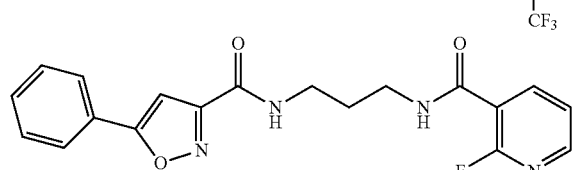
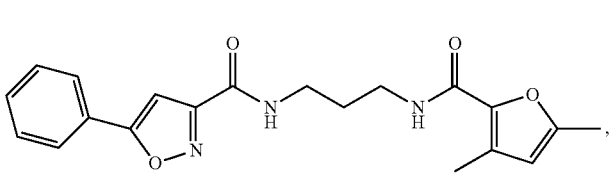
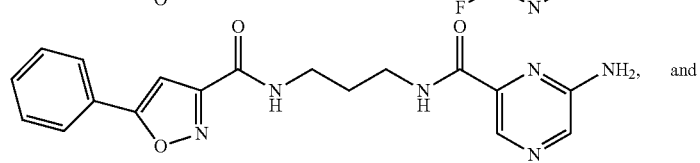
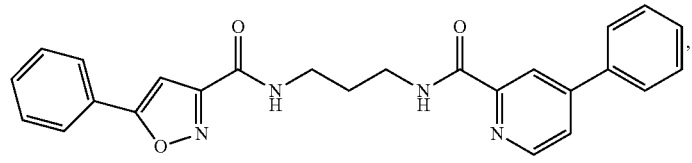
or a pharmaceutically acceptable salt thereof.

In an even further aspect, a compound is:
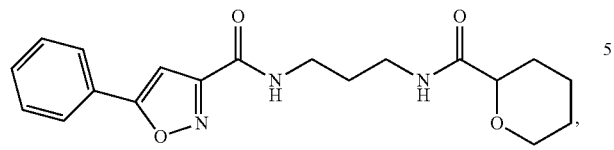
or a pharmaceutically acceptable salt thereof.
In a further aspect, a compound is selected from:
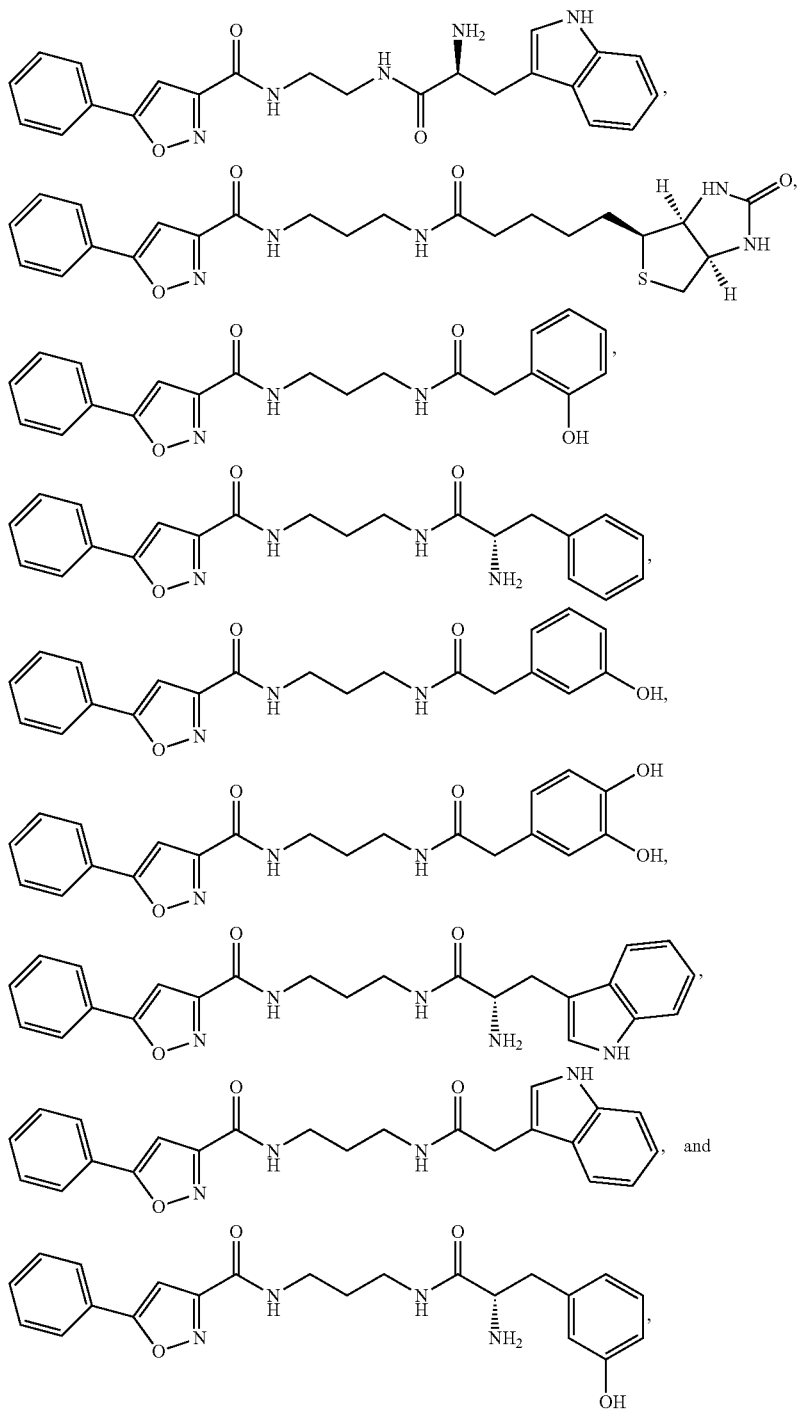
or a pharmaceutically acceptable salt thereof.

In a further aspect, a compound is selected from:
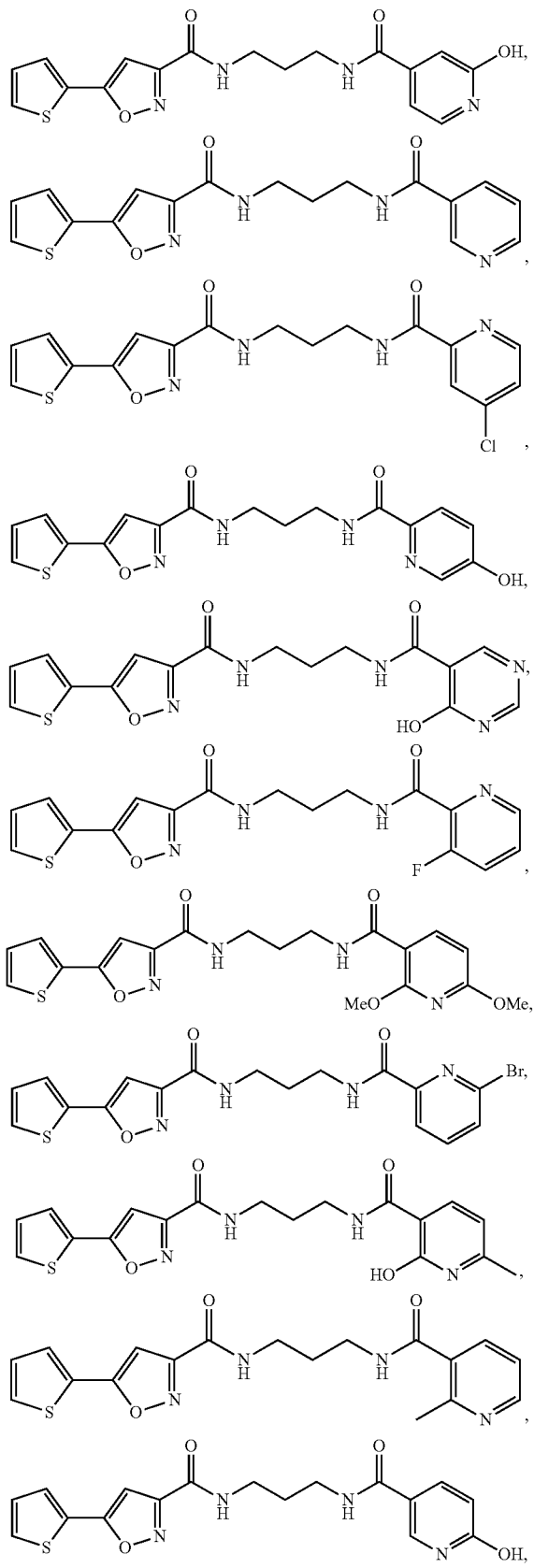
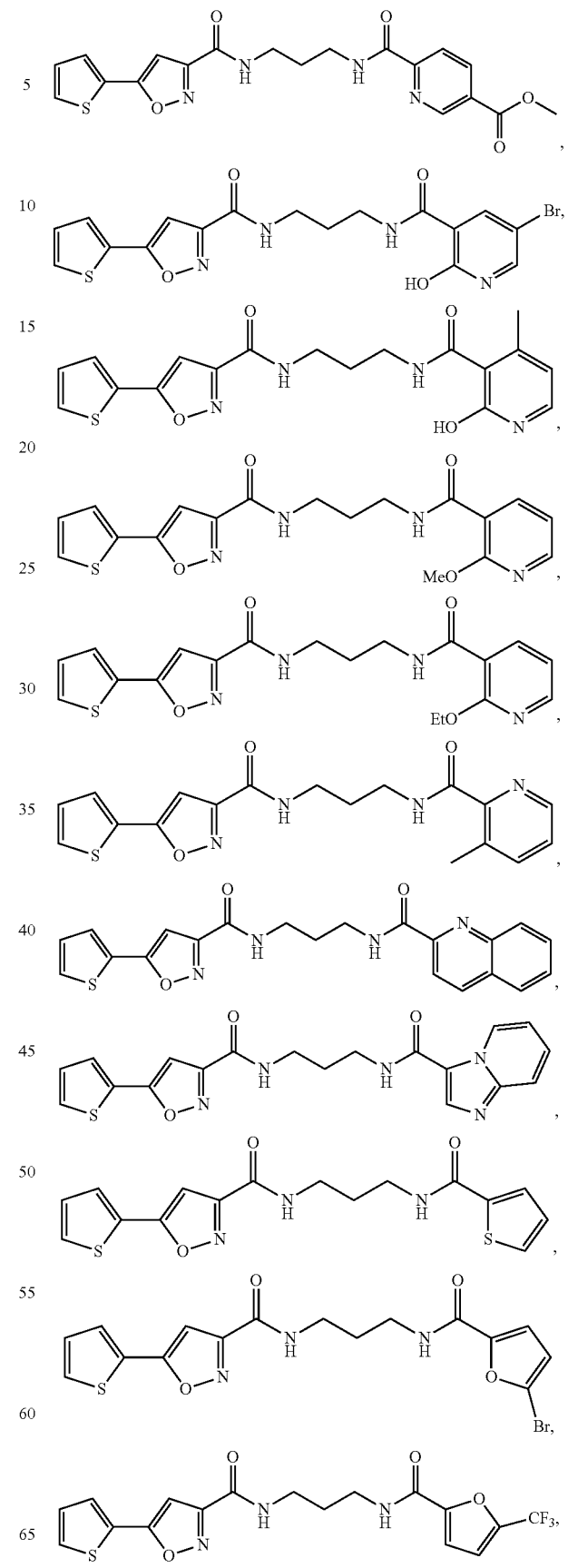

-continued
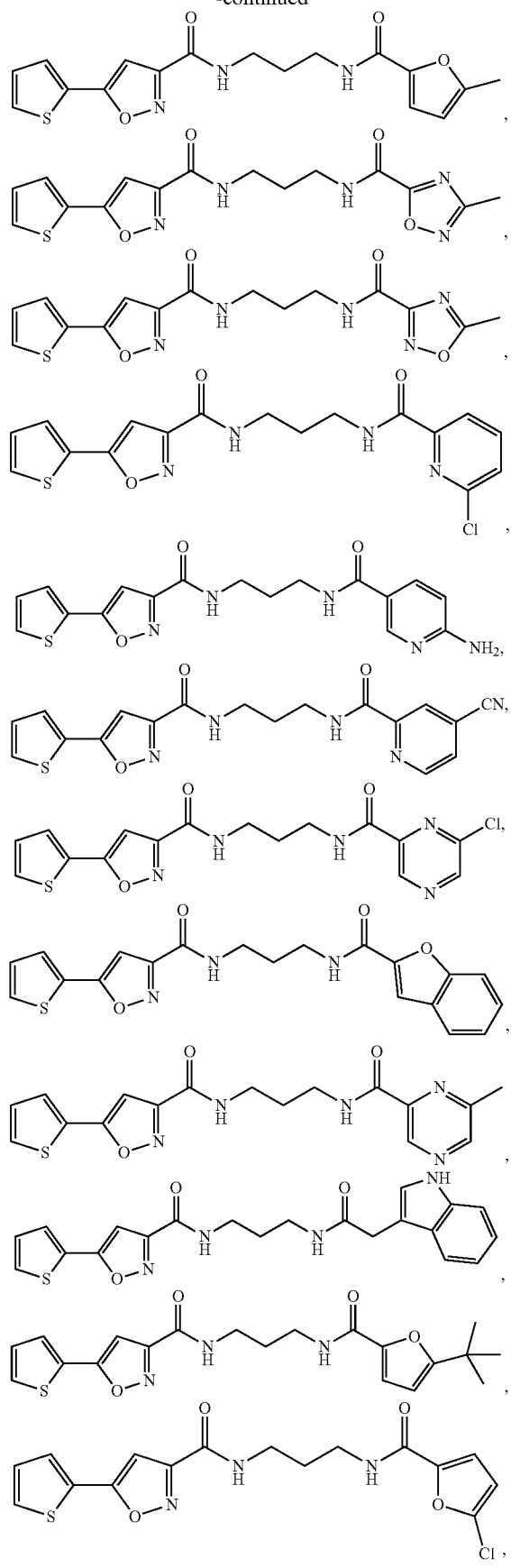
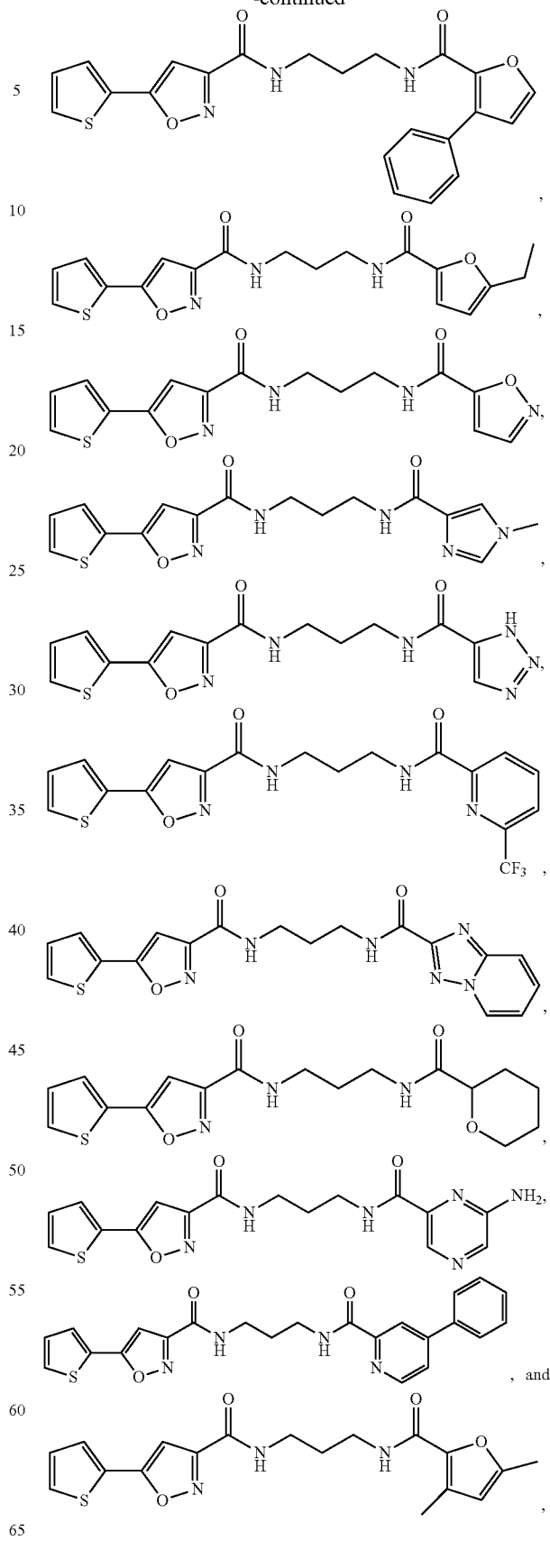
or a pharmaceutically acceptable salt thereof.

In a still further aspect, a compound is selected from:
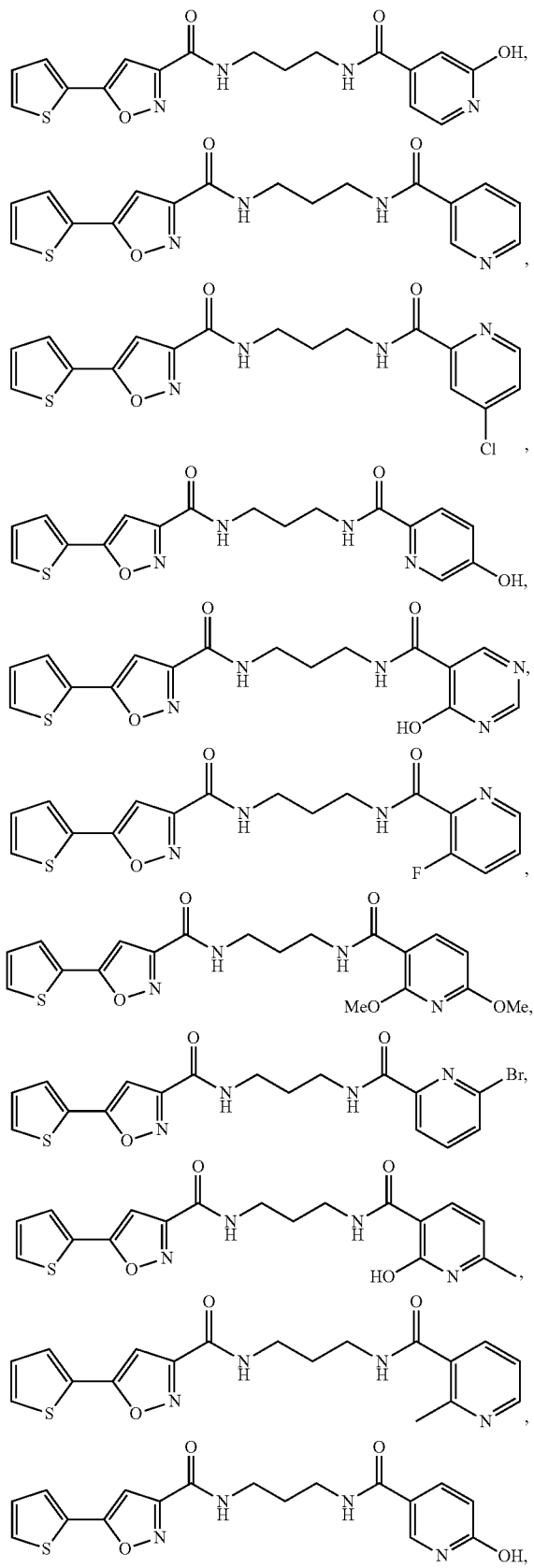
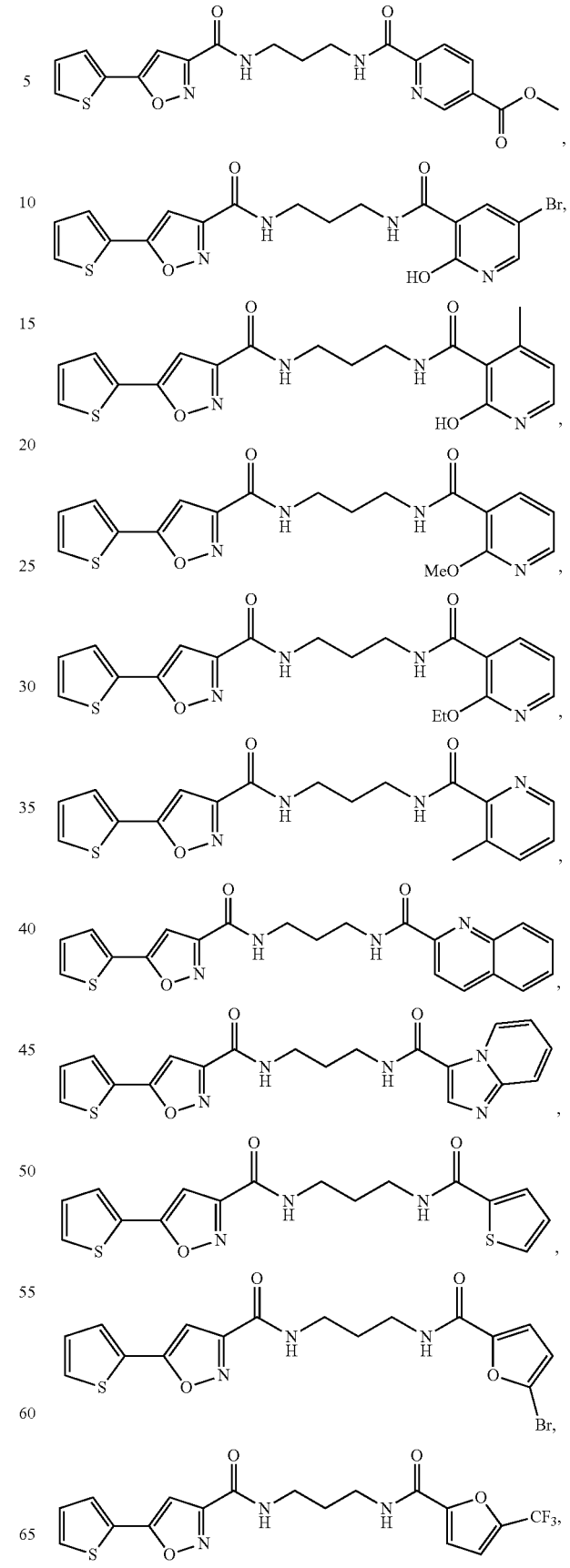

123
-continued
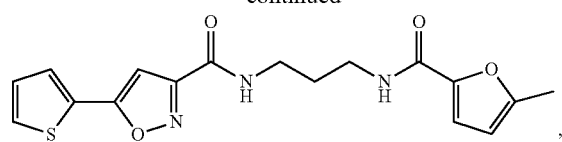,
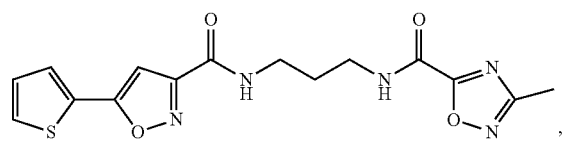,
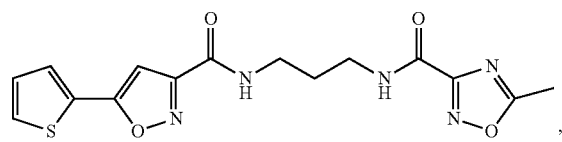,
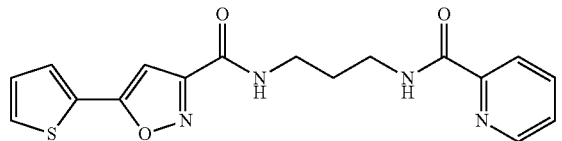,
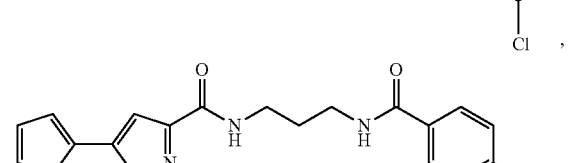,
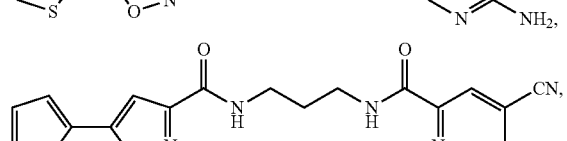,
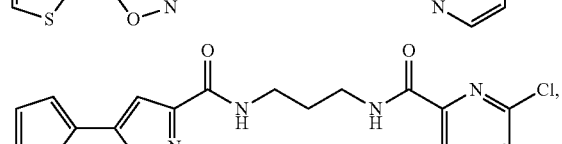,
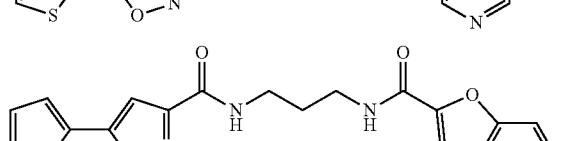,
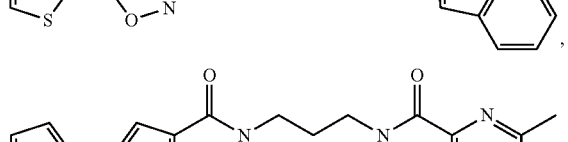,
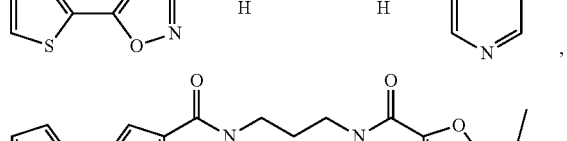,
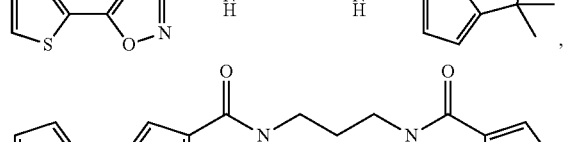,
124
-continued
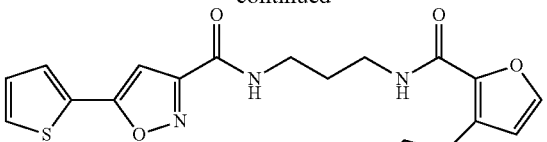,
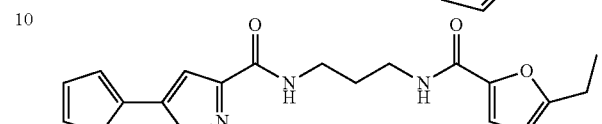,
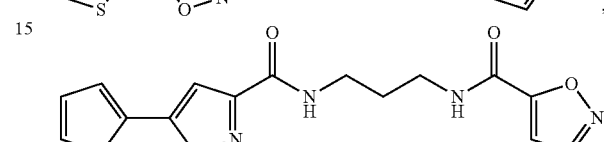,
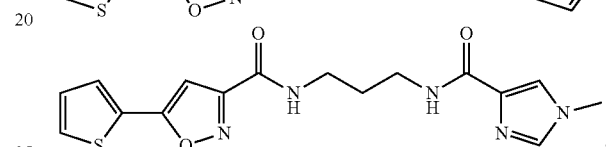,
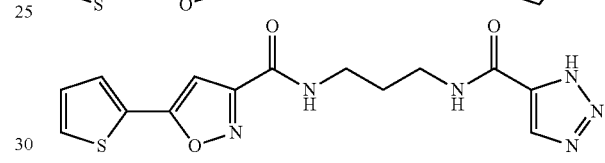,
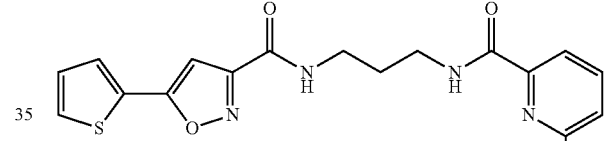,
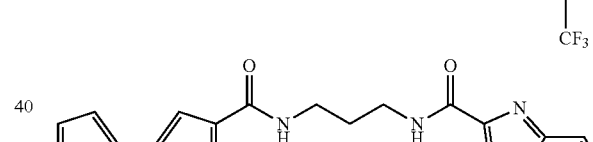,
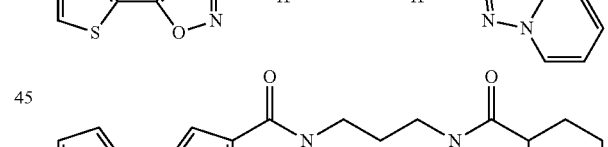,
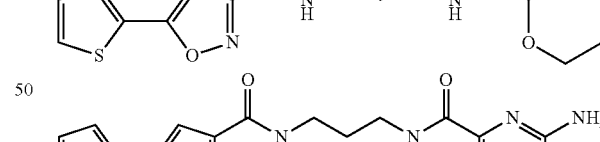,
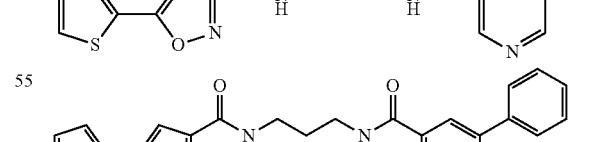, and
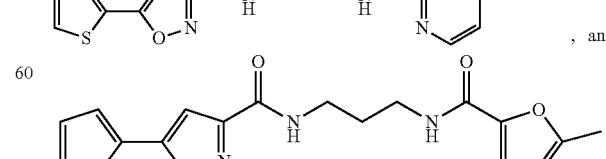,
or a pharmaceutically acceptable salt thereof.

In yet a further aspect, a compound is selected from:
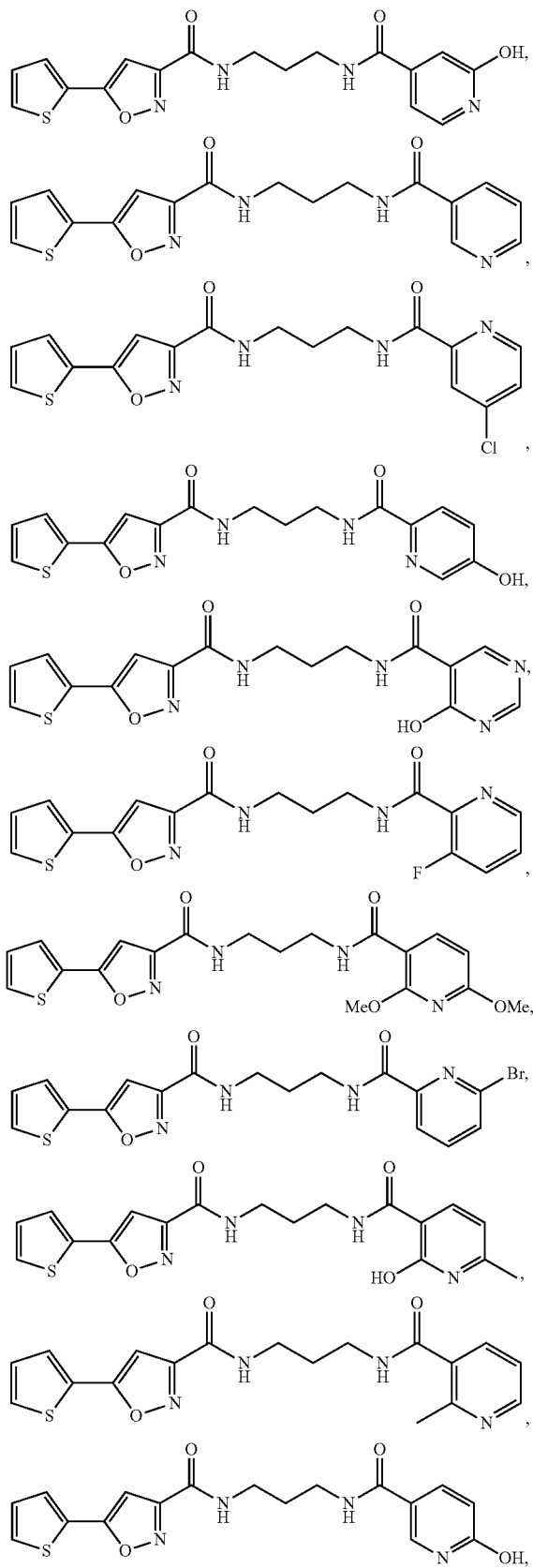
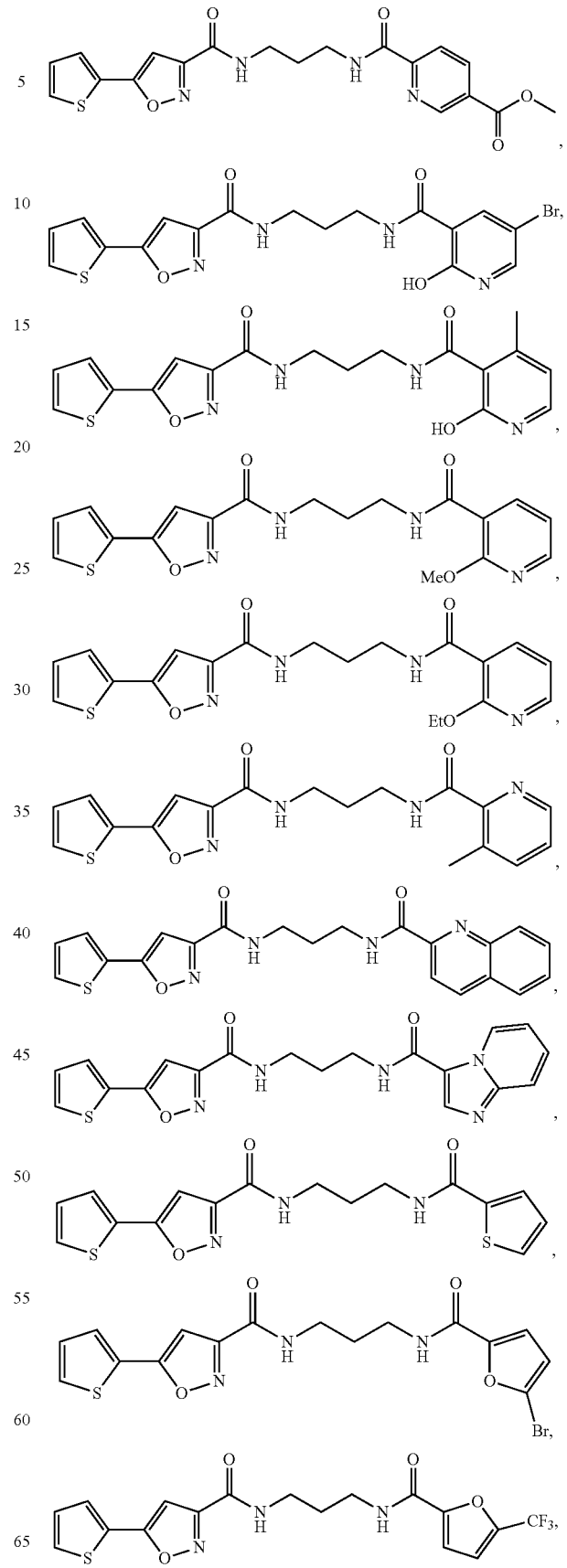

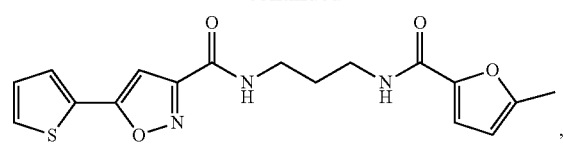,
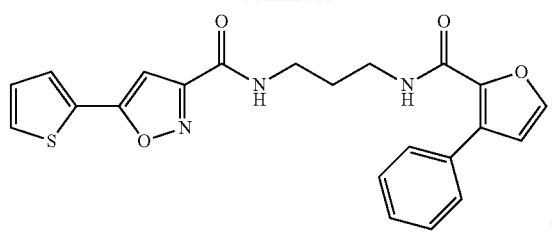,
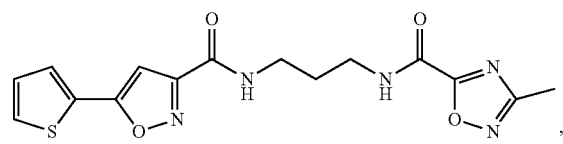,
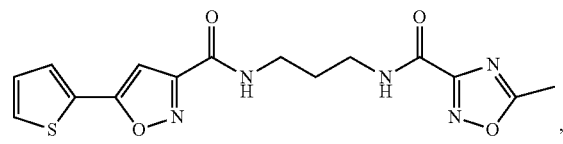,
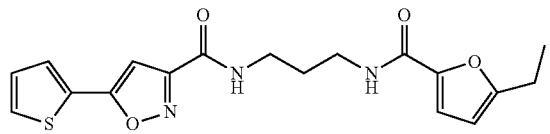,
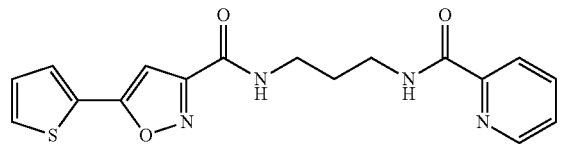,
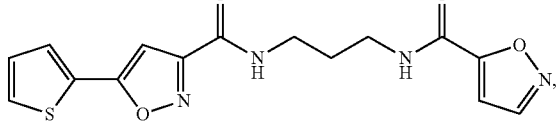,
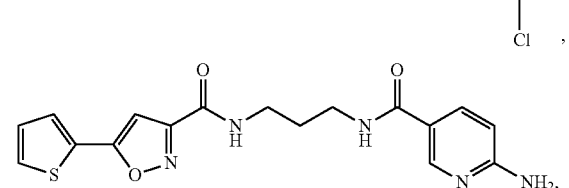,
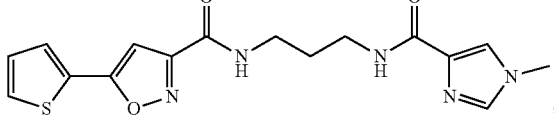,
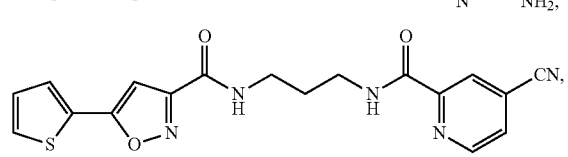,
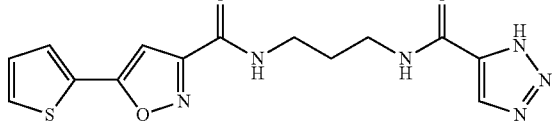,
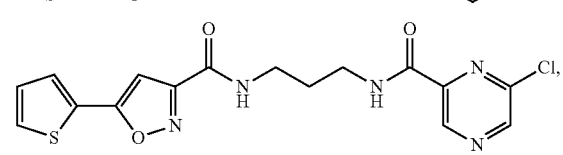,
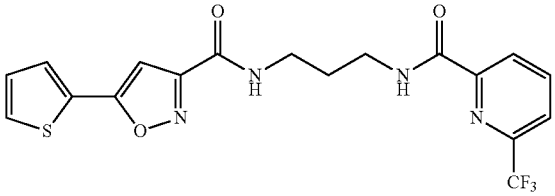,
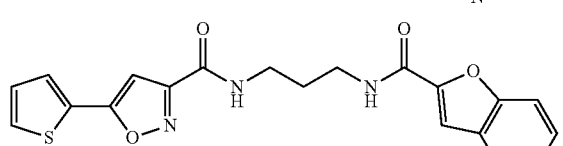,
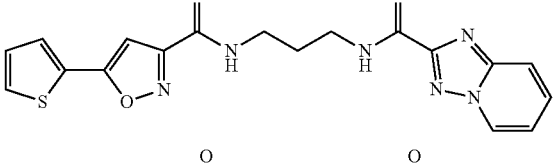,
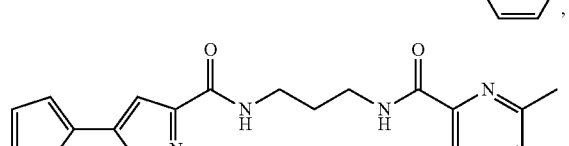,
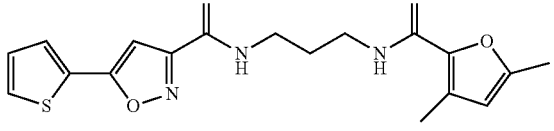,
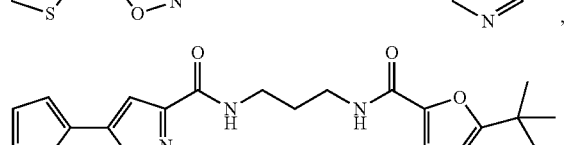,
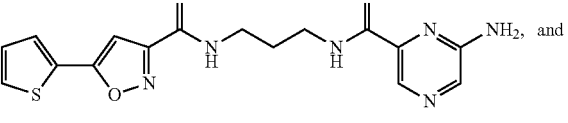,
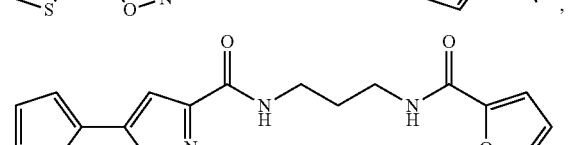,
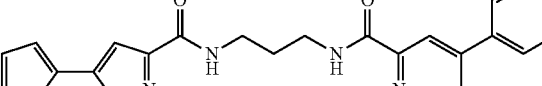 and
,
,
or a pharmaceutically acceptable salt thereof.

In an even further aspect, a compound is:
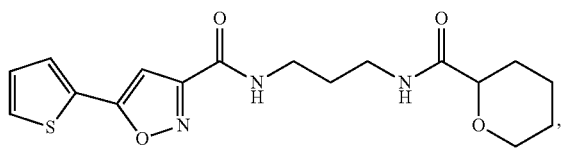 [SMILES: O=C(NCCCNC(=O)C1CCCCO1)c1cc(-c2cccs2)on1]
or a pharmaceutically acceptable salt thereof.
In a further aspect, a compound is:
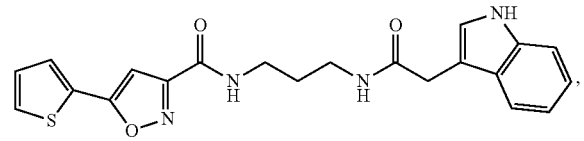 [SMILES: O=C(Cc1c[nH]c2ccccc12)NCCCNC(=O)c1cc(-c2cccs2)on1]
or a pharmaceutically acceptable salt thereof.
In one aspect, a compound is selected from:
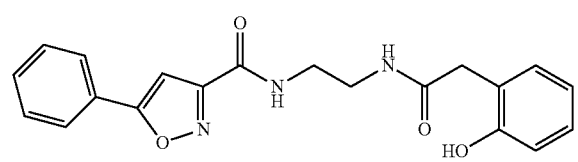
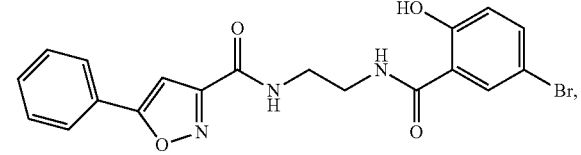
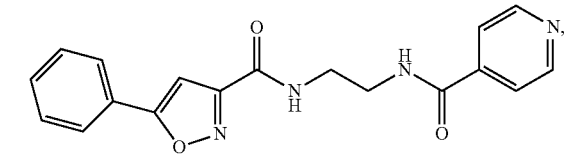
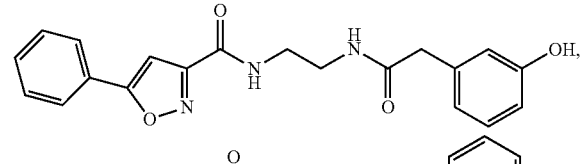
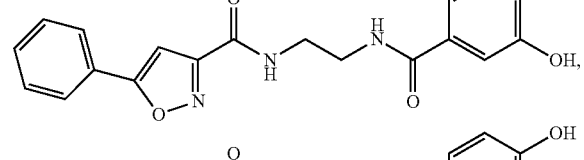
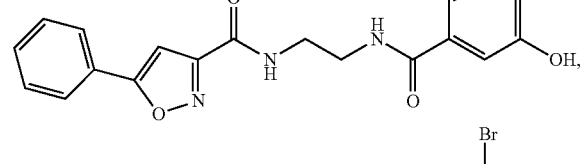
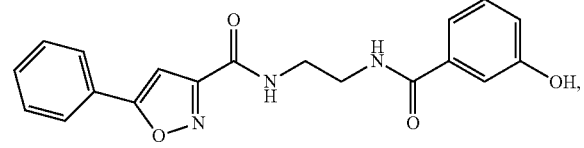
-continued
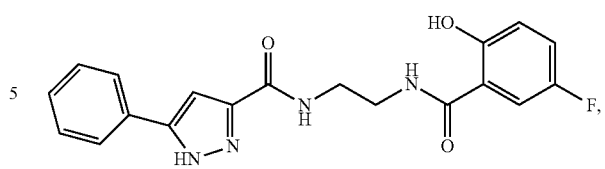
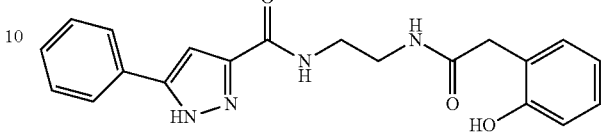
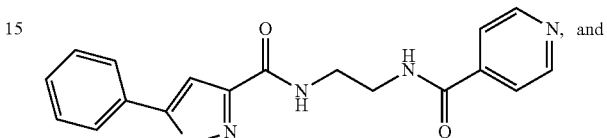
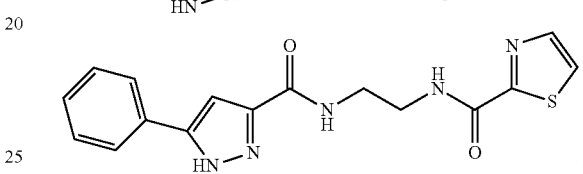
or a pharmaceutically acceptable salt thereof.
In a further aspect, a compound is selected from:
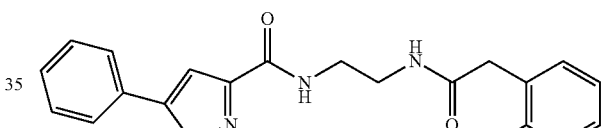
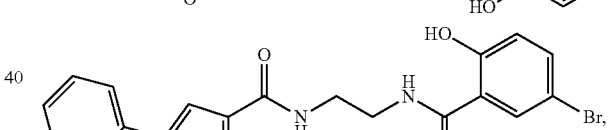
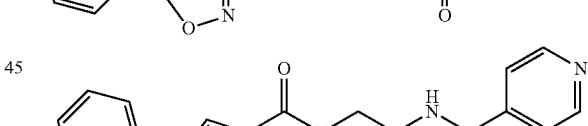
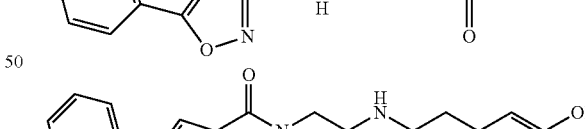
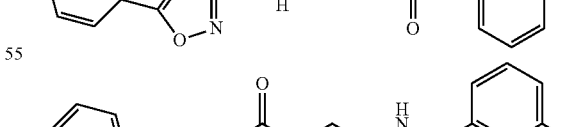
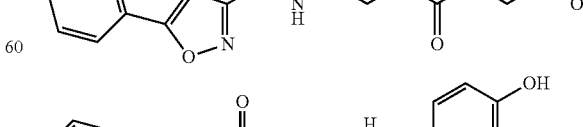
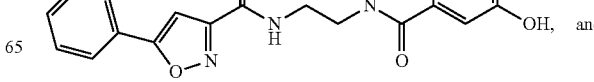

-continued

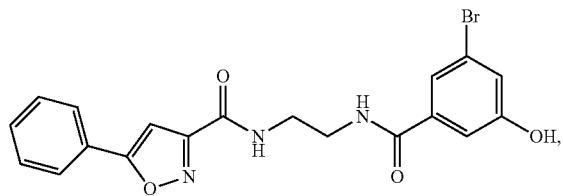

or a pharmaceutically acceptable salt thereof.

In a still further aspect, a compound is selected from:

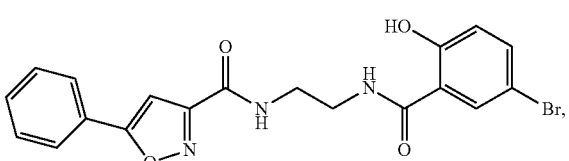

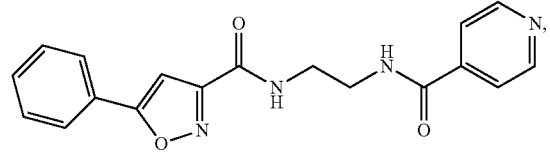

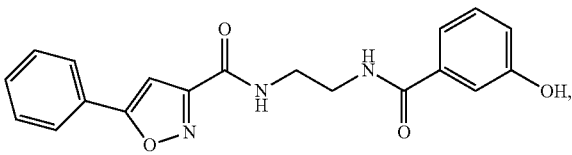

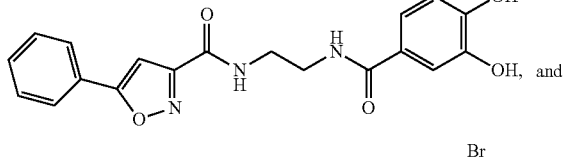

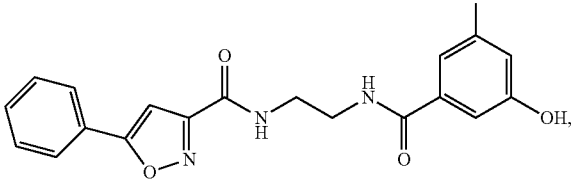

or a pharmaceutically acceptable salt thereof.

In yet a further aspect, a compound is selected from:

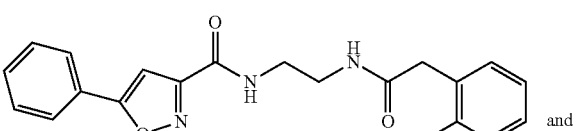

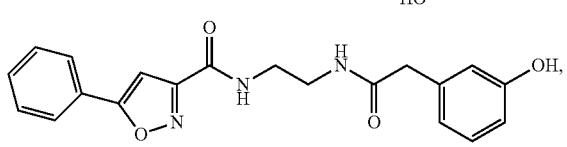

or a pharmaceutically acceptable salt thereof.

In a further aspect, a compound is selected from:

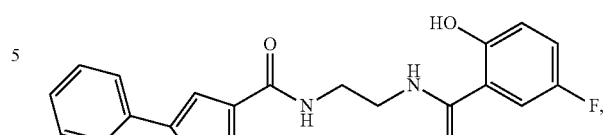

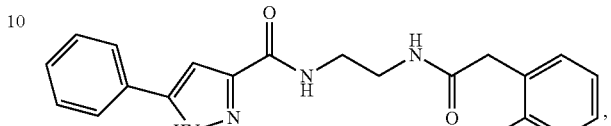

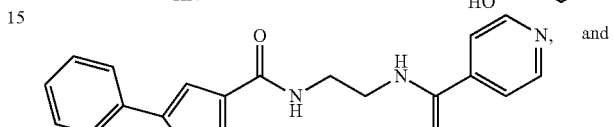

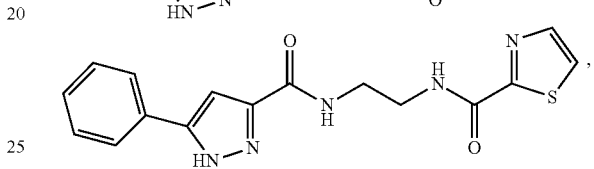

or a pharmaceutically acceptable salt thereof.

In a still further aspect, a compound is selected from:

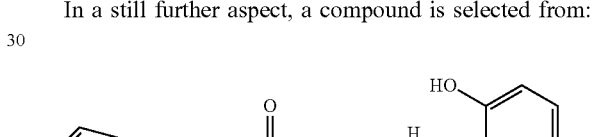

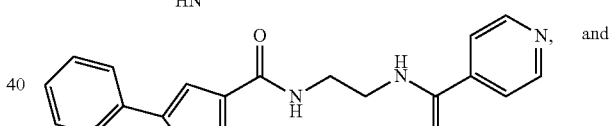

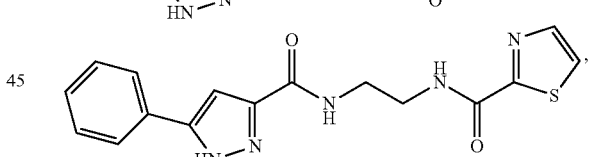

or a pharmaceutically acceptable salt thereof.

In yet a further aspect, a compound is:

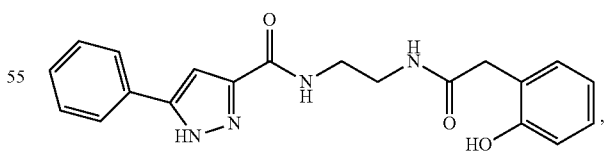

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as mediators of transcriptional induction of E-cadherin, and such activity can be determined using the assay methods described herein above.

In one aspect, a compound can be selected from:
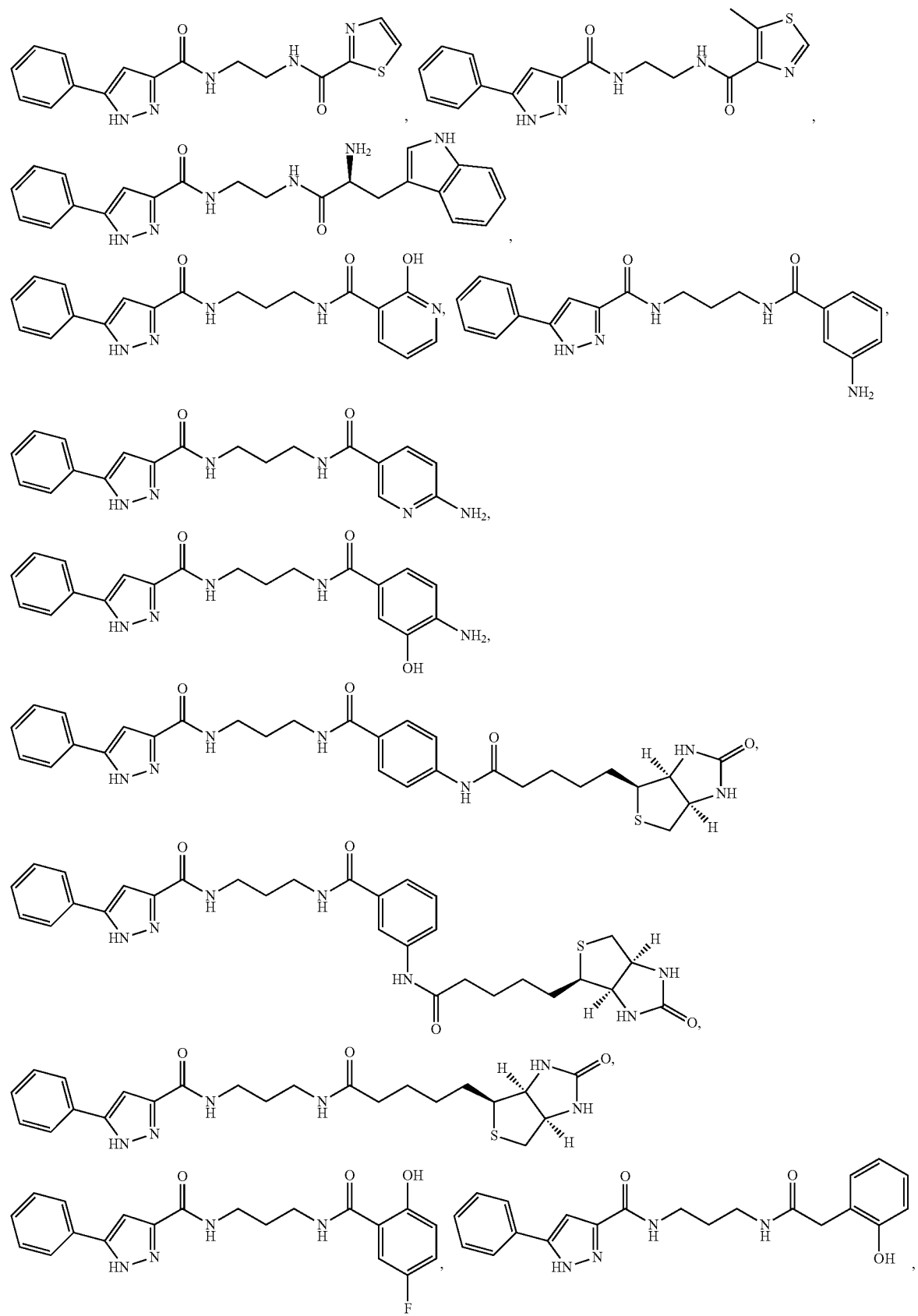

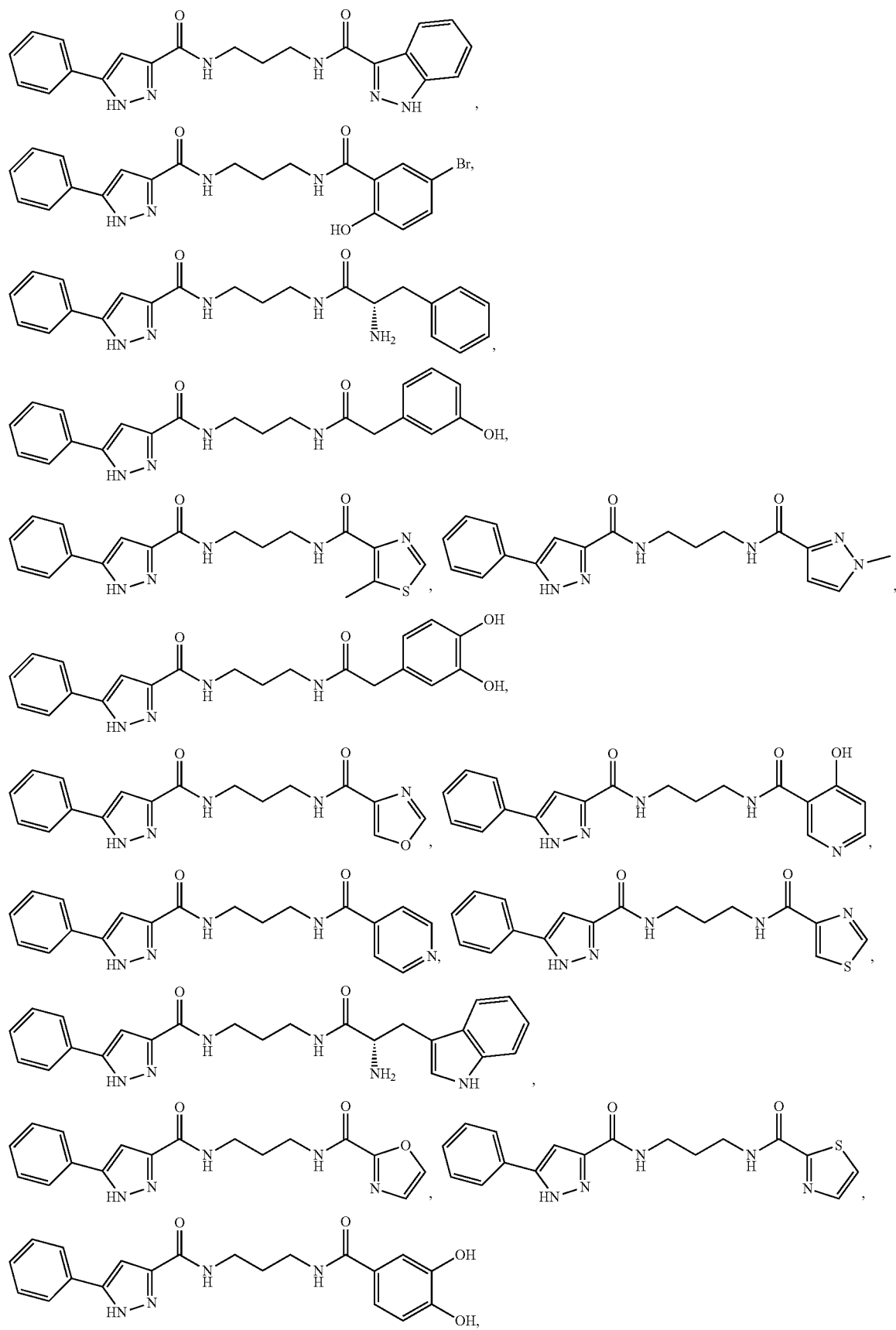

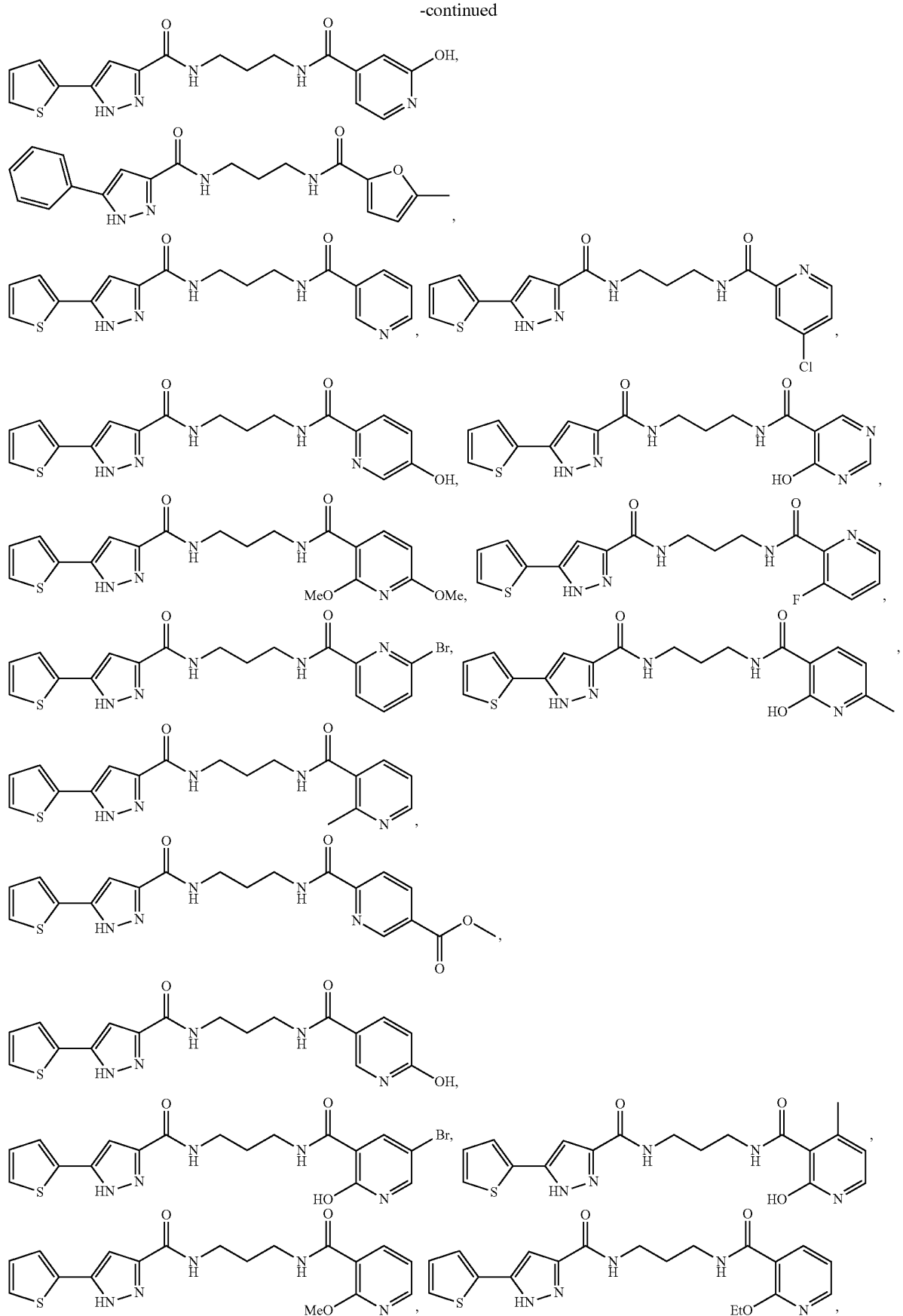

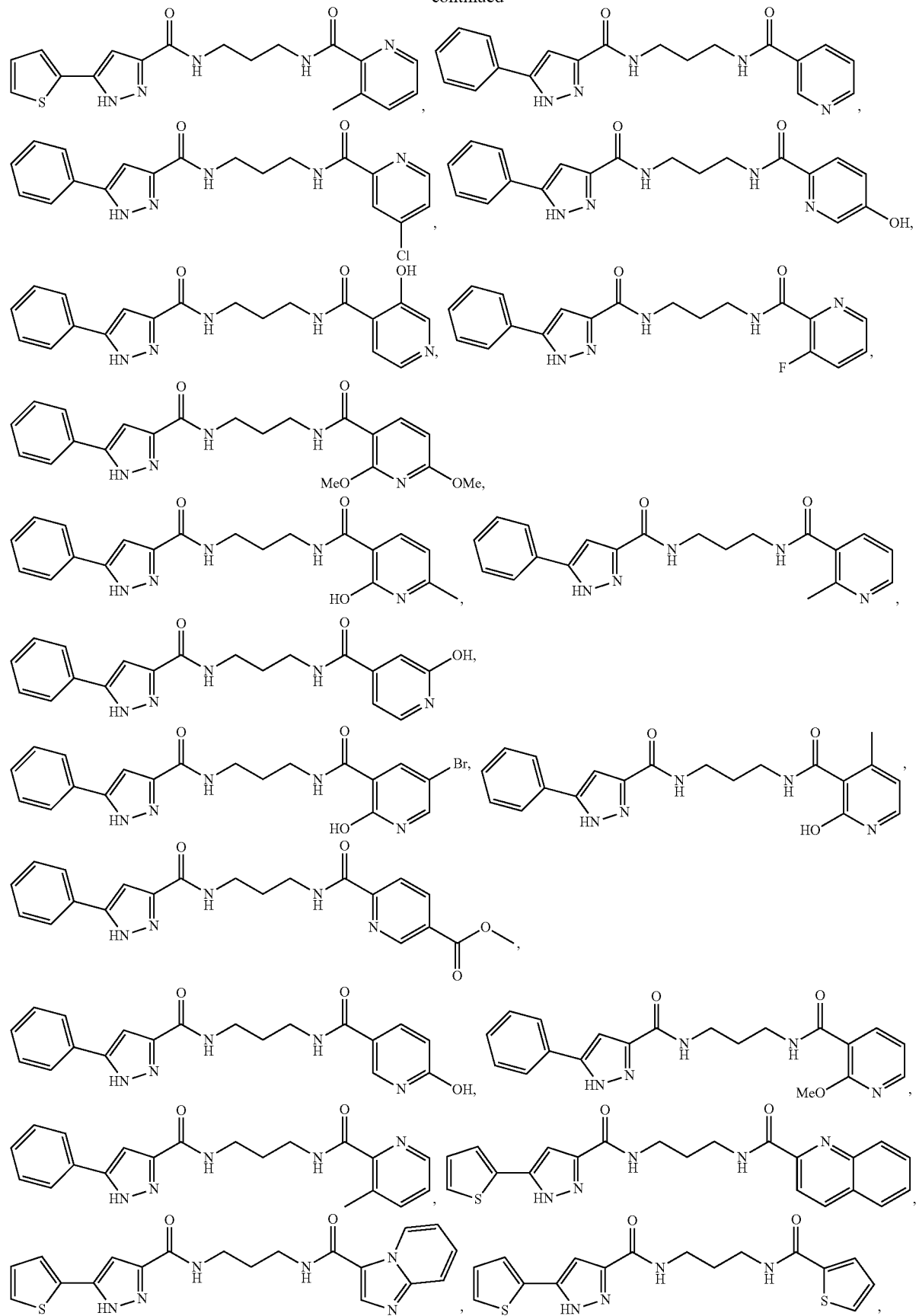

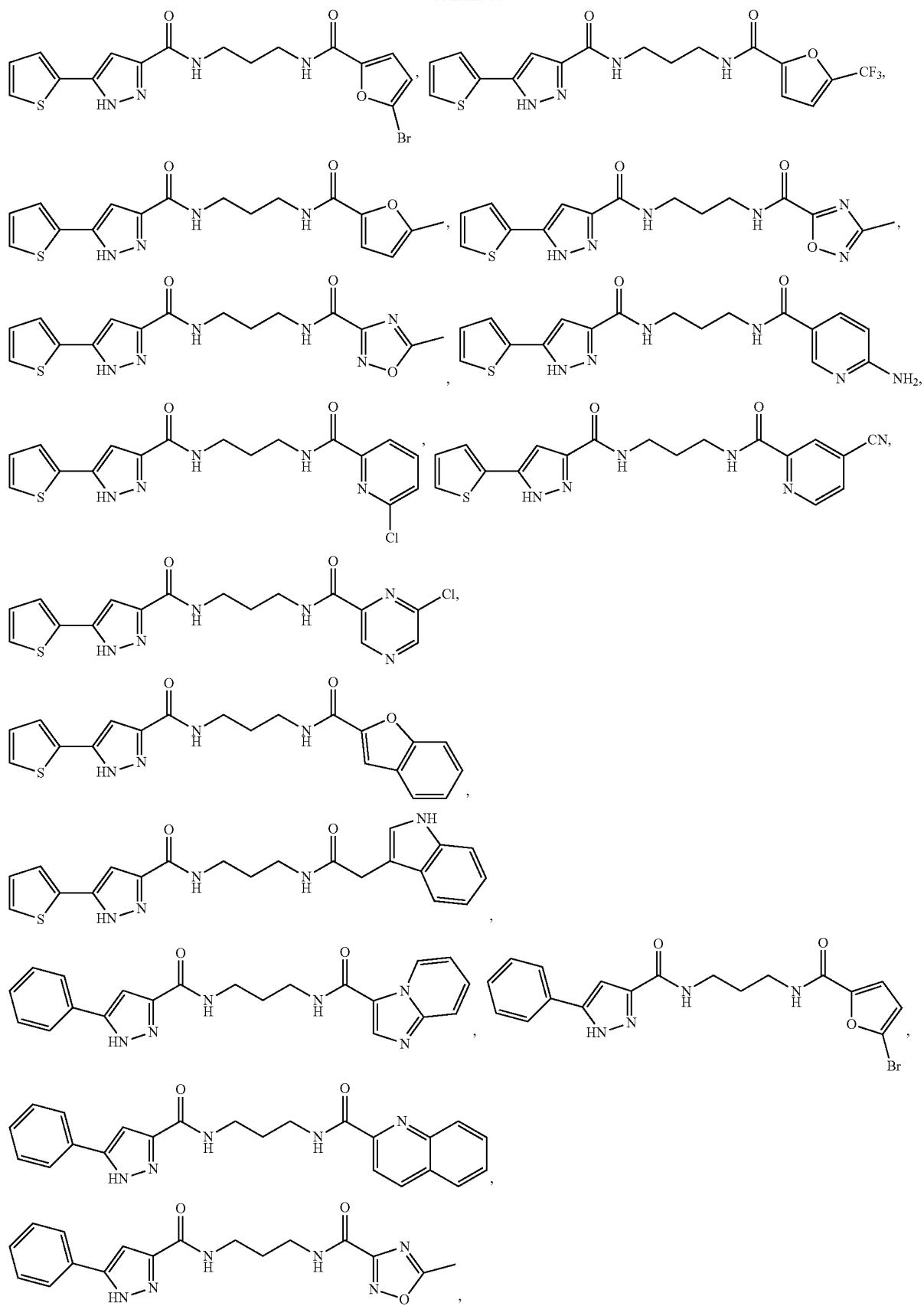

-continued
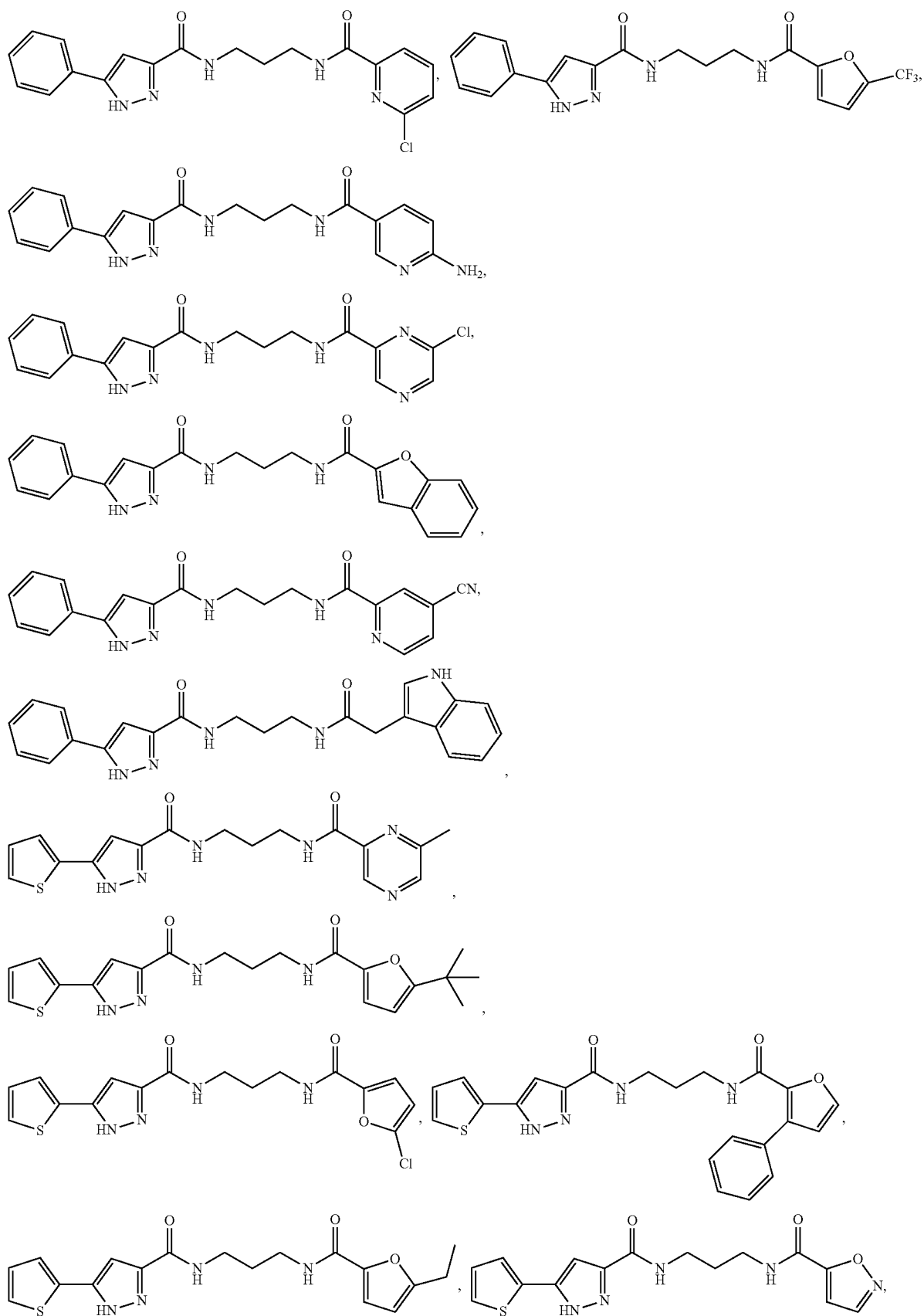

145 146
-continued
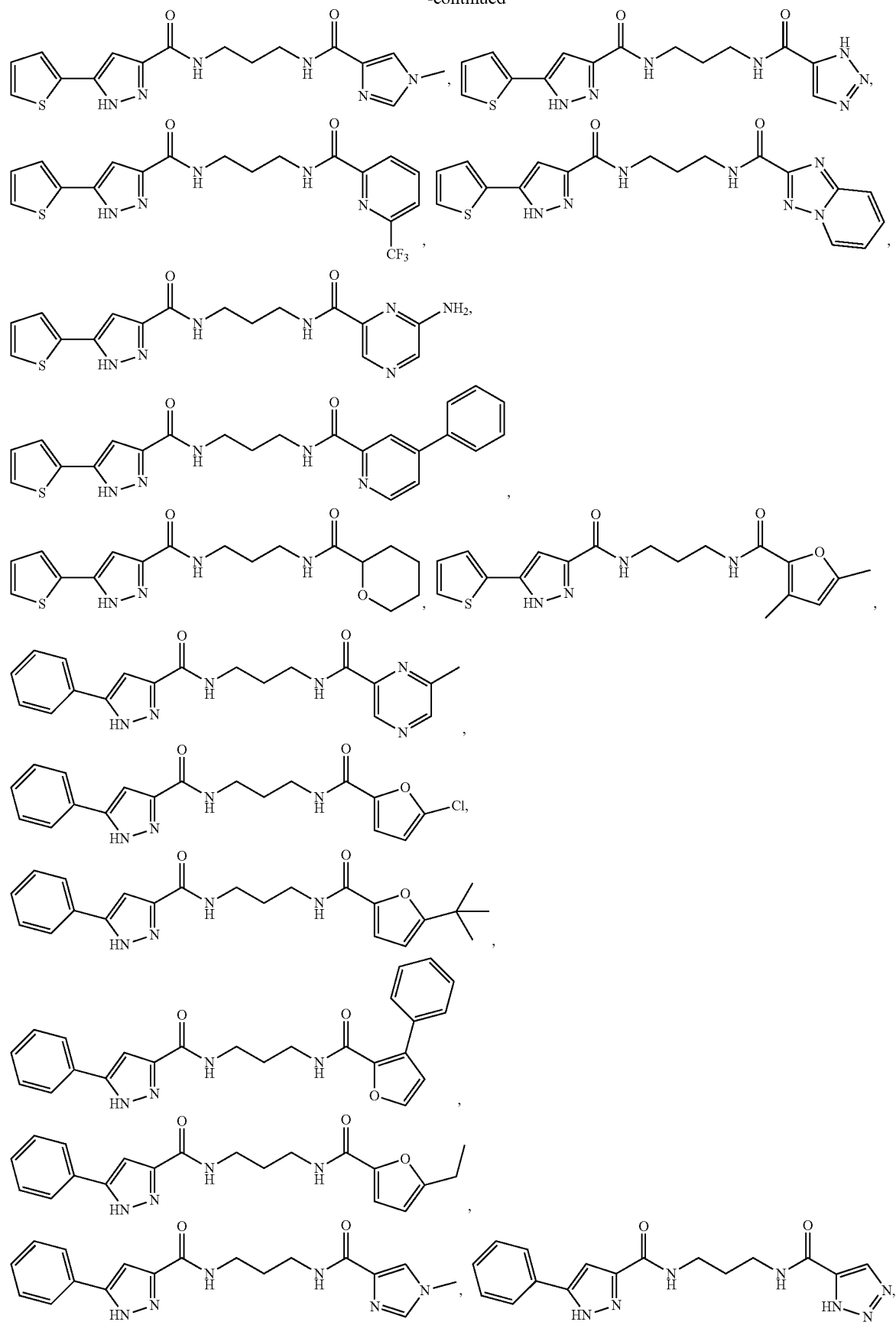

147
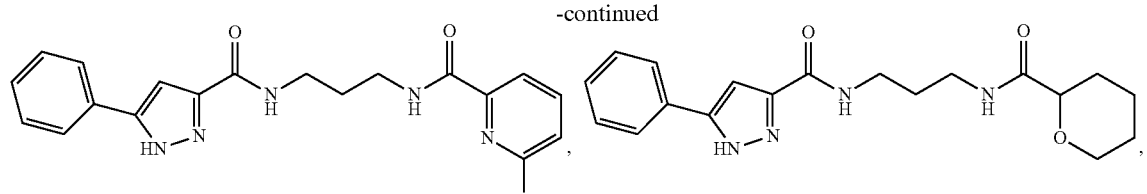
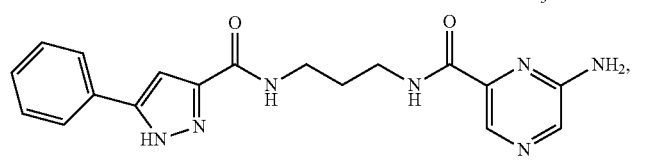
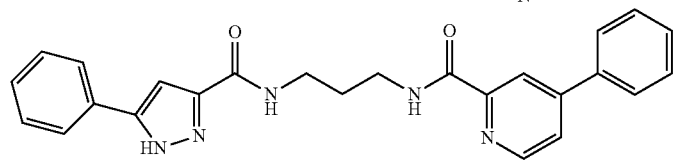
-continued
148
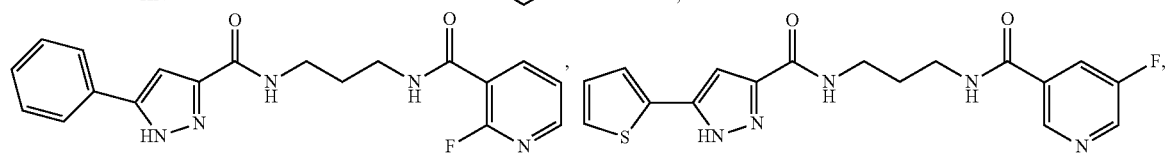
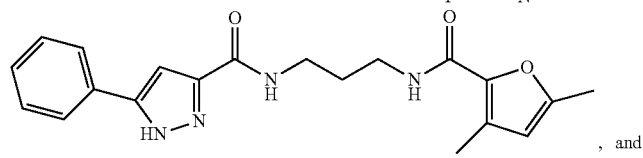
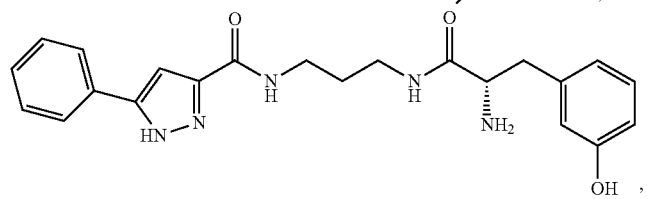
or a pharmaceutically acceptable salt thereof.
In a further aspect, a compound can be selected from:
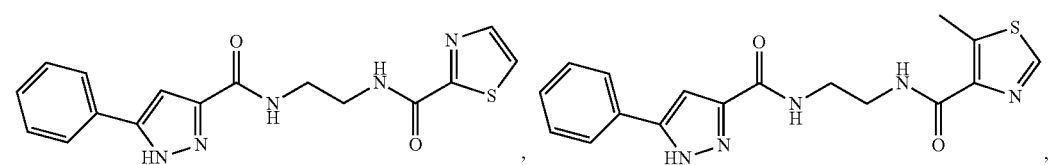
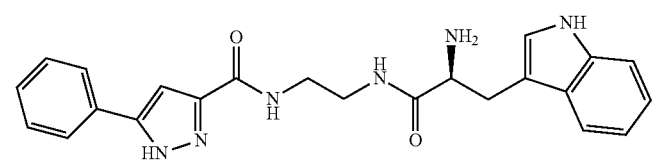
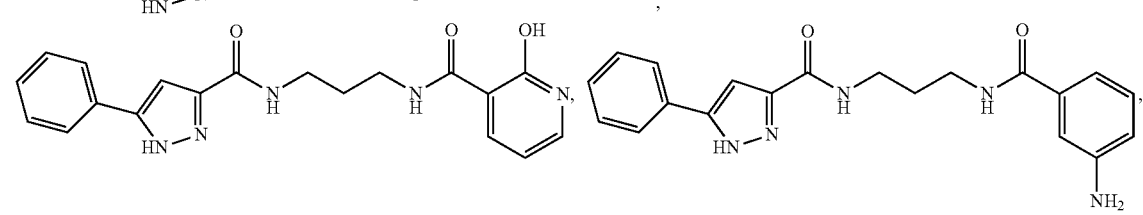

-continued
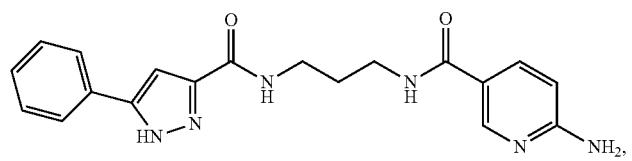
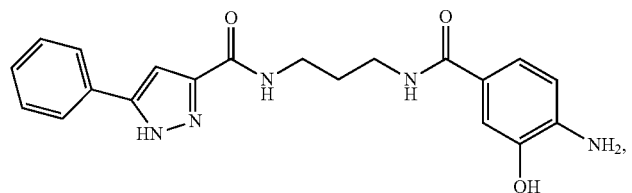
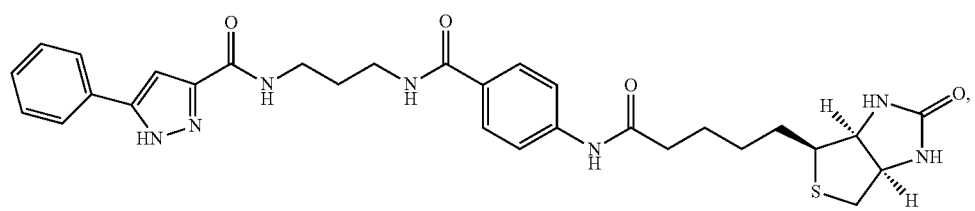
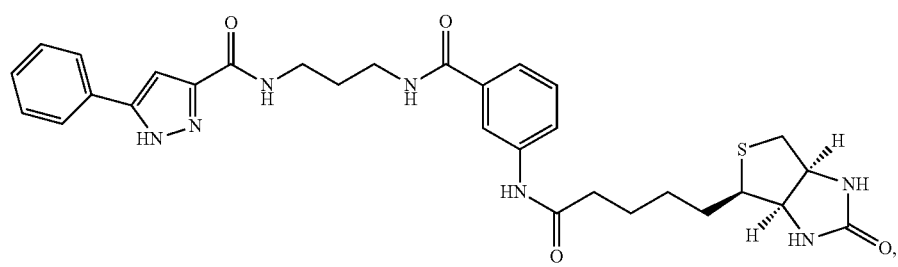
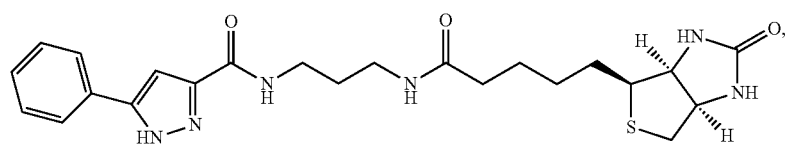
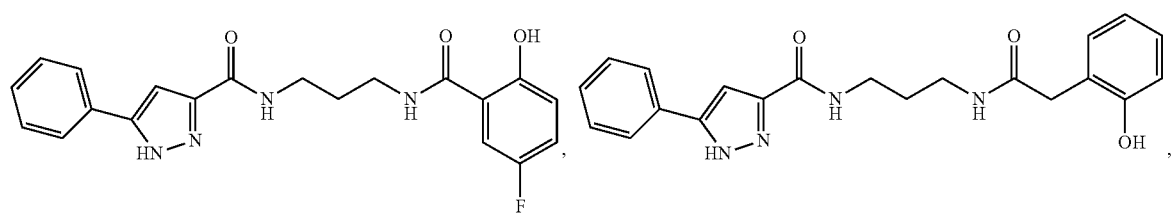
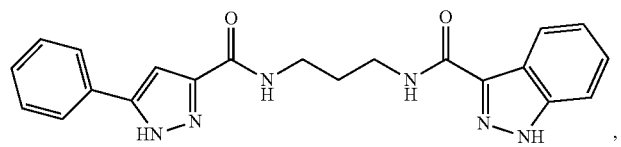
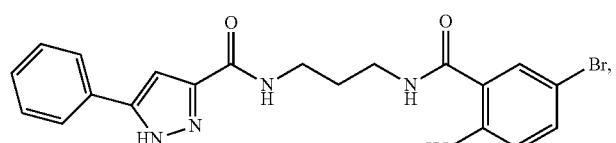
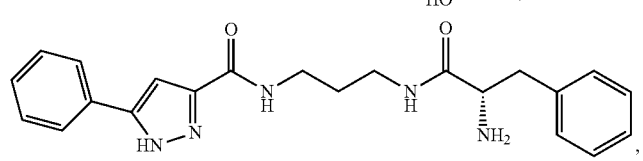

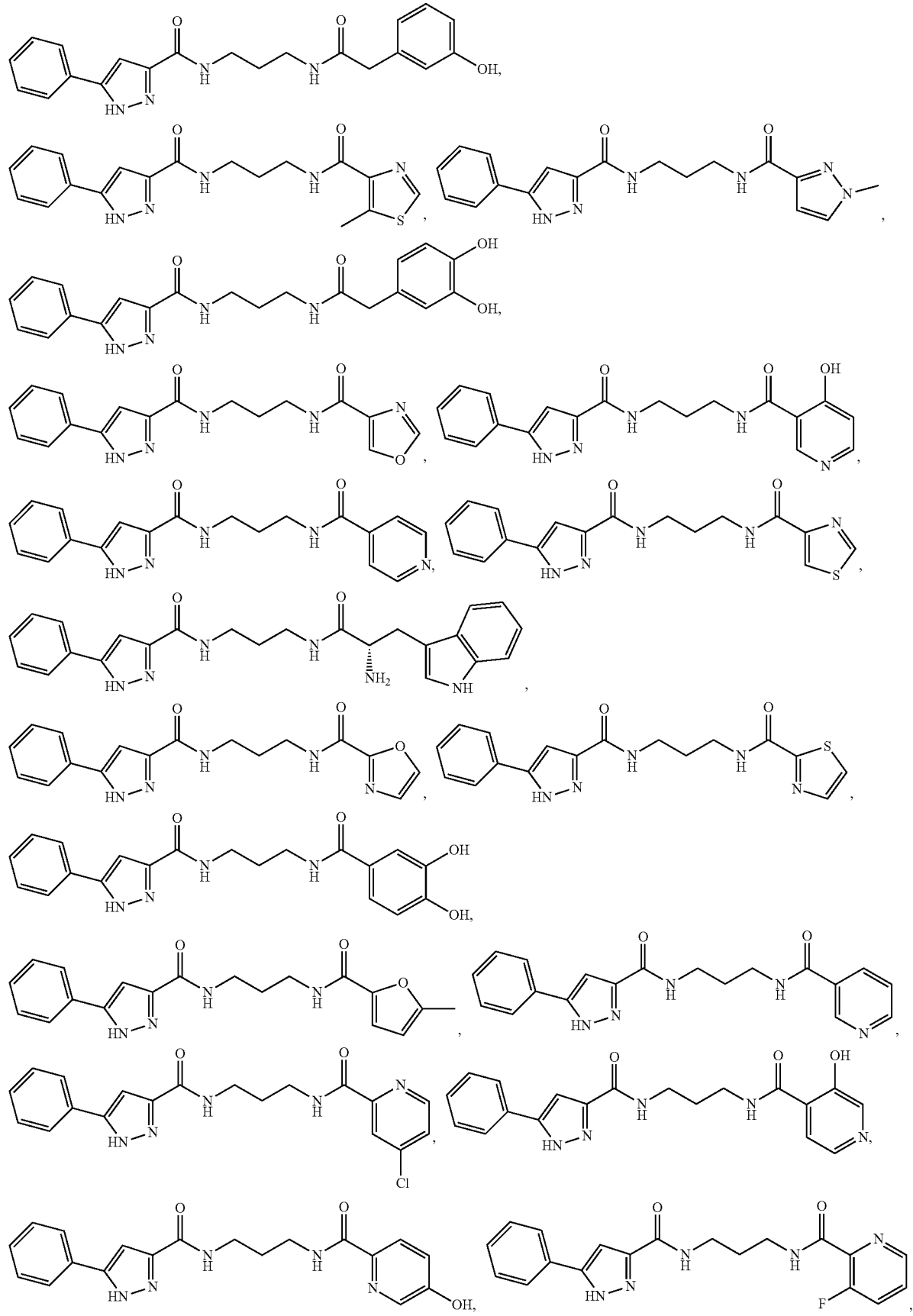

-continued
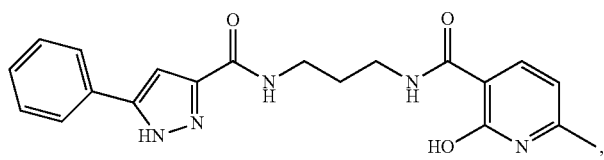
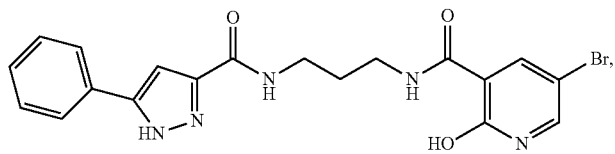
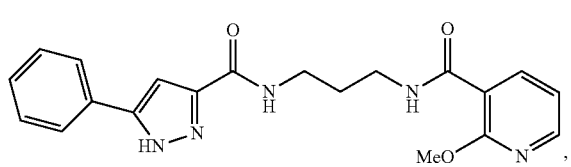
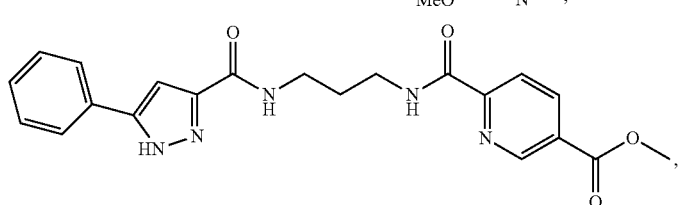
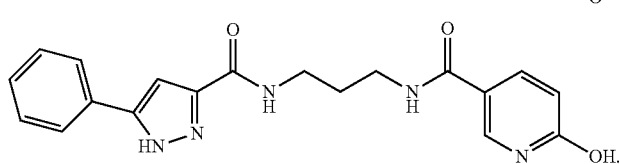
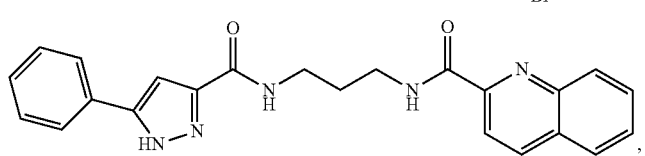
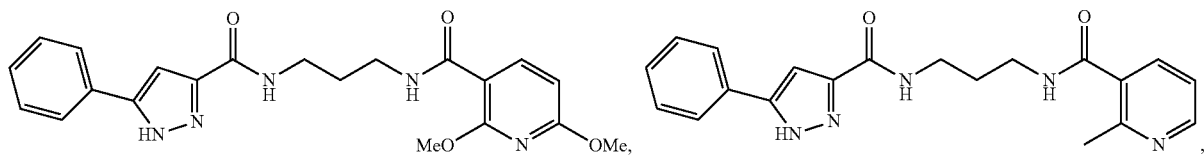
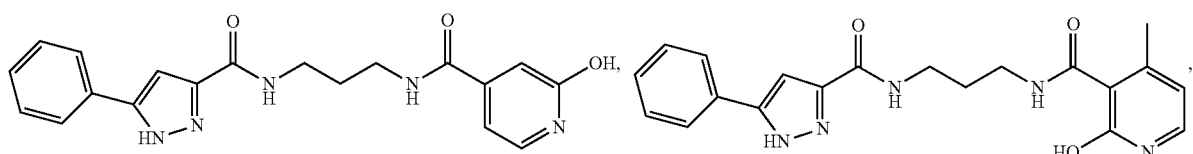
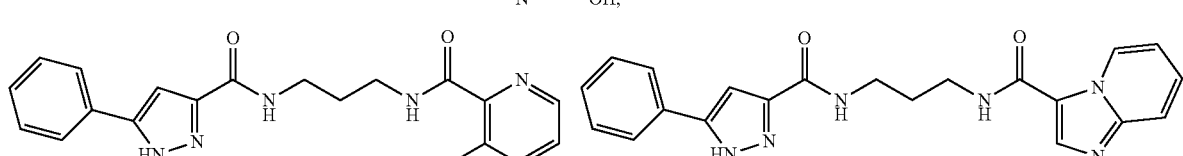
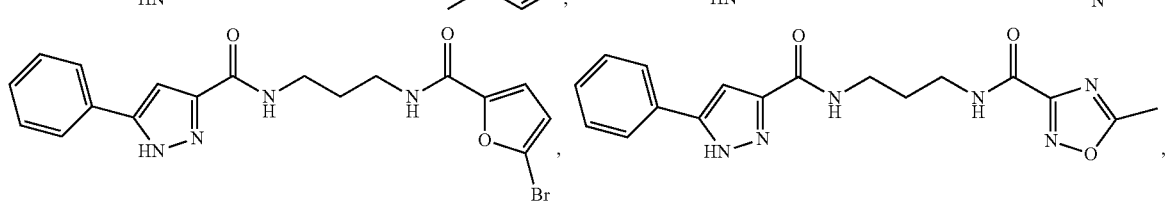

-continued
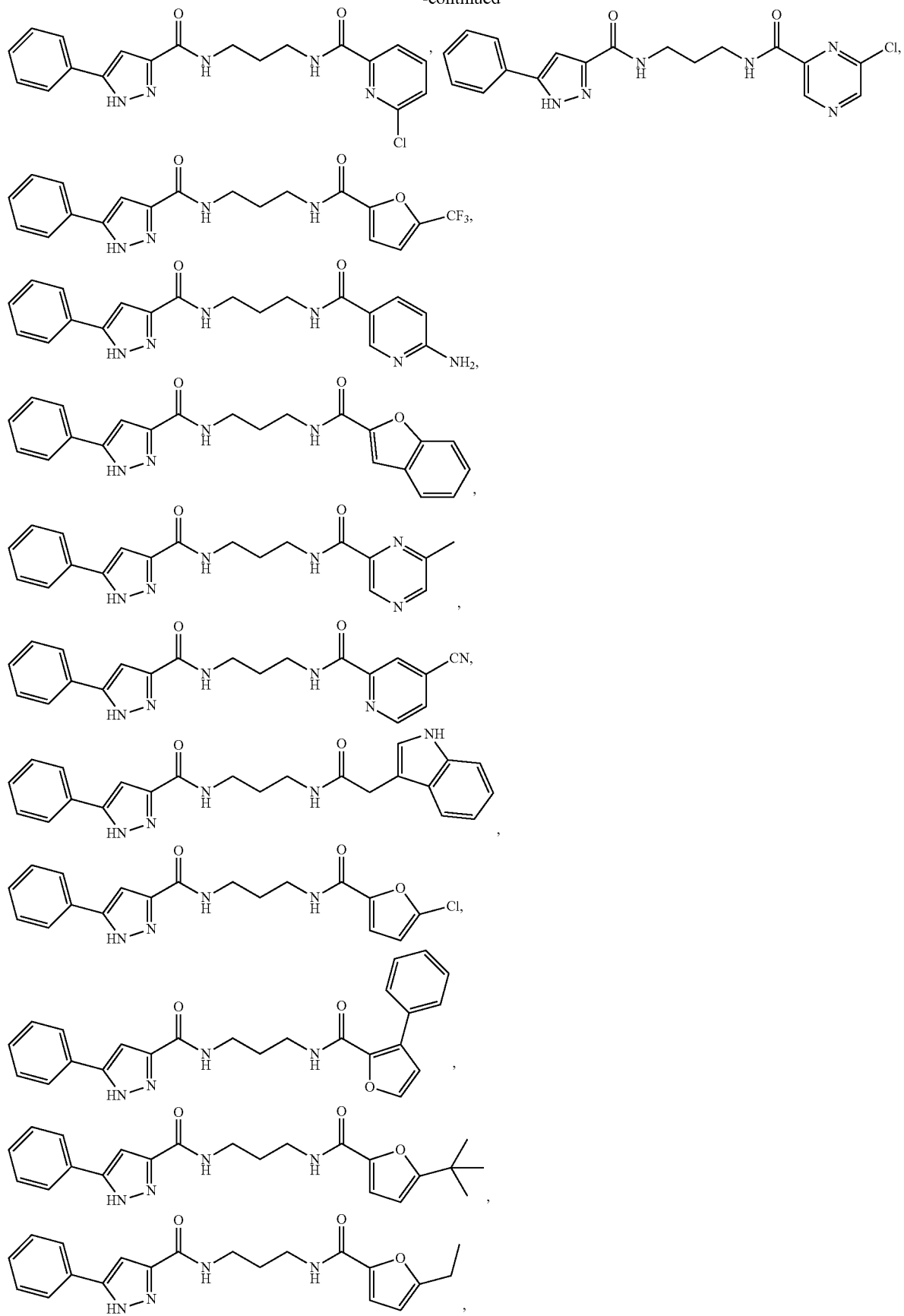

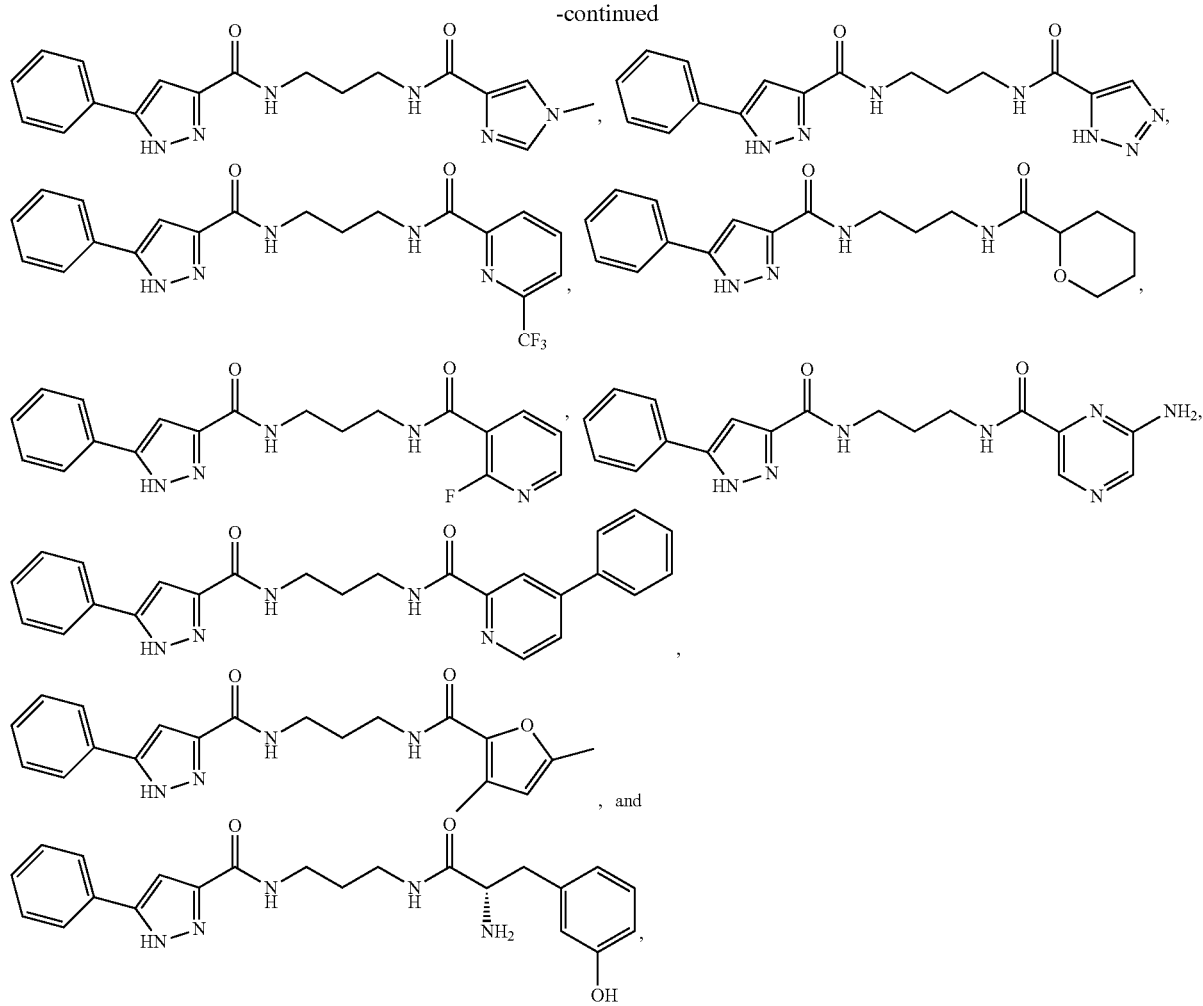
or a pharmaceutically acceptable salt thereof.
In a still further aspect, a compound can be selected from:
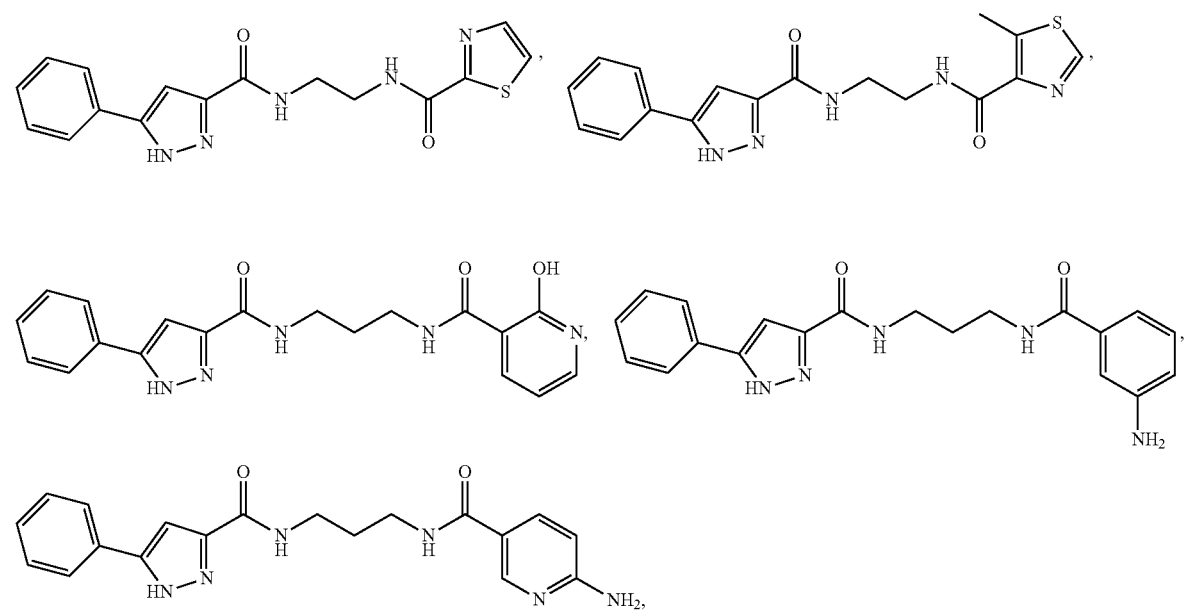

-continued
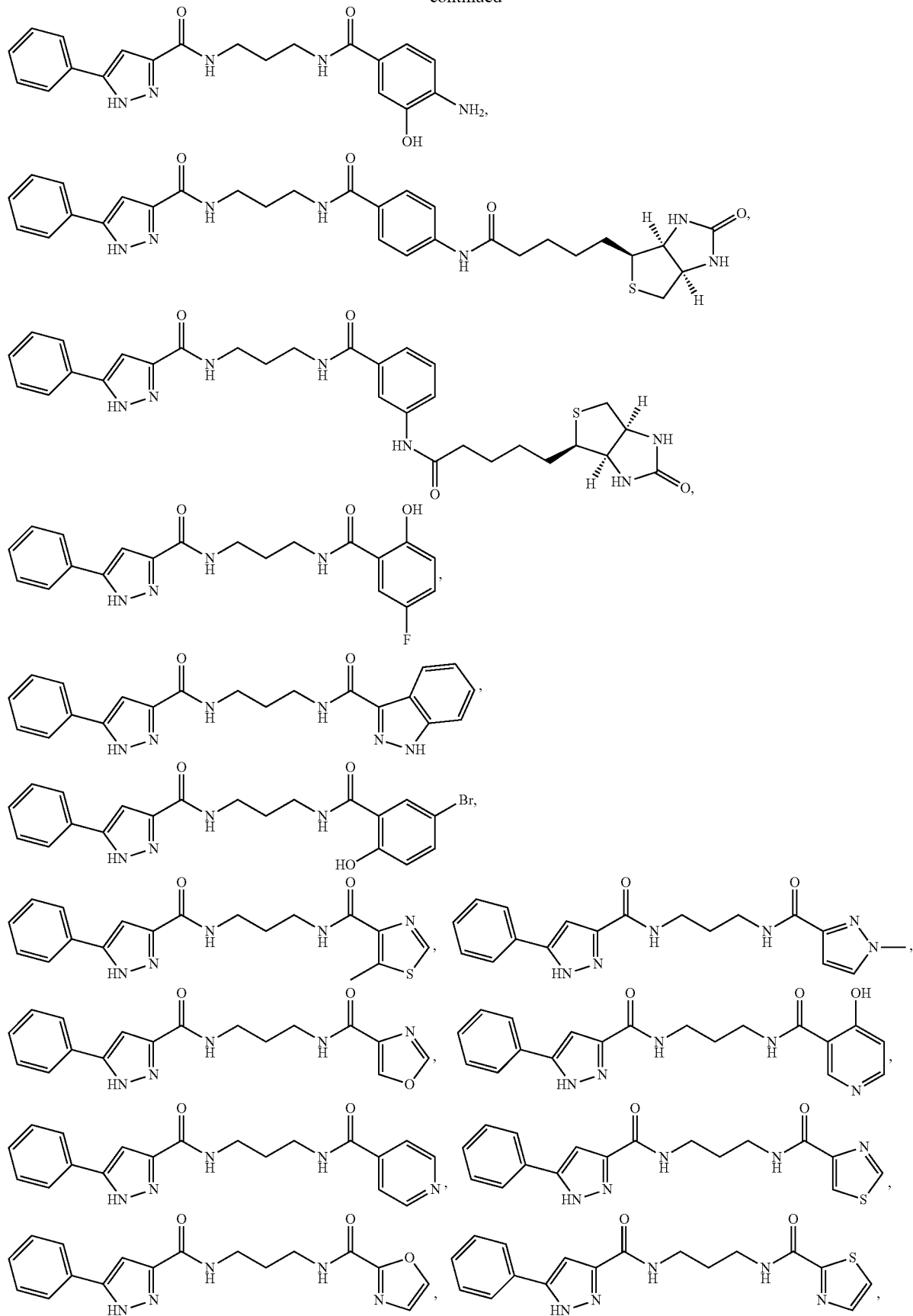

-continued
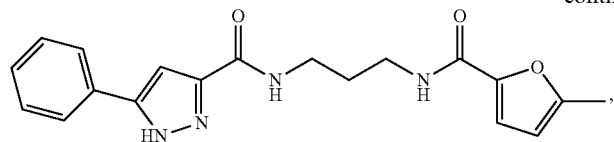
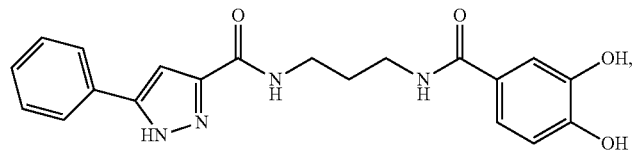
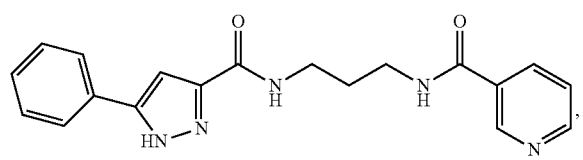
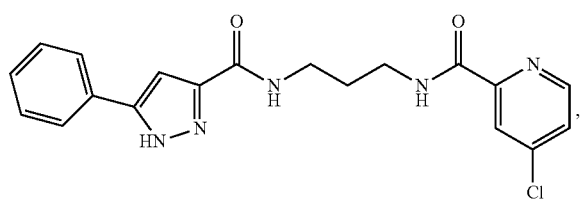
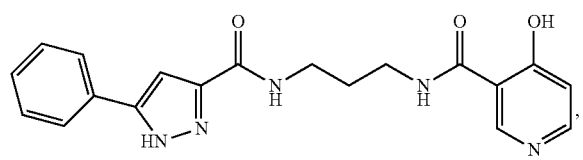
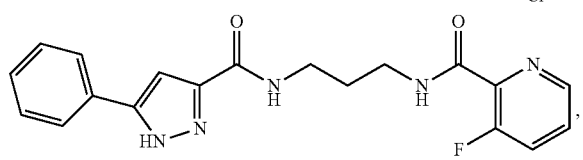
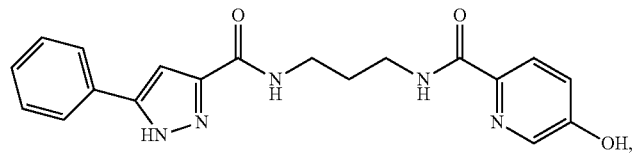
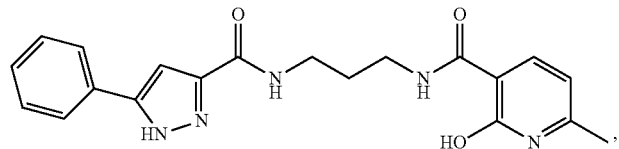
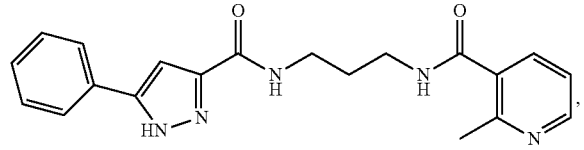
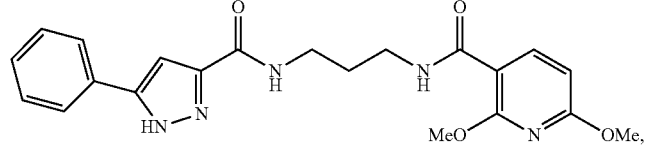
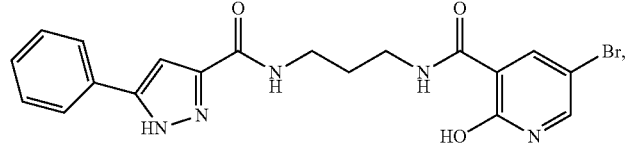
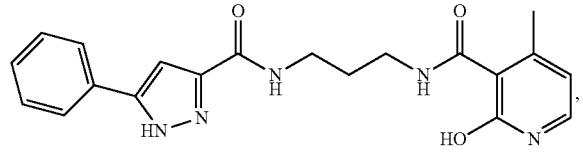
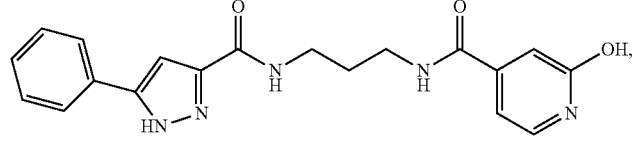

163 164
-continued
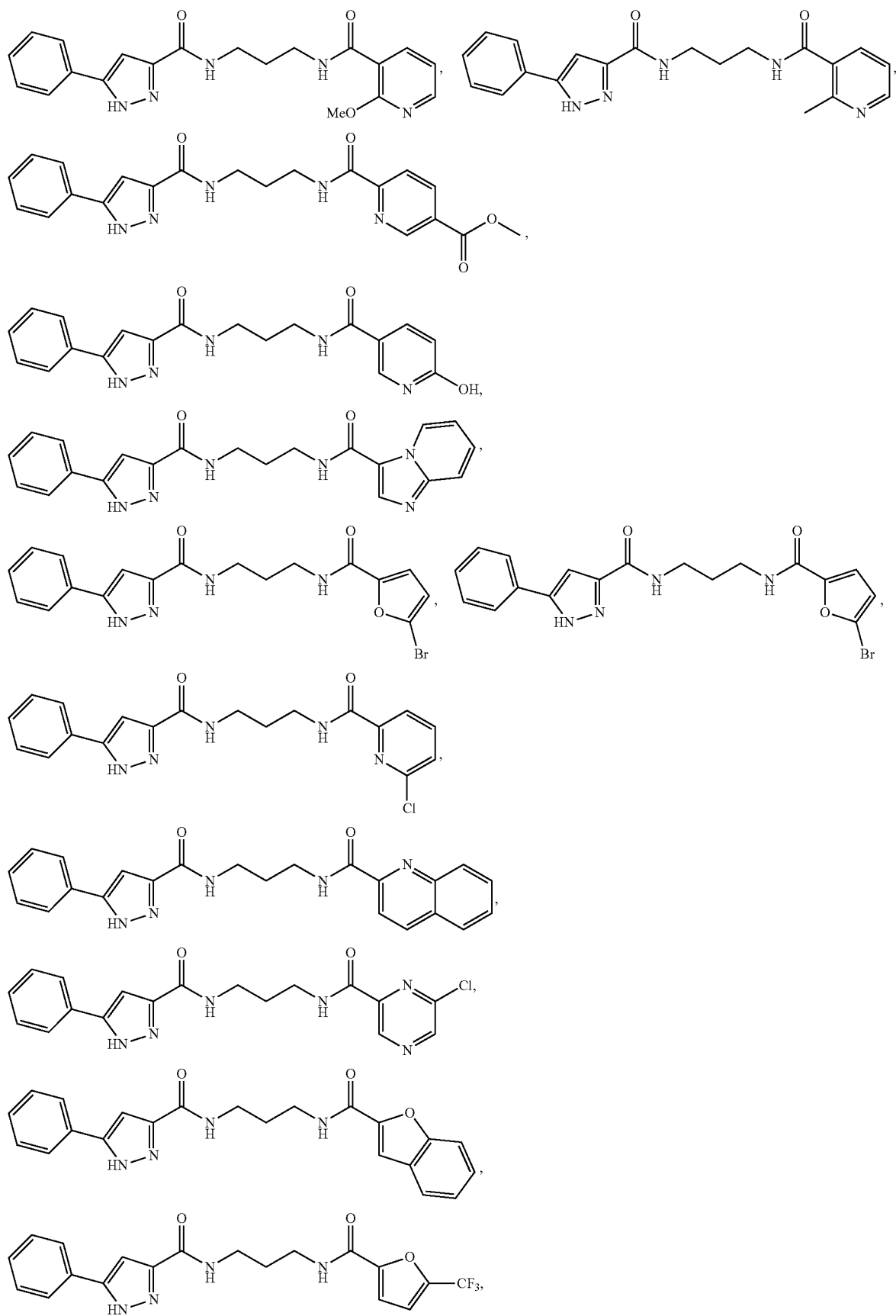

-continued
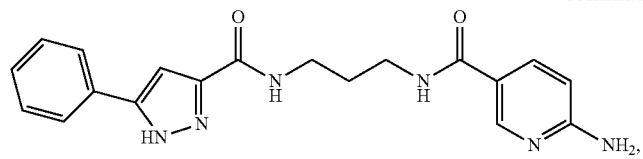
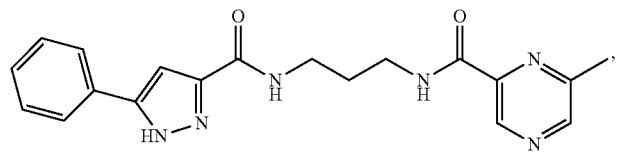
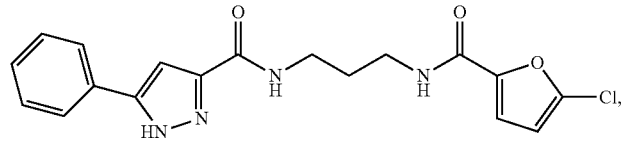
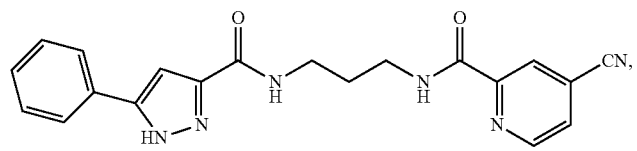
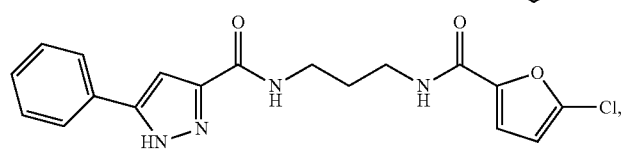
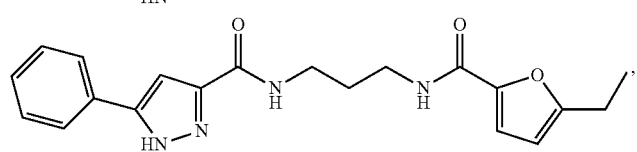
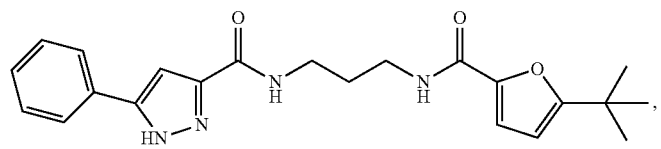
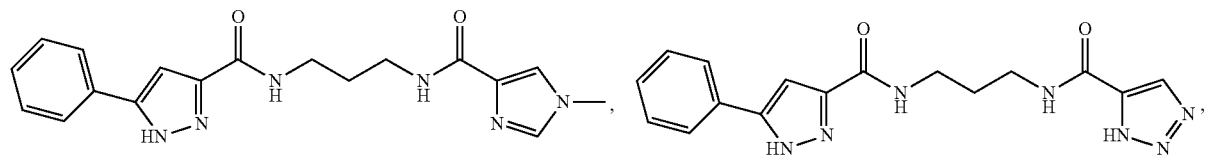
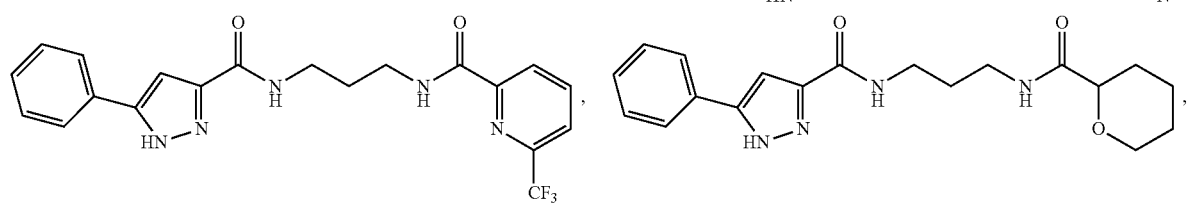
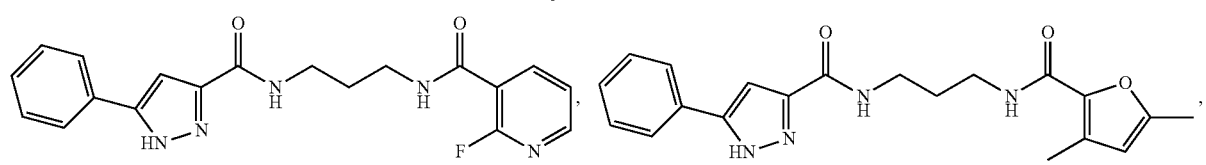
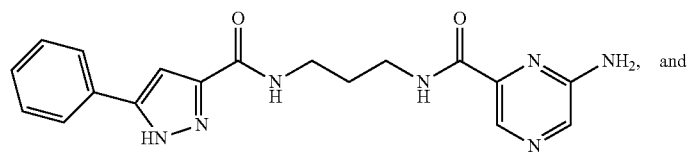

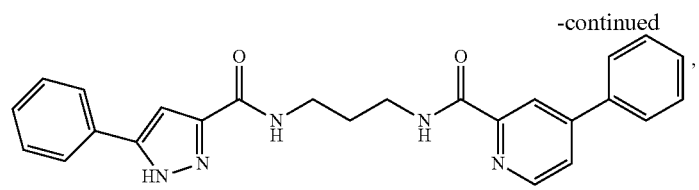
or a pharmaceutically acceptable salt thereof.
In yet a further aspect, a compound can be selected from:
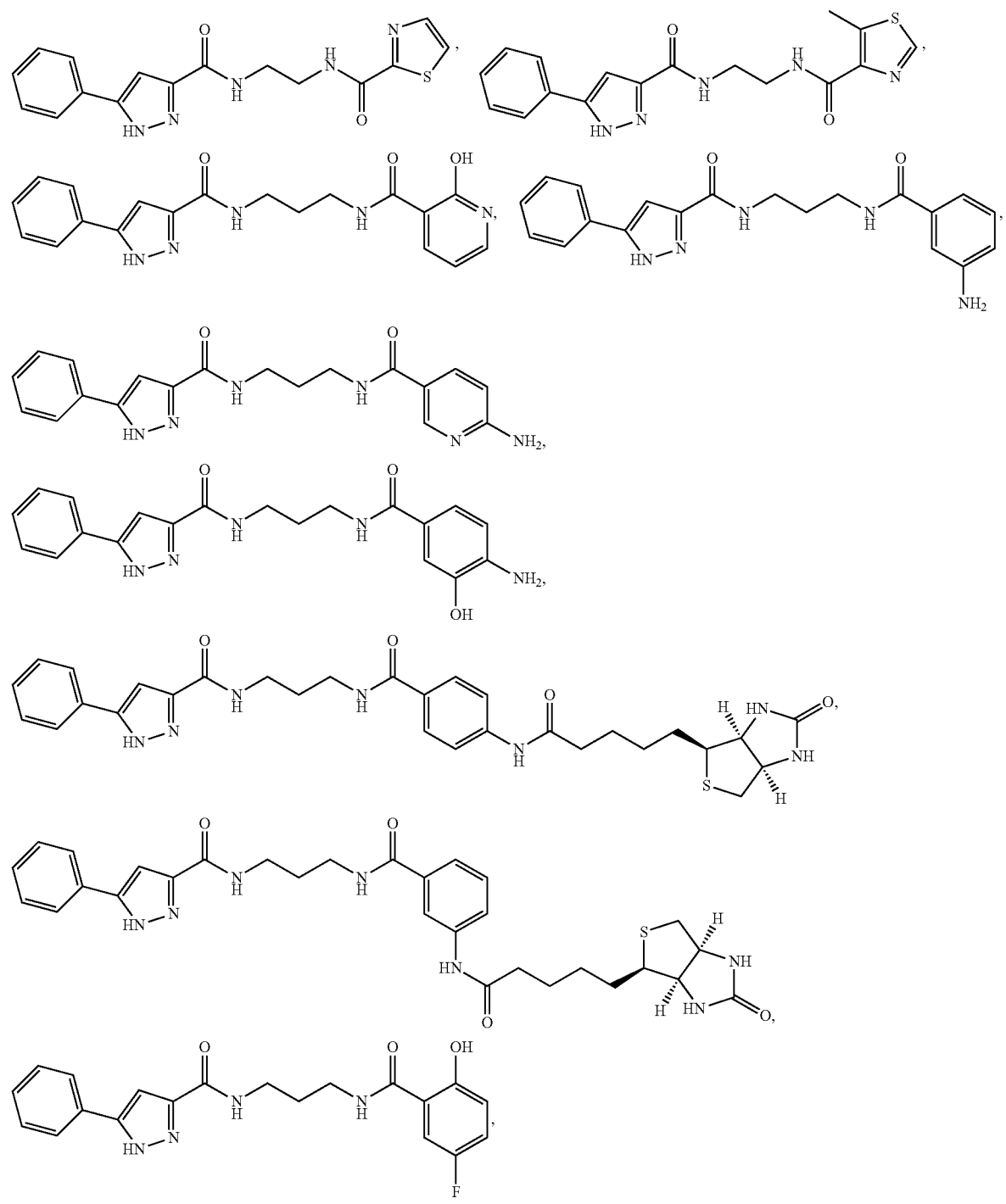

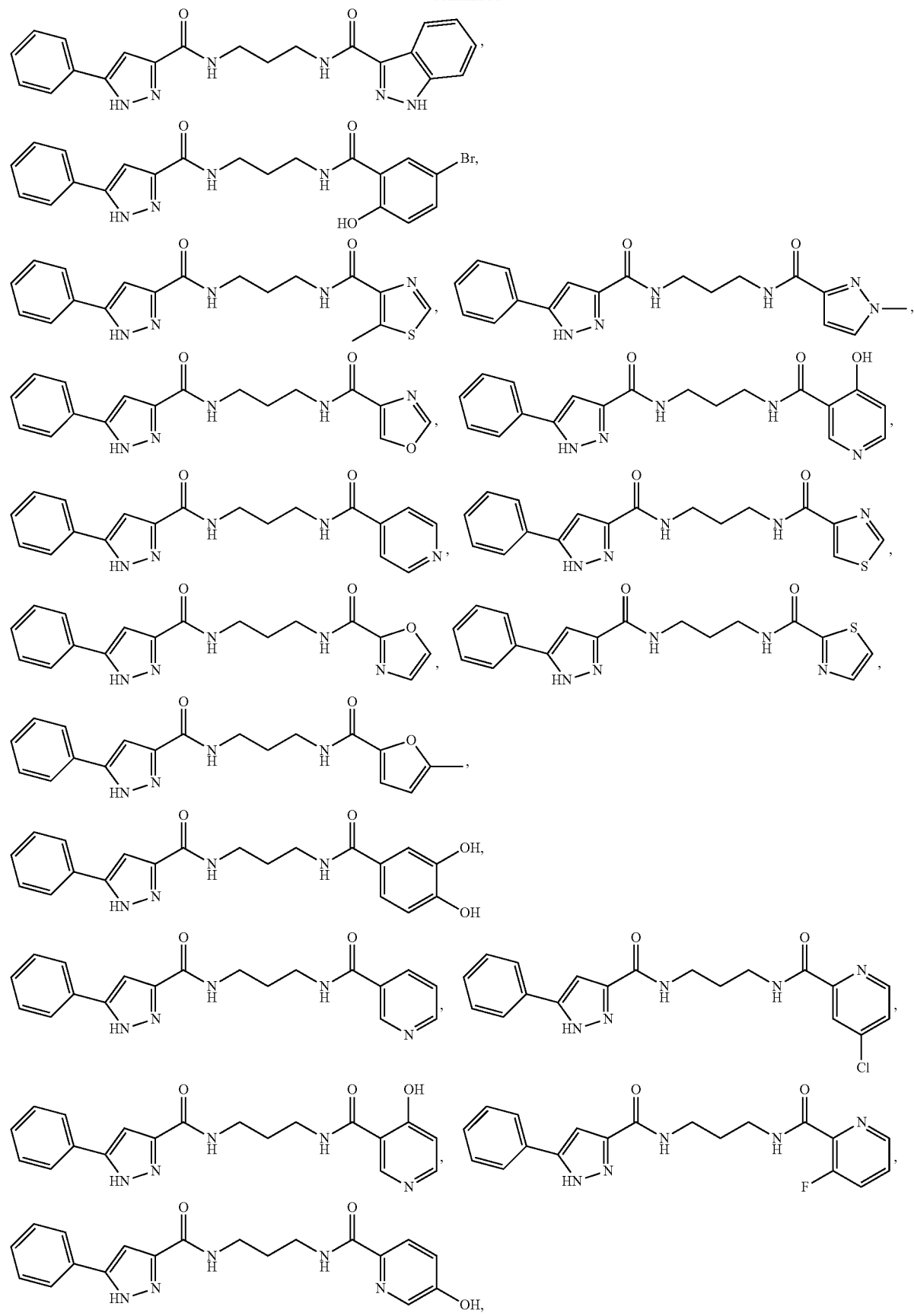

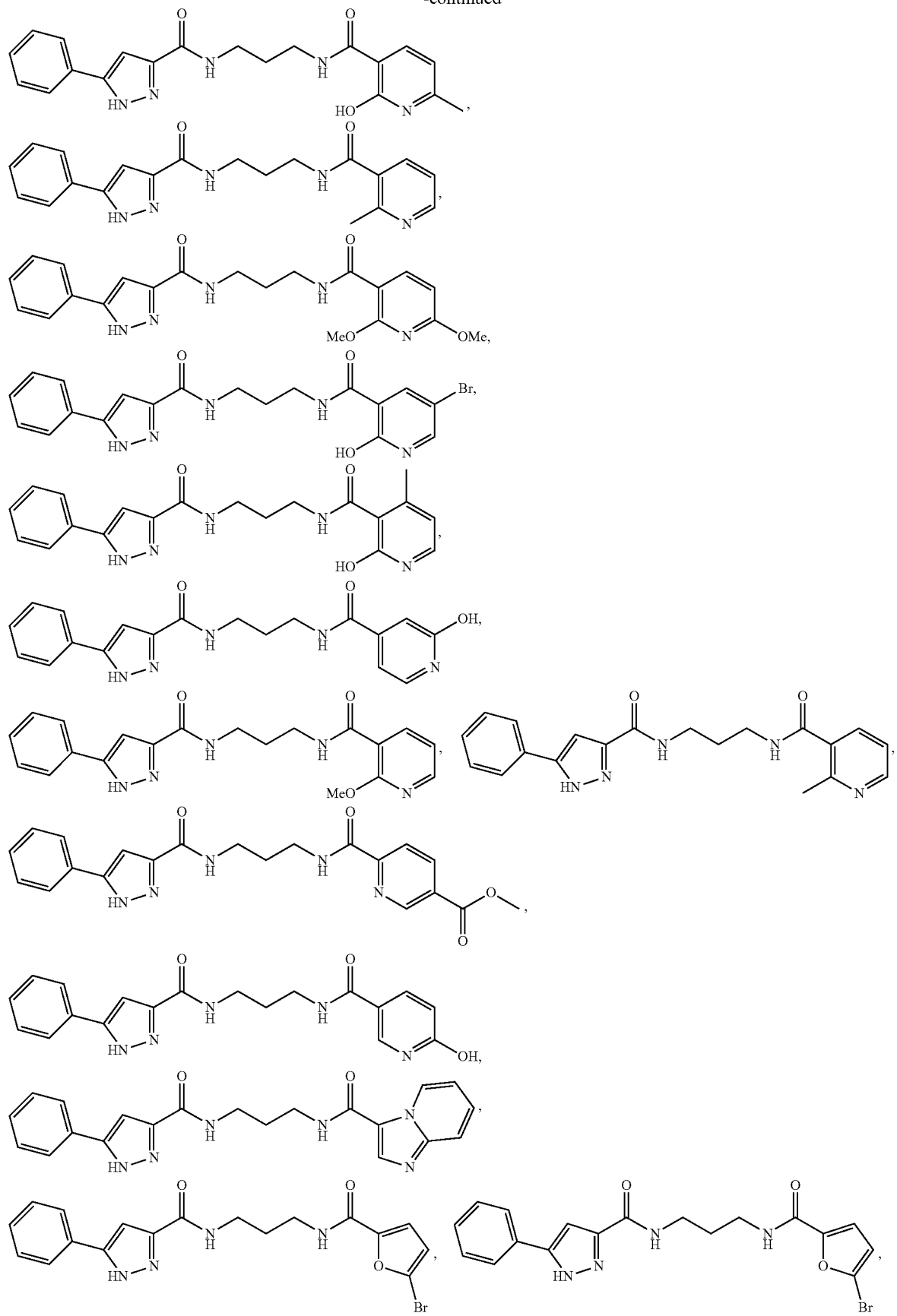

-continued
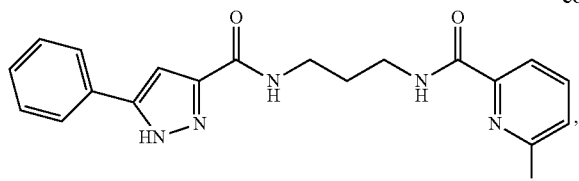
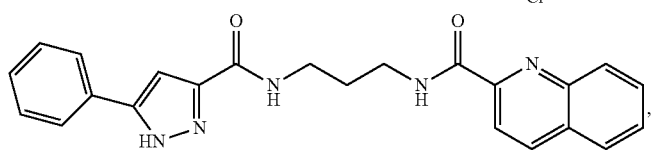
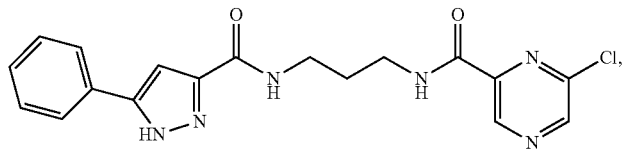
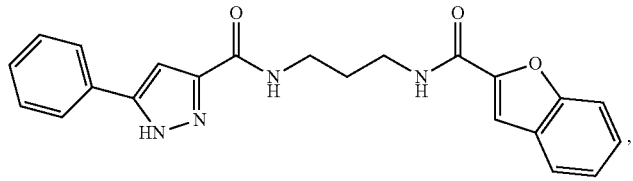
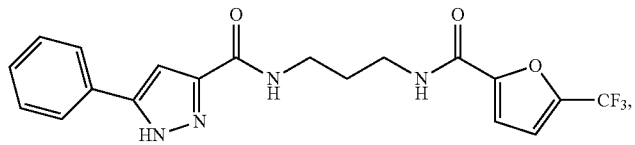
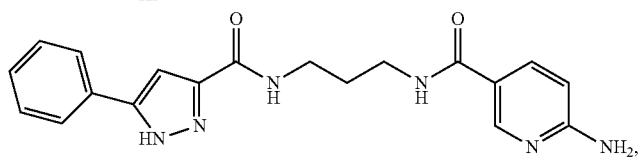
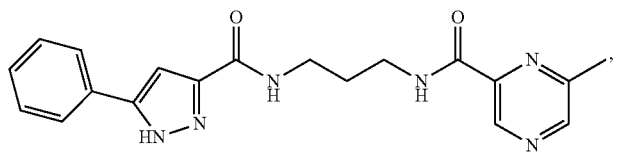
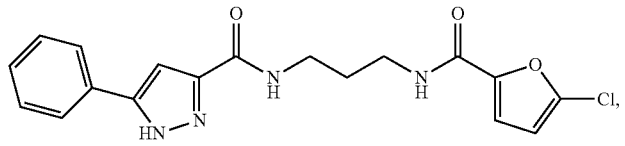
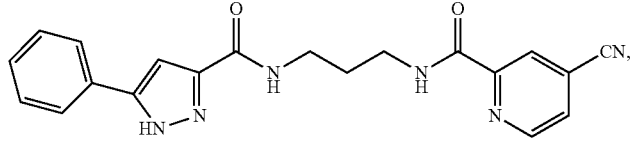
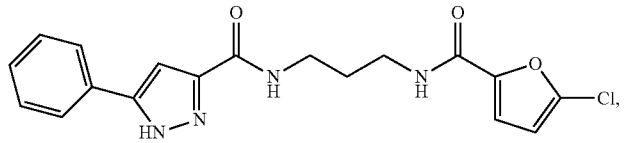
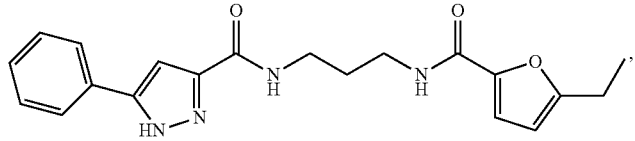

-continued
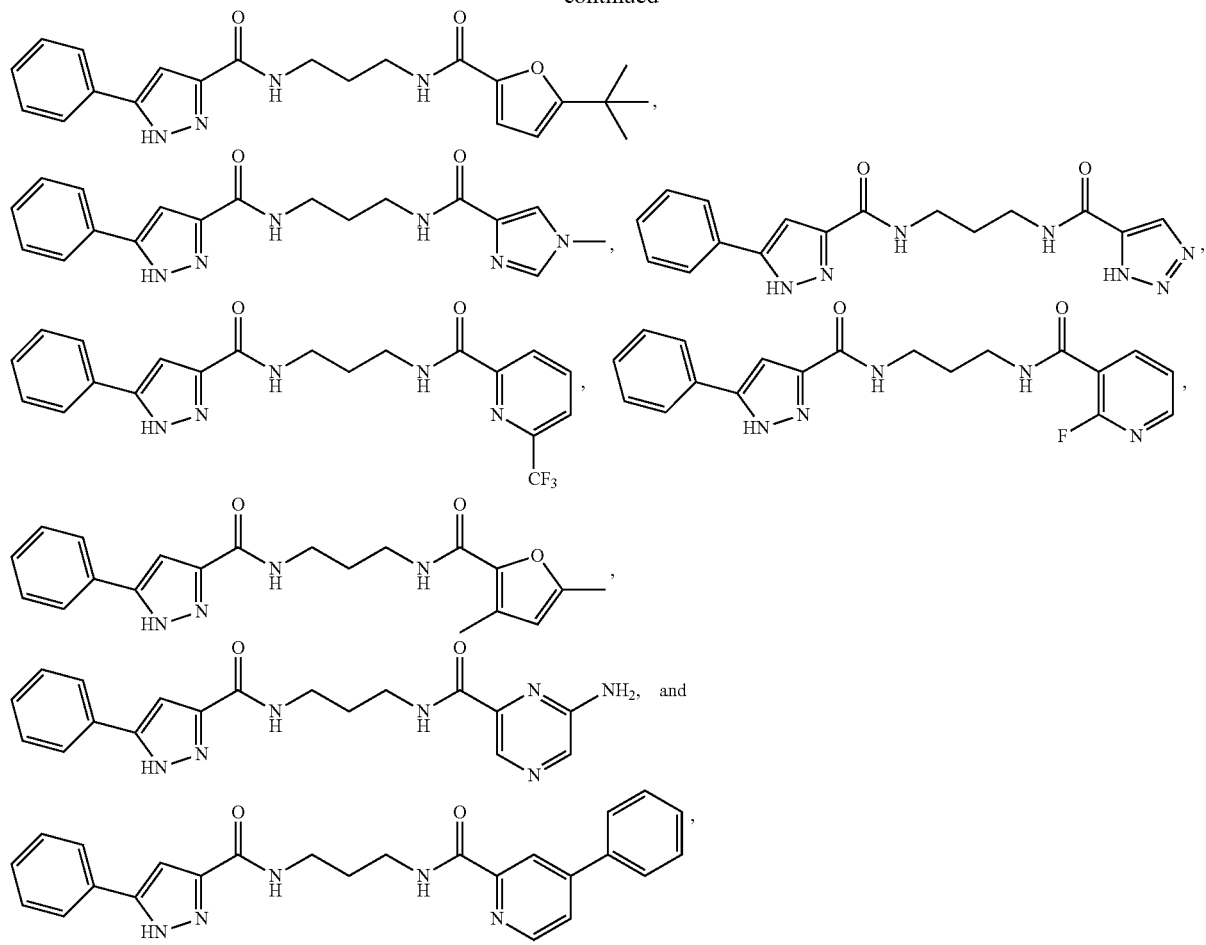
or a pharmaceutically acceptable salt thereof.
In an even further aspect, a compound can be:
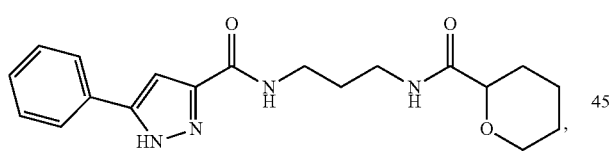
or a pharmaceutically acceptable salt thereof.
In a further aspect, a compound can be selected from:
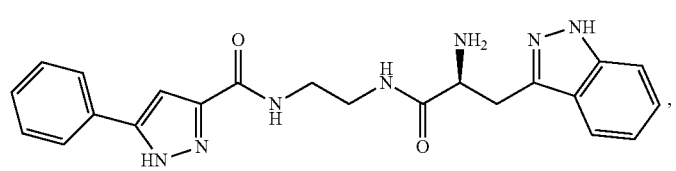
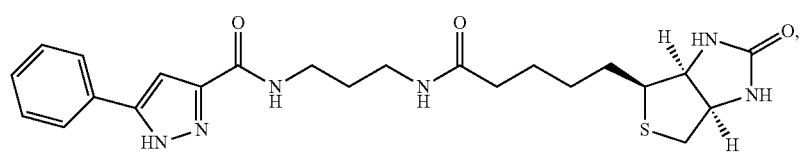

-continued
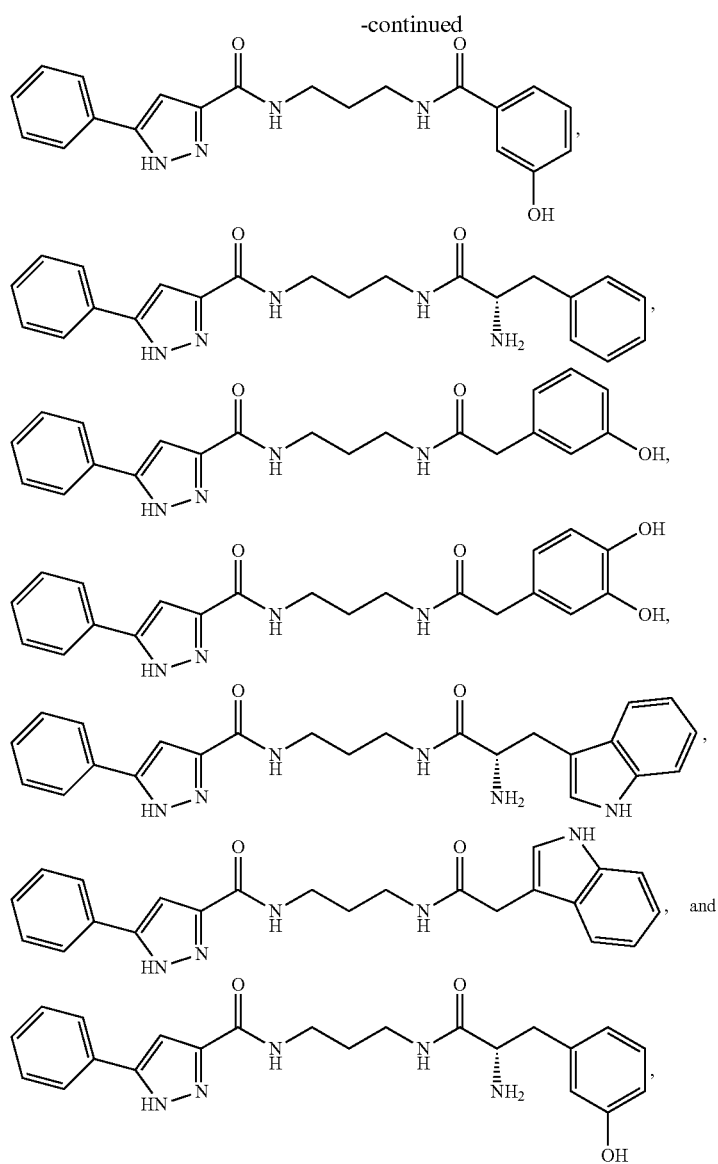
or a pharmaceutically acceptable salt thereof.
In a further aspect, a compound can be selected from:
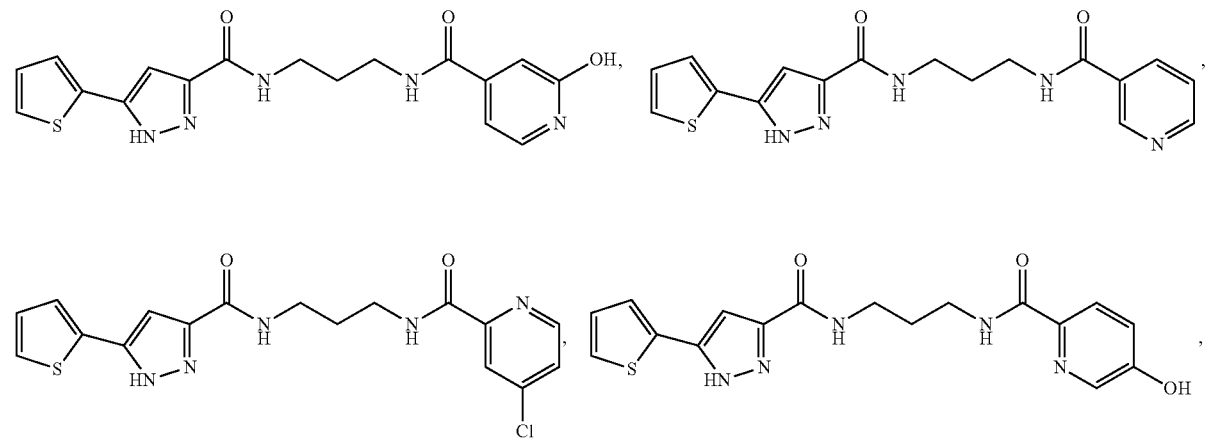

-continued

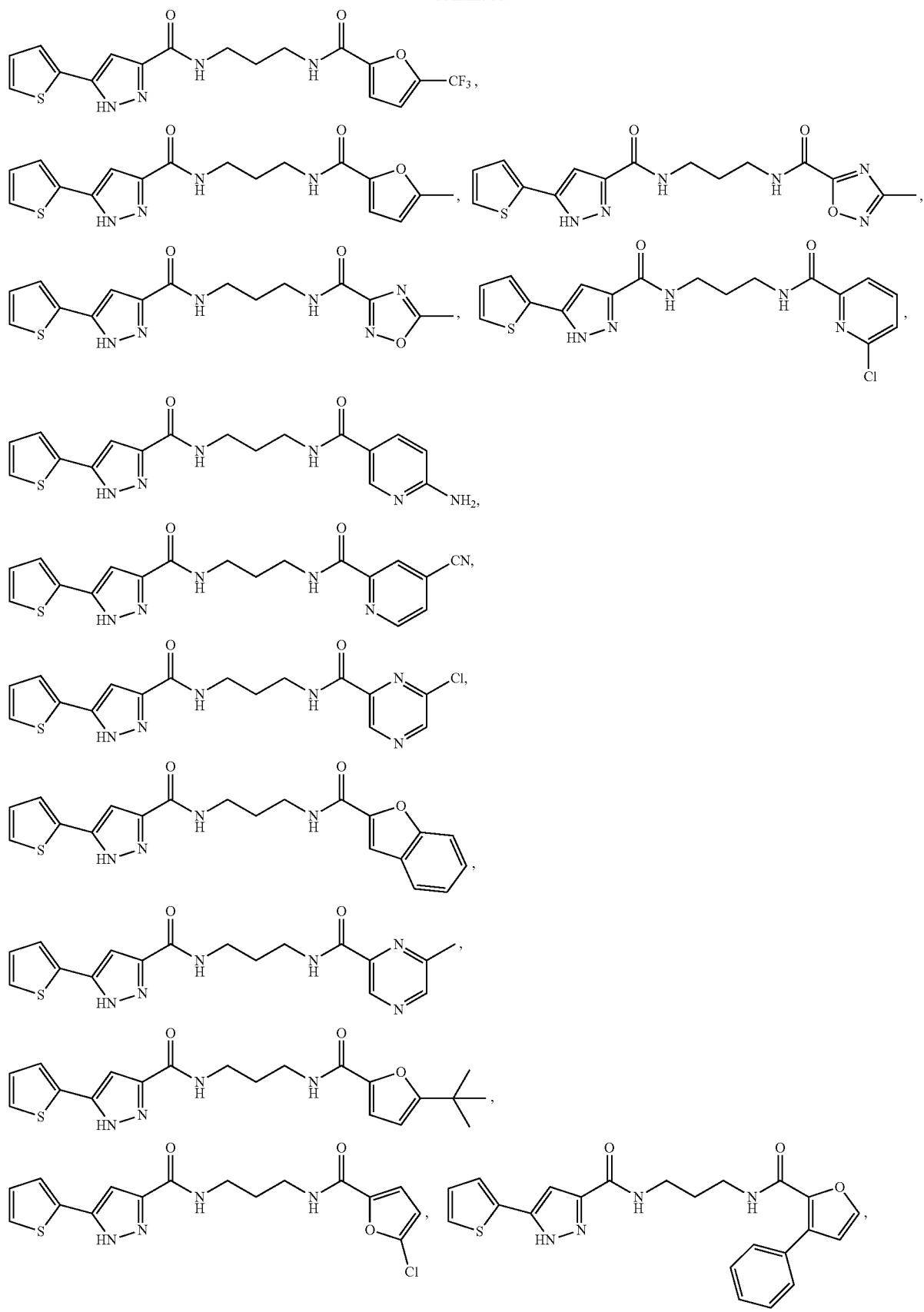

183
-continued
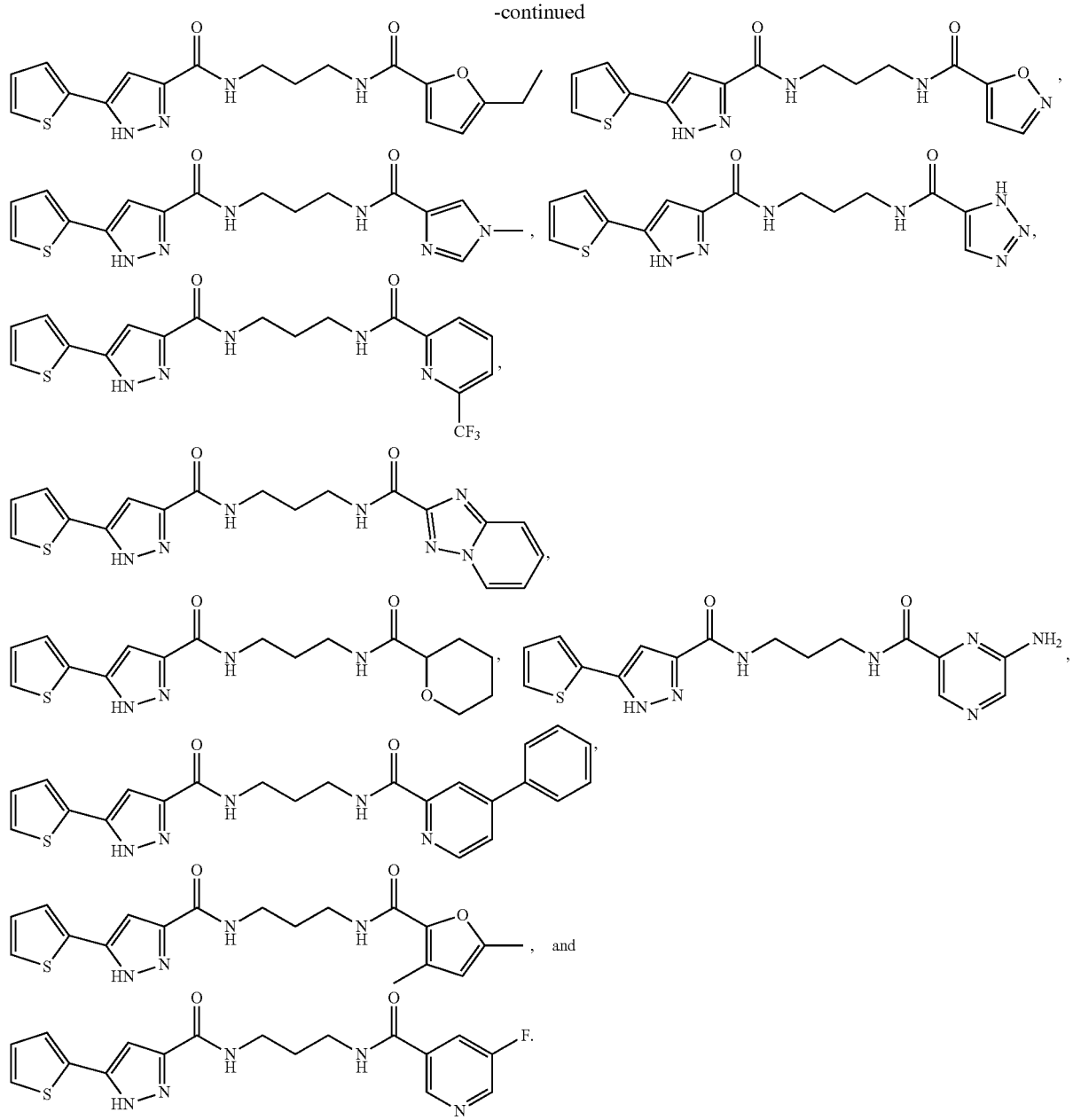
or a pharmaceutically acceptable salt thereof.
184
In a still further aspect, a compound can be selected from:
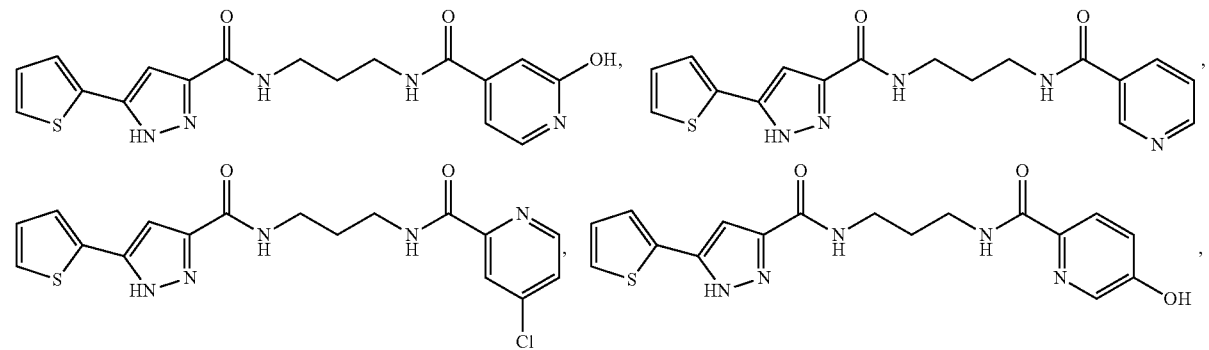

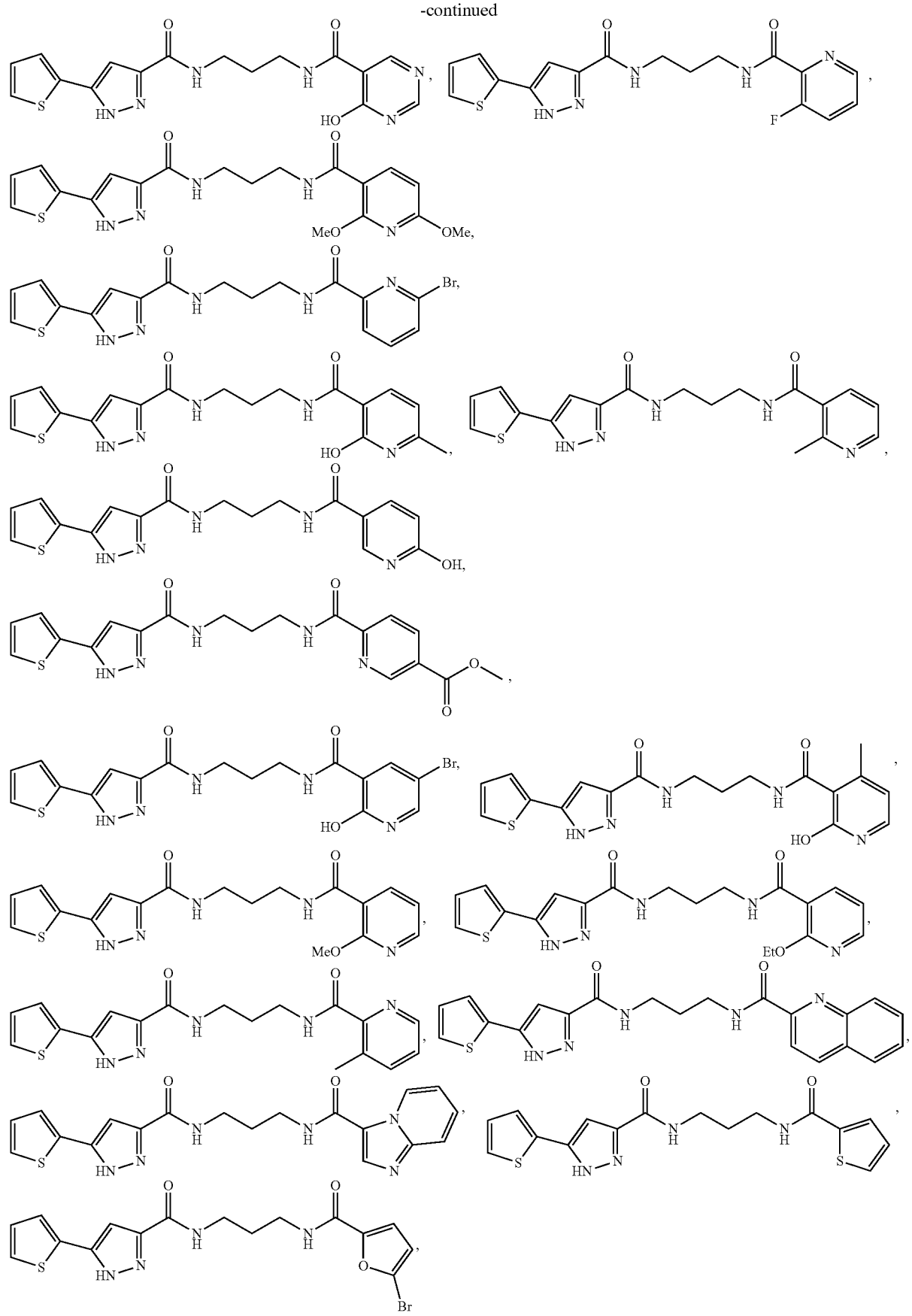
-continued

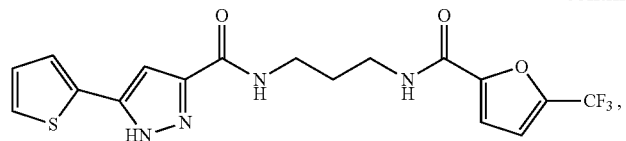
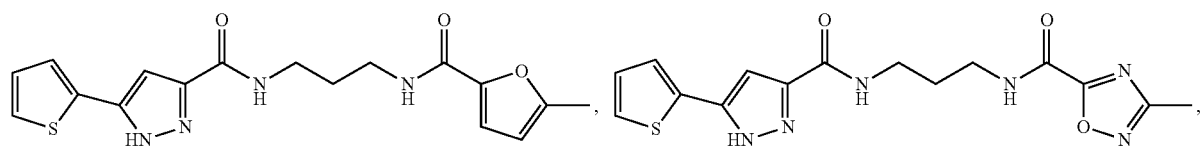
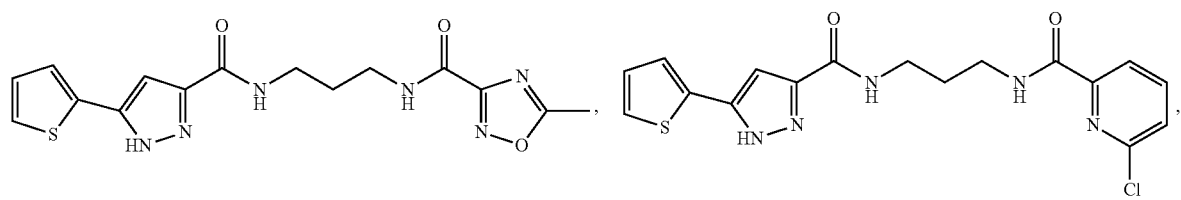
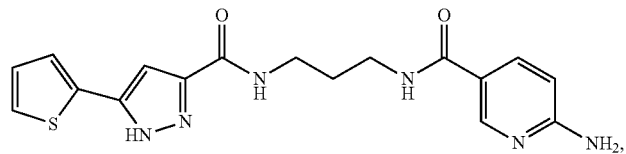
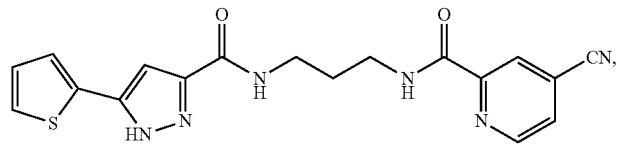
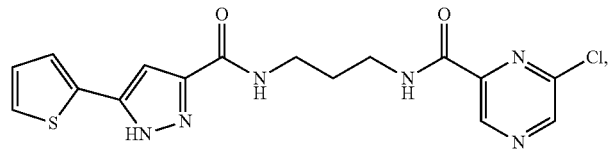
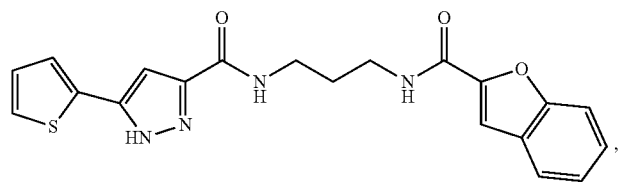
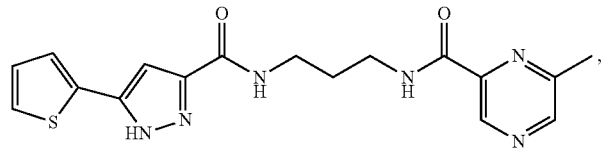
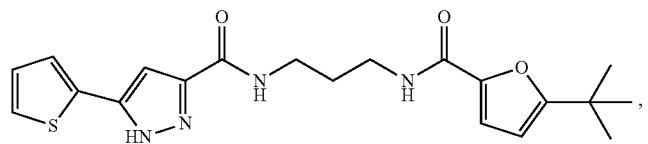
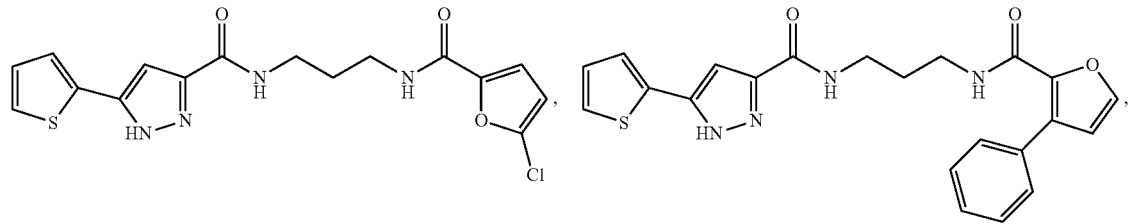

-continued
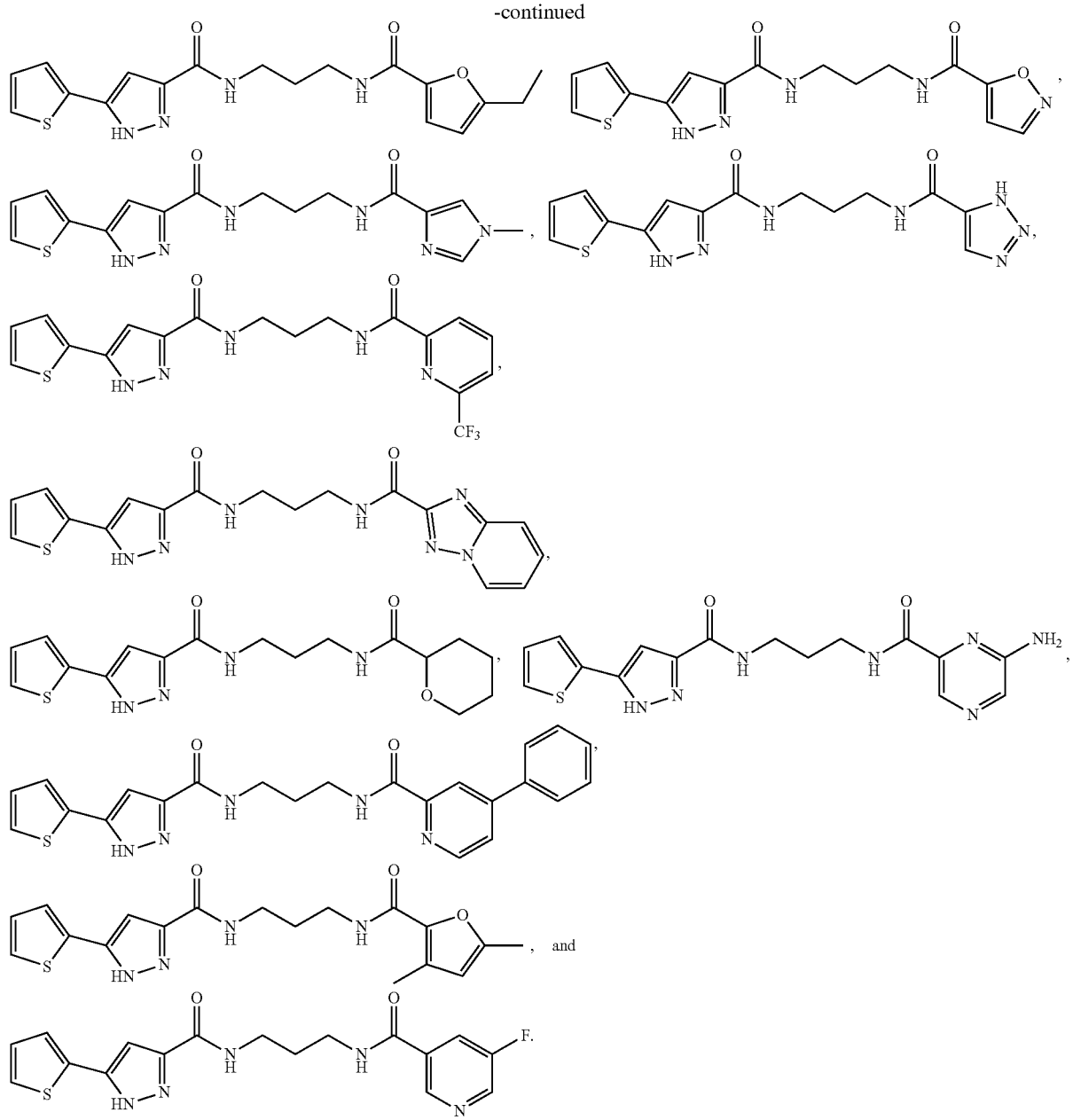
or a pharmaceutically acceptable salt thereof.
In yet a further aspect, a compound can be selected from:
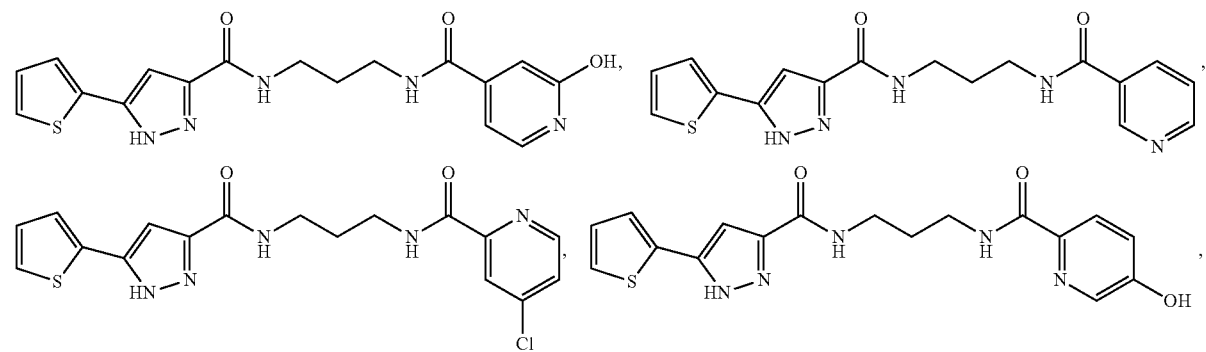

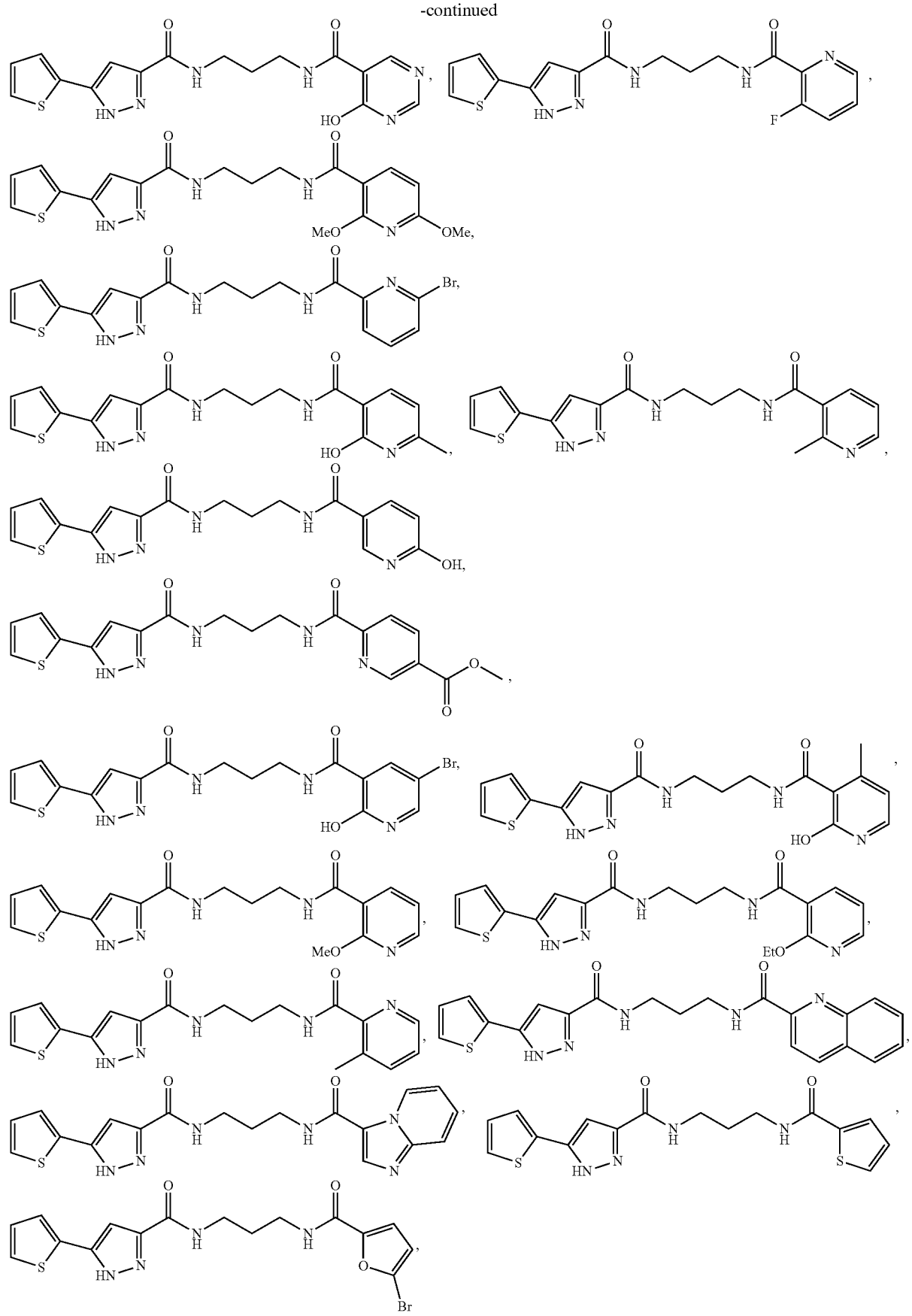

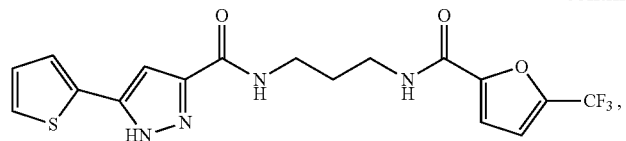
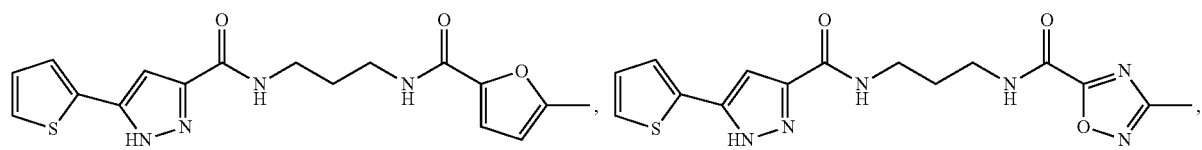
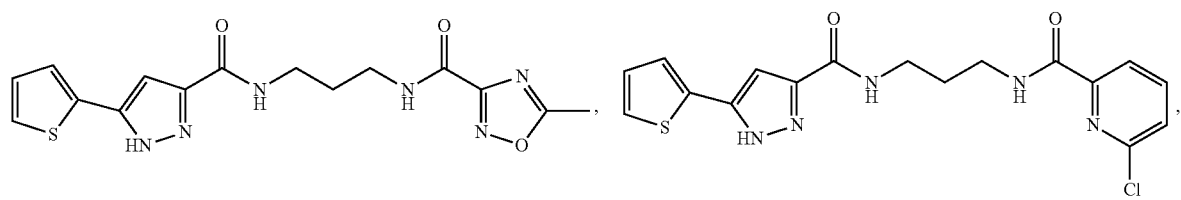
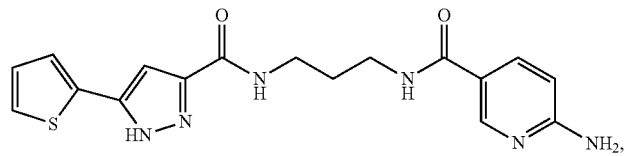
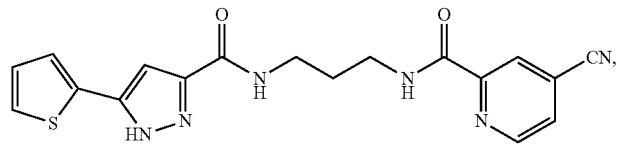
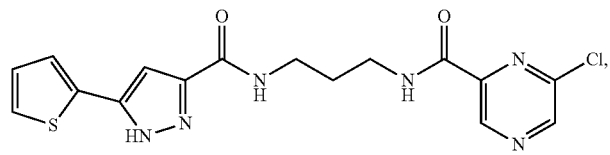
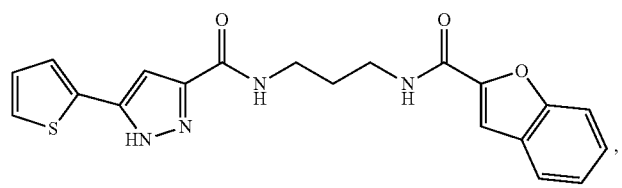
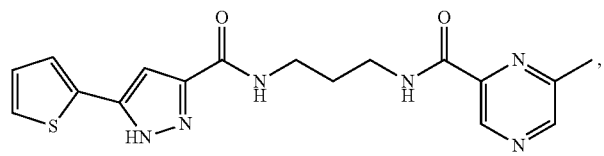
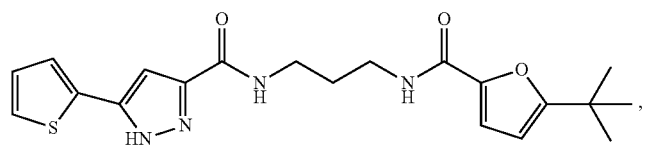
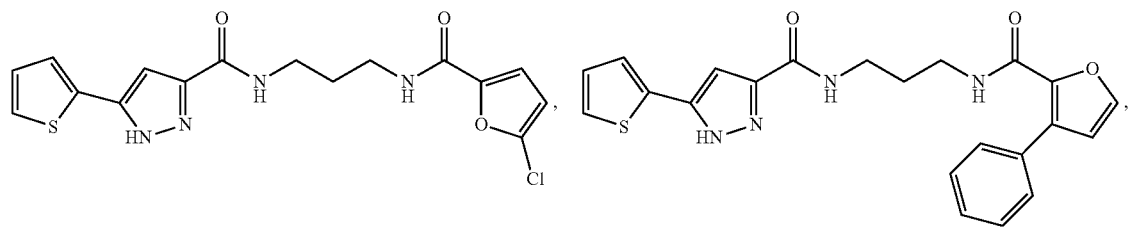

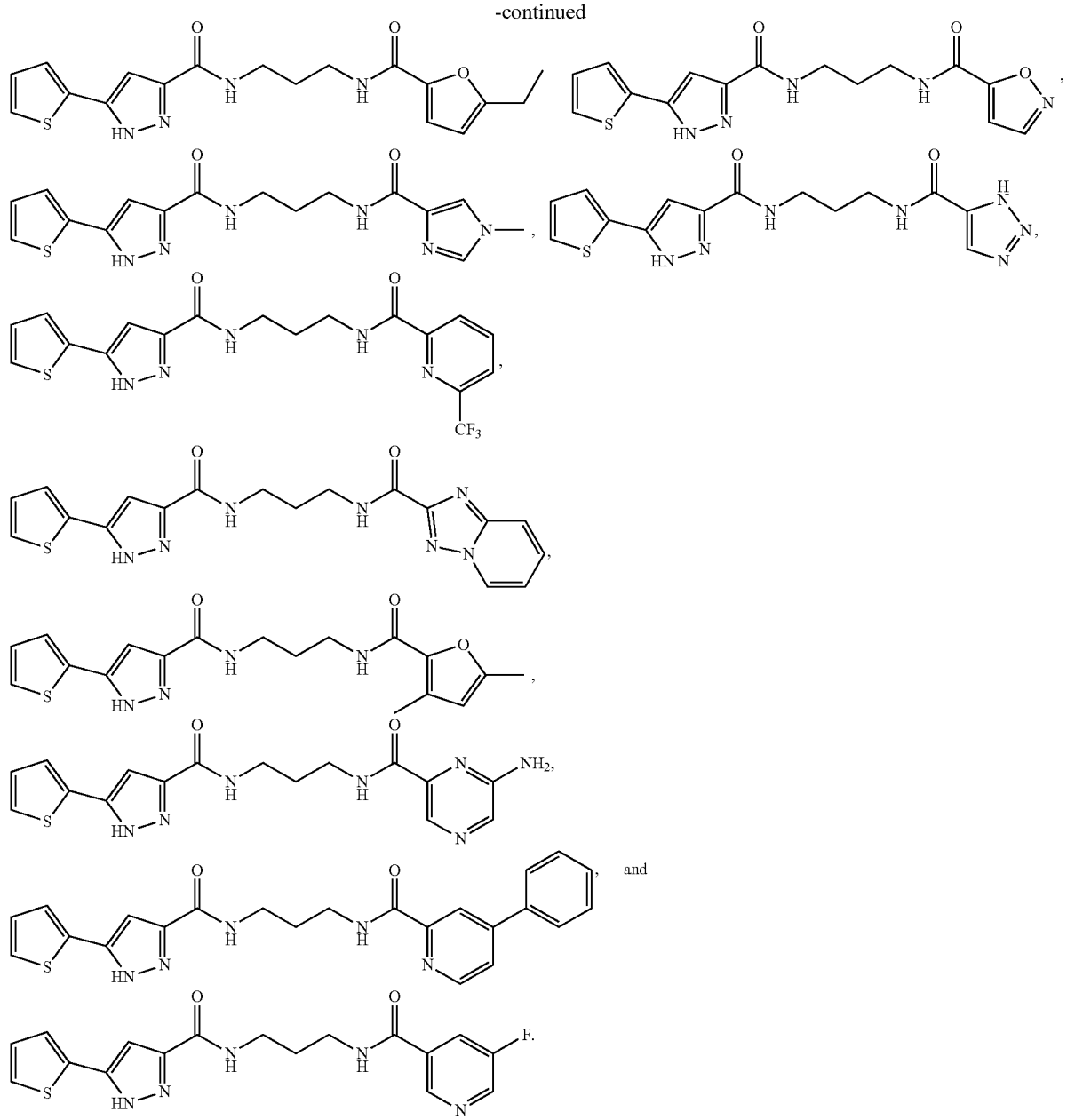

-continued or a pharmaceutically acceptable salt thereof.

In an even further aspect, a compound can be:

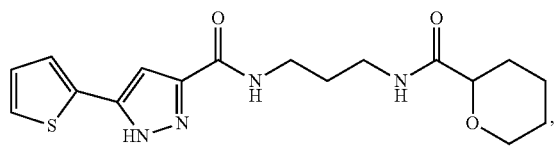 [SMILES: O=C(NCCCNC(=O)C1CCCCO1)c1cc(-c2cccs2)[nH]n1]

or a pharmaceutically acceptable salt thereof.

In a further aspect, a compound can be:

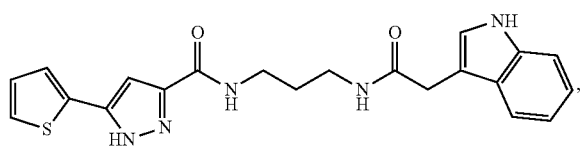

or a pharmaceutically acceptable salt thereof.

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. METHODS OF MAKING THE COMPOUNDS

In one aspect, the invention relates to methods of making compounds useful as mediators of transcriptional induction of E-cadherin, which can be useful in the treatment of disorders of uncontrolled cellular proliferation and other diseases in which E-cadherin is involved. In one aspect, the invention relates to the disclosed synthetic manipulations. In a further aspect, the disclosed compounds comprise the products of the synthetic methods described herein.

In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one product of the disclosed methods with a pharmaceutically acceptable carrier or diluent.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Route I

In one aspect, N-(aminoalkyl)-5-arylisoxazole-3-carboxamide analogs of the present invention can be prepared generically by the synthesis scheme as shown below. All positions are defined herein.

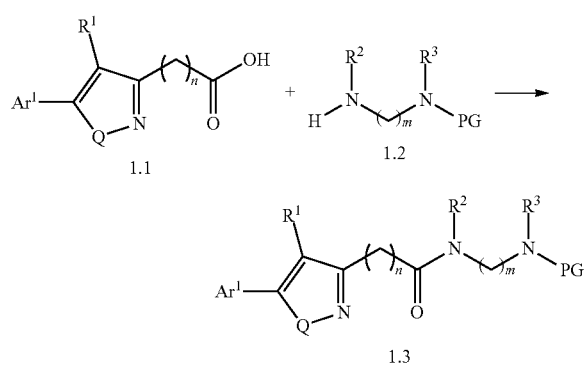

SCHEME 1A.

Compounds are represented in generic form, with substituents as noted in compound descriptions elsewhere herein. A more specific example is set forth below.

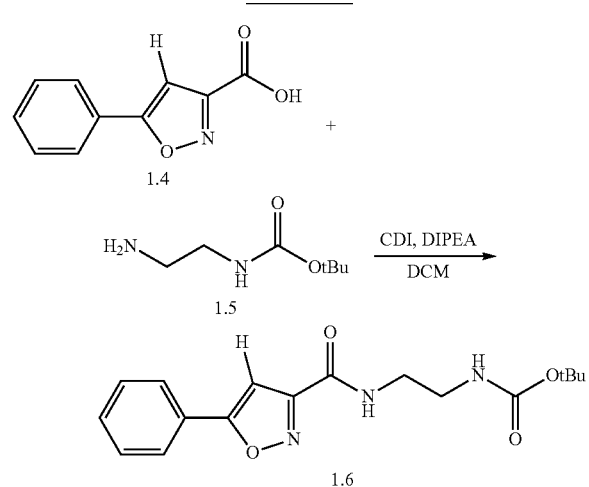

SCHEME 1B.

In one aspect, compounds of type 1.3, and similar compounds, can be prepared according to reaction Scheme 1B above. Thus, compounds of type 1.6 can be prepared by a coupling reaction of an appropriate carboxylic acid, e.g., 1.4 as shown above. Appropriate carboxylic acids are commercially available or prepared by methods known to one skilled in the art. The coupling reaction is carried out with a suitable coupling agent e.g., 1,1'-carbonyldiimidazole (CDI), in the presence of a suitable base, e.g., N,N-diisopropylethylamine (DIPEA), in a suitable solvent, e.g., dichloromethane (DCM), and with a suitable amine, e.g., tert-butyl (2-aminoethyl)carbamate (1.5) as shown above, which is commercially available or prepared by methods known to one skilled in the art. As can be appreciated by one skilled in the art, the above reaction provides an example of a generalized approach wherein compounds similar in structure to the specific reactants above (compounds similar to compounds of type 1.1 and 1.2), can be substituted in the reaction to provide N-(aminoalkyl)-5-arylisoxazole-3-carboxamide analogs similar to Formula 1.3.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

2. Route II

In one aspect, N-(aminoalkyl)-5-arylisoxazole-3-carboxamide analogs of the present invention can be prepared generically by the synthesis scheme as shown below. All positions are defined herein.

SCHEME 2A.

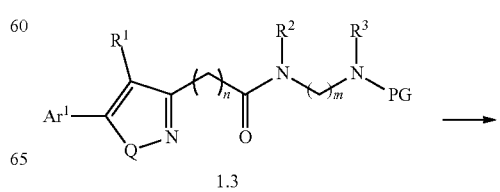

-continued

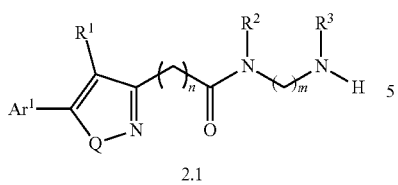

2.1

Compounds are represented in generic form, with substituents as noted in compound descriptions elsewhere herein. A more specific example is set forth below.

SCHEME 2B.

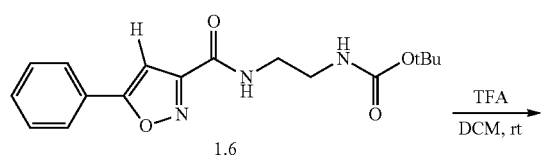

In one aspect, compounds of type 2.1, and similar compounds, can be prepared according to reaction Scheme 2B above. Thus, compounds of type 2.2 can be prepared by removal of an appropriate carbamate, e.g., 1.6 as shown above. The removal is carried out in the presence of a suitable acid, e.g., trifluoroacetic acid (TFA) as shown above, in a suitable solvent, e.g., dichloromethane. As can be appreciated by one skilled in the art, the above reaction provides an example of a generalized approach wherein compounds similar in structure to the specific reactants above (compounds similar to compounds of type 1.3), can be substituted in the reaction to provide N-(aminoalkyl)-5-arylisoxazole-3-carboxamide analogs similar to Formula 2.1.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

3. Route III

In one aspect, N-(3-(((aryl)methyl)amino)alkyl)-5-arylisoxazole-3-carboxamide analogs of the present invention can be prepared generically by the synthesis scheme as shown below. All positions are defined herein.

SCHEME 3A.

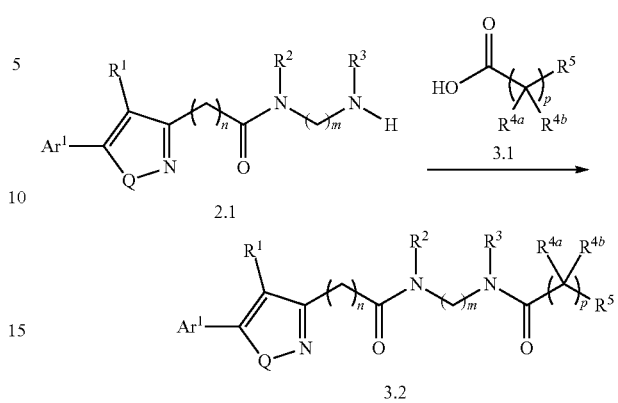

Compounds are represented in generic form, with substituents as noted in compound descriptions elsewhere herein. A more specific example is set forth below.

SCHEME 3B.

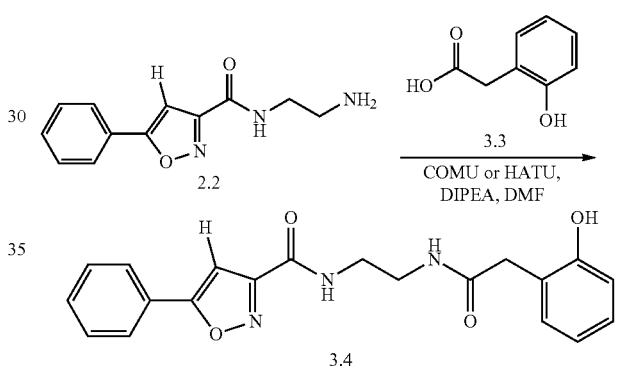

In one aspect, compounds of type 3.2, and similar compounds, can be prepared according to reaction Scheme 3B above. Thus, compounds of type 3.4 can be prepared by a coupling reaction of an appropriate amine, e.g., 2.2 as shown above. The coupling reaction is carried out in the presence of a suitable carboxylic acid, e.g., 2-(2-hydroxyphenyl) acetic acid (3.3), which is commercially available or prepared by methods known to one skilled in the art, and a suitable coupling agent, e.g., (1-cyano-2-ethoxy-2-oxoethylidenaminooxy)dimethylamino-morpholino-carbenium hexafluorophosphate (COMU) or 1-[bis(dimethylamino)methylene]-1H-1,2,3-triazolo[4,5-b]pyridinium 3-oxide hexafluorophosphate (HATU), in the presence of a suitable base, e.g., N,N-diisopropylethyl amine (DIPEA), in a suitable solvent, e.g., dimethylformamide (DMF). As can be appreciated by one skilled in the art, the above reaction provides an example of a generalized approach wherein compounds similar in structure to the specific reactants above (compounds similar to compounds of type 2.1 and 3.1), can be substituted in the reaction to provide N-acetamidoalkyl-5-arylisoxazole-3-carboxamide analogs similar to Formula 3.2.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

4. Route IV

In one aspect, N-(3-(((aryl)methyl)amino)alkyl)-5-arylisoxazole-3-carboxamide analogs of the present invention can be prepared generically by the synthesis scheme as shown below. All positions are defined herein.

SCHEME 4A.

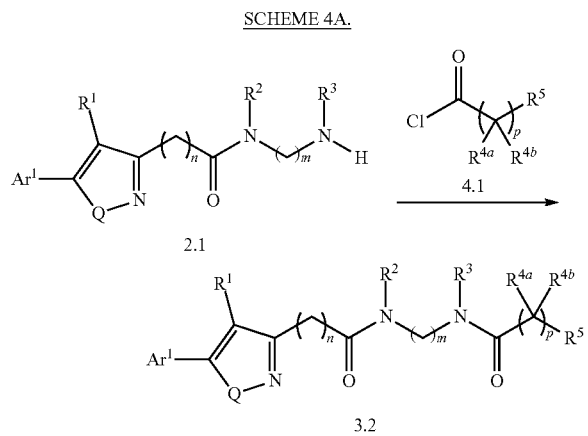

Compounds are represented in generic form, with substituents as noted in compound descriptions elsewhere herein. A more specific example is set forth below.

SCHEME 4B.

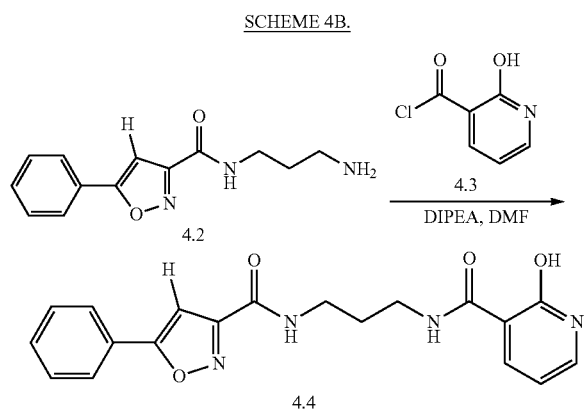

In one aspect, compounds of type 3.2, and similar compounds, can be prepared according to reaction Scheme 4B above. Thus, compounds of type 4.4 can be prepared by a coupling reaction of an appropriate amine, e.g., 4.2 as shown above. The coupling reaction is carried out in the presence of a suitable acyl chloride, e.g., 2-hydroxynicotinoyl chloride (4.3), which is commercially available or prepared by methods known to one skilled in the art, and a suitable base, e.g., N,N-diisopropylethyl amine (DIPEA), in a suitable solvent, e.g., dimethylformamide (DMF). As can be appreciated by one skilled in the art, the above reaction provides an example of a generalized approach wherein compounds similar in structure to the specific reactants above (compounds similar to compounds of type 2.1 and 3.1), can be substituted in the reaction to provide N-acetamidoalkyl-5-arylisoxazole-3-carboxamide analogs similar to Formula 3.2.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

D. PHARMACEUTICAL COMPOSITIONS

In one aspect, the invention relates to pharmaceutical compositions comprising the disclosed compounds. That is, a pharmaceutical composition can be provided comprising an effective amount of at least one disclosed compound, at least one product of a disclosed method of making, or a pharmaceutically acceptable salt, solvate, hydrate, or polymorph thereof, and a pharmaceutically acceptable carrier. In one aspect, the invention relates to pharmaceutical compositions comprising an effective amount of at least one disclosed compound, or a pharmaceutically acceptable salt thereof, and a pharmaceutically acceptable carrier.

In one aspect, the invention relates to pharmaceutical compositions comprising an effective amount of a disclosed compound, a product of a disclosed method of making, or a pharmaceutically acceptable salt thereof, and a pharmaceutically acceptable carrier.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition exhibits potentiation of E-cadherin expression with an $EC_{50}$ of less than about $30 \times 10^{-6}$ M. In a still further aspect, the pharmaceutical composition exhibits potentiation of E-cadherin expression with an $EC_{50}$ of less than about $20 \times 10^{-6}$ M. In an even further aspect the pharmaceutical composition exhibits potentiation of E-cadherin expression with an $EC_{50}$ of less than about $10 \times 10^{-6}$ M. In yet a further aspect, the pharmaceutical composition exhibits potentiation of E-cadherin expression with an $EC_{50}$ of less than about $5 \times 10^{-6}$ M. In an even further aspect, the pharmaceutical composition exhibits potentiation of E-cadherin expression with an $EC_{50}$ of less than about $1 \times 10^{-6}$ M. In a still further aspect, the pharmaceutical composition exhibits potentiation of E-cadherin expression with an $EC_{50}$ of between from about $30 \times 10^{-6}$ M to about $1 \times 10^{-6}$ M. In a yet further aspect, the pharmaceutical composition exhibits potentiation of E-cadherin expression with an $EC_{50}$ of between from about $20 \times 10^{-6}$ M to about $1 \times 10^{-6}$ M. In an even further aspect, the pharmaceutical composition exhibits potentiation of E-cadherin expression with an $EC_{50}$ of between from about $10 \times 10^{-6}$ M to about $1 \times 10^{-6}$ M. In a still further aspect, the pharmaceutical composition exhibits potentiation of E-cadherin expression with an $EC_{50}$ of between from about $5 \times 10^{-6}$ M to about $1 \times 10^{-6}$ M. In a still further aspect, potentiation of the expression of E-cadherin is restoration of the E-cadherin expression.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The present invention is further directed to a method for the manufacture of a medicament for modulating the expression of E-cadherin (e.g., treatment of one or more disorders of cellular proliferation associated with E-cadherin activity) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Methods for Modulating the Expression of E-Cadherin in Cells

In one aspect, the invention relates to a method for modulating the expression of E-cadherin in at least one cell, the method comprising the step of contacting the at least one cell with at least one compound having a structure represented by a formula:

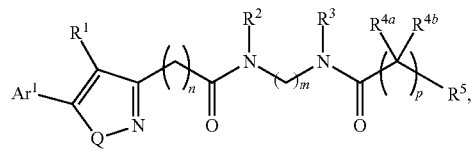

wherein m is an integer selected from 2, 3, and 4; wherein n is an integer selected from 0 and 1; wherein p is an integer selected 0, 1, 2, 3, and 4; wherein Q is selected from $NR^6$, O, and S; wherein $R^6$ is selected from hydrogen and C1-C4 alkyl; wherein $R^1$ is selected from hydrogen and C1-C4 alkyl; wherein each of $R^2$ and $R^3$ is independently selected from hydrogen and C1-C4 alkyl; wherein each occurrence of $R^{4a}$ and $R^{4b}$ is independently selected from hydrogen, halogen, —OH, —CN, —$N_3$, —$NH_2$, and C1-C4 alkyl; wherein $R^5$ is selected from $Cy^2$ and $Ar^2$; wherein $Cy^2$, when present, is selected from cycloalkyl and heterocycloalkyl, and $Cy^2$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein $Ar^2$, when present, is selected from aryl and heteroaryl, and $Ar^2$ is substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, C1-C4 dialkylamino, $Cy^3$, $Ar^3$, and —NH(C=O)(C1-C4 alkyl)$Cy^3$; wherein $Cy^3$, when present, is selected from cycloalkyl and heterocycloalkyl, and $Cy^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; and wherein $Ar^1$, when present, is selected from aryl and heteroaryl, and $Ar^1$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

In a further aspect, modulating is increasing. In a still further aspect, modulating is restoring.

In a further aspect, the cell is mammalian. In a still further aspect, the cell is human. In yet a further aspect, the cell has been isolated from a mammal prior to the contacting step.

In a further aspect, contacting is via administration to a mammal.

F. METHODS FOR TREATING A DISORDER ASSOCIATED WITH E-CADHERIN ACTIVITY

In one aspect, the invention relates to a method for treating a disorder associated with E-cadherin activity in a subject, the method comprising administering to the subject an effective amount of at least one compound having a structure represented by a formula:

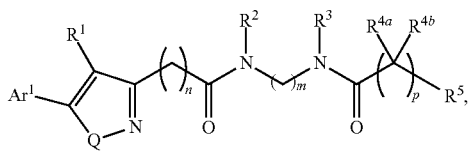

wherein m is an integer selected from 2, 3, and 4; wherein n is an integer selected from 0 and 1; wherein p is an integer selected 0, 1, 2, 3, and 4; wherein Q is selected from $NR^6$, O, and S; wherein $R^6$ is selected from hydrogen and C1-C4 alkyl; wherein $R^1$ is selected from hydrogen and C1-C4 alkyl; wherein each of $R^2$ and $R^3$ is independently selected from hydrogen and C1-C4 alkyl; wherein each occurrence of $R^{4a}$ and $R^{4b}$ is independently selected from hydrogen, halogen, —OH, —CN, —$N_3$, —$NH_2$, and C1-C4 alkyl; wherein $R^5$ is selected from $Cy^2$ and $Ar^2$; wherein $Cy^2$, when present, is selected from cycloalkyl and heterocycloalkyl, and $Cy^2$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein $Ar^2$, when present, is selected from aryl and heteroaryl, and $Ar^2$ is substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, C1-C4 dialkylamino, $Cy^3$, $Ar^3$, and —NH(C=O)(C1-C4 alkyl)$Cy^3$; wherein $Cy^3$, when present, is selected from cycloalkyl and heterocycloalkyl, and $Cy^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; and wherein $Ar^1$, when present, is selected from aryl and heteroaryl, and $Ar^1$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof, thereby treating the disorder in the subject.

In a further aspect, the compound exhibits restoration of E-cadherin expression. In a still further aspect, the compound exhibits an increase in E-cadherin expression.

In a further aspect, the compound exhibits potentiation of E-cadherin expression with an $EC_{50}$ of less than about $30 \times 10^{-6}$ M. In a still further aspect, the compound exhibits potentiation of E-cadherin expression with an $EC_{50}$ of less than about $20 \times 10^{-6}$ M. In yet a further aspect, the compound exhibits potentiation of E-cadherin expression with an $EC_{50}$ of less than about $10 \times 10^{-6}$ M. In an even further aspect, the compound exhibits potentiation of E-cadherin expression with an $EC_{50}$ of less than about $1 \times 10^{-6}$ M. In a still further aspect, the compound exhibits potentiation of E-cadherin expression with an $EC_{50}$ of less than about $5 \times 10^{-6}$ M. In yet a further aspect, the compound exhibits potentiation of E-cadherin expression with an $EC_{50}$ of less than about $1 \times 10^{-6}$ M. In an even further aspect, the compound exhibits potentiation of E-cadherin expression with an $EC_{50}$ of between about $30 \times 10^{-6}$ M and about $1 \times 10^{-6}$ M. In a still further aspect, the compound exhibits potentiation of E-cadherin expression with an $EC_{50}$ of between about $20 \times 10^{-6}$ M and about $1 \times 10^{-6}$ M. In yet a further aspect, the compound exhibits potentiation of E-cadherin expression with an $EC_{50}$ of between about $10 \times 10^{-6}$ M and about $1 \times 10^{-6}$ M. In an even further aspect, the compound exhibits potentiation of E-cadherin expression with an $EC_{50}$ of between about $5 \times 10^{-6}$ M and about $1 \times 10^{-6}$ M.

In a further aspect, the subject is a mammal. In a still further aspect, the subject is a human.

In a further aspect, the subject has been diagnosed with a need for treatment of the disorder prior to the administering step. In a still further aspect, the method further comprises the step of identifying a subject in need of treatment of the disorder.

In a further aspect, the disorder associated with E-cadherin activity is a disorder of uncontrolled cellular proliferation. In a still further aspect, the disorder of uncontrolled cellular proliferation is cancer. In yet a further aspect, the disorder of uncontrolled cellular proliferation is selected from breast cancer, renal cancer, gastric cancer, and colorectal cancer. In an even further aspect, the disorder of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

G. USE OF COMPOUNDS

In one aspect, the invention relates to pharmaceutical compositions comprising the disclosed compounds. That is, a pharmaceutical composition can be provided comprising an effective amount of at least one disclosed compound, at least one product of a disclosed method of making, or a pharmaceutically acceptable salt, solvate, hydrate, or polymorph thereof, and a pharmaceutically acceptable carrier. In one aspect, the invention relates to pharmaceutical compositions comprising an effective amount of at least one disclosed compound, or a pharmaceutically acceptable salt thereof, and a pharmaceutically acceptable carrier.

In one aspect, the invention relates to pharmaceutical compositions comprising an effective amount of a disclosed compound, a product of a disclosed method of making, or a pharmaceutically acceptable salt thereof, and a pharmaceutically acceptable carrier.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition exhibits potentiation of E-cadherin expression with an $EC_{50}$ of less than about $30 \times 10^{-6}$ M. In a still further aspect, the pharmaceutical composition exhibits potentiation of E-cadherin expression with an $EC_{50}$ of less than about $20 \times 10^{-6}$ M. In an even further aspect the pharmaceutical composition exhibits potentiation of E-cadherin expression with an $EC_{50}$ of less than about $10 \times 10^{-6}$ M. In yet a further aspect, the pharmaceutical composition exhibits potentiation of E-cadherin expression with an $EC_{50}$ of less than about $5 \times 10^{-6}$ M. In an even further aspect, the pharmaceutical composition exhibits potentiation of E-cadherin expression with an $EC_{50}$ of less than about $1 \times 10^{-6}$ M. In a still further aspect, the pharmaceutical composition exhibits potentiation of E-cadherin expression with an $EC_{50}$ of between from about $30 \times 10^{-6}$ M to about $1 \times 10^{-6}$ M. In a yet further aspect, the pharmaceutical composition exhibits potentiation of E-cadherin expression with an $EC_{50}$ of between from about $20\times10^{-6}$ M to about $1\times10^{-6}$ M. In an even further aspect, the pharmaceutical composition exhibits potentiation of E-cadherin expression with an $EC_{50}$ of between from about $10\times10^{-6}$ M to about $1\times10^{-6}$ M. In a still further aspect, the pharmaceutical composition exhibits potentiation of E-cadherin expression with an $EC_{50}$ of between from about $5\times10^{-6}$ M to about $1\times10^{-6}$ M. In a still further aspect, potentiation of the expression of E-cadherin is restoration of the E-cadherin expression.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The present invention is further directed to a method for the manufacture of a medicament for modulating the expression of E-cadherin (e.g., treatment of one or more disorders of cellular proliferation associated with E-cadherin activity) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

H. KITS

In one aspect, the invention relates to a kit comprising at least one disclosed compound or at least one disclosed product and one or more of at least one agent known to increase E-cadherin expression; at least one agent known to decrease E-cadherin expression; at least one agent known to treat a disorder of uncontrolled cellular proliferation; or instructions for treating a disorder of uncontrolled cellular proliferation. In a further aspect, the at least one compound or the at least one product and the at least one agent are co-formulated. In a further aspect, the at least one compound or the at least one product and the at least one agent are co-packaged.

In one aspect, the invention relates to kits comprising at least one compound having a structure represented by a formula:

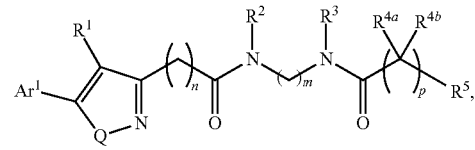

wherein m is an integer selected from 2, 3, and 4; wherein n is an integer selected from 0 and 1; wherein p is an integer selected 0, 1, 2, 3, and 4; wherein Q is selected from $NR^6$, O, and S; wherein $R^6$ is selected from hydrogen and C1-C4 alkyl; wherein $R^1$ is selected from hydrogen and C1-C4 alkyl; wherein each of $R^2$ and $R^3$ is independently selected from hydrogen and C1-C4 alkyl; wherein each occurrence of $R^{4a}$ and $R^{4b}$ is independently selected from hydrogen, halogen, —OH, —CN, —$N_3$, —$NH_2$, and C1-C4 alkyl; wherein $R^5$ is selected from $Cy^2$ and $Ar^2$; wherein $Cy^2$, when present, is selected from cycloalkyl and heterocycloalkyl, and $Cy^2$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein $Ar^2$, when present, is selected from aryl and heteroaryl, and $Ar^2$ is substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, C1-C4 dialkylamino, $Cy^3$, $Ar^3$, and —NH(C=O)(C1-C4 alkyl)$Cy^3$; wherein $Cy^3$, when present, is selected from cycloalkyl and heterocycloalkyl, and $Cy^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; and wherein Ar¹, when present, is selected from aryl and heteroaryl, and Ar¹ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof, and one or more of:

(a) at least one agent known to increase E-cadherin expression;

(b) at least one agent known to decrease E-cadherin expression;

(c) at least one agent known to treat a disorder of uncontrolled cellular proliferation; or (d) instructions for treating a disorder of uncontrolled cellular proliferation.

In a further aspect, the at least one compound and the at least one agent are co-formulated. In a still further aspect, the at least one compound and the at least one agent are co-packaged.

In a further aspect, the at least one agent known to increase E-cadherin expression is a histone deacetylase (HDAC) inhibitor. In a still further aspect, the HDAC inhibitor is selected from trichostatin A, vorinostat, romidepsin, and belinostat.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

I. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

1. Chemistry Experimental Methods

All non-aqueous reactions were performed in flame-dried or oven dried round-bottomed flasks under an atmosphere of argon. Stainless steel syringes or cannulae were used to transfer air- and moisture-sensitive liquids. Reaction temperatures were controlled using a thermocouple thermometer and analog hotplate stirrer. Reactions were conducted at room temperature (rt, approximately 23° C.) unless otherwise noted. Analytical thin-layer chromatography (TLC) was performed on E. Merck silica gel 60 F254 plates and visualized using UV, ceric ammonium molybdate, potassium permanganate, and anisaldehyde stains. Yields were reported as isolated, spectroscopically pure compounds.

HPLC was conducted on a Gilson HPLC system using a Gemini-NX 5u C18 column. ¹H NMR spectra were recorded on Bruker 400 MHz spectrometers and are reported relative to deuterated solvent signals. Data for ¹H NMR spectra are reported as follows: chemical shift (δ ppm), multiplicity (s=singlet, d=doublet, t=triplet, dd=double of doublets, dt=doublet of triplets, q=quartet, m=multiplet, br=broad, app=apparent), coupling constants (Hz), and integration. LC/MS was conducted and recorded on an Agilent Technologies 6140 Quadrupole instrument. Microwave reactions were conducted on a Biotage Initiator 2.0 microwave reactor.

A. Amide Bond Formation from a Carboxylic Acid (General Procedure A)

To a solution containing 1 equivalent of the required amine and 1.2 equivalents of the desired carboxylic acid in 2-5 mL of DMF or another suitable solvent was added 1.2-2.5 equivalents of an appropriate peptide coupling agent (e.g., COMU or HATU), along with 1.5 equiv of DIPEA. The reaction mixture was allowed to stir at rt until the reaction was complete and the solvents were removed under reduced pressure. The residue was subjected to purification by silica gel chromatography or by preparative HPLC purification to give the target compound.

(1) Synthesis of N-(2-(2-(2-hydroxyphenyl)acetamido)ethyl)-5-phenylisoxazole-3-carboxamide (Compound 1)

i) Preparation of tert-butyl (2-(5-phenylisoxazole-3-carboxamido)ethyl)carbamate

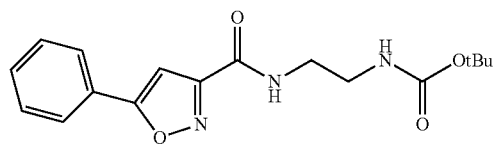 [SMILES: CC(C)(C)OC(=O)NCCNC(=O)c1cc(-c2ccccc2)on1]

To a solution containing 1.0 g (5.29 mmol) of 5-phenylisoxazole-3-carboxylic acid and 15 mL of DCM was added 0.943 g (5.82 mmol) of CDI. The reaction mixture was allowed to stir at rt for 15 min and a solution containing 0.889 g (5.56 mmol) of tert-butyl (2-aminoethyl)carbamate in 5 mL of DCM was added, followed by 2 mL (11 mmol) of DIPEA. The reaction mixture was allowed to stir at rt overnight, quenched by the addition of water, and extracted with DCM. The combined organic layers were dried by passage through a phase separator cartridge and the solvent was removed under reduced pressure. The residue was subjected to silica gel chromatography to give 1.21 g (71%) of tert-butyl (2-(5-phenylisoxazole-3-carboxamido)ethyl) carbamate as a white solid. LC/MS ret time: 1.201 min, m/z=276.2 [M–C(CH₃)₃)]⁺.

ii) Preparation of N-(2-aminoethyl)-5-phenylisoxazole-3-carboxamide trifluoroacetate

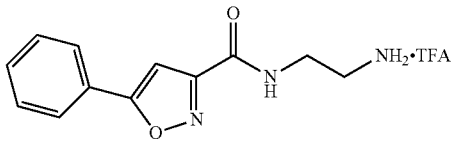

iii) Preparation of N-(2-(2-(2-hydroxyphenyl)acetamidoethyl)-5-phenylisoxazole-3-carboxamide (Compound 1)

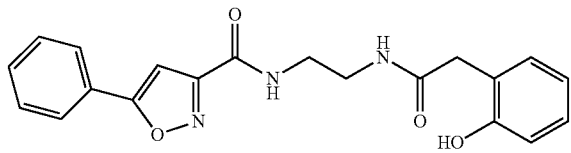 [SMILES: O=C(Cc1ccccc1O)NCCNC(=O)c1cc(-c2ccccc2)on1]

According to General Procedure A, N-(2-(2-(2-hydroxyphenyl)acetamido)ethyl)-5-phenylisoxazole-3-carboxamide was synthesized from N-(2-aminoethyl)-5-phenylisoxazole-3-carboxamide. $^1$HNMR (400 MHz, CD$_3$OD): δ 8.65 (br s, 1H), 7.95 (br s, 1H), 7.88 (dd, 2H, J=8.0, 2.0 Hz), 7.56-7.51 (m, 3H), 7.10 (d, 1H, J=8.0 Hz), 7.07-7.02 (m, 2H), 6.75 (t, 2H, J=8.0 Hz), 3.52 (s, 2H), 3.51 (t, 2H, J=5.6 Hz), 3.43 (t, 2H, J=5.6 Hz), LC/MS ret. Time 1.078 min, m/z=366.10 [M+H]$^+$.

(2) Synthesis of N-(2-(5-bromo-2-hydroxybenzamido)ethyl)-5-phenylisoxazole-3-carboxamide (Compound 2)

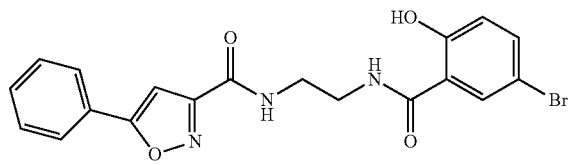 [SMILES: O=C(NCCNC(=O)c1cc(Br)ccc1O)c1cc(-c2ccccc2)on1]

According to General Procedure A, N-(2-(5-bromo-2-hydroxybenzamido)ethyl)-5-phenylisoxazole-3-carboxamide was synthesized from N-(2-aminoethyl)-5-phenylisoxazole-3-carboxamide. $^1$HNMR (400 MHz, CD$_3$OD): δ 7.94 (d, 1H, J=2.4 Hz), 7.88-7.86 (m, 2H), 7.52-7.45 (m, 3H), 7.46 (dd, 1H, J=8.8, 2.4 Hz), 7.07 (s, 1H), 6.83 (d, 1H, J=8.8 Hz), 3.63 (s, 4H); LC/MS ret. time: 1.330 min, m/z=432.10 [M+H]$^+$.

(3) Synthesis of N-(2-(nicotinamido)ethyl)-5-phenylisoxazole-3-carboxamide (Compound 3)

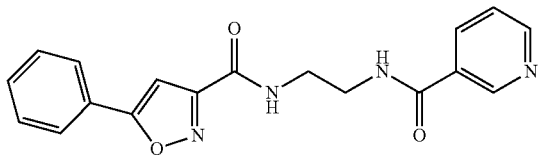 [SMILES: O=C(NCCNC(=O)c1cc(-c2ccccc2)on1)c1cccnc1]

According to General Procedure A, N-(2-(nicotinamido)ethyl)-5-phenylisoxazole-3-carboxamide was synthesized from N-(2-aminoethyl)-5-phenylisoxazole-3-carboxamide. LC/MS ret. time=0.876 min, m/z=337.20 [M+H]$^+$.

(4) Synthesis of N-(2-(isonicotinamido)ethyl)-5-phenylisoxazole-3-carboxamide (Compound 4)

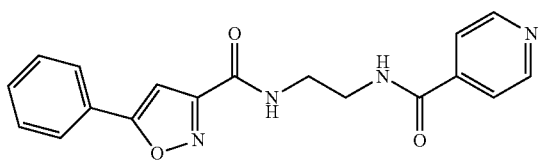 [SMILES: O=C(NCCNC(=O)c1cc(-c2ccccc2)on1)c1ccncc1]

According to General Procedure A, N-(2-(isonicotinamido)ethyl)-5-phenylisoxazole-3-carboxamide was synthesized from N-(2-aminoethyl)-5-phenylisoxazole-3-carboxamide. $^1$HNMR (400 MHz, CD$_3$OD): δ 8.83 (d, 2H, J=5.6 Hz), 8.06 (d, 2H, J=6.0 Hz), 7.86-7.84 (m, 2H), 7.52-7.50 (m, 3H), 7.05 (s, 1H), 3.67 (br s, 4H); LC/MS ret. time=0.867 min, m/z=337.20 [M+H]$^+$.

(5) Synthesis of 5-phenyl-N-(2-(thiazole-2-carboxamido)ethyl)isoxazole-3-carboxamide (Compound 5)

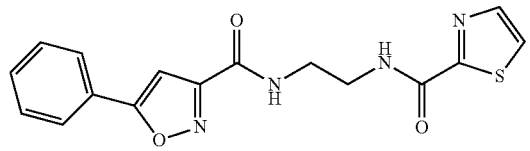 [SMILES: O=C(NCCNC(=O)c1nccs1)c1cc(-c2ccccc2)on1]

According to General Procedure A, 5-phenyl-N-(2-(thiazole-2-carboxamido)ethyl)isoxazole-3-carboxamide was synthesized from N-(2-aminoethyl)-5-phenylisoxazole-3-carboxamide. $^1$HNMR (400 MHz, CD$_3$OD): δ 7.93 (d, 1H, J=3.0 Hz), 7.87-7.85 (m, 2H), 7.81 (d, 1H, J=3.0 Hz), 7.54-7.48 (m, 3H), 7.06 (s, 1H), 3.65 (s, 4H); LC/MS ret. time=1.073 min, m/z=343.20 [M+H]$^+$.

(6) Synthesis of (S)—N-(2-(2-amino-3-(1H-idol-3-yl)propanamido)ethyl)-5-phenylisoxazole-3-carboxamide (Compound 6)

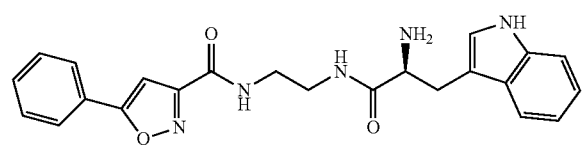 [SMILES: N[C@@H](Cc1c[nH]c2ccccc12)C(=O)NCCNC(=O)c1cc(-c2ccccc2)on1]

According to General Procedure A, (S)—N-(2-(2-amino-3-(1H-indol-3-yl)propanamido)ethyl)-5-phenylisoxazole-3-carboxamide was synthesized from N-(2-aminoethyl)-5-phenylisoxazole-3-carboxamide. $^1$HNMR (400 MHz, CD$_3$OD): δ 7.85-7.82 (m, 2H), 7.62 (d, 1H, J=8.0 Hz), 7.51-7.49 (m, 3H), 7.35 (d, 1H, J=8.4 Hz), 7.20 (s, 1H), 7.11 (dd, 1H, J=8.0, 7.2 Hz), 7.06-7.02 (m, 2H), 4.07 (t, 1H, J=7.2

Hz), 3.48-3.33 (m, 4H), 3.22 (dd, 1H, J=14.8, 8.0 Hz); LC/MS ret. time=0.983 min, m/z=418.20 [M+H]⁺.

(7) Synthesis of N-(2-(2-(3-hydroxyphenyl)acetamido)ethyl)-5-phenylisoxazole-3-carboxamide (Compound 7)

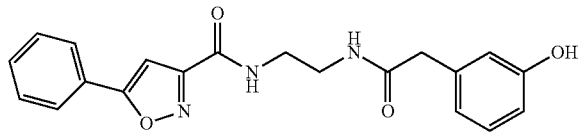 [SMILES: O=C(Cc1cccc(O)c1)NCCNC(=O)c1cc(-c2ccccc2)on1]

According to General Procedure A, N-(2-(2-(3-hydroxyphenyl)acetamido)ethyl)-5-phenylisoxazole-3-carboxamide was synthesized from N-(2-aminoethyl)-5-phenylisoxazole-3-carboxamide. LC/MS ret. time=1.010 min, m/z=366.10 [M+H]⁺.

(8) Synthesis of N-(2-(3-hydroxybenzamido)ethyl)-5-phenylisoxazole-3-carboxamide (Compound 8)

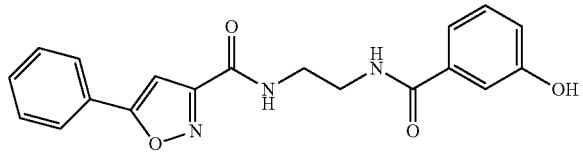 [SMILES: O=C(NCCNC(=O)c1cc(-c2ccccc2)on1)c1cccc(O)c1]

According to General Procedure A, N-(2-(3-hydroxybenzamido)ethyl)-5-phenylisoxazole-3-carboxamide was synthesized from N-(2-aminoethyl)-5-phenylisoxazole-3-carboxamide. ¹HNMR (400 MHz, CD₃OD): δ 7.87 (m, 2H), 7.53-7.50 (m, 3H), 7.26-7.23 (m, 3H), 7.08 (s, H), 6.94 (t, 1H, J=8.0 Hz), 3.63-3.61 (m, 4H); LC/MS ret. time=1.023 min; m/z=352.2 [M+H]⁺.

(9) Synthesis of N-(2-(3,4-dihydroxybenzamido)ethyl)-5-phenylisoxazole-3-carboxamide (Compound 9)

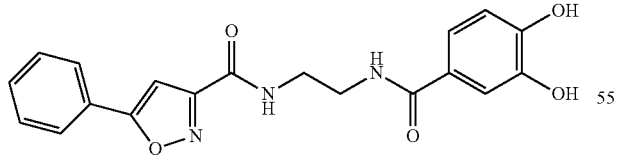

According to General Procedure A, N-(2-(3,4-dihydroxybenzamido)ethyl)-5-phenylisoxazole-3-carboxamide was synthesized from N-(2-aminoethyl)-5-phenylisoxazole-3-carboxamide. ¹HNMR (400 MHz, CD₃OD): δ 7.87 (dd, 2H, J=8.0, 2.4 Hz), 7.55-7.50 (m, 3H), 7.29 (d, 1H, J=2.0 Hz), 7.21 (dd, 1H, J=8.0, 2.0 Hz), 7.08 (s, 1H), 6.80 (d, 1H, J=8.4 Hz), 6.62-3.57 (m, 4H); LC/MS ret. time=0.956 min, m/z=368.20 [M+H]⁺.

(10) Synthesis of N-(2-(3-BROMO-5-hydroxybenzamido)ethyl)-5-phenylisoxazole-3-carboxamide (Compound 10)

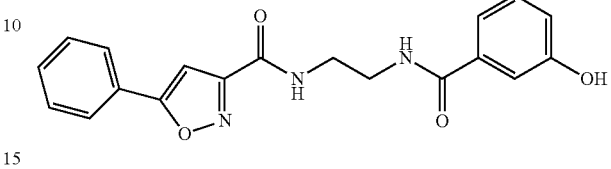

According to General Procedure A, N-(2-(3-bromo-5-hydroxybenzamido)ethyl)-5-phenylisoxazole-3-carboxamide was synthesized from N-(2-aminoethyl)-5-phenylisoxazole-3-carboxamide. LC/MS ret. time=1.147 min, m/z=432.10 [M+H]⁺.

(11) Synthesis of N-(2-(5-methylthiazole-4-carboxamido)ethyl)-5-phenylisoxazole-3-carboxamide (Compound 11)

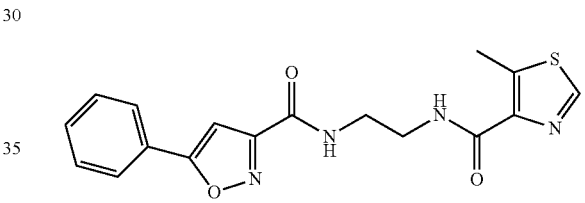

According to General Procedure A, N-(2-(5-methylthiazole-4-carboxamido)ethyl)-5-phenylisoxazole-3-carboxamide was synthesized from N-(2-aminoethyl)-5-phenylisoxazole-3-carboxamide. ¹HNMR (400 MHz, CD₃OD): δ 8.94 (s, 1H), 7.88-7.86 (m, 2H), 7.57-7.50 (m, 3H), 7.07 (s, 1H), 3.68-3.59 (m, 4H), 2.64 (s, 3H); LC/MS ret. time=1.010 min, m/z=357.10 [M+H]⁺.

(12) Synthesis of N-(2-(4-hydroxynicotinamido)ethyl)-5-phenylisoxazole-3-carboxamide (Compound 12)

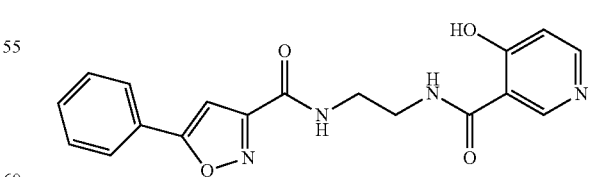

According to General Procedure A, N-(2-(4-hydroxynicotinamido)ethyl)-5-phenylisoxazole-3-carboxamide was synthesized from N-(2-aminoethyl)-5-phenylisoxazole-3-carboxamide. LC/MS ret. time=0.914 min, m/z=353.20 [M+H]⁺.

(13) Synthesis of N-(3-(2-hydroxynicotinamido)propyl)-5-phenylisoxazole-3-carboxamide (Compound 13)

i) Preparation of tert-butyl (3-(5-phenylisoxazole-3-carboxamido)propyl)carbamate

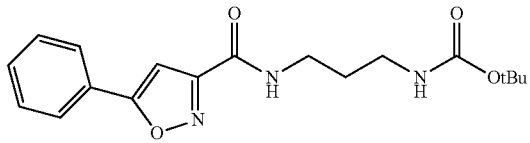 [SMILES: CC(C)(C)OC(=O)NCCCNC(=O)c1cc(-c2ccccc2)on1]

To a solution containing 1.0 g (5.29 mmol) of 3-phenylisoxazole-3-carboxylic acid and 0.89 g (5.56 mmol) of tert-butyl (3-aminopropyl)carbamate in 10 mL of DMF was added 2.5 g (5.82 mmol) of COMU, followed by 2.0 mL (11.1 mmol) of DIPEA. The reaction mixture was allowed to stir at rt overnight. The solvents were removed under reduced pressure and the residue was subjected to silica gel chromatography to give 1.55 g (85%) of tert-butyl (3-(5-phenylisoxazole-3-carboxamido)propyl)carbamate as a yellow solid. LC/MS: 1.22 min, m/z=368.2 [M+K]$^+$.

ii) Preparation of N-(3-aminopropyl)-5-phenylisoxazole-3-carboxamide hydrochloride

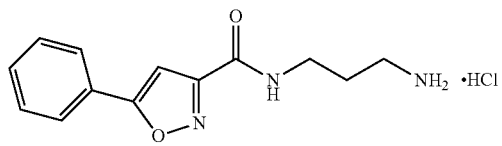 [SMILES: NCCCNC(=O)c1cc(-c2ccccc2)on1 ; Cl]

A mixture containing 1.5 g (4.35 mmol) of tert-butyl (3-(5-phenylisoxazole-3-carboxamido)propyl)carbamate, 50 mL of DCM, and 10 mL of a 4.0M solution of HCl in dioxane was allowed to stir at rt for 1 h. The solvents were removed under reduced pressure to give 1.22 g (100%) of N-(3-aminopropyl)-5-phenylisoxazole-3-carboxamide, which was used with no further purification. $^1$H NMR (400 MHz, CD$_3$OD): δ 7.89-7.87 (m, 2H), 7.54-7.51 (m, 3H), 7.10 (s, 1H), 3.51 (t, 2H, J=6.8 Hz), 3.02 (t, 2H, J=7.2 Hz), 2.01-1.94 (m, 2H); LC/MS: 0.79 min, m/z=246.3 [M+H]$^+$.

iii) Preparation of N-(3-(2-hydroxynicotinamido)propyl)-5-phenylisoxazole-3-carboxamide (Compound 13)

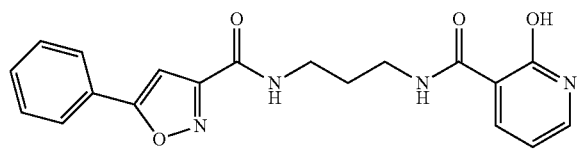 [SMILES: O=C(NCCCNC(=O)c1cccnc1O)c1cc(-c2ccccc2)on1]

To a solution containing 0.3 g (0.278 mmol) of N-(3-aminopropyl)-5-phenylisoxazole-3-carboxamide hydrochloride salt, 0.156 g (1.12 mmol) of 2-hydroxynicotinic acid, and 5 mL of DMF was added 0.50 g (1.17 mmol) of COMU followed by 289 µL (1.6 mmol) of DIPEA. The reaction mixture was allowed to stir at rt for 2 h. The solvents were removed under reduced pressure. The residue was subjected HPLC purification to give 92 mg (25%) of N-(3-(2-hydroxynicotinamido)propyl)-5-phenylisoxazole-3-carboxamide as a white solid. $^1$H NMR (400 MHz, d$^6$-DMSO): δ 9.81 (t, 1H, J=6 Hz), 8.87, (t, 1H, J=5.6 Hz), 8.32 (dd, 1H, J=7.2, 2 Hz), 7.93-7.91 (m, 2H), 7.69-7.67 (m, 1H), 7.56-7.53 (m, 3H), 7.34 (s, 1H), 6.45 (t, 1H, J=13.2 Hz), 3.37-3.28 (m, 4H), and 1.77-1.73, m, 2H); $^{13}$C NMR (125 MHz, d$^6$-DMSO): δ 170.7, 163.8, 132.6, 160.1, 158.8, 144.3, 139.7, 131.2, 129.7, 126.7, 126.2, 120.8, 106.6, 100.3, 37.1, 36.6, and 29.6. HRMS calcd for C$_{18}$H$_{18}$N$_5$O$_2$: 366.1461. found 366.1464.

(14) Synthesis of N-(3-(6-aminonicotinamido)propyl)-5-phenylisoxazole-3-carboxamide (Compound 14)

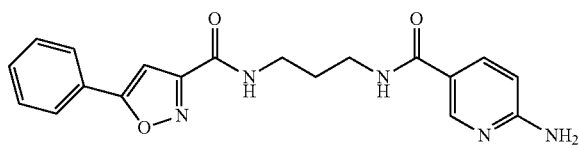 [SMILES: Nc1ccc(C(=O)NCCCNC(=O)c2cc(-c3ccccc3)on2)cn1]

According to General Procedure A, N-(3-(6-aminonicotinamido)propyl)-5-phenylisoxazole-3-carboxamide was synthesized from N-(3-aminopropyl)-5-phenylisoxazole-3-carboxamide hydrochloride salt. LC/MS ret. time=1.101 min, m/z=366.10 [M+H]$^+$.

(15) Synthesis of N-(3-(3-aminobenzamido)propyl)-5-phenylisoxazole-3-carboxamide (Compound 15)

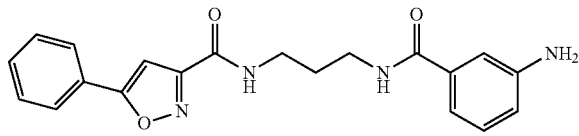 [SMILES: Nc1cccc(C(=O)NCCCNC(=O)c2cc(-c3ccccc3)on2)c1]

According to General Procedure A, N-(3-(3-aminobenzamido)propyl)-5-phenylisoxazole-3-carboxamide was synthesized from N-(3-aminopropyl)-5-phenylisoxazole-3-carboxamide hydrochloride salt. LC/MS ret. time=1.094 min, m/z=365.10 [M+H]$^+$.

(16) Synthesis of N-(3-(4-amino-3-hydroxybenzamido)propyl)-5-phenylisoxazole-3-carboxamide (Compound 16)

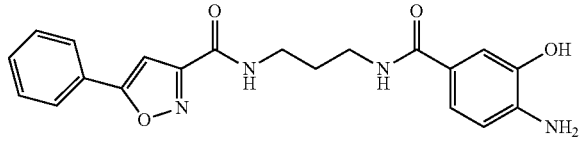 [SMILES: Nc1ccc(C(=O)NCCCNC(=O)c2cc(-c3ccccc3)on2)cc1O]

According to General Procedure A, N-(3-(4-amino-3-hydroxybenzamido)propyl)-5-phenylisoxazole-3-carboxamide was synthesized from N-(3-aminopropyl)-5-phenylisoxazole-3-carboxamide hydrochloride salt. LC/MS ret. time=1.091 min, m/z=381.10 [M+H]$^+$.

(17) Synthesis of N-(3-(4-(5-((3aS,4S,6aR)-2-oxohexahydro-1H-thieno[3,4-d]imidazol-4-yl)pentanamido)benzamido)propyl)-5-phenylisoxazole-3-carboxamide (Compound 17)

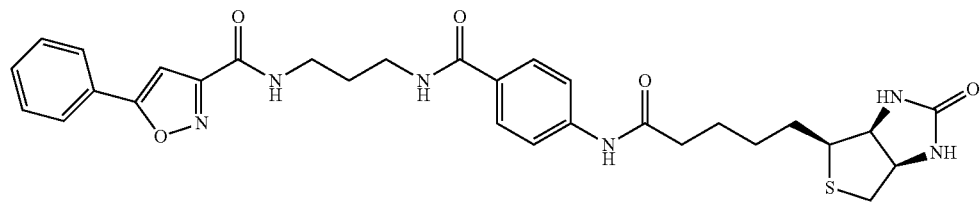 [SMILES: O=C(CCCC[C@@H]1SC[C@@H]2NC(=O)N[C@@H]21)Nc1ccc(C(=O)NCCCNC(=O)c2cc(-c3ccccc3)on2)cc1]

i) Preparation of N-(3-(4-aminobenzamido)propyl)-5-phenylisoxazole-3-carboxamide

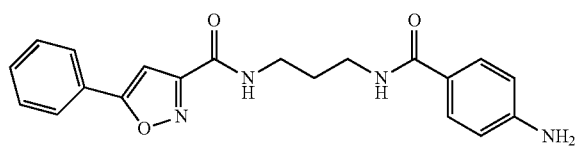 [SMILES: Nc1ccc(C(=O)NCCCNC(=O)c2cc(-c3ccccc3)on2)cc1]

According to General Procedure A, N-(3-(4-aminobenzamido)propyl)-5-phenylisoxazole-3-carboxamide was synthesized from N-(3-aminopropyl)-5-phenylisoxazole-3-carboxamide hydrochloride salt. LC/MS ret. time 1.128=min, m/z=365.10 [M+H]$^+$.

ii) Preparation of N-(3-(4-(5-((3aS,4S,6aR)-2-oxohexahydro-1h-thieno[3,4-d]imidazol-4-yl)pentanamido)benzamido)propyl)-5-phenylisoxazole-3-carboxamide (Compound 17)

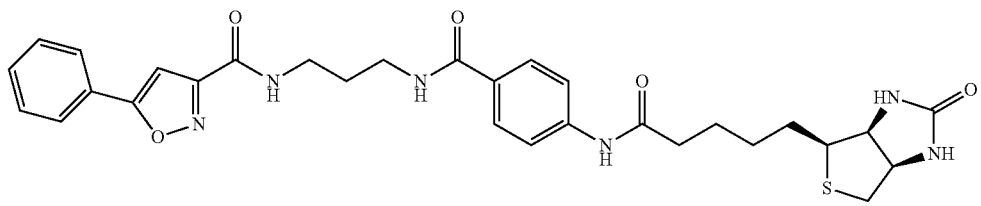 [SMILES: O=C(CCCC[C@@H]1SC[C@@H]2NC(=O)N[C@@H]21)Nc1ccc(C(=O)NCCCNC(=O)c2cc(-c3ccccc3)on2)cc1]

To a solution containing 20 mg (0.055 mmol) of N-(3-(4-aminobenzamido)propyl)-5-phenylisoxazole-3-carboxamide and 1 mL of DMF was added 20 mg (0.058 mmol) of 2,5-dioxopyrrolidin-1-yl 5-((3aS,4S,6aR)-2-oxohexahydro-1H-thieno[3,4-d]imidazol-4-yl)pentanoate, followed by 21 mg (0.13 mmol) of DIPEA. The reaction mixture was allowed to stir at rt for 4 h and then heated at 70° C. overnight. The solvents were removed under reduced pressure and the residue was subjected to HPLC purification to give N-(3-(4-(5-((3aS,4S,6aR)-2-oxohexahydro-1H-thieno[3,4-d]imidazol-4-yl)pentanamido)benzamido)propyl)-5-phenylisoxazole-3-carboxamide. LC/MS ret. time=1.268 min, m/z=591.10 [M+H]⁺.

(18) Synthesis of N-(3-(3-(5-((3aS,4S,6aR)-2-oxohexahydro-1H-thieno[3,4-d]imidazol-4-yl)pentanamido)benzamido)propyl)-5-phenylisoxazole-3-carboxamide (Compound 18)

To a solution containing 20 mg (0.057 mmol) of N-(3-aminopropyl)-5-phenylisoxazole-3-carboxamide hydrochloride salt and 1 mL of DMF was added 20 mg (0.058 mmol) of 2,5-dioxopyrrolidin-1-yl 5-((3aS,4S,6aR)-2-oxohexahydro-1H-thieno[3,4-d]imidazol-4-yl)pentanoate, followed by 21 mg (0.13 mmol) of DIPEA. The reaction mixture was allowed to stir at rt for 4 h and then heated at 70° C. overnight. The solvents were removed under reduced pressure and the residue was subjected to HPLC purification to give N-(3-(5-((3aS,4S,6aR)-2-oxohexahydro-1H-thieno[3,4-d]imidazol-4-yl)pentanamido)propyl)-5-phenylisoxazole-3-carboxamide. LC/MS ret. time=1.208 min, m/z=472.00 [M+H]⁺.

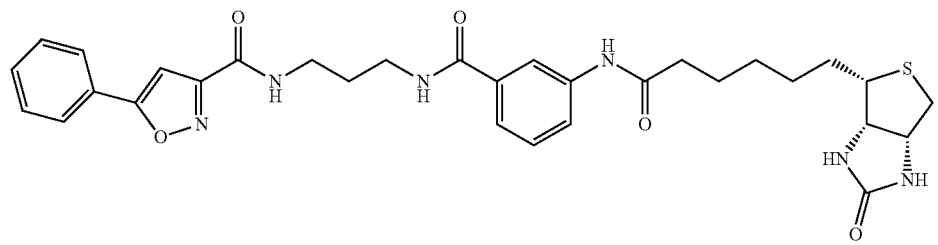 [SMILES: O=C(CCCCC[C@@H]1SC[C@@H]2NC(=O)N[C@@H]21)Nc1cccc(C(=O)NCCCNC(=O)c2cc(-c3ccccc3)on2)c1]

To a solution containing 20 mg (0.055 mmol) of N-(3-(3-aminobenzamido)propyl)-5-phenylisoxazole-3-carboxamide and 1 mL of DMF was added 20 mg (0.058 mmol) of 2,5-dioxopyrrolidin-1-yl 5-((3aS,4S,6aR)-2-oxohexahydro-1H-thieno[3,4-d]imidazol-4-yl)pentanoate, followed by 21 mg (0.13 mmol) of DIPEA. The reaction mixture was allowed to stir at rt for 4 h and then heated at 70° C. overnight. The solvents were removed under reduced pressure and the residue was subjected to HPLC purification to give N-(3-(3-(5-((3aS,4S,6aR)-2-oxohexahydro-1H-thieno[3,4-d]imidazol-4-yl)pentanamido)benzamido)propyl)-5-phenylisoxazole-3-carboxamide. LC/MS ret. time=1.298 min, m/z=591.10 [M+H]⁺.

(19) Synthesis of N-(3-(5-((3aS,4S,6aR)-2-oxohexahydro-1h-thieno[3,4-d]imidazol-4-yl)pentanamido)propyl)-5-phenylisoxazole-3-carboxamide (Compound 19)

(20) Synthesis of N-(3-(5-fluoro-2-hydroxybenzamido)propyl)-5-phenylisoxazole-3-carboxamide (Compound 20)

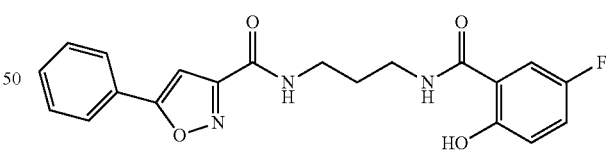

According to General Procedure A, N-(3-(5-fluoro-2-hydroxybenzamido)propyl)-5-phenylisoxazole-3-carboxamide was synthesized from N-(3-aminopropyl)-5-phenylisoxazole-3-carboxamide hydrochloride salt. ¹H NMR (400 MHz, CD₃OD): δ 7.88-7.86 (m, 2H), 7.55-7.51 (m, 3H), 7.12 (ddd, 1H, J=9.0, 8.0, 3.1 Hz), 7.072 (s, 1H), 6.88 (dd, 1H, J=9.0, 5.6 Hz), 3.50, (t, 4H, J=6.7 Hz), 1.93 (t, 2H, J=6.7 Hz); LC/MS ret. time=1.261 min, m/z=384.10 [M+H]⁺.

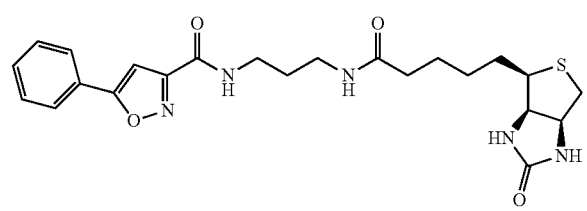 [SMILES: O=C(CCCC[C@H]1SC[C@H]2NC(=O)N[C@H]21)NCCCNC(=O)c1cc(-c2ccccc2)on1]

(21) Synthesis of N-(3-(2-(2-hydroxyphenyl)acetamido)propyl)-5-phenylisoxazole-3-carboxamide (Compound 21)

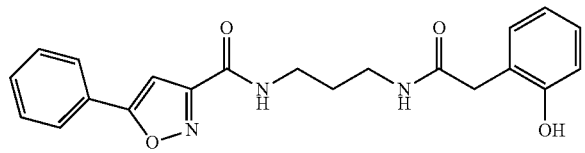 [SMILES: O=C(Cc1ccccc1O)NCCCNC(=O)c1cc(-c2ccccc2)on1]

According to General Procedure A, N-(3-(2-(2-hydroxyphenyl)acetamido)propyl)-5-phenylisoxazole-3-carboxamide was synthesized from N-(3-aminopropyl)-5-phenylisoxazole-3-carboxamide hydrochloride salt. LC/MS ret. time=1.121 min, m/z=380.20 [M+H]$^+$.

(22) Synthesis of N-(3-(1H-indazole-3-carboxamido)propyl)-5-phenylisoxazole-3-carboxamide (Compound 22)

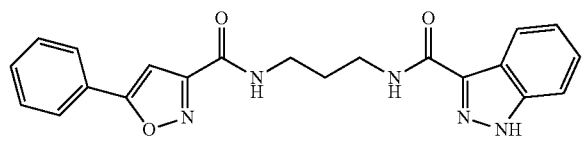 [SMILES: O=C(NCCCNC(=O)c1n[nH]c2ccccc12)c1cc(-c2ccccc2)on1]

According to General Procedure A, N-(3-(1H-indazole-3-carboxamido)propyl)-5-phenylisoxazole-3-carboxamide was synthesized from N-(3-aminopropyl)-5-phenylisoxazole-3-carboxamide hydrochloride salt. LC/MS ret. time=1.155 min, m/z=390.10 [M+H]$^+$.

(23) Synthesis of (S)—N-(2-(2-amino-3-phenylpropanamido)ethyl)-5-phenylisoxazole-3-carboxamide (Compound 23)

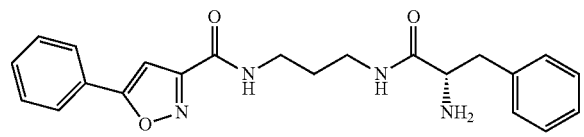 [SMILES: N[C@@H](Cc1ccccc1)C(=O)NCCCNC(=O)c1cc(-c2ccccc2)on1]

According to General Procedure A, (S)—N-(2-(2-amino-3-phenylpropanamido)ethyl)-5-phenylisoxazole-3-carboxamide was synthesized from N-(3-aminopropyl)-5-phenylisoxazole-3-carboxamide hydrochloride salt. $^1$H NMR (400 MHz, CD$_3$OD): δ 7.87-7.84 (m, 2H), 7.53-7.51 (m, 1H), 7.36-7.26 (m, 5H), 7.07 (s, 1H), 4.03 (t, 1H, J=8.4 Hz), 3.53-3.38 (m, 4H), 3.20 (dd, 1H, J=14.0, 7.2 Hz), 3.05 (dd, 1H, J=13.6, 8.0 Hz); LC/MS ret. time=0.983 min, m/z=379.30 [M+H]$^+$.

(24) Synthesis of N-(3-(5-bromo-2-hydroxybenzamido)propyl)-5-phenylisoxazole-3-carboxamide (Compound 24)

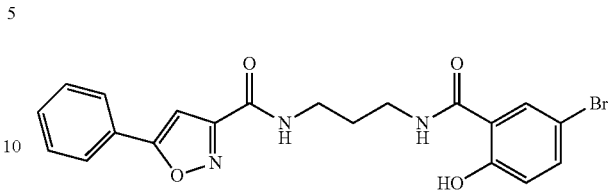

According to General Procedure A, N-(3-(5-bromo-2-hydroxybenzamido)propyl)-5-phenylisoxazole-3-carboxamide was synthesized from N-(3-aminopropyl)-5-phenylisoxazole-3-carboxamide hydrochloride salt. $^1$H NMR (400 MHz, CD$_3$OD): δ 7.93 (d, 1H, J=2.4 Hz), 7.88-7.86 (m, 2H), 7.56-7.51 (m, 3H), 7.45 (dd, 1H, J=8.8, 2.4 Hz), 7.06 (s, 1H), 6.83 (d, 1H, J=8.8 Hz), 3.50 (t, 4H, J=6.7 Hz), 1.96-1.89 (m, 2H); LC/MS ret. time=1.342 min, m/z=446.10 [M+H]$^+$.

(25) Synthesis of N-(3-(2-(3-hydroxyphenyl)acetamido)propyl)-5-phenylisoxazole-3-carboxamide (Compound 25)

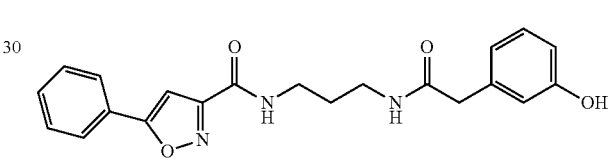

According to General Procedure A, N-(3-(2-(3-hydroxyphenyl)acetamido)propyl)-5-phenylisoxazole-3-carboxamide was synthesized from N-(3-aminopropyl)-5-phenylisoxazole-3-carboxamide hydrochloride salt. $^1$H NMR (400 MHz, CD$_3$OD): δ 8.71 (br s, 1H), 7.87-7.84 (m, 2H), 7.55-7.5\47 (m, 3H), 7.11 (t, 1H, J=8.0 Hz), 7.06 (s, 1H), 6.77-6.75 (2H), 6.67 (dd, 1H, J=8.2, 1.8 Hz), 3.39 (t, 2H, J=6.8 Hz), 3.31 (t, 2H, J=1.6 Hz), 3.28 (t, 2H, J=6.8 Hz), 1.83-1.76 (m, 2H); LC/MS ret. time=1.047 min, m/z=380.20 [M+H]$^+$.

(26) Synthesis of N-(3-(5-methylthiazole-4-carboxamido)propyl)-5-phenylisoxazole-3-carboxamide (Compound 26)

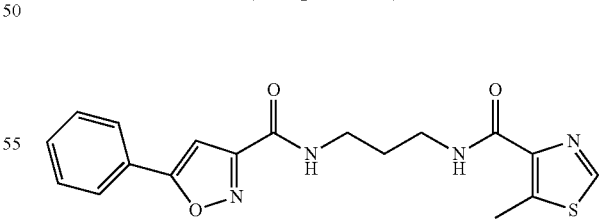

According to General Procedure A, N-(3-(5-methylthiazole-4-carboxamido)propyl)-5-phenylisoxazole-3-carboxamide was synthesized from N-(3-aminopropyl)-5-phenylisoxazole-3-carboxamide hydrochloride salt. $^1$H NMR (400 MHz, CD$_3$OD): δ 8.95 (s, 1H), 7.90-7.86 (m, 2H), 7.57-7.49 (m, 3H), 7.08 (s, 1H), 3.50 (t, 2H, J=6.7 Hz), 3.46 (t, 2H, J=6.7 Hz), 2.67 (s, 3H), 1.95-1.87 (m, 2H); LC/MS ret. time=1.045 min, m/z=371.20 [M+H]$^+$.

(27) Synthesis of N-(3-(3,4-dihydroxybenzamido)propyl)-5-phenylisoxazole-3-carboxamide (Compound 27)

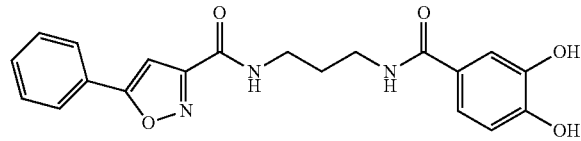 [SMILES: O=C(NCCCNC(=O)c1cc(-c2ccccc2)on1)c1ccc(O)c(O)c1]

According to General Procedure A, N-(3-(3,4-dihydroxybenzamido)propyl)-5-phenylisoxazole-3-carboxamide was synthesized from N-(3-aminopropyl)-5-phenylisoxazole-3-carboxamide hydrochloride salt. $^1$H NMR (400 MHz, CD$_3$OD): δ 7.90-7.86 (m, 2H), 7.55-7.49 (m, 3H), 7.30 (d, 1H, J=2.0 Hz), 7.22 (dd, 1H, J=8.3, 2.0 Hz), 7.08 (s, 1H), 6.79 (d, 1H, J=8.2 Hz), 3.49 (t, 2H, J=6.7 Hz), 3.45 (t, 2H, J=6.6 Hz), 1.93-1.85 (m, 2H); LC/MS ret. time=0.984 min, m/z=382.20 [M+H]$^+$.

(28) Synthesis of N-(3-(1-methyl-1h-pyrazole-3-carboxamido)propyl)-5-phenylisoxazole-3-carboxamide (Compound 28)

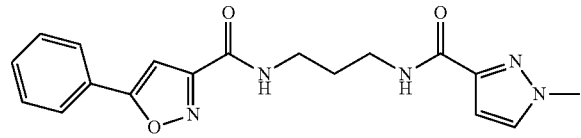 [SMILES: Cn1ccc(C(=O)NCCCNC(=O)c2cc(-c3ccccc3)on2)n1]

According to General Procedure A, N-(3-(1-methyl-1H-pyrazole-3-carboxamido)propyl)-5-phenylisoxazole-3-carboxamide was synthesized from N-(3-aminopropyl)-5-phenylisoxazole-3-carboxamide hydrochloride salt. LC/MS ret. time=1.010 min, m/z=354.30 [M+H]$^+$.

(29) Synthesis of N-(3-(oxazole-4-carboxamido)propyl)-5-phenylisoxazole-3-carboxamide (Compound 29)

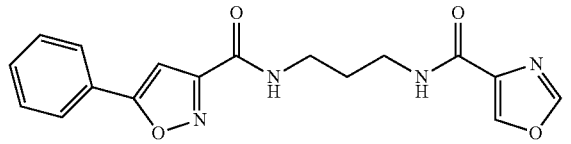 [SMILES: O=C(NCCCNC(=O)c1cc(-c2ccccc2)on1)c1cocn1]

According to General Procedure A, N-(3-(oxazole-4-carboxamido)propyl)-5-phenylisoxazole-3-carboxamide was synthesized from N-(3-aminopropyl)-5-phenylisoxazole-3-carboxamide hydrochloride salt. $^1$H NMR (400 MHz, CD$_3$OD): δ 8.78 (br s, 1H), 8.72 (br s, 1H), 8.32 (s, 1H), 7.89-7.85 (m, 2H), 7.72 (s, 1H), 7.56-7.49 (m, 3H), 7.08 (s, 1H), 3.52-3.44 (m, 4H), 1.95-1.88 (m, 2H); LC/MS ret. time=0.975 min, m/z=341.20 [M+H]$^+$.

(30) Synthesis of N-(3-(4-hydroxynicotinamido)propyl)-5-phenylisoxazole-3-carboxamide (Compound 30)

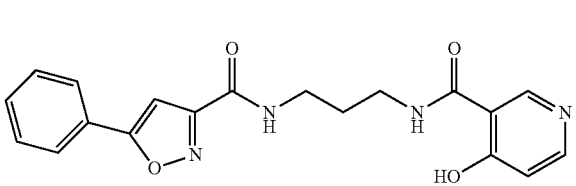 [SMILES: O=C(NCCCNC(=O)c1cnccc1O)c1cc(-c2ccccc2)on1]

According to General Procedure A, N-(3-(4-hydroxynicotinamido)propyl)-5-phenylisoxazole-3-carboxamide was synthesized from N-(3-aminopropyl)-5-phenylis oxazole-3-carboxamide hydrochloride salt. LC/MS ret. time=1.015 min, m/z=367.20 [M+H]$^+$.

(31) Synthesis of N-(3-(isonicotinamido)propyl)-5-phenylisoxazole-3-carboxamide (Compound 31)

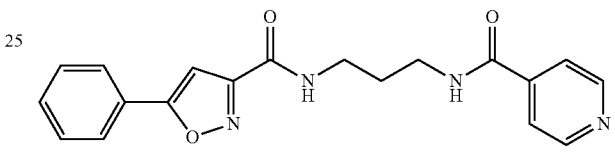

According to General Procedure A, N-(3-(isonicotinamido)propyl)-5-phenylisoxazole-3-carboxamide was synthesized from N-(3-aminopropyl)-5-phenylisoxazole-3-carboxamide hydrochloride salt. LC/MS ret. time=0.953 min, m/z=351.20 [M+H]$^+$.

(32) Synthesis of (S)—N-(3-(2-amino-3-(1H-indol-3-yl)propanamido)propyl)-5-phenylisoxazole-3-carboxamide (Compound 32)

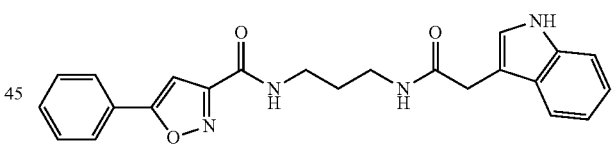

According to General Procedure A, (S)—N-(3-(2-amino-3-(1H-indol-3-yl)propanamido)propyl)-5-phenylisoxazole-3-carboxamide was synthesized from N-(3-aminopropyl)-5-phenylisoxazole-3-carboxamide hydrochloride salt. LC/MS ret. time=1.092 min, m/z=432.20 [M+H]$^+$.

(33) Synthesis of 5-phenyl-N-(3-(thiazole-4-carboxamido)propyl)isoxazole-3-carboxamide (Compound 33)

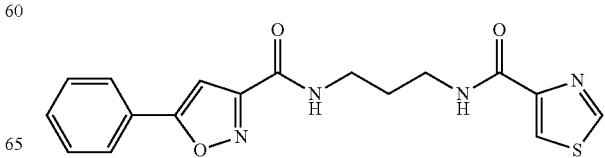

According to General Procedure A, 5-phenyl-N-(3-(thiazole-4-carboxamido)propyl)isoxazole-3-carboxamide was synthesized from N-(3-aminopropyl)-5-phenylisoxazole-3-carboxamide hydrochloride salt. $^1$H NMR (400 MHz, CD$_3$OD): δ 8.98 (d, 1H, J=1.9 Hz), 8.82 (br s, 1H, 8.73 (br s, 1H), 8.24 (d, 1H, J=1.9 Hz), 7.90-7.85 (m, 2H), 7.57-7.47 (m, 3H), 7.07, s, 1H), 3.55-3.45 (m, 4H, 1.95-1.89 (m, 2H); LC/MS ret. time=1.053 min, m/z=357.10 [M+H]$^+$.

(34) Synthesis of N-(3-(oxazole-2-carboxamido)propyl)-5-phenylisoxazole-3-carboxamide (Compound 34)

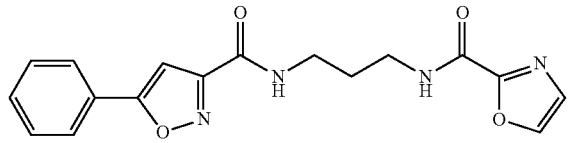 [SMILES: O=C(NCCCNC(=O)c1nccs1)c1cc(-c2ccccc2)on1]

According to General Procedure A, N-(3-(oxazole-2-carboxamido)propyl)-5-phenylisoxazole-3-carboxamide was synthesized from N-(3-aminopropyl)-5-phenylisoxazole-3-carboxamide hydrochloride salt. LC/MS ret. time=1.008 min, m/z=341.20 [M+H]$^+$.

(35) Synthesis of 5-phenyl-N-(3-(thiazole-2-carboxamido)propyl)isoxazole-3-carboxamide (Compound 35)

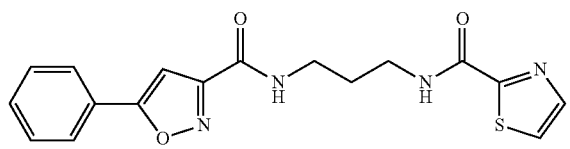

According to General Procedure A, 5-phenyl-N-(3-(thiazole-2-carboxamido)propyl)isoxazole-3-carboxamide was synthesized from N-(3-aminopropyl)-5-phenylisoxazole-3-carboxamide hydrochloride salt. LC/MS ret. time=1.118 min, m/z=342.10 [M+H]$^+$.

(36) Synthesis of N-(3-(3,4-dihydroxybenzamido)propyl)-5-phenylisoxazole-3-carboxamide (Compound 36)

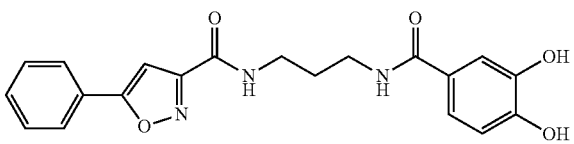 [SMILES: O=C(NCCCNC(=O)c1cc(-c2ccccc2)on1)c1ccc(O)c(O)c1]

According to General Procedure A, N-(3-(3,4-dihydroxybenzamido)propyl)-5-phenylisoxazole-3-carboxamide was synthesized from N-(3-aminopropyl)-5-phenylisoxazole-3-carboxamide hydrochloride salt. $^1$H NMR (400 MHz, CD$_3$OD): δ 7.89-7.85 (m, 2H), 7.56-7.49 (m, 3H), 7.30 (d, 1H, J=2.0 Hz), 7.22 (dd, 1H, J=8.2 Hz, 2.0 Hz), 7.07 s, 1H), 6.79 (d, 1H, J=8.3 Hz), 3.48 (t, 2H, J=6.7 Hz), 3.45 (t, 2H, J=6.6 Hz), 1.93-1.85 (m, 2H); LC/MS ret. time=0.984 min, m/z=382.20 [M+H]$^+$.

(37) Synthesis of N-(3-(2-hydroxyisonicotinamido)propyl)-5-(thiophen-2-yl)isoxazole-3-carboxamide (Compound 37)

i) Preparation of N-(3-aminopropyl)-5-(thiophen-2-yl)isoxazole-3-carboxamide

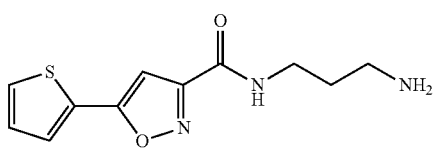 [SMILES: NCCCNC(=O)c1cc(-c2cccs2)on1]

In a manner analogous to the preparation of N-(3-aminopropyl)-5-phenylisoxazole-3-carboxamide, N-(3-aminopropyl)-5-(thiophen-2-yl)isoxazole-3-carboxamide was prepared from 5-(thiophen-2-yl)isoxazole-3-carboxylic acid, m/z=252.1 [M+H]$^+$.

ii) Preparation of N-(3-(2-hydroxyisonicotinamido)propyl)-5-(thiophen-2-yl)isoxazole-3-carboxamide (Compound 37)

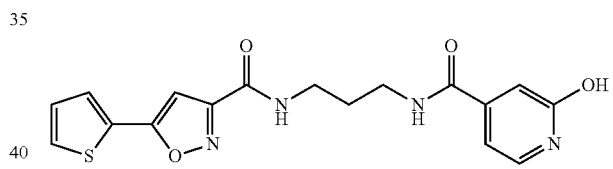

According to General Procedure A, N-(3-(2-hydroxyisonicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.731 min, m/z=373.1 [M+H]$^+$.

(38) Synthesis of N-(3-(5-methylfuran-2-carboxamido)propyl)-5-phenylisoxazole-3-carboxamide (Compound 38)

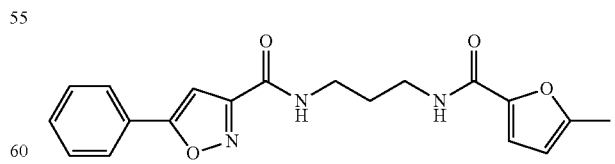

According to General Procedure A, N-(3-(5-methylfuran-2-carboxamido)propyl)-5-phenylisoxazole-3-carboxamide was synthesized from N-(3-aminopropyl)-5-phenylisoxazole-3-carboxamide. LC/MS ret. time=0.896 min, m/z=355.8 [M+H]$^+$.

(39) Synthesis of N-(3-(nicotinamido)propyl)-5-(thiophen-2-yl)isoxazole-3-carboxamide (Compound 39)

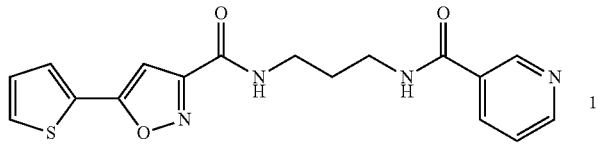

According to General Procedure A, N-(3-(nicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.733 min, m/z=357.1 [M+H]$^+$.

(40) Synthesis of N-(3-(4-chloropicolinamido)propyl)-5-(thiophen-2-yl)isoxazole-3-carboxamide (Compound 40)

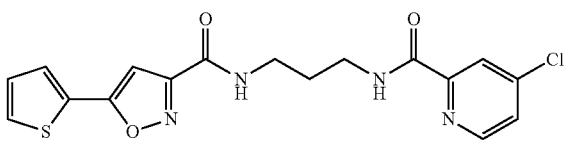 [SMILES: O=C(NCCCNC(=O)c1cc(-c2cccs2)on1)c1cc(Cl)ccn1]

According to General Procedure A, N-(3-(4-chloropicolinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.916 min, m/z=371.1 [M+H]$^+$.

(41) Synthesis of N-(3-(5-hydroxypicolinamido)propyl)-5-(thiophen-2-yl)isoxazole-3-carboxamide (Compound 41)

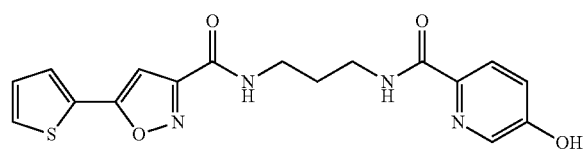 [SMILES: O=C(NCCCNC(=O)c1cc(-c2cccs2)on1)c1ccc(O)cn1]

According to General Procedure A, N-(3-(5-hydroxypicolinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.813 min, m/z=373.1 [M+H]$^+$.

(42) Synthesis of N-(3-(4-hydroxypyrimidine-5-carboxamido)propyl)-5-(thiophen-2-yl)isoxazole-3-carboxamide (Compound 42)

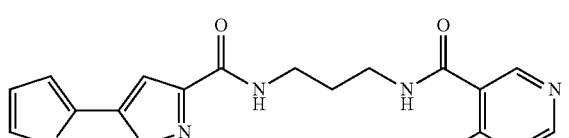

According to General Procedure A, N-(3-(4-hydroxypyrimidine-5-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.731 min, m/z=374.0 [M+H]$^+$.

(43) Synthesis of N-(3-(2,6-dimethoxynicotinamido)propyl)-5-(thiophen-2-yl)isoxazole-3-carboxamide (Compound 43)

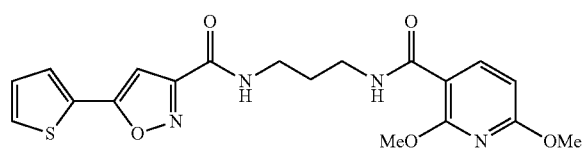 [SMILES: COc1ccc(C(=O)NCCCNC(=O)c2cc(-c3cccs3)on2)c(OC)n1]

According to General Procedure A, N-(3-(2,6-dimethoxynicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=1.041 min, m/z=417.1 [M+H]$^+$.

(44) Synthesis of N-(3-(3-fluoropicolinamido)propyl)-5-(thiophen-2-yl)isoxazole-3-carboxamide (Compound 44)

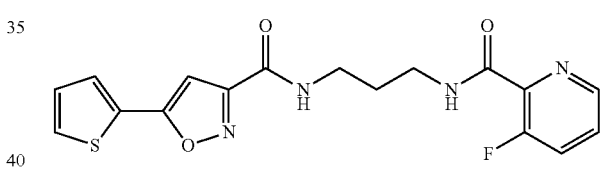

According to General Procedure A, N-(3-(3-fluoropicolinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.879 min, m/z=375.1 [M+H]$^+$.

(45) Synthesis of N-(3-(6-bromopicolinamido)propyl)-5-(thiophen-2-yl)isoxazole-3-carboxamide (Compound 45)

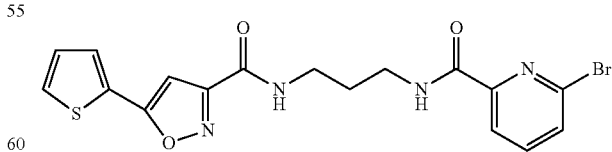

According to General Procedure A, N-(3-(6-bromopicolinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=1.023 min, m/z=437.0 [M+H]$^+$.

(46) Synthesis of N-(3-(2-hydroxy-6-methylnicotinamido)propyl)-5-(thiophen-2-yl)isoxazole-3-carboxamide (Compound 46)

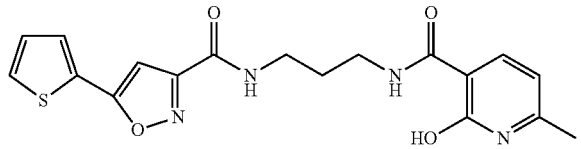 [SMILES: Cc1ccc(C(=O)NCCCNC(=O)c2cc(-c3cccs3)on2)c(O)n1]

According to General Procedure A, N-(3-(2-hydroxy-6-methylnicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.807 min, m/z=387.0 [M+H]$^+$.

(47) Synthesis of N-(3-(2-methylnicotinamido)propyl)-5-(thiophen-2-yl)isoxazole-3-carboxamide (Compound 47)

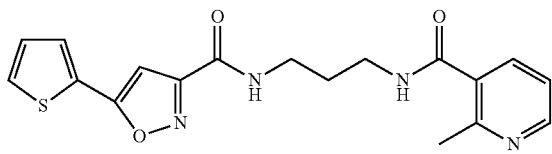 [SMILES: Cc1ncccc1C(=O)NCCCNC(=O)c1cc(-c2cccs2)on1]

According to General Procedure A, N-(3-(2-methylnicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.694 min, m/z=371.1 [M+H]$^+$.

(48) Synthesis of methyl 6-((3-(5-(thiophen-2-yl)isoxazole-3-carboxamido)propyl)carbamoyl)nicotinate (Compound 48)

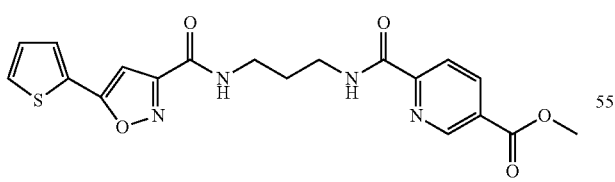

According to General Procedure A, methyl 6-((3-(5-(thiophen-2-yl)isoxazole-3-carboxamido)propyl)carbamoyl)nicotinate was synthesized from N-(3-aminopropyl)-5-(thiophen-2-yl)isoxazole-3-carboxamide. LC/MS ret. time=0.954 min, m/z=415.0 [M+H]$^+$.

(49) Synthesis of N-(3-(6-hydroxynicotinamido)propyl)-5-(thiophen-2-yl)isoxazole-3-carboxamide (Compound 49)

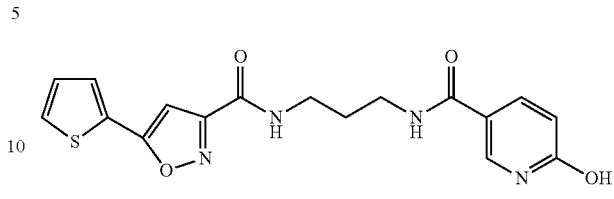

According to General Procedure A, N-(3-(6-hydroxynicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.816 min, m/z=373.1 [M+H]$^+$.

(50) Synthesis of N-(3-(5-bromo-2-hydroxynicotinamido)propyl)-5-(thiophen-2-yl)isoxazole-3-carboxamide (Compound 50)

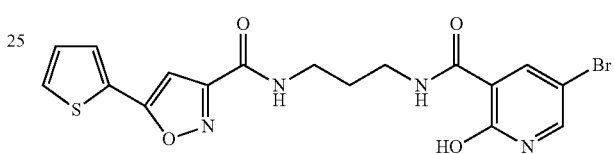

According to General Procedure A, N-(3-(5-bromo-2-hydroxynicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.888 min, m/z=452.9 [M+H]$^+$.

(51) Synthesis of N-(3-(2-hydroxy-4-methylnicotinamido)propyl)-5-(thiophen-2-yl)isoxazole-3-carboxamide (Compound 51)

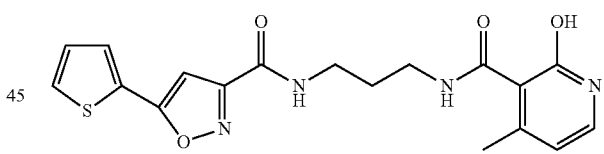

According to General Procedure A, N-(3-(2-hydroxy-4-methylnicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.942 min, m/z=387.1 [M+H]$^+$.

(52) Synthesis of N-(3-(2-methoxynicotinamido)propyl)-5-(thiophen-2-yl)isoxazole-3-carboxamide (Compound 52)

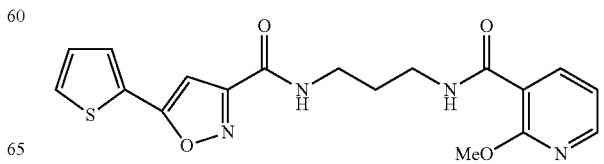

According to General Procedure A, N-(3-(2-methoxynicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.807 min, m/z=387.0 [M+H]⁺.

(53) Synthesis of N-(3-(2-ethoxynicotinamido)propyl)-5-(thiophen-2-yl)isoxazole-3-carboxamide (Compound 53)

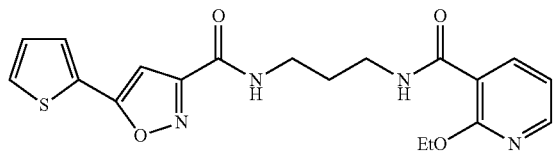 [SMILES: CCOc1ncccc1C(=O)NCCCNC(=O)c1cc(-c2cccs2)on1]

According to General Procedure A, N-(3-(2-ethoxynicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=1.013 min, m/z=401.1 [M+H]⁺.

(54) Synthesis of N-(3-(5-fluoronicotinamido)propyl)-5-(thiophen-2-yl)isoxazole-3-carboxamide (Compound 54)

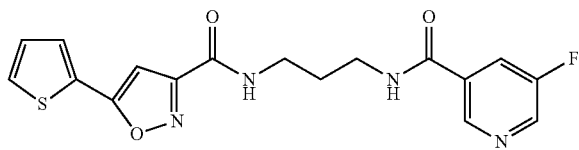 [SMILES: O=C(NCCCNC(=O)c1cc(-c2cccs2)on1)c1cncc(F)c1]

According to General Procedure A, N-(3-(5-fluoronicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.868 min, m/z=401.1 [M+H]⁺.

(55) Synthesis of N-(3-(3-methylpicolinamido)propyl)-5-(thiophen-2-yl)isoxazole-3-carboxamide (Compound 55)

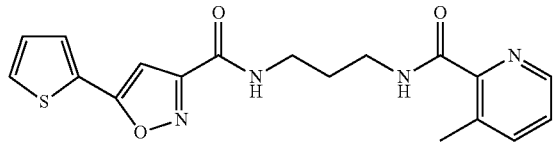 [SMILES: Cc1cccnc1C(=O)NCCCNC(=O)c1cc(-c2cccs2)on1]

According to General Procedure A, N-(3-(3-methylpicolinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.916 min, m/z=371.1 [M+H]⁺.

(56) Synthesis of N-(3-(nicotinamido)propyl)-5-phenylisoxazole-3-carboxamide (Compound 56)

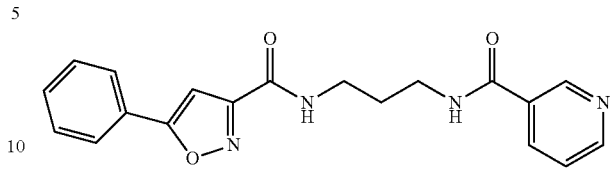

According to General Procedure A, N-(3-(nicotinamido)propyl)-5-phenylisoxazole-3-carboxamide was synthesized from N-(3-aminopropyl)-5-phenylisoxazole-3-carboxamide. LC/MS ret. time=0.770 min, m/z=351.1 [M+H]⁺.

(57) Synthesis of N-(3-(4-chloropicolinamido)propyl)-5-phenylisoxazole-3-carboxamide (Compound 57)

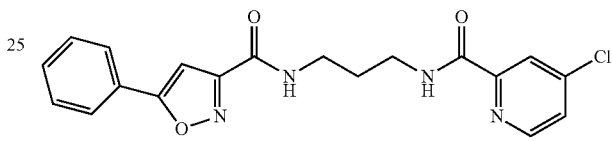

According to General Procedure A, N-(3-(4-chloropicolinamido)propyl)-5-phenylisoxazole-3-carboxamide was synthesized from N-(3-aminopropyl)-5-phenylisoxazole-3-carboxamide. LC/MS ret. time=1.043 min, m/z=385.1 [M+H]⁺.

(58) Synthesis of N-(3-(5-hydroxypicolinamido)propyl)-5-phenylisoxazole-3-carboxamide (Compound 58)

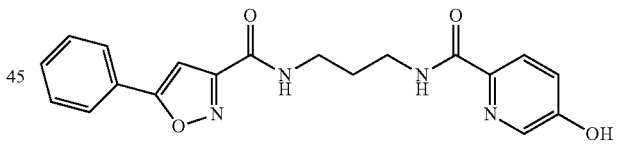

According to General Procedure A, N-(3-(5-hydroxypicolinamido)propyl)-5-phenylisoxazole-3-carboxamide was synthesized from N-(3-aminopropyl)-5-phenylisoxazole-3-carboxamide. LC/MS m/z=367.2 [M+H]⁺.

(59) Synthesis of N-(3-(3-hydroxyisonicotinamido)propyl)-5-phenylisoxazole-3-carboxamide (Compound 59)

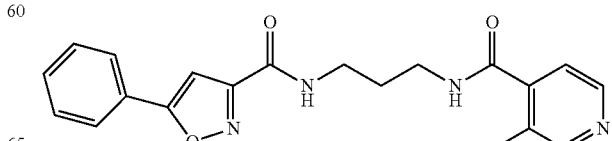

According to General Procedure A, N-(3-(3-hydroxy-isonicotinamido)propyl)-5-phenylisoxazole-3-carboxamide was synthesized from N-(3-aminopropyl)-5-phenylisoxazole-3-carboxamide. LC/MS ret. time=0.861 min, m/z=367.1 [M+H]+.

(60) Synthesis of N-(3-(2,6-dimethoxynicotinamido)propyl)-5-phenylisoxazole-3-carboxamide (Compound 60)

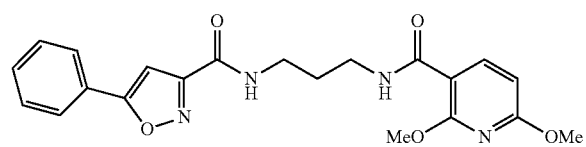 [SMILES: COc1ccc(C(=O)NCCCNC(=O)c2cc(-c3ccccc3)on2)c(OC)n1]

According to General Procedure A, N-(3-(2,6-dimethoxynicotinamido)propyl)-5-phenylisoxazole-3-carboxamide was synthesized from N-(3-aminopropyl)-5-phenylisoxazole-3-carboxamide. LC/MS ret. time=1.069 min, m/z=411.1 [M+H]+.

(61) Synthesis of N-(3-(3-fluoropicolinamido)propyl)-5-phenylisoxazole-3-carboxamide (Compound 61)

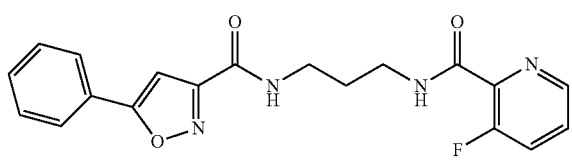 [SMILES: O=C(NCCCNC(=O)c1ncccc1F)c1cc(-c2ccccc2)on1]

According to General Procedure A, N-(3-(3-fluoropicolinamido)propyl)-5-phenylisoxazole-3-carboxamide was synthesized from N-(3-aminopropyl)-5-phenylisoxazole-3-carboxamide. LC/MS ret. time=0.911 min, m/z=369.1 [M+H]+.

(62) Synthesis of N-(3-(6-bromopicolinamido)propyl)-5-phenylisoxazole-3-carboxamide (Compound 62)

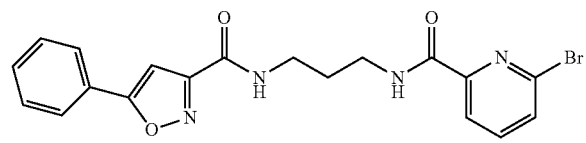 [SMILES: O=C(NCCCNC(=O)c1cccc(Br)n1)c1cc(-c2ccccc2)on1]

According to General Procedure A, N-(3-(6-bromopicolinamido)propyl)-5-phenylisoxazole-3-carboxamide was synthesized from N-(3-aminopropyl)-5-phenylisoxazole-3-carboxamide. LC/MS ret. time=1.050 min, m/z=431.0 [M+H]+.

(63) Synthesis of N-(3-(2-hydroxy-6-methylnicotinamido)propyl)-5-phenylisoxazole-3-carboxamide (Compound 63)

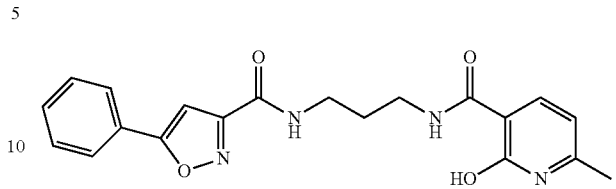

According to General Procedure A, N-(3-(2-hydroxy-6-methylnicotinamido)propyl)-5-phenylisoxazole-3-carboxamide was synthesized from N-(3-aminopropyl)-5-phenylisoxazole-3-carboxamide. LC/MS ret. time=0.840 min, m/z=381.1 [M+H]+.

(64) Synthesis of N-(3-(2-hydroxyisonicotinamido)propyl)-5-phenylisoxazole-3-carboxamide (Compound 64)

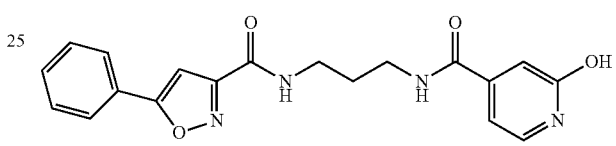

According to General Procedure A, N-(3-(2-hydroxyisonicotinamido)propyl)-5-phenylisoxazole-3-carboxamide was synthesized from N-(3-aminopropyl)-5-phenylisoxazole-3-carboxamide. LC/MS ret. time=0.767 min, m/z=367.1 [M+H]+.

(65) Synthesis of N-(3-(2-methylnicotinamido)propyl)-5-phenylisoxazole-3-carboxamide (Compound 65)

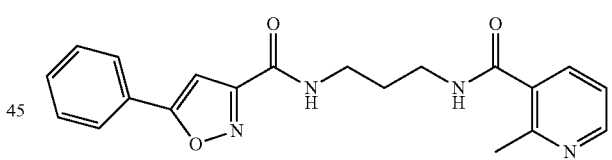

According to General Procedure A, N-(3-(2-methylnicotinamido)propyl)-5-phenylisoxazole-3-carboxamide was synthesized from N-(3-aminopropyl)-5-phenylisoxazole-3-carboxamide. LC/MS ret. time=0.941 min, m/z=365.1 [M+H]+.

(66) Synthesis of methyl 6-((3-(5-phenylisoxazole-3-carboxamido)propyl)carbamoyl)nicotinate (Compound 66)

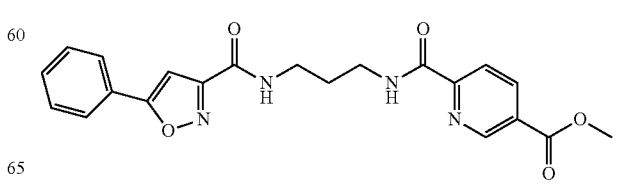

According to General Procedure A, methyl 6-((3-(5-phenylisoxazole-3-carboxamido)propyl)carbamoyl)nicotinate was synthesized from N-(3-aminopropyl)-5-phenylisoxazole-3-carboxamide. LC/MS ret. time=0.982 min, m/z=409.1 [M+H]⁺.

(67) Synthesis of N-(3-(6-hydroxynicotinamido)propyl)-5-phenylisoxazole-3-carboxamide (Compound 67)

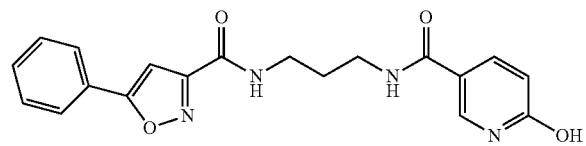 [SMILES: O=C(NCCCNC(=O)c1cc(-c2ccccc2)on1)c1ccc(O)nc1]

According to General Procedure A, N-(3-(6-hydroxynicotinamido)propyl)-5-phenylisoxazole-3-carboxamide was synthesized from N-(3-aminopropyl)-5-phenylisoxazole-3-carboxamide. LC/MS ret. time=1.088 min, m/z=367.2 [M+H]⁺.

(68) Synthesis of N-(3-(5-bromo-2-hydroxynicotinamido)propyl)-5-phenylisoxazole-3-carboxamide (Compound 68)

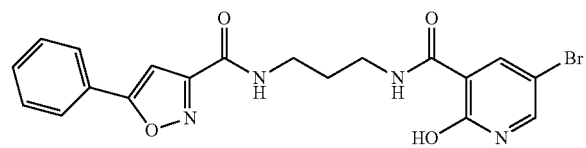 [SMILES: O=C(NCCCNC(=O)c1cc(Br)cnc1O)c1cc(-c2ccccc2)on1]

According to General Procedure A, N-(3-(5-bromo-2-hydroxynicotinamido)propyl)-5-phenylisoxazole-3-carboxamide was synthesized from N-(3-aminopropyl)-5-phenylisoxazole-3-carboxamide. LC/MS ret. time=0.913 min, m/z=446.9 [M+H]⁺.

(69) Synthesis of N-(3-(2-hydroxy-4-methylnicotinamido)propyl)-5-phenylisoxazole-3-carboxamide (Compound 69)

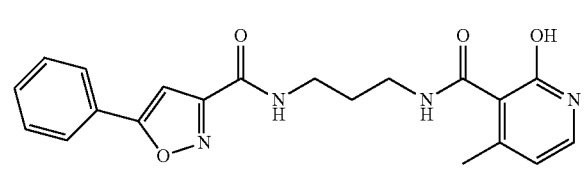 [SMILES: Cc1ccnc(O)c1C(=O)NCCCNC(=O)c1cc(-c2ccccc2)on1]

According to General Procedure A, N-(3-(2-hydroxy-4-methylnicotinamido)propyl)-5-phenylisoxazole-3-carboxamide was synthesized from N-(3-aminopropyl)-5-phenylisoxazole-3-carboxamide. LC/MS ret. time=0.711 min, m/z=367.1 [M+H]⁺.

(70) Synthesis of N-(3-(2-methoxynicotinamido)propyl)-5-phenylisoxazole-3-carboxamide (Compound 70)

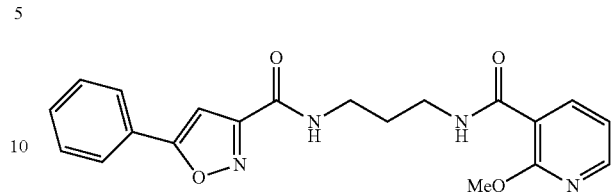

According to General Procedure A, N-(3-(2-methoxynicotinamido)propyl)-5-phenylisoxazole-3-carboxamide was synthesized from N-(3-aminopropyl)-5-phenylisoxazole-3-carboxamide. LC/MS ret. time=0.979 min, m/z=381.1 [M+H]⁺.

(71) Synthesis of N-(3-(3-methylpicolinamido)propyl)-5-phenylisoxazole-3-carboxamide (Compound 71)

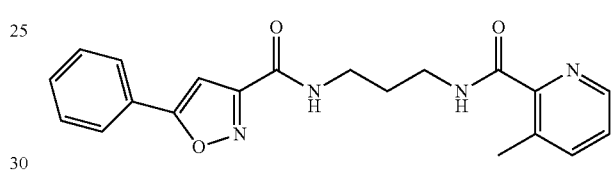

According to General Procedure A, N-(3-(3-methylpicolinamido)propyl)-5-phenylisoxazole-3-carboxamide was synthesized from N-(3-aminopropyl)-5-phenylisoxazole-3-carboxamide. LC/MS ret. time=0.762 min, m/z=365.1 [M+H]⁺.

(72) Synthesis of N-(3-(quinoline-2-carboxamido)propyl)-5-(thiophen-2-yl)isoxazole-3-carboxamide (Compound 72)

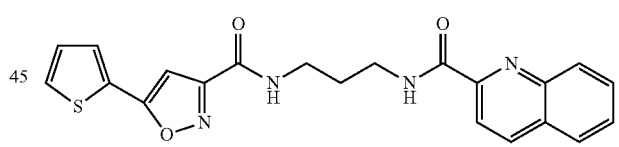

According to General Procedure A, N-(3-(quinoline-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=1.045 min, m/z=407.1 [M+H]⁺.

(73) Synthesis of N-(3-(imidazo[1,2-a]pyridine-3-carboxamido)propyl)-5-(thiophen-2-yl)isoxazole-3-carboxamide (Compound 73)

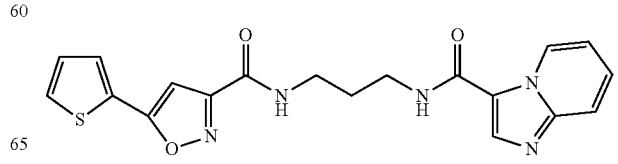

According to General Procedure A, N-(3-(imidazo[1,2-a]pyridine-3-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=1.035 min, m/z=396.1 [M+H]$^+$.

(74) Synthesis of N-(3-(5-bromofuran-2-carboxamido)propyl)-5-(thiophen-2-yl)isoxazole-3-carboxamide (Compound 74)

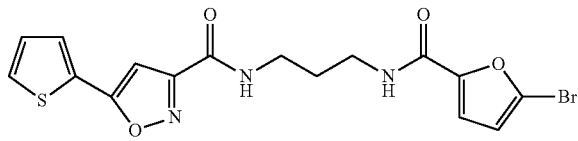 [SMILES: O=C(NCCCNC(=O)c1ccc(Br)o1)c1cc(-c2cccs2)on1]

According to General Procedure A, N-(3-(5-bromofuran-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.979 min, m/z=426.0 [M+H]$^+$.

(75) Synthesis of 5-(thiophen-2-yl)-N-(3-(thiophene-2-carboxamido)propyl)isoxazole-3-carboxamide (Compound 75)

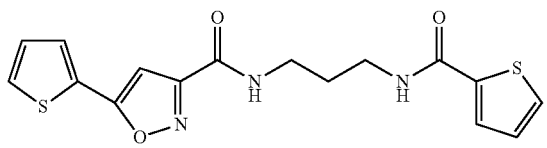 [SMILES: O=C(NCCCNC(=O)c1cccs1)c1cc(-c2cccs2)on1]

According to General Procedure A, 5-(thiophen-2-yl)-N-(3-(thiophene-2-carboxamido)propyl)isoxazole-3-carboxamide was synthesized from N-(3-aminopropyl)-5-(thiophen-2-yl)isoxazole-3-carboxamide. LC/MS ret. time=0.926 min, m/z=362.0 [M+H]$^+$.

(76) Synthesis of 5-(thiophen-2-YL)-N-(3-(5-(trifluoromethyl)furan-2-carboxamido)propyl)isoxazole-3-carboxamide (Compound 76)

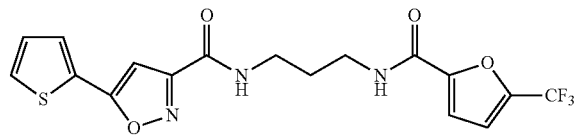 [SMILES: O=C(NCCCNC(=O)c1ccc(C(F)(F)F)o1)c1cc(-c2cccs2)on1]

According to General Procedure A, 5-(thiophen-2-yl)-N-(3-(5-(trifluoromethyl)furan-2-carboxamido)propyl)isoxazole-3-carboxamide was synthesized from N-(3-aminopropyl)-5-(thiophen-2-yl)isoxazole-3-carboxamide. LC/MS ret. time=1.042 min, m/z=414.0 [M+H]$^+$.

(77) Synthesis of N-(3-(5-methylfuran-2-carboxamido)propyl)-5-(thiophen-2-yl)isoxazole-3-carboxamide (Compound 77)

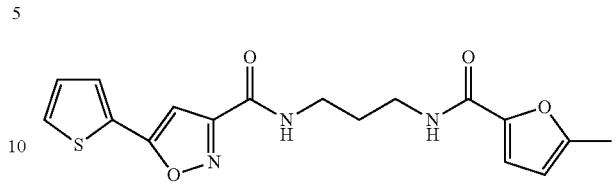

According to General Procedure A, N-(3-(5-methylfuran-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.928 min, m/z=360.1 [M+H]$^+$.

(78) Synthesis of 3-methyl-N-(3-(5-(thiophen-2-yl)isoxazole-3-carboxamido)propyl)-1,2,4-oxadiazole-5-carboxamide (Compound 78)

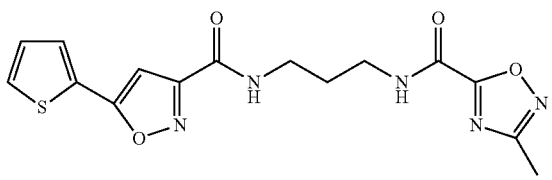 [SMILES: Cc1noc(C(=O)NCCCNC(=O)c2cc(-c3cccs3)on2)n1]

According to General Procedure A, 3-methyl-N-(3-(5-(thiophen-2-yl)isoxazole-3-carboxamido)propyl)-1,2,4-oxadiazole-5-carboxamide was synthesized from N-(3-aminopropyl)-5-(thiophen-2-yl)isoxazole-3-carboxamide. LC/MS ret. time=0.882 min, m/z=362.1 [M+H]$^+$.

(79) Synthesis of N-(3-(6-aminonicotinamido)propyl)-5-(thiophen-2-yl)isoxazole-3-carboxamide (Compound 79)

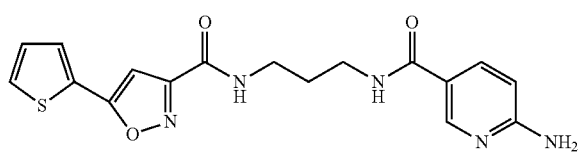 [SMILES: Nc1ccc(C(=O)NCCCNC(=O)c2cc(-c3cccs3)on2)cn1]

According to General Procedure A, N-(3-(6-aminonicotinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.663 min, m/z=372.1 [M+H]$^+$.

(80) Synthesis of 5-methyl-N-(3-(5-(thiophen-2-yl)isoxazole-3-carboxamido)propyl)-1,2,4-oxadiazole-3-carboxamide (Compound 80)

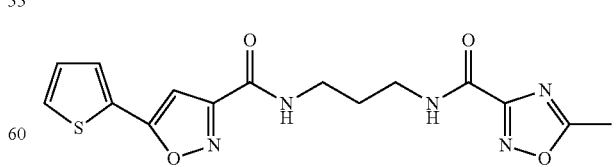

According to General Procedure A, 5-methyl-N-(3-(5-(thiophen-2-yl)isoxazole-3-carboxamido)propyl)-1,2,4-oxadiazole-3-carboxamide was synthesized from N-(3-aminopropyl)-5-(thiophen-2-yl)isoxazole-3-carboxamide. LC/MS ret. time=0.844 min, m/z=362.1 [M+H]$^+$.

(81) Synthesis of N-(3-(6-chloropicolinamido)propyl)-5-(thiophen-2-yl)isoxazole-3-carboxamide (Compound 81)

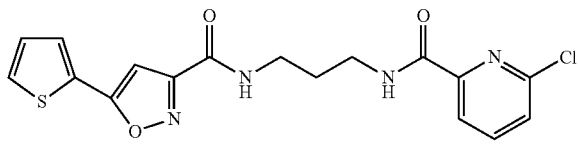 [SMILES: O=C(NCCCNC(=O)c1cccc(Cl)n1)c1cc(-c2cccs2)on1]

According to General Procedure A, N-(3-(6-chloropicolinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=1.005 min, m/z=391.0 [M+H]$^+$.

(82) Synthesis of N-(3-(4-cyanopicolinamido)propyl)-5-(thiophen-2-yl)isoxazole-3-carboxamide (Compound 82)

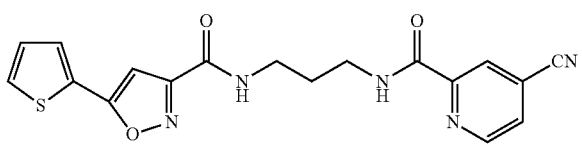 [SMILES: N#Cc1ccnc(C(=O)NCCCNC(=O)c2cc(-c3cccs3)on2)c1]

According to General Procedure A, N-(3-(4-cyanopicolinamido)propyl)-5-(thiophen-2-yl)isoxazole-3-carboxamide was synthesized from N-(3-aminopropyl)-5-(thiophen-2-yl)isoxazole-3-carboxamide LC/MS ret. time=0.932 min, m/z=382.1 [M+H]$^+$.

(83) Synthesis of N-(3-(6-chloropyrazine-2-carboxamido)propyl)-5-(thiophen-2-yl)isoxazole-3-carboxamide (Compound 83)

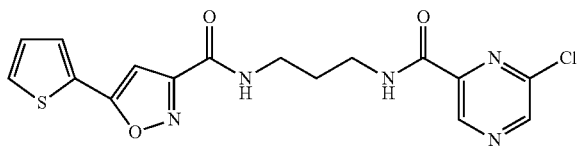 [SMILES: O=C(NCCCNC(=O)c1cncc(Cl)n1)c1cc(-c2cccs2)on1]

According to General Procedure A, N-(3-(6-chloropyrazine-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.946 min, m/z=392.4 [M+H]$^+$.

(84) Synthesis of N-(3-(2-(1H-indol-3-yl)acetamido)propyl)-5-(thiophen-2-yl)isoxazole-3-carboxamide (Compound 84)

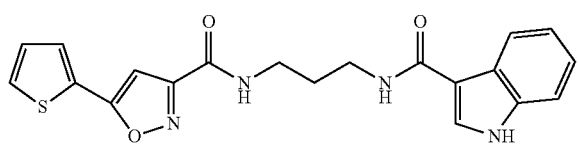 [SMILES: O=C(NCCCNC(=O)c1c[nH]c2ccccc12)c1cc(-c2cccs2)on1]

According to General Procedure A, N-(3-(2-(1H-indol-3-yl)acetamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.960 min, m/z=409.1 [M+H]$^+$.

(85) Synthesis of N-(3-(benzofuran-2-carboxamido)propyl)-5-(thiophen-2-yl)isoxazole-3-carboxamide (Compound 85)

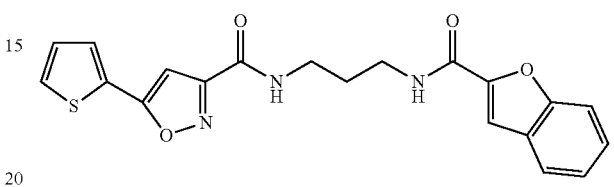

According to General Procedure A, N-(3-(benzofuran-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.757 min, m/z=396.1 [M+H]$^+$.

(86) Synthesis of 5-phenyl-n-(3-(quinoline-2-carboxamido)propyl)isoxazole-3-carboxamide (Compound 86)

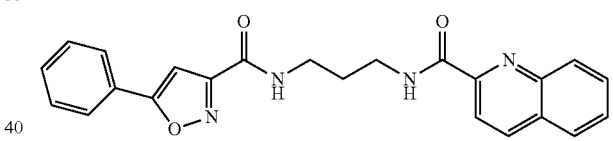

According to General Procedure A, 5-phenyl-N-(3-(quinoline-2-carboxamido)propyl)isoxazole-3-carboxamide was synthesized from N-(3-aminopropyl)-5-phenylisoxazole-3-carboxamide. LC/MS ret. time=1.089 min, m/z=400.7 [M+H]$^+$.

(87) Synthesis of N-(3-(imidazo[1,2-a]pyridine-3-carboxamido)propyl)-5-phenylisoxazole-3-carboxamide (Compound 87)

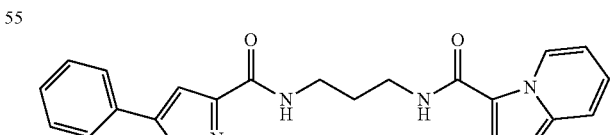

According to General Procedure A, N-(3-(imidazo[1,2-c]pyridine-3-carboxamido)propyl)-5-phenylisoxazole-3-carboxamide was synthesized from N-(3-aminopropyl)-5-phenylisoxazole-3-carboxamide. LC/MS ret. time=1.022 min, m/z=390.7 [M+H]$^+$.

(88) Synthesis of N-(3-(5-bromofuran-2-carboxamido)propyl)-5-phenylisoxazole-3-carboxamide (Compound 88)

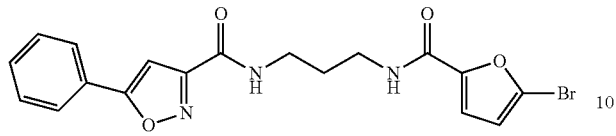

According to General Procedure A, N-(3-(5-bromofuran-2-carboxamido)propyl)-5-phenylisoxazole-3-carboxamide was synthesized from N-(3-aminopropyl)-5-phenylisoxazole-3-carboxamide. LC/MS ret. time=1.036 min, m/z=419.6 [M+H]$^+$.

(89) Synthesis of 5-PHENYL-N-(3-(5-(trifluoromethyl)furan-2-carboxamido)propyl)isoxazole-3-carboxamide (Compound 89)

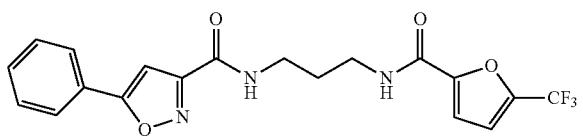 [SMILES: O=C(NCCCNC(=O)c1ccc(C(F)(F)F)o1)c1cc(-c2ccccc2)on1]

According to General Procedure A, 5-phenyl-N-(3-(5-(trifluoromethyl)furan-2-carboxamido)propyl)isoxazole-3-carboxamide was synthesized from N-(3-aminopropyl)-5-phenylisoxazole-3-carboxamide. LC/MS ret. time=1.101 min, m/z=407.7 [M+H]$^+$.

(90) Synthesis of N-(3-(6-aminonicotinamido)propyl)-5-phenylisoxazole-3-carboxamide (Compound 90)

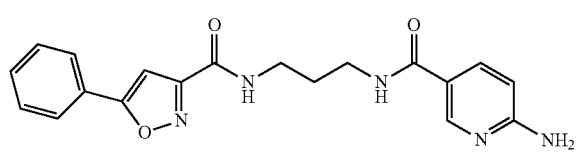 [SMILES: Nc1ccc(C(=O)NCCCNC(=O)c2cc(-c3ccccc3)on2)cn1]

According to General Procedure A, N-(3-(6-aminonicotinamido)propyl)-5-phenylisoxazole-3-carboxamide was synthesized from N-(3-aminopropyl)-5-phenylisoxazole-3-carboxamide. LC/MS ret. time=0.756 min, m/z=365.7 [M+H]$^+$.

(91) Synthesis of 5-methyl-N-(3-(5-phenylisoxazole-3-carboxamido)propyl)-1,2,4-oxadiazole-3-carboxamide (Compound 91)

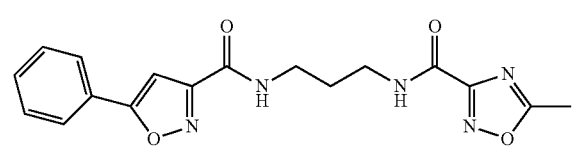 [SMILES: Cc1nc(C(=O)NCCCNC(=O)c2cc(-c3ccccc3)on2)no1]

According to General Procedure A, 5-methyl-N-(3-(5-phenylisoxazole-3-carboxamido)propyl)-1,2,4-oxadiazole-3-carboxamide was synthesized from N-(3-aminopropyl)-5-phenylisoxazole-3-carboxamide. LC/MS ret. time=0.896 min, m/z=355.8 [M+H]$^+$.

(92) Synthesis of N-(3-(6-chloropicolinamido)propyl)-5-phenylisoxazole-3-carboxamide (Compound 92)

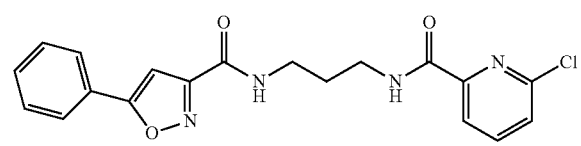 [SMILES: O=C(NCCCNC(=O)c1cccc(Cl)n1)c1cc(-c2ccccc2)on1]

According to General Procedure A, N-(3-(6-chloropicolinamido)propyl)-5-phenylisoxazole-3-carboxamide was synthesized from N-(3-aminopropyl)-5-phenylisoxazole-3-carboxamide. LC/MS ret. time=0.991 min, m/z=385.6 [M+H]$^+$.

(93) Synthesis of N-(3-(4-cyanopicolinamido)propyl)-5-phenylisoxazole-3-carboxamide (Compound 93)

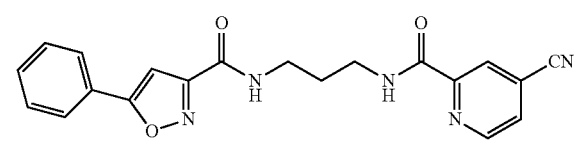 [SMILES: N#Cc1ccnc(C(=O)NCCCNC(=O)c2cc(-c3ccccc3)on2)c1]

According to General Procedure A, N-(3-(4-cyanopicolinamido)propyl)-5-phenylisoxazole-3-carboxamide was synthesized from N-(3-aminopropyl)-5-phenylisoxazole-3-carboxamide. LC/MS ret. time=min, m/z=355.8 [M+H]$^+$.

(94) Synthesis of N-(3-(6-chloropyrazine-2-carboxamido)propyl)-5-phenylisoxazole-3-carboxamide (Compound 94)

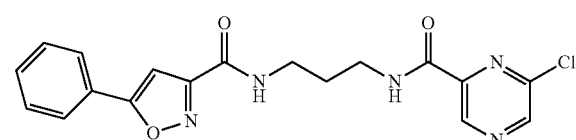

According to General Procedure A, N-(3-(6-chloropyrazine-2-carboxamido)propyl)-5-phenylisoxazole-3-carboxamide was synthesized from N-(3-aminopropyl)-5-phenylisoxazole-3-carboxamide. LC/MS ret. time=1.032 min, m/z=386.7 [M+H]$^+$.

(95) Synthesis of N-(3-(2-(1H-indol-3-yl)acetamido)propyl)-5-phenylisoxazole-3-carboxamide (Compound 95)

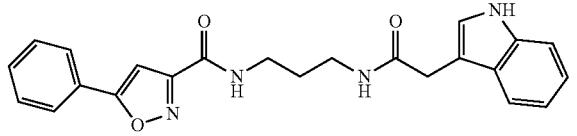 [SMILES: O=C(Cc1c[nH]c2ccccc12)NCCCNC(=O)c1cc(-c2ccccc2)on1]

According to General Procedure A, N-(3-(2-(1H-indol-3-yl)acetamido)propyl)-5-phenylisoxazole-3-carboxamide was synthesized from N-(3-aminopropyl)-5-phenylisoxazole-3-carboxamide. LC/MS ret. time=1.002 min, m/z=402.8 [M+H]$^+$.

(96) Synthesis of N-(3-(benzofuran-2-carboxamido)propyl)-5-phenylisoxazole-3-carboxamide (Compound 96)

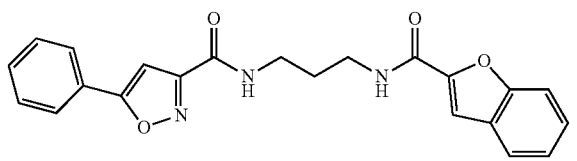 [SMILES: O=C(NCCCNC(=O)c1cc2ccccc2o1)c1cc(-c2ccccc2)on1]

According to General Procedure A, N-(3-(benzofuran-2-carboxamido)propyl)-5-phenylisoxazole-3-carboxamide was synthesized from N-(3-aminopropyl)-5-phenylisoxazole-3-carboxamide. LC/MS ret. time=1.081 min, m/z=389.7 [M+H]$^+$.

(97) Synthesis of N-(3-(6-methylpyrazine-2-carboxamido)propyl)-5-(thiophen-2-yl)isoxazole-3-carboxamide (Compound 97)

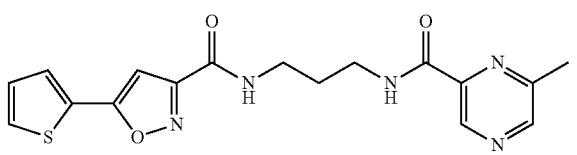 [SMILES: Cc1cncc(C(=O)NCCCNC(=O)c2cc(-c3cccs3)on2)n1]

According to General Procedure A, N-(3-(6-methylpyrazine-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.884 min, m/z=372.1 [M+H]$^+$.

(98) Synthesis of N-(3-(5-(tert-butyl)furan-2-carboxamido)propyl)-5-(thiophen-2-yl)isoxazole-3-carboxamide (Compound 98)

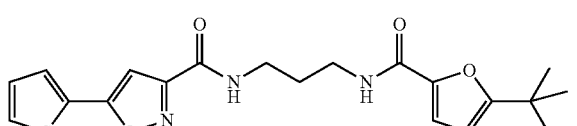

According to General Procedure A, N-(3-(5-(tert-butyl)furan-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=1.104 min, m/z=402.1 [M+H]$^+$.

(99) Synthesis of N-(3-(5-chlorofuran-2-carboxamido)propyl)-5-(thiophen-2-yl)isoxazole-3-carboxamide (Compound 99)

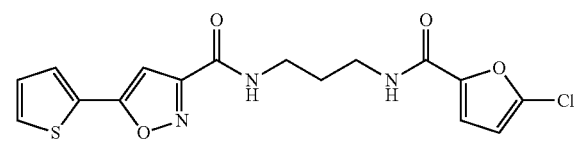 [SMILES: O=C(NCCCNC(=O)c1ccc(Cl)o1)c1cc(-c2cccs2)on1]

According to General Procedure A, N-(3-(5-chlorofuran-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.970 min, m/z=380.0 [M+H]$^+$.

(100) Synthesis of N-(3-(3-phenylfuran-2-carboxamido)propyl)-5-(thiophen-2-yl)isoxazole-3-carboxamide (Compound 100)

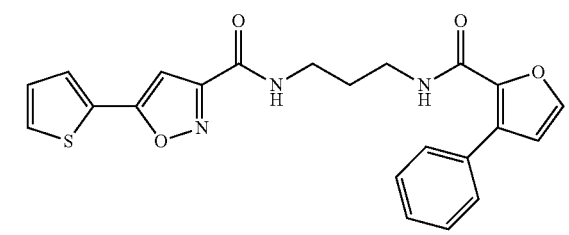 [SMILES: O=C(NCCCNC(=O)c1occc1-c1ccccc1)c1cc(-c2cccs2)on1]

According to General Procedure A, N-(3-(3-phenylfuran-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=1.083 min, m/z=422.1 [M+H]$^+$.

(101) Synthesis of N-(3-(5-ethylfuran-2-carboxamido)propyl)-5-(thiophen-2-yl)isoxazole-3-carboxamide (Compound 101)

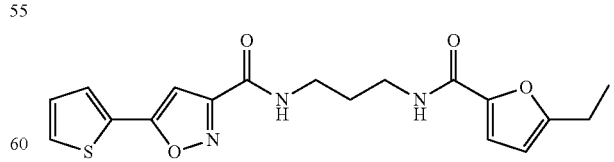

According to General Procedure A, N-(3-(5-ethylfuran-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.995 min, m/z=374.1 [M+H]$^+$.

(102) Synthesis of N-(3-(isoxazole-5-carboxamido)propyl)-5-(thiophen-2-yl)isoxazole-3-carboxamide (Compound 102)

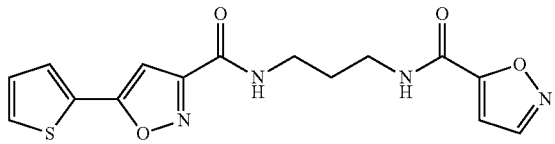 [SMILES: O=C(NCCCNC(=O)c1ccno1)c1cc(-c2cccs2)on1]

According to General Procedure A, N-(3-(isoxazole-5-carboxamido)propyl)-5-(thiophen-2-yl)isoxazole-3-carboxamide was synthesized from N-(3-aminopropyl)-5-(thiophen-2-yl)isoxazole-3-carboxamide LC/MS ret. time=0.845 min, m/z=347.1 [M+H]$^+$.

(103) Synthesis of N-(3-(1-methyl-1H-imidazole-4-carboxamido)propyl)-5-(thiophen-2-yl)isoxazole-3-carboxamide (Compound 103)

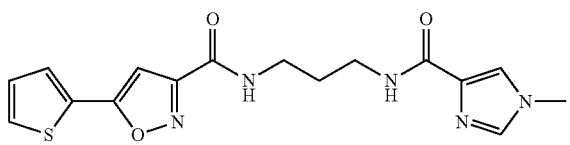 [SMILES: Cn1cnc(C(=O)NCCCNC(=O)c2cc(-c3cccs3)on2)c1]

According to General Procedure A, N-(3-(1-methyl-1H-imidazole-4-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.647 min, m/z=360.1 [M+H]$^+$.

(104) Synthesis of N-(3-(1H-1,2,3-triazole-5-carboxamido)propyl)-5-(thiophen-2-yl)isoxazole-3-carboxamide (Compound 104)

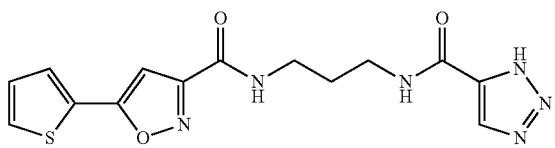 [SMILES: O=C(NCCCNC(=O)c1cnn[nH]1)c1cc(-c2cccs2)on1]

According to General Procedure A, N-(3-(1H-1,2,3-triazole-5-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.753 min, m/z=347.1 [M+H]$^+$.

(105) Synthesis of N-(3-(6-aminopyrazine-2-carboxamido)propyl)-5-(thiophen-2-yl)isoxazole-3-carboxamide (Compound 105)

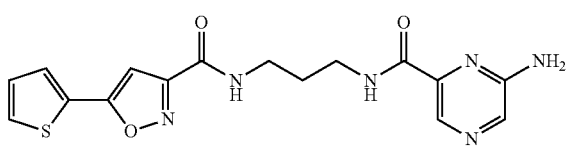 [SMILES: Nc1cncc(C(=O)NCCCNC(=O)c2cc(-c3cccs3)on2)n1]

According to General Procedure A, N-(3-(6-aminopyrazine-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.779 min, m/z=373.1 [M+H]$^+$.

(106) Synthesis of N-(3-(4-phenylpicolinamido)propyl)-5-(thiophen-2-yl)isoxazole-3-carboxamide (Compound 106)

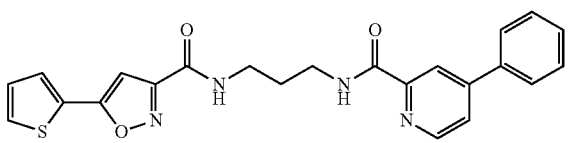 [SMILES: O=C(NCCCNC(=O)c1cc(-c2cccs2)on1)c1cc(-c2ccccc2)ccn1]

According to General Procedure A, N-(3-(4-phenylpicolinamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=1.089 min, m/z=433.1 [M+G]$^+$.

(107) Synthesis of 5-(thiophen-2-YL)-N-(3-(6-(trifluoromethyl)picolinamido)propyl)isoxazole-3-carboxamide (Compound 107)

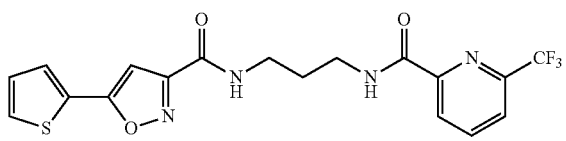 [SMILES: O=C(NCCCNC(=O)c1cccc(C(F)(F)F)n1)c1cc(-c2cccs2)on1]

According to General Procedure A, 5-(thiophen-2-yl)-N-(3-(6-(trifluoromethyl)picolinamido)propyl)isoxazole-3-carboxamide was synthesized from N-(3-aminopropyl)-5-(thiophen-2-yl)isoxazole-3-carboxamide. LC/MS ret. time=1.059 min, m/z=425.0 [M+H]$^+$.

(108) Synthesis of N-(3-([1,2,4]triazolo[1,5-a]pyrimidine-2-carboxamido)propyl)-5-(thiophen-2-yl)isoxazole-3-carboxamide (Compound 108)

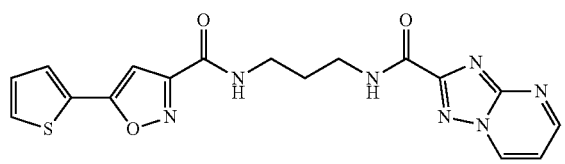 [SMILES: O=C(NCCCNC(=O)c1nc2ncccn2n1)c1cc(-c2cccs2)on1]

According to General Procedure A, N-(3-([1,2,4]triazolo[1,5-a]pyrimidine-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.763 min, m/z=398.0 [M+H]$^+$.

(109) Synthesis of N-(3-(TETRAHYDRO-2H-PYRAN-2-CARBOXAMIDO)PROPYL)-5-(THIOPHEN-2-YL)ISOXAZOLE-3-CARBOXAMIDE (Compound 109)

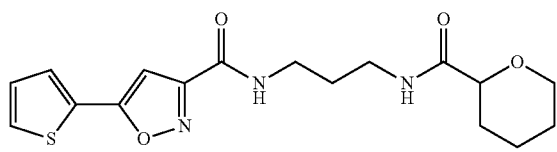 [SMILES: O=C(NCCCNC(=O)C1CCCCO1)c1cc(-c2cccs2)on1]

According to General Procedure A, N-(3-(tetrahydro-2H-pyran-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=0.806 min, m/z=364.1 [M+H]$^+$.

(110) Synthesis of N-(3-(3,5-dimethylfuran-2-carboxamido)propyl)-5-(thiophen-2-yl)isoxazole-3-carboxamide (Compound 110)

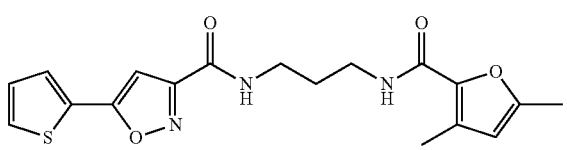 [SMILES: Cc1cc(C)c(C(=O)NCCCNC(=O)c2cc(-c3cccs3)on2)o1]

According to General Procedure A, N-(3-(3,5-dimethylfuran-2-carboxamido)propyl)-5-(thiophen-2-yl)isoxazole-3-carboxamide was synthesized from N-(3-aminopropyl)-5-(thiophen-2-yl)isoxazole-3-carboxamide. LC/MS ret. time=1.004 min, m/z=374.1 [M+H]$^+$.

(111) Synthesis of N-(3-(6-methylpyrazine-2-carboxamido)propyl)-5-phenylisoxazole-3-carboxamide (Compound 111)

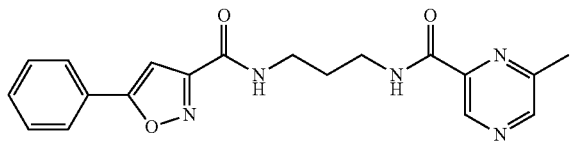 [SMILES: Cc1cncc(C(=O)NCCCNC(=O)c2cc(-c3ccccc3)on2)n1]

According to General Procedure A, N-(3-(6-methylpyrazine-2-carboxamido)propyl)-5-phenylisoxazole-3-carboxamide was synthesized from N-(3-aminopropyl)-5-phenylisoxazole-3-carboxamide. LC/MS ret. time=0.832 min, m/z=366.7 [M+H]$^+$.

(112) Synthesis of N-(3-(5-(tert-butyl)furan-2-carboxamido)propyl)-5-phenylisoxazole-3-carboxamide (Compound 113)

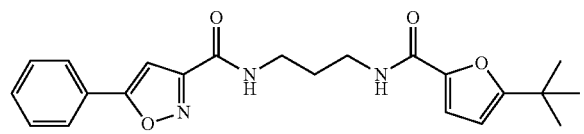 [SMILES: CC(C)(C)c1ccc(C(=O)NCCCNC(=O)c2cc(-c3ccccc3)on2)o1]

According to General Procedure A, N-(3-(5-(tert-butyl)furan-2-carboxamido)propyl)-5-phenylisoxazole-3-carboxamide was synthesized from N-(3-aminopropyl)-5-phenylisoxazole-3-carboxamide. LC/MS ret. time=1.130 min, m/z=396.2 [M+H]$^+$.

(113) Synthesis of N-(3-(5-chlorofuran-2-carboxamido)propyl)-5-phenylisoxazole-3-carboxamide (Compound 113)

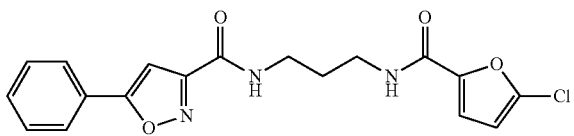 [SMILES: O=C(NCCCNC(=O)c1ccc(Cl)o1)c1cc(-c2ccccc2)on1]

According to General Procedure A, N-(3-(5-chlorofuran-2-carboxamido)propyl)-5-phenylisoxazole-3-carboxamide was synthesized from N-(3-aminopropyl)-5-phenylisoxazole-3-carboxamide. LC/MS ret. time=1.000 min, m/z=374.1 [M+H]$^+$.

(114) Synthesis of 5-phenyl-N-(3-(3-phenylfuran-2-carboxamido)propyl)isoxazole-3-carboxamide (Compound 114)

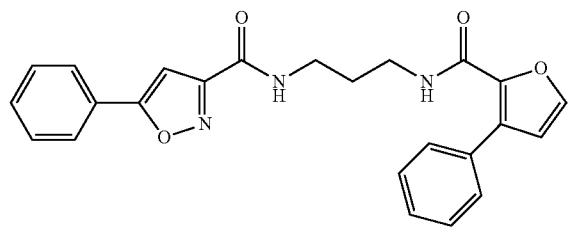 [SMILES: O=C(NCCCNC(=O)c1occc1-c1ccccc1)c1cc(-c2ccccc2)on1]

According to General Procedure A, 5-phenyl-N-(3-(3-phenylfuran-2-carboxamido)propyl)isoxazole-3-carboxamide was synthesized from N-(3-aminopropyl)-5-phenylisoxazole-3-carboxamide. LC/MS ret. time=1.114 min, m/z=416.1 [M+H]$^+$.

(115) Synthesis of N-(3-(5-ethylfuran-2-carboxamido)propyl)-5-phenylisoxazole-3-carboxamide (Compound 115)

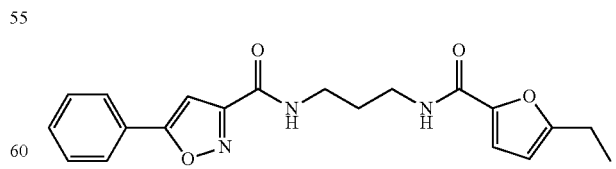

According to General Procedure A, N-(3-(5-ethylfuran-2-carboxamido)propyl)-5-phenylisoxazole-3-carboxamide was synthesized from N-(3-aminopropyl)-5-phenylisoxazole-3-carboxamide. LC/MS ret. time=1.033 min, m/z=368.1 [M+H]$^+$.

(116) Synthesis of N-(3-(1-methyl-1H-imidazole-4-carboxamido)propyl)-5-phenylisoxazole-3-carboxamide (Compound 116)

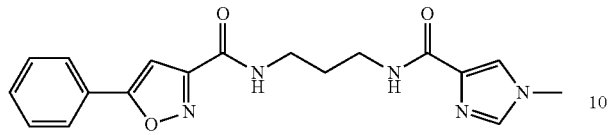

According to General Procedure A, N-(3-(1-methyl-1H-imidazole-4-carboxamido)propyl)-5-phenylisoxazole-3-carboxamide was synthesized from N-(3-aminopropyl)-5-phenylisoxazole-3-carboxamide. LC/MS ret. time=0.737 min, m/z=354.1 [M+H]$^+$.

(117) Synthesis of N-(3-(1H-1,2,3-triazole-5-carboxamido)propyl)-5-phenylisoxazole-3-carboxamide (Compound 117)

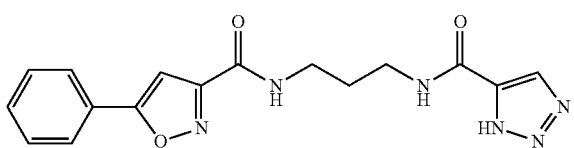 [SMILES: O=C(NCCCNC(=O)c1cnn[nH]1)c1cc(-c2ccccc2)on1]

According to General Procedure A, N-(3-(1H-1,2,3-triazole-5-carboxamido)propyl)-5-phenylisoxazole-3-carboxamide was synthesized from N-(3-aminopropyl)-5-phenylisoxazole-3-carboxamide. LC/MS ret. time=0.807 min, m/z=341.1 [M+H]$^+$.

(118) Synthesis of N-(3-(6-aminopyrazine-2-carboxamido)propyl)-5-phenylisoxazole-3-carboxamide (Compound 118)

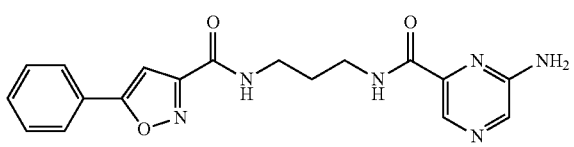 [SMILES: Nc1cncc(C(=O)NCCCNC(=O)c2cc(-c3ccccc3)on2)n1]

According to General Procedure A, N-(3-(6-aminopyrazine-2-carboxamido)propyl)-5-phenylisoxazole-3-carboxamide was synthesized from N-(3-aminopropyl)-5-phenylisoxazole-3-carboxamide. LC/MS ret. time=1.005 min, m/z=367.8 [M+H]$^+$.

(119) Synthesis of 5-phenyl-N-(3-(4-phenylpicolinamido)propyl)isoxazole-3-carboxamide (Compound 119)

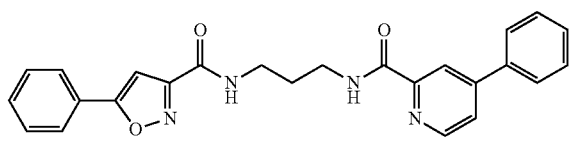 [SMILES: O=C(NCCCNC(=O)c1cc(-c2ccccc2)on1)c1cc(-c2ccccc2)ccn1]

According to General Procedure A, 5-phenyl-N-(3-(4-phenylpicolinamido)propyl)isoxazole-3-carboxamide was synthesized from N-(3-aminopropyl)-5-phenylisoxazole-3-carboxamide. LC/MS ret. time=1.131 min, m/z=426.7 [M+H]$^+$.

(120) Synthesis of 5-phenyl-N-(3-(6-(trifluoromethyl)picolinamido)propyl)isoxazole-3-carboxamide (Compound 120)

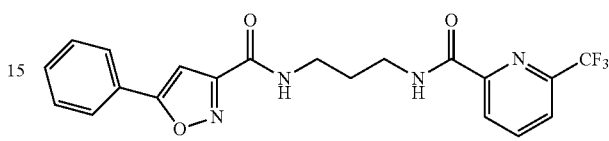

According to General Procedure A, 5-phenyl-N-(3-(6-(trifluoromethyl)picolinamido)propyl)isoxazole-3-carboxamide was synthesized from N-(3-aminopropyl)-5-phenylisoxazole-3-carboxamide. LC/MS ret. time=1.104 min, m/z=418.7 [M+H]$^+$.

(121) Synthesis of 5-PHENYL-N-(3-(tetrahydro-2H-pyran-2-carboxamido)propyl)isoxazole-3-carboxamide (Compound 121)

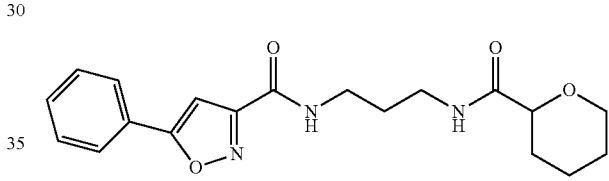

According to General Procedure A, 5-phenyl-N-(3-(tetrahydro-2H-pyran-2-carboxamido)propyl)isoxazole-3-carboxamide was synthesized from N-(3-aminopropyl)-5-phenylisoxazole-3-carboxamide. LC/MS ret. time=0.978 min, m/z=357.1 [M+H]$^+$.

(122) Synthesis of N-(2-(5-fluoro-2-hydroxybenzamido)ethyl)-5-phenyl-1H-pyrazole-3-carboxamide (Compound 122)

i) Preparation of tert-butyl (2-(5-phenyl-1H-pyrazole-3-carboxamido)ethyl)carbamate

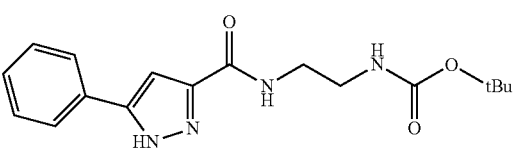 [SMILES: CC(C)(C)OC(=O)NCCNC(=O)c1cc(-c2ccccc2)[nH]n1]

To a solution containing 0.2 g (1.0 mmol) of 5-phenyl-1H-pyrazole-3-carboxylic acid and 3 mL of DCM, and 3 mL of DMF was added 0.19 g (1.15 mmol) of CDI. The reaction mixture was allowed to stir at rt for 30 min and a solution containing 0.2 g (1.15 mmol) of tert-butyl (2-aminoethyl) carbamate in 2 mL of DCM was added. The reaction mixture was allowed to stir at rt overnight, quenched by the addition of water, and extracted with DCM. The combined organic layers were dried by passage through a phase separator cartridge and the solvent was removed under reduced pressure. The residue was subjected to silica gel chromatography to give 0.32 g (91%) of tert-butyl (2-(5-phenyl-1H-pyrazole-3-carboxamido)ethyl)carbamate as a white solid. LC/MS ret time: 1.254 min, m/z=246.30 [M−C(CH$_3$)$_3$)]$^+$.

ii) Preparation of N-(2-aminoethyl)-5-phenyl-1H-pyrazole-3-carboxamide trifluoroacetate

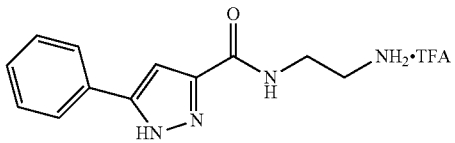

A solution containing 0.31 g (0.93 mmol) of tert-butyl (2-(5-phenyl-1H-pyrazole-3-carboxamido)ethyl)carbamate, 8 mL of DCM and 3 mL of TFA was allowed to stir at rt overnight. The solvents were removed under reduced pressure to give the trifluoroacetate salt of N-(2-aminoethyl)-5-phenyl-1H-pyrazole-3-carboxamide as a white solid. $^1$HNMR (400 MHz, CD$_3$OD): δ 7.68 (d, 2H, J=7.2 Hz), 7.44 (t, 2H, J=7.2 Hz), 7.38-7.32 (m, 1H), 7.04 (s, 1H), 3.64 (t, 2H, J=6.0 Hz), 3.15 (t, 2H, J=6.0 Hz); LC/MS ret time: 0.671 min, m/z=231.20 [M+H]$^+$.

iii) Preparation of N-(2-(5-fluoro-2-hydroxybenzamido)ethyl)-5-phenyl-1H-pyrazole-3-carboxamide (Compound 122)

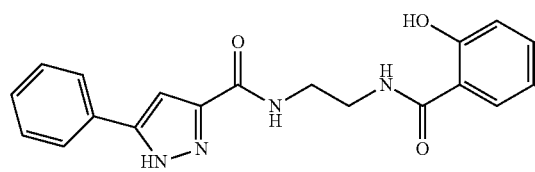

According to General Procedure A, N-(2-(5-fluoro-2-hydroxybenzamido)ethyl)-5-phenyl-1H-pyrazole-3-carboxamide was synthesized from N-(2-aminoethyl)-5-phenyl-1H-pyrazole-3-carboxamide. $^1$H NMR (400 MHz, CD$_3$OD): δ 7.71 (d, 2H, J=7.2 Hz), 7.53 (dd, 1H, J=9.5, 3.0 Hz), 7.45 (t, 2H, J=7.2 Hz), 7.37 (t, 1H, J=7.3), 7.14 (ddd, 1H, J=9.0, 8.0, 3.1 Hz), 7.03 (s, 1H), 6.88 (dd, 1H, J=9.0, 4.6 Hz), 3.62 (s, 4H); LC/MS ret. time=1.095 min, m/z=369.10 [M+H]$^+$.

(123) Synthesis of N-(2-(2-(2-hydroxyphenyl)acetamido)ethyl)-5-phenyl-1H-pyrazole-3-carboxamide (Compound 123)

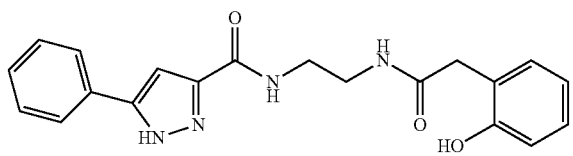 [SMILES: O=C(Cc1ccccc1O)NCCNC(=O)c1cc(-c2ccccc2)[nH]n1]

According to General Procedure A, N-(2-(2-(2-hydroxyphenyl)acetamido)ethyl)-5-phenyl-1H-pyrazole-3-carbox-amide was synthesized from N-(2-aminoethyl)-5-phenyl-1H-pyrazole-3-carboxamide. $^1$H NMR (400 MHz, CD$_3$OD): δ 7.72 (d, 2H, J=7.3 Hz), 7.45 (t, 2H, J=7.3 Hz). 7.11-7.03 (m, 3H), 6.99 (s, 1H), 6.76 (t, 2H, J=8.1 Hz), 3.53 (s, 1H), 3.50 (t, 2H, J=6.0 Hz), 3.42 (t, 2H, J=6.0 Hz), 3.34 (s, 1H). LC/MS ret. time=0.971 min, m/z=365.20 [M+H]$^+$.

(124) Synthesis of N-(2-(5-phenyl-1H-pyrazole-3-carboxamido)ethyl)isonicotinamide (Compound 124)

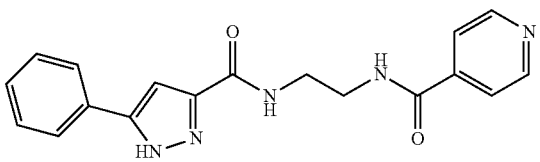 [SMILES: O=C(NCCNC(=O)c1cc(-c2ccccc2)[nH]n1)c1ccncc1]

According to General Procedure A, N-(2-(5-phenyl-1H-pyrazole-3-carboxamido)ethyl)isonicotinamide was synthesized from N-(2-aminoethyl)-5-phenyl-1H-pyrazole-3-carboxamide. $^1$H NMR (400 MHz, CD$_3$OD): δ 8.83 (d, 1H, J=5.6 Hz), 8.07 (d, 1H, J=6.2 Hz), 7.70 (d, 1H, J=8.0 Hz), 7.45 (t, 2H, J=7.4 Hz), 7.37 (t, 1H, J=7.4 Hz), 7.03 (s, 1H), 3.66 (s, 4H); LC/MS ret. time=0.768 min, m/z=336.20 [M+H]$^+$.

(125) Synthesis of N-(2-(5-phenyl-1H-pyrazole-3-carboxamido)ethyl)thiazole-2-carboxamide (Compound 125)

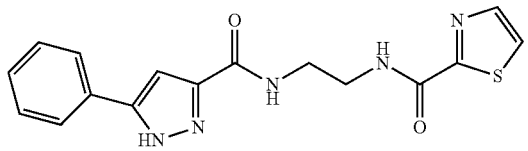 [SMILES: O=C(NCCNC(=O)c1nccs1)c1cc(-c2ccccc2)[nH]n1]

According to General Procedure A, N-(2-(5-phenyl-1H-pyrazole-3-carboxamido)ethyl)thiazole-2-carboxamide was synthesized from N-(2-aminoethyl)-5-phenyl-1H-pyrazole-3-carboxamide. LC/MS ret. time=0.949 min, m/z=342.10 [M+H]$^+$.

B. Amide Bond Formation from an Acyl Chloride (General Procedure B)

To a solution containing 1 equivalent of the required amine in 2-5 mL of DCM or another suitable solvent was added 1.2 equivalents of the desired acyl chloride along with 1.5 equiv of DIPEA. The reaction mixture was allowed to stir at rt until the reaction was complete and the solvents were removed under reduced pressure. The residue was subjected to purification by silica gel chromatography or by preparative HPLC purification to give the target compound.

2. Biology Experimental Methods

A. Evaluation of E-Cadherin Expression in a Cell-Based Assay

SW620 and H520 cells (5×10$^4$/100 μL) were seeded in a 96-well plate prior to treatment. Cells were treated with 10 μM concentration of synthesized compound in quadruplicate for 24 hours in RPMI 1640 supplemented medium and 100 μg/mL penicillin-streptomycin. The cells were then fixed with 100% methanol for 20 minutes at 4° C. The wells were then washed 2 times with PBS, permeabilized in 2% bovine serum albumin (BSA) and 0.2% TritonX-100 in PBS for 30 minutes at room temperature with gentle agitation, and blocked in LI-COR blocking buffer for 30 minutes at room temperature with gentle agitation. The cells were then incubated with the following primary antibodies: anti-E-Cadherin (1:500) and anti-α-Tubulin (1:1000) diluted in blocking buffer (1:1 dilution in PBS) for 2 hours at room temperature with gentle agitation. The cells were washed 4 times in PBS-T for 5 minutes each, and then incubated with the following secondary antibodies conjugated to a fluorescent entity: IRDye 800-conjugated goat anti-rabbit IgG (1:1000) and IRDye-700-conjugated goat anti-mouse IgG (1:2000) in blocking buffer (1:1 dilution in PBS) with gentle agitation for 1 h at room temperature. The cells were washed 4 times in PBS-T for 5 minutes each followed by a single wash with PBS. All liquid was removed from the wells and the plates were visualized and analyzed on the Odyssey IR imaging system (LI-COR Biosciences).

The assay was further optimized in the following manner. The cells were washed 2 times with PBS, fixed in 100% methanol at room temperature for 15 minutes, and again washed 2 times with PBS. The cells were then incubated with the following primary antibodies: anti-E-Cadherin (1:200) and anti-α-Tubulin (1:2000) diluted in ice cold 2% bovine serum albumin (BSA) and 0.2% TritonX-100 in PBS for 1 hour at room temperature with gentle agitation. The cells were washed 2 times in PBS and then incubated with the following secondary antibodies conjugated to a fluorescent entity: Licor 800-conjugated goat anti-rabbit IgG (1:2000) and IRDye-700-conjugated goat anti-mouse IgG (1:2000) in ice cold 2% BSA and 0.2% TritonX-100 in PBS with gentle agitation for 45 minutes at room temperature. The wells were washed 2 times in PBS, dried, and analyzed as previously mentioned.

B. Cell Culture

A colorectal adenocarcinoma cell line, SW620, a lung squamous carcinoma cell line, H520, Murine mammary epithelial NMuMG cells, were obtained from the American Type Culture Collection (ATCC) (Manassas, Va.), and the immortalized human microvascular endothelial cell line, HMEC-1 was obtained from F. Candl Center for Disease Control. All cells were maintained on a humidified atmosphere of 5% $CO_2$ in air at 37° C. SW620 and H520 cells were routinely cultured in RPMI 1640 supplemented with 10% fetal bovine serum, FBS (Atlanta Biologicals, 511550) and 1% penicillin/streptomycine (Cellgro, 30-004-C1). NMuMG cells were cultured in DMEM (Gibco, 11965-092) supplemented with 10% FBS, 1% L-glutamine (Gibco 25030-081) and 1% Penicillin/Streptomycin. HMEC-1 cells were cultured in MCDB131 (Gibco), supplemented with 10% FBS, 10 ng/mL epidermal growth factor (Becton-Dickson), 100 U/mL 1-glutamine (Gibco), 1 μm/mL hydrocortisone (Sigma Chemical), and 1% Penicillin/Streptomycin.

c. Cell Immunostaining (In-Cell-Western)

SW620inv cells were used for ICW analysis as described (Stoops, S. L., et al. (2011) *ACS Chemical Biology* 6, 452-465).

D. Isolation of Low E-Cadherin "Invasive" SW620 Cells

SW620 cells (ATCC p92) were grown in RPMI+10% FBS+P/S to sub-confluence. The cells were washed with PBS, trypsinized, and re-suspended in serum-free RPMI at a concentration of one million cells/mL. The cells were then added to the upper chamber of 24 mm transwell (Costar#3428) that had been coated with 400 μL of 2.5 mg/mL matrigel (BD Biosciences). One milliliter of 10% FBS+P/S was added to the lower chamber. The cells were incubated at 37° C. for 72 hours in order to allow the cells to invade. Four biological replicate transwells were prepared for invasion. After 72 hours, the invading cells were trypsinized from the bottom portion of the transwell membranes and plated in 6 $cm^2$ tissue culture plates. These invasive cells were then analyzed by western blot, matrigel invasion assay, and immunofluorescence for E-cadherin levels with and without TSA treatments. Cells from biological replicate B were used in subsequent assays.

NMuMG breast cancer cells were obtained from ATCC and were maintained at <20 passages in the laboratory and were cultured in DMEM (Gibco, 11965-092) supplemented with 10% FBS (Atlanta Biologicals, S11550), 1% L-glutamine (Gibco 25030-081) and 1% Penicillin/Streptomycin (Cellgro, 30-004-C1). For EMT studies, nMuMg cells ($5 \times 10^4$/well) were seeded on 8-well chamber slides for 24 h prior to treatment. After treatments, the cells were rinsed with PBS and fixed with 100% methanol for 15 min at 4° C. The cells were rinsed with PBS and blocked and permeabilized with 2% BSA and 0.2% TritonX-100 in PBS. The cells were then incubated with anti-E-cadherin antibody (BD Transduction Laboratories) and diluted in (1:50) 1% BSA in PBS blocking solution overnight at 4° C. After 3 washes with PBS, the cells were incubated with appropriate secondary antibodies conjugated to fluorescein (1:200; Sigma, St. Louis, Mo.) or Texas Red (1:500; Invitrogen, Carlsbad, Calif.) and DAPI (1:2000, Sigma, St. Louis, Mo.) for 40 min at RT. The cells were washed 3 times with PBS and then mounted with Vectashield mounting medium (Vector Laboratories, Burlingame, Calif.). Images were captured on an Olympus FV-1000 fluorescent microscope.

HMEC-1 cells (F. Candl, Center for Disease Control) were cultured in MCDB131 (Gibco), supplemented with 10% FBS, 10 ng/mL epidermal growth factor (Becton-Dickson), 100 U/mL 1-glutamine (Gibco), and 1 μm/mL hydrocortisone (Sigma Chemical). For tube assays and scratch assays, HMEC1 cells in complete media were plated on top of growth factor reduced matrigel (BD Biosciences) with or without DMSO or 10 μM Compound 13 (259Y). Experiments were performed in triplicate at least three times according to previously reported methods (Al-Greene, N. T., et al. (2013) *PLoS One* 8, e69660). Significance was determined by Mann-Whitney, ANOVA, or Student's t test as noted.

E. Animal Studies

All murine experiments were approved by the Vanderbilt Institutional Animal Care and Use Committee and performed in accordance with the standards of the Association of Assessment and Accreditation of Laboratory Care (AAALAC) (i.e., tumor establishment, time course of treatments, measures of tumor growth, tumor excision and protein extraction, concentration applied with conditions, and time applied relative to compound treatment).

F. Molecular Analysis

The 1.4 kbp E-cadherin promoter plasmid (E1) and deletion plasmids E2-E8 were a gift from Dr. Eric Fearon at The University of Michigan (Liu, Y. N., et al. (2005) *Onocogene* 24, 8277-8290). All plasmid constructs were sequenced at the Vanderbilt University Sequencing Core to confirm the E-cadherin promoter fragments using the PCR primers listed in Table I and herein below. Luciferase assays were performed as previously described (Freeman, T. J., et al. (2012) *Gastroenterology* 142, 562-572).

RNA extraction was conducted using RNAeasy (Qiagen) and qPCR (primers are synthesized at IDT Biotechnology, UPL probes are from Roche Biologicals: E-cadherin (F:

TTG ACG CCG AGA GCT ACA C, R: GTC GAC CGG TGC AAT CTT, UPL probe 80), PMM1 (F: TTC TCC GAA CTG GAC AAG AAA, R: CTC TGT TTT CAG GGC TTC CA, UPL probe 7), Occludin (F: AGG AAC CGA GAG CCA GGT, R: GGA TGA GCA ATG CCC TTT AG, UPL probe 84), Vimentin (F: GAC CAG CTA ACC AAC GAC AAA, R: GTC GAC CGG TGC AAT CTT, UPL probe 39). For the chromatin Immunoprecipitation (ChIP) assay on the E-cadherin promoter, the following primers were used: E-Cadherin (-76/64) forward: 5'-GTG AAC CCT CAG CCA ATC AGC GGT-3'; reverse: 5'-GGA GCG GGC TGG AGT CTG AAC TG-3'. Protein extraction was conducted using RIPA buffer (150 mM NaCl, 1% NP-40, 0.5% Na deoxycholate, 0.1% SDS, 50 mM Tris-Cl, pH=8.0) supplemented with a protease inhibitor cocktail consisting of 1 µg/mL aprotinin, 1 µg/mL leupeptin, 3 µg/mL Pepstatin, 1 mM NaVO3, 1 mM NaF, 0.5 µM DTT. Gel electrophoresis was conducted on 10-15% polyacrylamide gels, depending on the size of the protein of interest. Antibodies used in this study were as follows: E-cadherin (BD Transduction Laboratories), VE-cadherin (Santa Cruz Biotech., WB) and Vimentin (Sigma Chemical), for H3K9Ac (Millipore, WB and ChIP), H3K4Me3 (Millipore, WB and ChIP), H3K4Me (Cell Signaling, Western blot), H3K27Me3 (Millipore, western blot and ChIP), H3 (abcam, WB and ChIP), Pol2 antibody (Millipore, ChIP), and Normal Rabbit IgG (Cell Signaling, ChIP). Quantification of protein bands on Western blot was conducted in ImageJ.

TABLE I

| PCR primer | Sequence | SEQ. ID NO. |
| --- | --- | --- |
| E-cadherin forward primer | TTG ACG CCG AGA GCT ACA C | 1 |
| E-cadherin reverse primer | GTC GAC CGG TGC AAT CTT | 2 |
| PMM1 forward primer | TTC TCC GAA CTG GAC AAG AAA | 3 |
| PMM1 reverse primer | CTC TGT TTT CAG GGC TTC CA | 4 |
| Occludin forward primer | AGG AAC CGA GAG CCA GGT | 5 |
| Occludin reverse primer | GGA TGA GCA ATG CCC TTT AG | 6 |
| Vimentin forward primer | GAC CAG CTA ACC AAC GAC AAA | 7 |
| Vimentin reverse primer | GTC GAC CGG TGC AAT CTT | 8 |
| E-Cadherin forward primer | GTG AAC CCT CAG CCA ATC AGC GGT | 9 |
| E-Cadherin reverse primer | GGA GCG GGC TGG AGT CTG AAC TG | 10 |

3. Characterization of Exemplary Compounds

The compounds below in Table II were synthesized with methods identical or analogous to those described herein. The requisite starting materials were commercially available, described in the literature, or readily synthesized by one skilled in the art of organic synthesis. The mass spectrometry data were obtained using the general LC-MS methods as described above. LC-MS [M+H]$^+$ means the protonated mass of the free base of the compound.

TABLE II

| No. | Compound | LC-MS [M + H]$^+$ |
| --- | --- | --- |
| 1 | (structure) | 366.10 |
| 2 | (structure) | 432.10 |

TABLE II-continued

| No. | Compound | LC-MS [M + H]+ |
|---|---|---|
| 3 | 5-phenylisoxazole-3-carboxamide-ethylene-nicotinamide | 337.20 |
| 4 | 5-phenylisoxazole-3-carboxamide-ethylene-isonicotinamide | 337.20 |
| 5 | 5-phenylisoxazole-3-carboxamide-ethylene-thiazole-2-carboxamide | 343.20 |
| 6 | 5-phenylisoxazole-3-carboxamide-ethylene-tryptophanamide | 418.20 |
| 7 | 5-phenylisoxazole-3-carboxamide-ethylene-(3-hydroxyphenyl)acetamide | 366.10 |
| 8 | 5-phenylisoxazole-3-carboxamide-ethylene-3-hydroxybenzamide | 352.2 |
| 9 | 5-phenylisoxazole-3-carboxamide-ethylene-3,4-dihydroxybenzamide | 368.20 |
| 10 | 5-phenylisoxazole-3-carboxamide-ethylene-3-bromo-5-hydroxybenzamide | 432.10 |
| 11 | 5-phenylisoxazole-3-carboxamide-ethylene-5-methylthiazole-4-carboxamide | 357.10 |

TABLE II-continued

| No. | Compound | LC-MS [M + H]+ |
|---|---|---|
| 12 | | 353.20 |
| 13 | | 366.15 |
| 14 | | 366.10 |
| 15 | | 365.10 |
| 16 | | 381.10 |
| 17 | | 591.10 |
| 18 | | 591.10 |
| 19 | | 472.00 |

TABLE II-continued
| No. | Compound | LC-MS [M + H]+ |
|---|---|---|
| 20 | 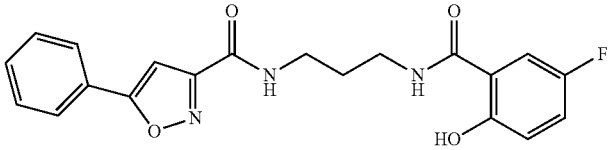 [SMILES: O=C(NCCCNC(=O)c1cc(F)ccc1O)c1cc(-c2ccccc2)on1] | 384.10 |
| 21 | 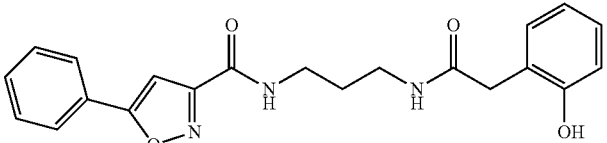 | 380.20 |
| 22 | 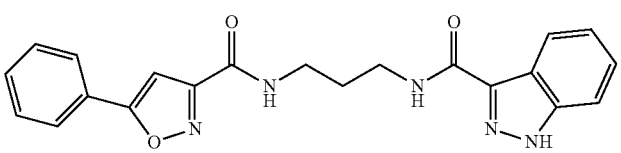 [SMILES: O=C(NCCCNC(=O)c1n[nH]c2ccccc12)c1cc(-c2ccccc2)on1] | 390.10 |
| 23 | 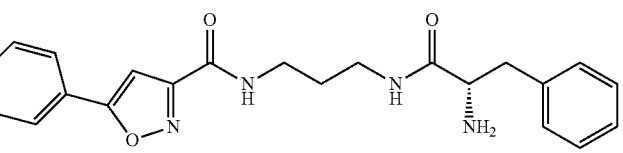 | 379.30 |
| 24 | 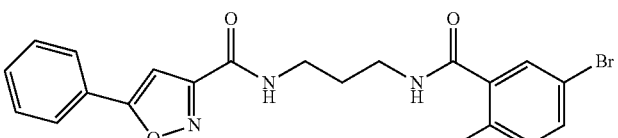 | 446.10 |
| 25 | 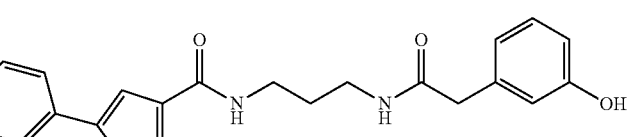 | 380.20 |
| 26 | 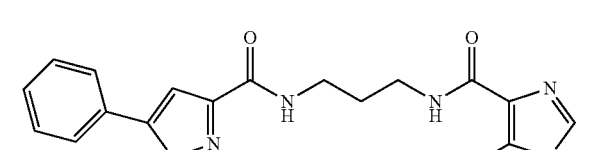 | 371.20 |
| 27 | 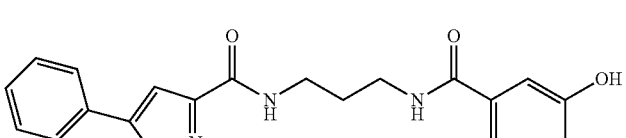 | 382.20 |
| 28 | 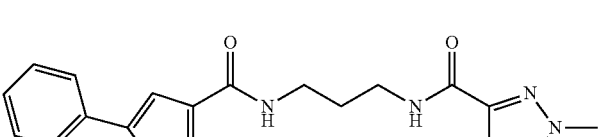 | 354.30 |

TABLE II-continued
| No. | Compound | LC-MS [M + H]+ |
|---|---|---|
| 29 | 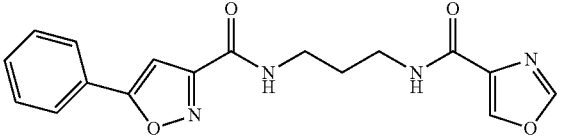 [SMILES: O=C(NCCCNC(=O)c1cc(-c2ccccc2)on1)c1cocn1] | 341.20 |
| 30 | 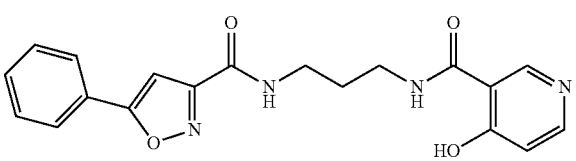 [SMILES: O=C(NCCCNC(=O)c1cnccc1O)c1cc(-c2ccccc2)on1] | 367.20 |
| 31 | 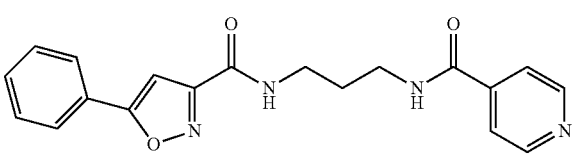 [SMILES: O=C(NCCCNC(=O)c1cc(-c2ccccc2)on1)c1ccncc1] | 351.20 |
| 32 | 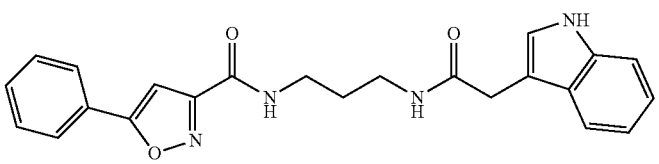 [SMILES: O=C(Cc1c[nH]c2ccccc12)NCCCNC(=O)c1cc(-c2ccccc2)on1] | 432.20 |
| 33 | 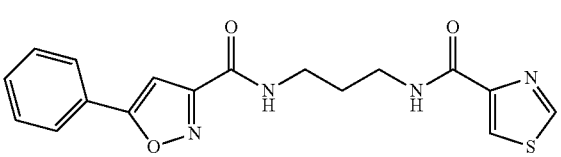 [SMILES: O=C(NCCCNC(=O)c1cc(-c2ccccc2)on1)c1cscn1] | 357.10 |
| 34 | 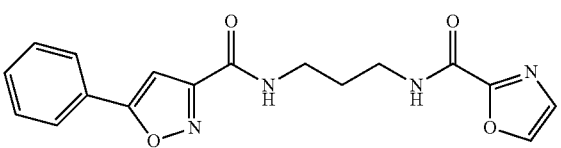 [SMILES: O=C(NCCCNC(=O)c1ncco1)c1cc(-c2ccccc2)on1] | 341.20 |
| 35 | 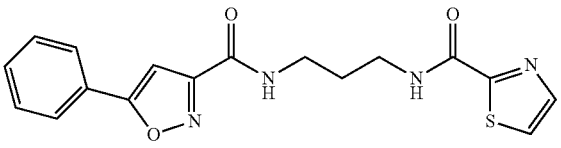 [SMILES: O=C(NCCCNC(=O)c1nccs1)c1cc(-c2ccccc2)on1] | 342.10 |
| 36 | 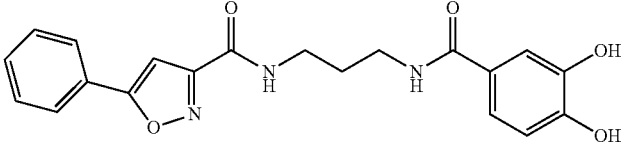 [SMILES: O=C(NCCCNC(=O)c1cc(-c2ccccc2)on1)c1ccc(O)c(O)c1] | 382.20 |
| 37 | 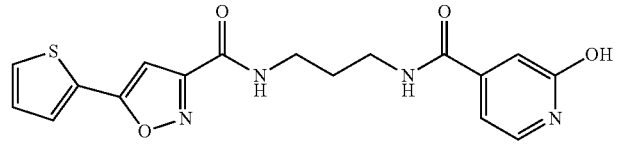 [SMILES: O=C(NCCCNC(=O)c1cc(-c2cccs2)on1)c1ccnc(O)c1] | 373.10 |
| 38 | 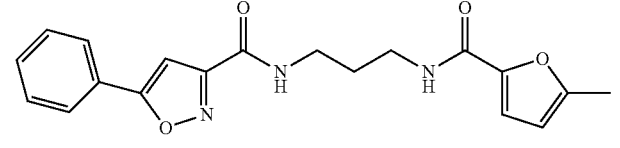 [SMILES: Cc1ccc(C(=O)NCCCNC(=O)c2cc(-c3ccccc3)on2)o1] | 355.80 |

TABLE II-continued

| No. | Compound | LC-MS [M + H]+ |
|---|---|---|
| 39 | | 357.10 |
| 40 | | 371.10 |
| 41 | | 373.10 |
| 42 | | 374.00 |
| 43 | | 417.10 |
| 44 | | 375.10 |
| 45 | | 437.00 |
| 46 | | 387.00 |
| 47 | | 371.10 |

TABLE II-continued

| No. | Compound | LC-MS [M + H]+ |
|---|---|---|
| 48 | | 415.00 |
| 49 | | 373.10 |
| 50 | | 452.90 |
| 51 | | 387.10 |
| 52 | | 387.00 |
| 53 | | 401.10 |
| 54 | | 401.10 |
| 55 | | 371.10 |
| 56 | | 351.10 |

TABLE II-continued

| No. | Compound | LC-MS [M + H]+ |
|---|---|---|
| 57 | 5-phenylisoxazole-3-carboxamide-N-(CH2)3-NH-C(O)-(4-chloropyridin-2-yl) | 385.10 |
| 58 | 5-phenylisoxazole-3-carboxamide-N-(CH2)3-NH-C(O)-(5-hydroxypyridin-2-yl) | 367.20 |
| 59 | 5-phenylisoxazole-3-carboxamide-N-(CH2)3-NH-C(O)-(3-hydroxypyridin-4-yl) | 367.10 |
| 60 | 5-phenylisoxazole-3-carboxamide-N-(CH2)3-NH-C(O)-(2,6-dimethoxypyridin-3-yl) | 411.10 |
| 61 | 5-phenylisoxazole-3-carboxamide-N-(CH2)3-NH-C(O)-(3-fluoropyridin-2-yl) | 369.10 |
| 62 | 5-phenylisoxazole-3-carboxamide-N-(CH2)3-NH-C(O)-(6-bromopyridin-2-yl) | 431.10 |
| 63 | 5-phenylisoxazole-3-carboxamide-N-(CH2)3-NH-C(O)-(2-hydroxy-6-methylpyridin-3-yl) | 381.10 |
| 64 | 5-phenylisoxazole-3-carboxamide-N-(CH2)3-NH-C(O)-(6-hydroxypyridin-3-yl) | 367.10 |
| 65 | 5-phenylisoxazole-3-carboxamide-N-(CH2)3-NH-C(O)-(2-methylpyridin-3-yl) | 365.10 |

TABLE II-continued

| No. | Compound | LC-MS [M + H]+ |
|---|---|---|
| 66 | | 409.10 |
| 67 | | 367.20 |
| 68 | | 446.90 |
| 69 | | 367.10 |
| 70 | | 381.10 |
| 71 | | 365.10 |
| 72 | | 407.10 |
| 73 | | 396.10 |
| 74 | | 426.00 |

TABLE II-continued

| No. | Compound | LC-MS [M + H]+ |
|---|---|---|
| 75 | 5-(thiophen-2-yl)-N-(3-(thiophene-2-carboxamido)propyl)isoxazole-3-carboxamide | 362.00 |
| 76 | 5-(thiophen-2-yl)-N-(3-(5-(trifluoromethyl)furan-2-carboxamido)propyl)isoxazole-3-carboxamide | 414.00 |
| 77 | N-(3-(5-methylfuran-2-carboxamido)propyl)-5-(thiophen-2-yl)isoxazole-3-carboxamide | 360.10 |
| 78 | N-(3-(3-methyl-1,2,4-oxadiazole-5-carboxamido)propyl)-5-(thiophen-2-yl)isoxazole-3-carboxamide | 362.10 |
| 79 | N-(3-(6-aminonicotinamido)propyl)-5-(thiophen-2-yl)isoxazole-3-carboxamide | 372.10 |
| 80 | N-(3-(5-methyl-1,2,4-oxadiazole-3-carboxamido)propyl)-5-(thiophen-2-yl)isoxazole-3-carboxamide | 362.10 |
| 81 | N-(3-(6-chloropicolinamido)propyl)-5-(thiophen-2-yl)isoxazole-3-carboxamide | 391.00 |
| 82 | N-(3-(4-cyanopicolinamido)propyl)-5-(thiophen-2-yl)isoxazole-3-carboxamide | 382.10 |
| 83 | N-(3-(5-chloropyrazine-2-carboxamido)propyl)-5-(thiophen-2-yl)isoxazole-3-carboxamide | 392.40 |
| 84 | N-(3-(2-(1H-indol-3-yl)acetamido)propyl)-5-(thiophen-2-yl)isoxazole-3-carboxamide | 409.10 |

TABLE II-continued

| No. | Compound | LC-MS [M + H]+ |
|---|---|---|
| 85 | | 396.10 |
| 86 | | 400.70 |
| 87 | | 390.70 |
| 88 | | 419.60 |
| 89 | | 407.70 |
| 90 | | 365.70 |
| 91 | | 355.80 |
| 92 | | 385.60 |
| 93 | | 355.80 |

TABLE II-continued

| No. | Compound | LC-MS [M + H]+ |
|---|---|---|
| 94 | | 386.70 |
| 95 | | 402.80 |
| 96 | | 389.70 |
| 97 | | 372.10 |
| 98 | | 402.10 |
| 99 | | 380.00 |
| 100 | | 422.10 |
| 101 | | 374.10 |
| 102 | | 347.10 |

TABLE II-continued

| No. | Compound | LC-MS [M + H]+ |
|---|---|---|
| 103 | | 360.10 |
| 104 | | 347.10 |
| 105 | | 373.10 |
| 106 | | 433.10 |
| 107 | | 425.00 |
| 108 | | 398.00 |
| 109 | | 364.10 |
| 110 | | 374.10 |
| 111 | | 366.70 |

TABLE II-continued

| No. | Compound | LC-MS [M + H]+ |
|---|---|---|
| 112 | | 396.20 |
| 113 | | 374.10 |
| 114 | | 416.10 |
| 115 | | 368.10 |
| 116 | | 354.10 |
| 117 | | 341.10 |
| 118 | | 367.80 |
| 119 | | 426.70 |
| 120 | | 418.70 |

TABLE II-continued

| No. | Compound | LC-MS [M + H]+ |
|---|---|---|
| 121 | 5-phenylisoxazole-3-carboxamide-NH-(CH2)3-NH-C(O)-tetrahydropyran-2-yl | 357.10 |
| 122 | 5-phenyl-1H-pyrazole-3-carboxamide-NH-(CH2)2-NH-C(O)-(2-hydroxy-5-fluorophenyl) | 369.10 |
| 123 | 5-phenyl-1H-pyrazole-3-carboxamide-NH-(CH2)2-NH-C(O)-CH2-(2-hydroxyphenyl) | 365.20 |
| 124 | 5-phenyl-1H-pyrazole-3-carboxamide-NH-(CH2)2-NH-C(O)-(pyridin-4-yl) | 336.20 |
| 125 | 5-phenyl-1H-pyrazole-3-carboxamide-NH-(CH2)2-NH-C(O)-(thiazol-2-yl) | 342.10 |

4. Activity of N-acetamidoalkyl-5-arylisoxazole-3-carboxamide Analogs Analogs in a Cell-Based Assay N-Acetamidoalkyl-5-arylisoxazole-3-carboxamide analogs were synthesized as described above. Changes in expression level of E-cadherin in response to 10 μM compound in SW620 cells was determined in a cell-based functional assay as described above, and the data are shown in Table III. The compound number corresponds to the compound numbers used in Table II.

TABLE III

| Compound No. | fold change SW620 ICW |
|---|---|
| 1 | 3.40 |
| 2 | 1.18 |
| 3 | 3.05 |
| 4 | 2.79 |
| 5 | 8.98 |
| 6 | 0.92 |
| 7 | 2.92 |
| 8 | 2.44 |
| 9 | 1.89 |
| 10 | 2.35 |
| 11 | 2.08 |
| 12 | 3.25 |
| 13 | 5.23 |
| 14 | 0.70 |
| 15 | 3.94 |
| 16 | 3.72 |
| 17 | 1.04 |
| 18 | 1.05 |
| 19 | 1.25 |
| 20 | 2.43 |
| 21 | 4.92 |
| 22 | 1.62 |
| 23 | 0.84 |
| 28 | 3.42 |
| 29 | 3.35 |
| 30 | 2.69 |
| 31 | 3.51 |
| 32 | 2.70 |
| 33 | 3.70 |
| 34 | 2.77 |
| 35 | 2.61 |
| 36 | 2.69 |
| 37 | 1.83 |
| 38 | 3.37 |
| 39 | 4.56 |
| 40 | 1.95 |
| 41 | 2.77 |
| 42 | 0.95 |
| 43 | 1.45 |
| 44 | 3.36 |
| 45 | 3.35 |
| 46 | 3.48 |
| 47 | 2.72 |
| 48 | 1.48 |
| 49 | 1.71 |
| 50 | 1.40 |

TABLE III-continued

| Compound No. | fold change SW620 ICW |
|---|---|
| 51 | 2.73 |
| 52 | 3.99 |
| 53 | 3.52 |
| 54 | 2.22 |
| 55 | 2.98 |
| 56 | 3.43 |
| 57 | 3.30 |
| 58 | 3.57 |
| 59 | 1.26 |
| 60 | 2.32 |
| 61 | 2.94 |
| 62 | 2.59 |
| 63 | 4.59 |
| 64 | 1.80 |
| 65 | 2.05 |
| 66 | 1.55 |
| 67 | 1.22 |
| 68 | 1.61 |
| 69 | 2.00 |
| 70 | 2.62 |
| 71 | 3.61 |
| 72 | 3.13 |
| 73 | 3.04 |
| 74 | 3.06 |
| 75 | 3.05 |
| 76 | 2.68 |
| 77 | 2.99 |
| 78 | 1.97 |
| 79 | 3.58 |
| 80 | 2.83 |
| 81 | 3.09 |
| 82 | 2.80 |
| 83 | 2.64 |
| 84 | 4.59 |
| 85 | 3.26 |
| 86 | 3.48 |
| 87 | 2.40 |
| 88 | 4.43 |
| 89 | 2.13 |
| 90 | 2.50 |
| 91 | 3.47 |
| 92 | 3.13 |
| 93 | 2.88 |
| 94 | 3.69 |
| 95 | 4.20 |
| 96 | 2.58 |
| 97 | 3.82 |
| 98 | 3.65 |
| 99 | 3.66 |
| 100 | 2.37 |
| 101 | 4.24 |
| 102 | 2.87 |
| 103 | 3.02 |
| 104 | 3.13 |
| 105 | 4.26 |
| 106 | 3.69 |
| 107 | 4.15 |
| 108 | 2.45 |
| 109 | 4.02 |
| 110 | 3.74 |
| 111 | 4.13 |
| 112 | 3.86 |
| 113 | 4.09 |
| 114 | 4.70 |
| 115 | 3.83 |
| 116 | 2.60 |
| 117 | 3.71 |
| 118 | 4.38 |
| 119 | 4.13 |
| 120 | 3.08 |
| 121 | 3.74 |
| 122 | 1.45 |
| 123 | 1.37 |
| 124 | 1.29 |
| 125 | 1.77 |

Changes in expression level of E-cadherin in response to 10 μM compound in H520 cells was determined in a cell-based functional assay as described above, and the data are shown in Table IV. The compound number corresponds to the compound numbers used in Table II.

TABLE IV

| Compound No. | fold change H520 ICW |
|---|---|
| 1 | 3.51 |
| 2 | 1.14 |
| 4 | 2.87 |
| 5 | 4.22 |
| 13 | 5.54 |
| 20 | 5.27 |
| 21 | 5.92 |
| 22 | 1.88 |
| 122 | 1.04 |
| 123 | 1.24 |
| 124 | 1.22 |
| 125 | 1.10 |

$EC_{50}$ of induceunce of E-cadherin expression in SW620 cells was determined in a cell-based functional assay as described above, and the data are shown in Table V. The compound number corresponds to the compound numbers used in Table IV.

TABLE V

| Compound No. | $EC_{50}$ SW620 ICW |
|---|---|
| 1 | 3.70 |
| 3 | 7.10 |
| 4 | 8.80 |
| 5 | 4.80 |
| 13 | 4.10 |
| 20 | 5.00 |
| 21 | 4.97 |
| 39 | 5.02 |
| 63 | 5.64 |
| 84 | 1.65 |
| 88 | 6.16 |
| 95 | 2.57 |
| 101 | 4.12 |
| 105 | 5.65 |
| 107 | 6.95 |
| 109 | 9.29 |
| 111 | 7.20 |
| 113 | 4.59 |
| 114 | 6.35 |
| 118 | 5.45 |
| 119 | 5.64 |

$EC_{50}$ of induceunce of E-cadherin expression in H520 cells was determined in a cell-based functional assay as described above, and the data are shown in Table VI. The compound number corresponds to the compound numbers used in Table II.

TABLE VI

| Compound No. | $EC_{50}$ H520 ICW |
|---|---|
| 1 | 5.6 |
| 4 | 5.1 |
| 13 | 1.00 |
| 20 | 1.4 |
| 21 | 1.5 |

5. Compound 13 Modulates E-Cadherin mRNA Levels

Figure 1B:
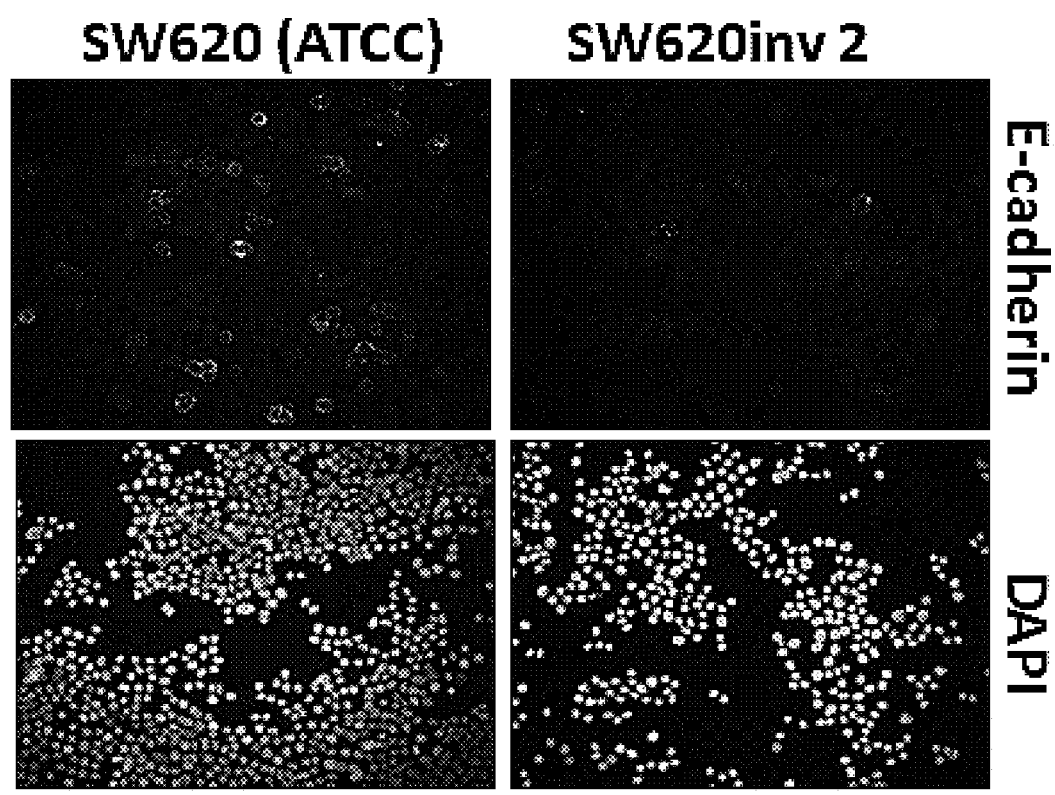
Figure 1C:
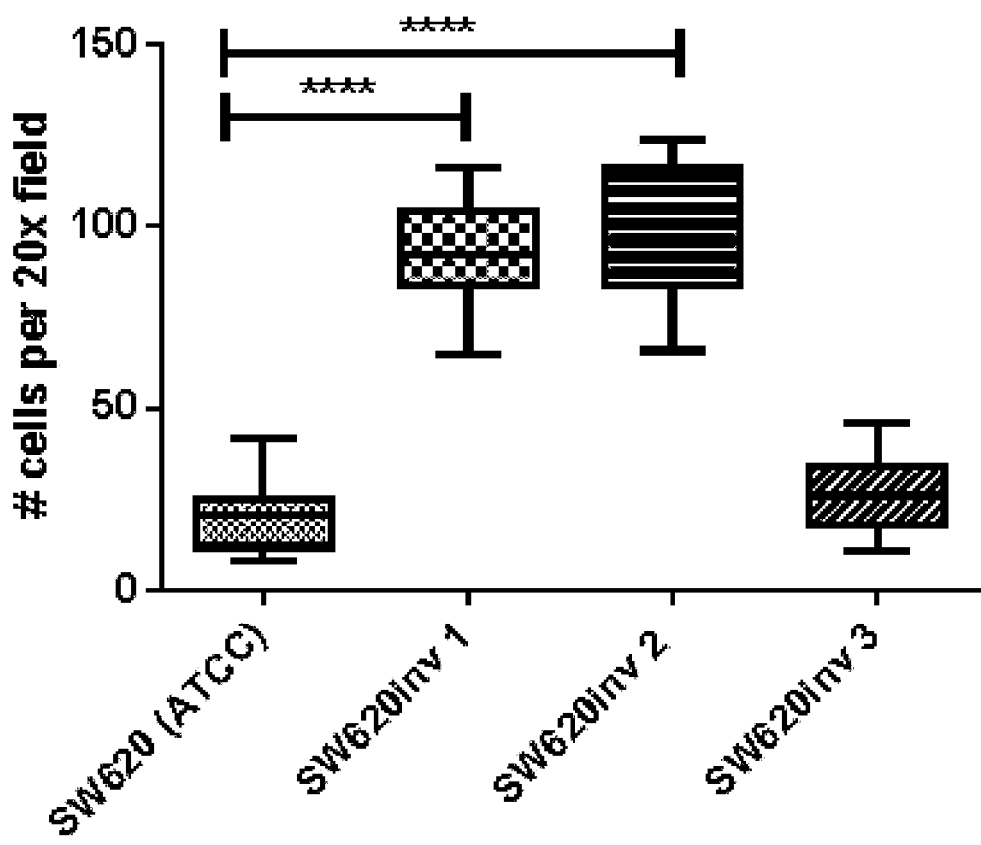

Compounds of the present invention restore E-cadherin protein to the surface of selected aggressive colon and lung cancer cells. This effect is associated with inhibition of the invasive potential of the cells (Stoops, S. L., et al. (2011) *ACS Chemical Biology* 6, 452-465). To further investigate the kinetics and dose dependence of the E-cadherin restoration activity in highly invasive colon and lung cancer cells a population of SW620 colon cancer cells (herein referred to as "SW620inv", Stoops, S. L., et al. (2011) *ACS Chemical Biology* 6, 452-465) were used that were selected for high invasive potential and low E-cadherin expression by passage through matrigel (FIG. 1A-C). The kinetics of altered E-cadherin expression in SW620inv cells was determined by quantitative Western blot, using the Odyssey imaging system. By 6 hours post-treatment with Compound 13, E-cadherin protein levels in lysates from the SW260inv cells were doubled when compared with DMSO vehicle or Compound 124 treatment. The protein levels continued increasing through the 12, 18, and 24 hour time-points (FIG. 2A) and E-cadherin protein levels were maintained at >10× that of control vehicle treated cells. Using the quantitative in-cell Western (ICW) assay (Stoops, S. L., et al. (2011) *ACS Chemical Biology* 6, 452-465) in SW620inv colon cancer cells, an $EC_{50}$ value of 2.22 µM±0.25 was determined for the E-Cadherin restoration activity of Compound 13 (FIG. 2B and FIG. 2C).

Referring to FIG. 1A-C, SW620 p92 from ATCC and 3 independently prepared populations of SW620inv cells (1, 2, 3) were treated with either DMSO or 0.33 µM trichostatin A (TSA) in serum free culture media and cultured for 24 h. FIG. 1A shows a Western blot of E-cadherin and β-actin from 24 h protein lysates. FIG. 1B shows an immunofluorescence of E-cadherin staining comparing SW620 and SW620inv clone B. Images were taken at 200× magnification. FIG. 1C shows a matrigel transwell invasion assay of SW620 cells compared with 4 clones of SW620inv. The number of invading cells is graphed for each group. A Student's t-test was used for statistical comparison of results from each group. **=p<0.00005, =p<0.005.

Figure 2A:
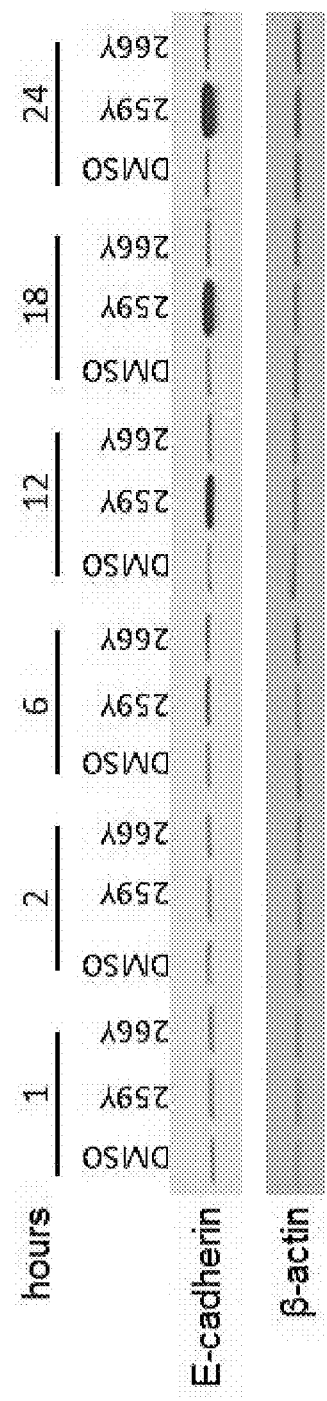
FIG. 2A-C show representative data pertaining to the time dependent (2A) and concentration dependent (2B and 2C) changes in E-cadherin expression following treatment with Compound 13 (259Y).

Referring to FIG. 2A, time dependent changes in SW620inv E-cadherin expression following Compound 13 (259Y) treatment are shown by Western blot.

Figure 2C:
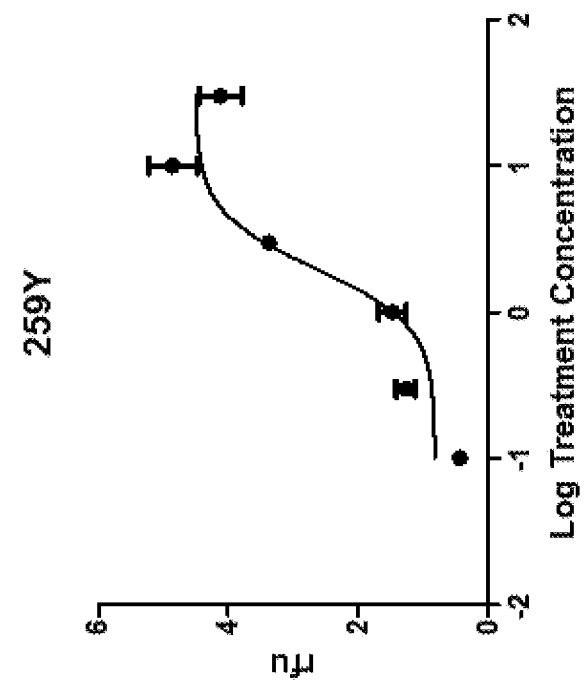
Figure 2B:
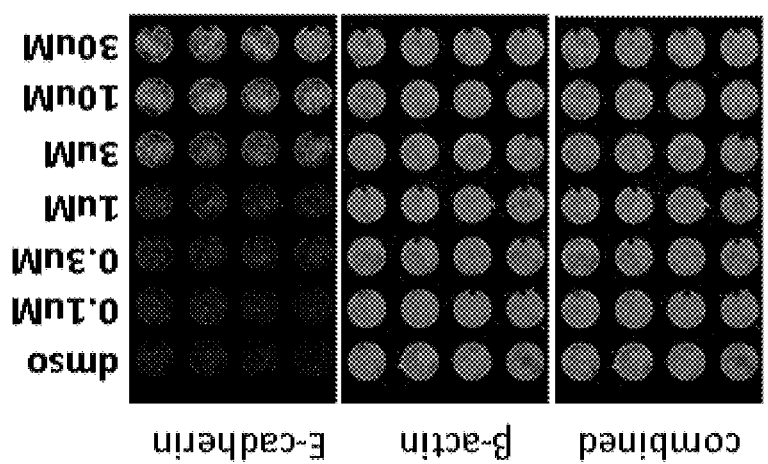

Referring to FIG. 2B and FIG. 2C, concentration dependent changes in E-cadherin expression following 24 hours of Compound 13 (259Y) treatment as determined by quantitative in cell Western (ICW) are shown. The graph shows mean values with standard error bars from 3 biological replicates.

Figure 3A:
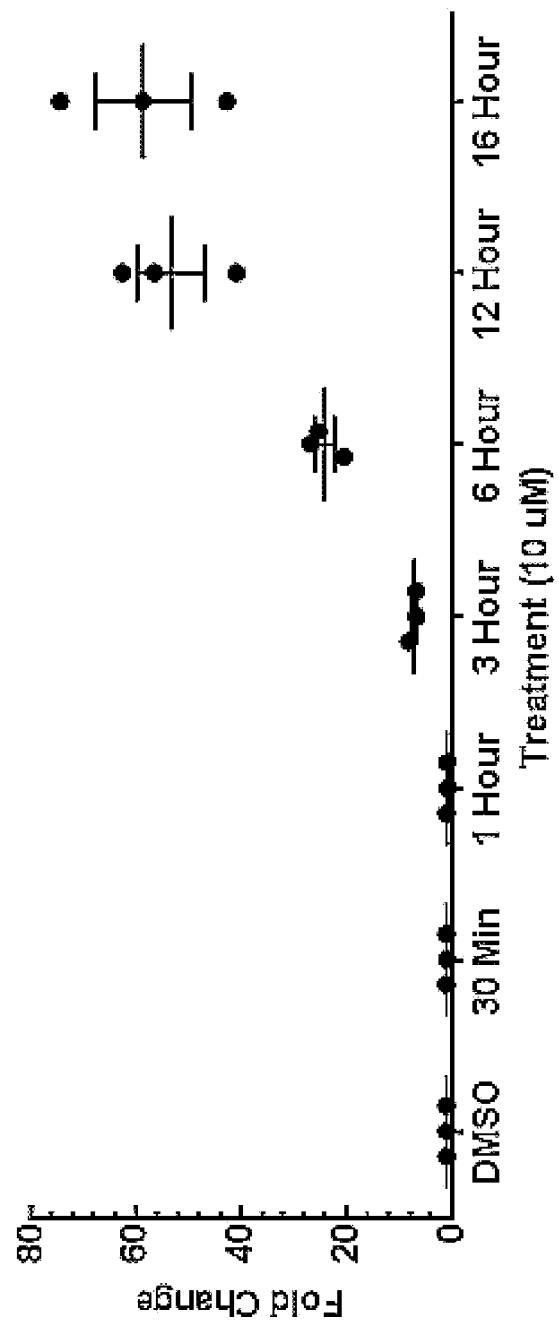
FIG. 3A-C show representative data demonstrating that treatment with Compound 13 (259Y) increases E-cadherin mRNA level.

The effect of Compound 13 treatment on E-cadherin mRNA expression was also determined Compound 13 induced detectable increases in E-cadherin mRNA levels by 3 hours after treatment in the SW620inv cells (FIG. 3A). Compound 13 increased the mRNA levels of E-cadherin specific mRNA by 27-fold in SW620inv cells (FIG. 3B) and by 20-fold in H520 cells (FIG. 3C) by 6 hours post-treatment. Thus, E-cadherin specific mRNA expression increases as early as 3 hours following Compound 13 treatment, while detectable increases in E-cadherin protein levels occur later, at 6-12 hours, consistent with a mechanism involving mRNA transcription or stability. Whether de novo protein synthesis was required for the effect of Compound 13 on E-cadherin mRNA expression was determined. For these experiments, cells were treated with cycloheximide prior to application of Compound 13 and the expression of E-cadherin mRNA was evaluated 6 hours post-treatment for best sensitivity. The levels of cyclin D1 protein, known to have a very short half-life of ~20 minutes (Diehl, J. A., et al. (1998) *Genes & Development* 12, 3499-3511), were analyzed as a positive control for the effectiveness of cycloheximide (CHX) treatment. CHX treatment did not prevent the increase in E-cadherin mRNA levels in response to Compound 13 treatment (FIG. 4A). As shown in FIG. 4B and FIG. 4C, cyclin D1 levels were markedly reduced within the 7 hour experimental interval, but the more stable β-actin protein levels were not significantly altered. Thus, without wishing to be bound by theory, these data suggest that de novo protein synthesis may not be required for Compound 13 activity on E-cadherin mRNA expression.

Referring to FIG. 3A, E-cadherin transcriptional effect with 10 µM Compound 13 (259Y) treatment at the indicated timing is shown. E-cadherin specific mRNA species were measured for each of four biological replicates by qPCR. Fold change relative to DMSO treatment (set to 1) is determined by the formula $\log_2^{-\Delta\Delta C_p}$.

Figures 3B, 3C:
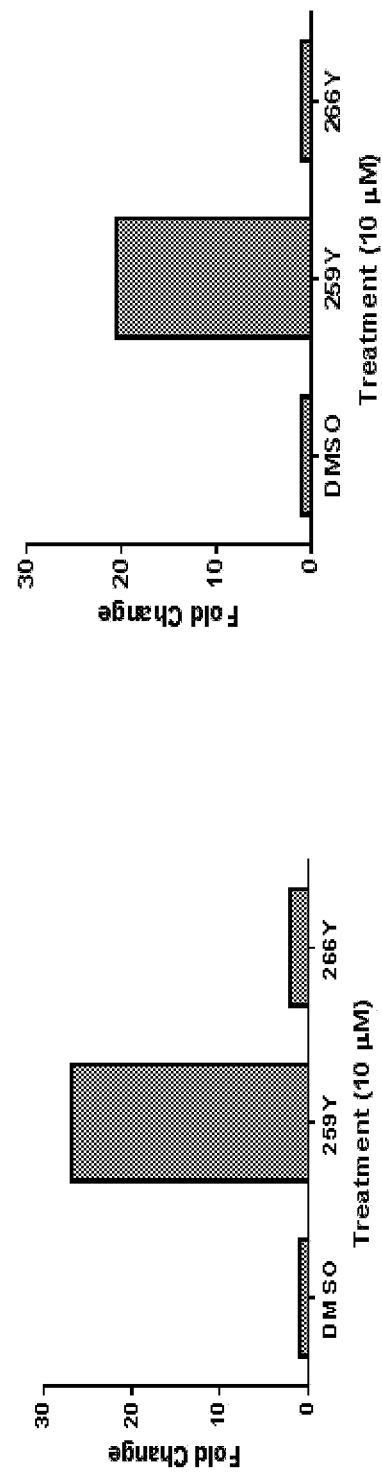
Figure 4A:
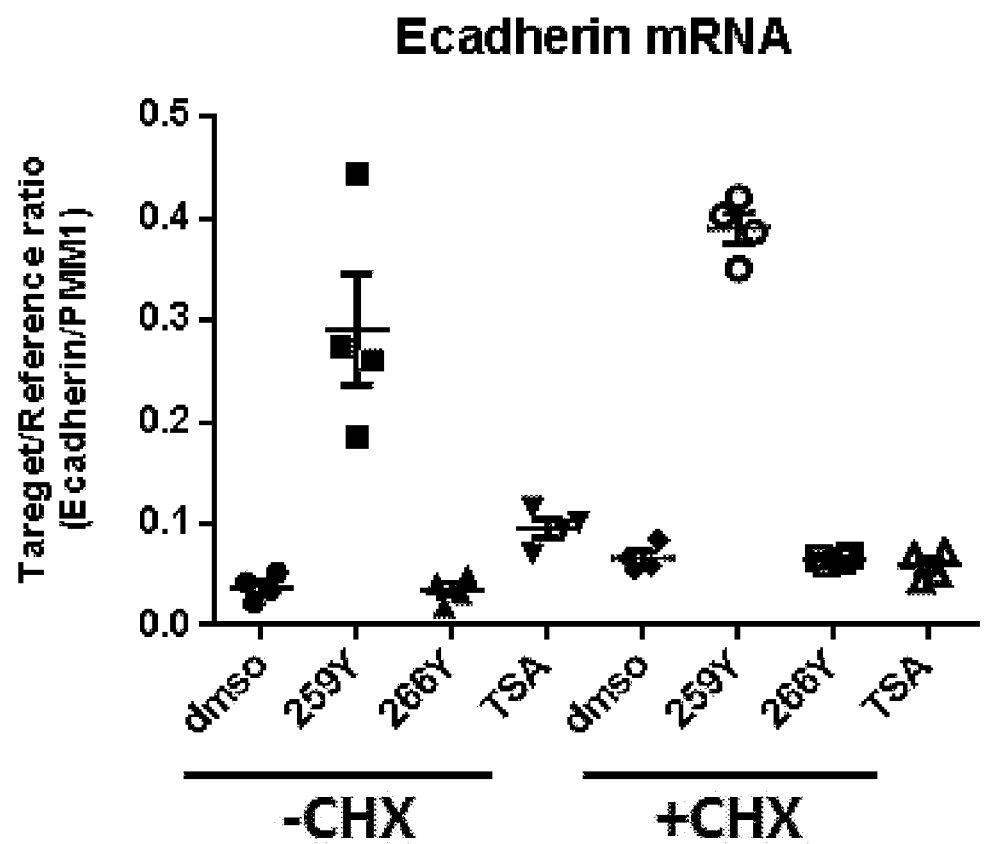
FIG. 4A-C show representative data pertaining to the activity of Compound 13 (259Y) and Compound 124 (266Y). Specifically, the quantification of E-cadherin specific mRNA by qPCR (4A) and the quantification of cyclin D1 protein by ICW (4B and 4C) are shown.
Figure 4C:
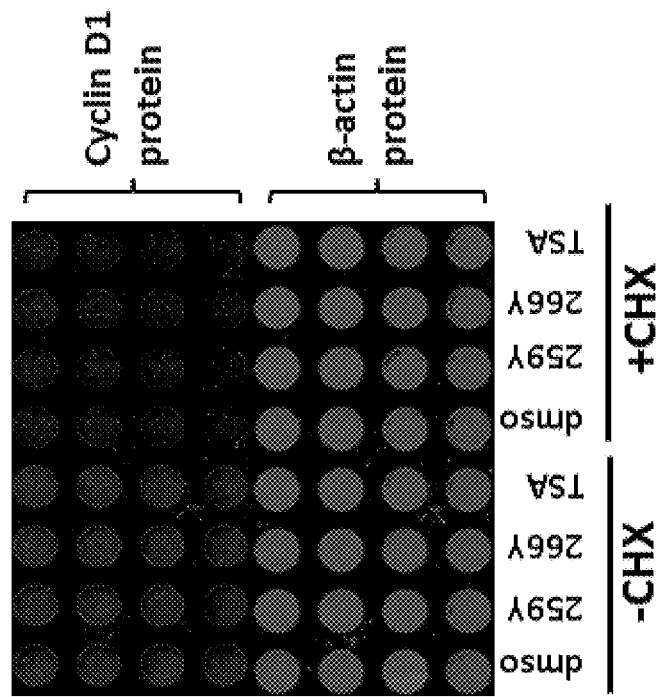
Figure 4B:
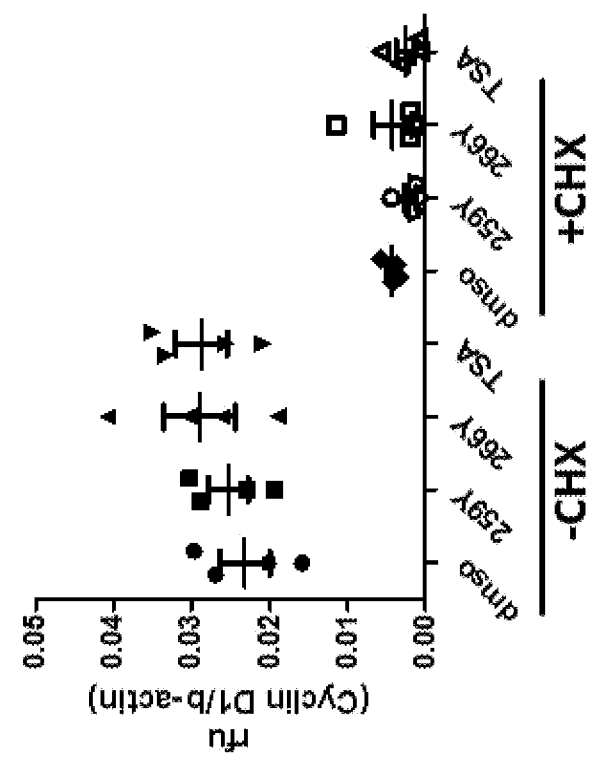

Referring to FIG. 3B and FIG. 3C, changes in E-cadherin cellular mRNA levels in SW620inv (3B) and H520 cells (3C) are shown following treatment for 6 hours with 10 µM Compound 13 (259Y), fold change as above.

Referring to FIG. 4A, quantification of E-cadherin specific mRNA by qPCR is shown. Cells were treated for 1 hour with DMSO or 100 µM/mL cycloheximide, then DMSO, 10 µM Compound 13 (259Y), 10 µM Compound 124 (266Y), or 0.33 µM TSA were added for 6 hours prior to harvest RNA. Fold change relative to DMSO without cycloheximide was calculated by the formula $\log_2^{-\Delta\Delta C_p}$.

Referring to FIG. 4B and FIG. 4C, quantification of cyclin D1 protein by ICW, as described above, and under similar conditions as in (4A) at 6 h post-treatment with or without cyclohexamide.

Figure 5:
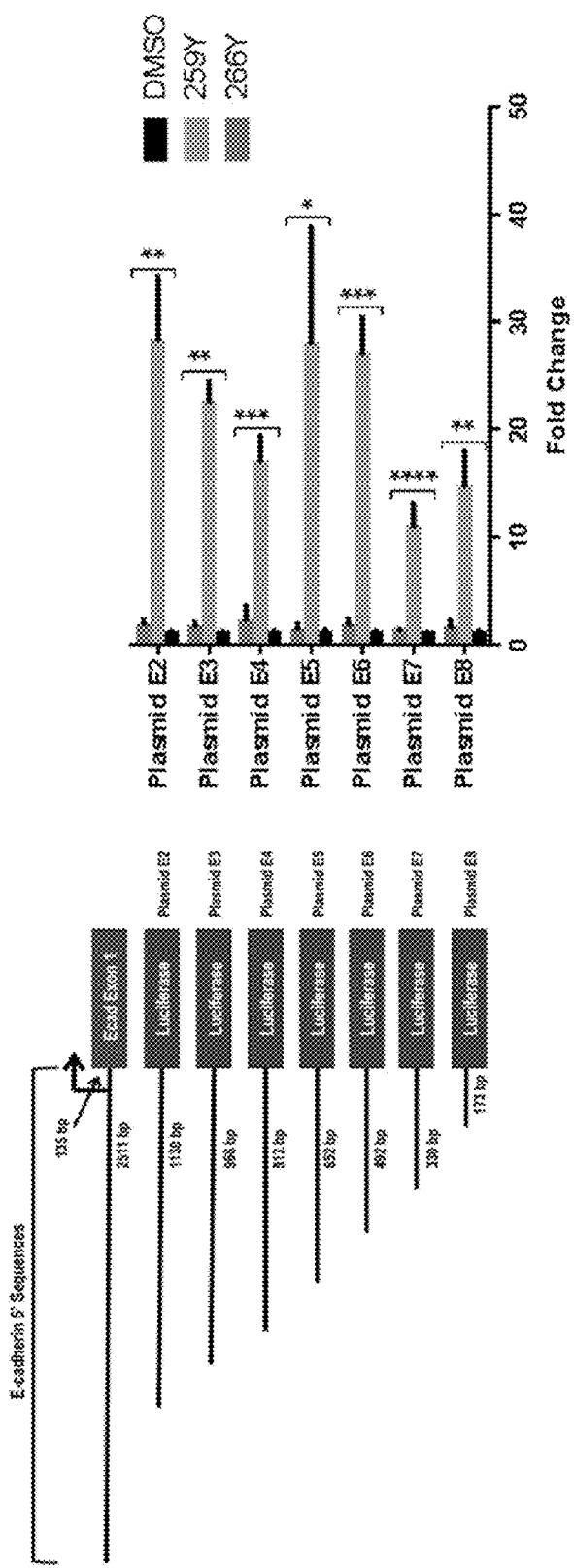
FIG. 5 shows a representative schematic of the eight E-cadherin promoter reporter plasmids (full length and truncated) used to identify the promoter elements critical for promoter activity.

6. Compound 13 Activity is Associated with a Proximal Region of the CDH1 Promoter and Increases Binding of Transcription Activated Markers Compound 13 (259Y) induces>20-fold increases in reporter activation driven by the 1130 bp promoter region in an assay in which an exogenous firefly luciferase gene is driven by defined regions of the human E-cadherin promoter. This region includes consensus binding sequences for several known transcription factors, including AML1, P300, Snail and SP1 (Liu, Y. N., et al. (2005) *Oncogene* 24, 8277-8290). Serial deletion of the distal regions of the promoter reduced the efficiency of the Compound 13 effect to >10× above control, particularly when the region between −492 bp to −330 bp, containing consensus binding sequences for HNF3, P300, AML1 and Snail transcription factors, were deleted. Importantly, significant Compound 13 specific promoter-responsive activity was retained with the proximal (173 bp) region of the E-cadherin promoter (FIG. 5). This 173 bp region of the E-cadherin promoter contains multiple consensus binding sequences for SP1 and Snail transcription factors (FIG. 6) and was used for further transcriptional studies.

Referring to FIG. 5, a diagram of the 8 E-cadherin promoter reporter plasmids (full length and truncations) utilized to determine promoter elements critical for promoter activity is shown. SW620inv cells were transfected for 4 hours with one of the 8 reporter plasmids and a CMV-β-gal plasmid for purposes of normalization, then treated for 24 hours with DMSO, 10 µM Compound 13 (259Y), or 10 µM Compound 124 (266Y). Fold change is $\log_2^{-\Delta\Delta C_p}$ of the normalized fluorescence signal relative to the mean of the DMSO treated group. Statistical significance was calculated using a two-way ANOVA (Holm-Sidak method): **=p<0.00005, *=p<0.0005, **=p<0.005,

*=p<0.05. Data points represent technical replicates (n=3) from a representative experiment.

Figure 6:
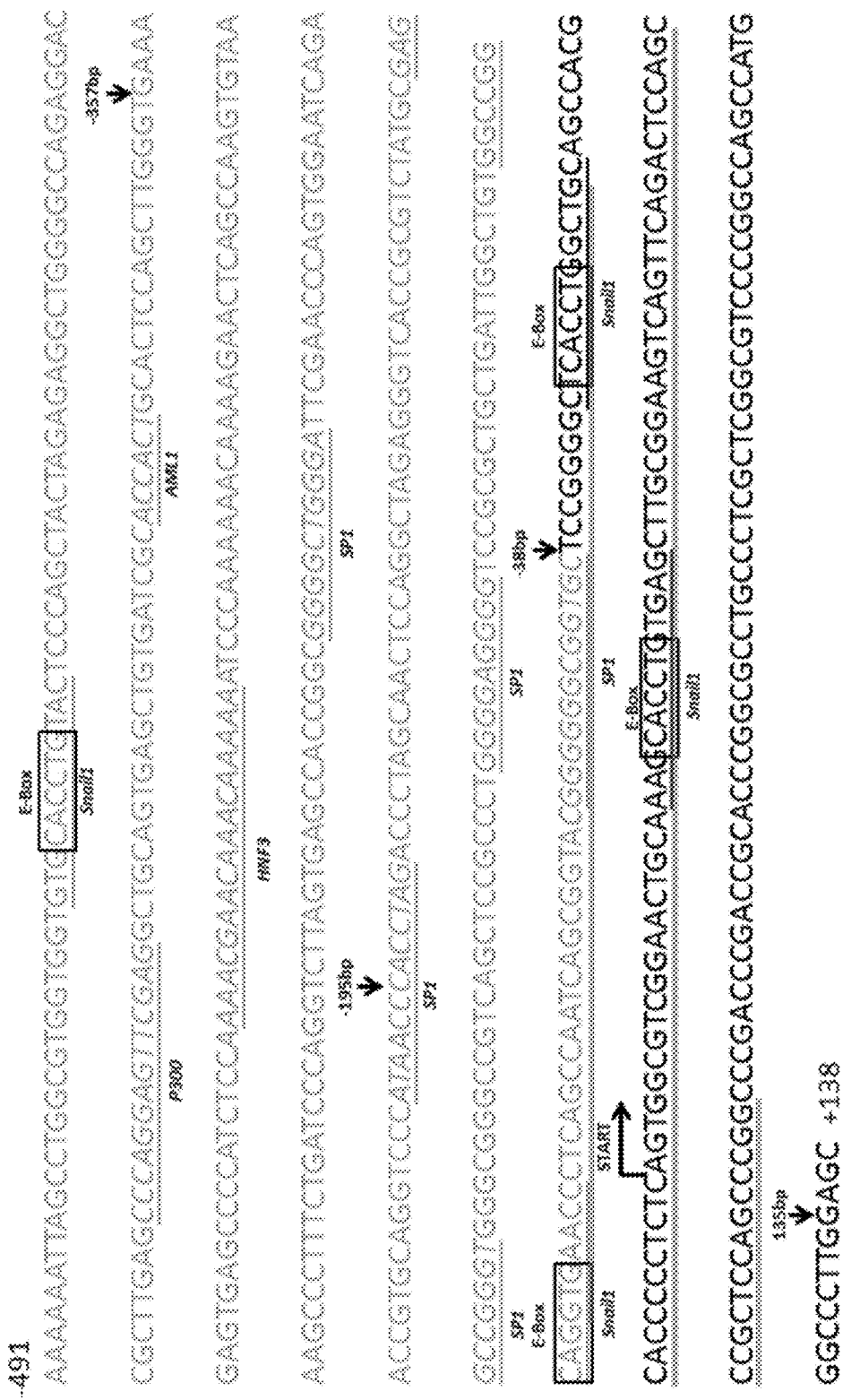
FIG. 6 shows a representative schematic of the human E-cadherin promoter region important for Compound 13 (259Y) studies.

Referring to FIG. 6, a schematic showing the sequence of the −491 to +138 bp promoter region of the human E-cadherin promoter (adapted from Liu, et al. (2005) *Oncogene* 24, 8277-8290). Downward pointing arrows with base pair (bp) position numbers indicating the boundaries of plasmids E6, E7 and E8 are indicated. The transcriptional start site (codon AGT) is marked with a bold arrow, E-boxes (CACCTG or CAGGTG) are designated by boxes and Snail1 binding sites are underlined and indicated below the sequence. The sequence of the PCR product used in the ChIP assays (139 bp product from -74 bp to +64 bp) is indicated by a bold underline. Other consensus binding sequences for additional transcription factors of interest including P300, AML1, HNF3 and SP1 are underlined and indicated by italics. The sequence with dark black typing represents E-cadherin regulatory sequences E8 (−38/+135).

Figure 7A:
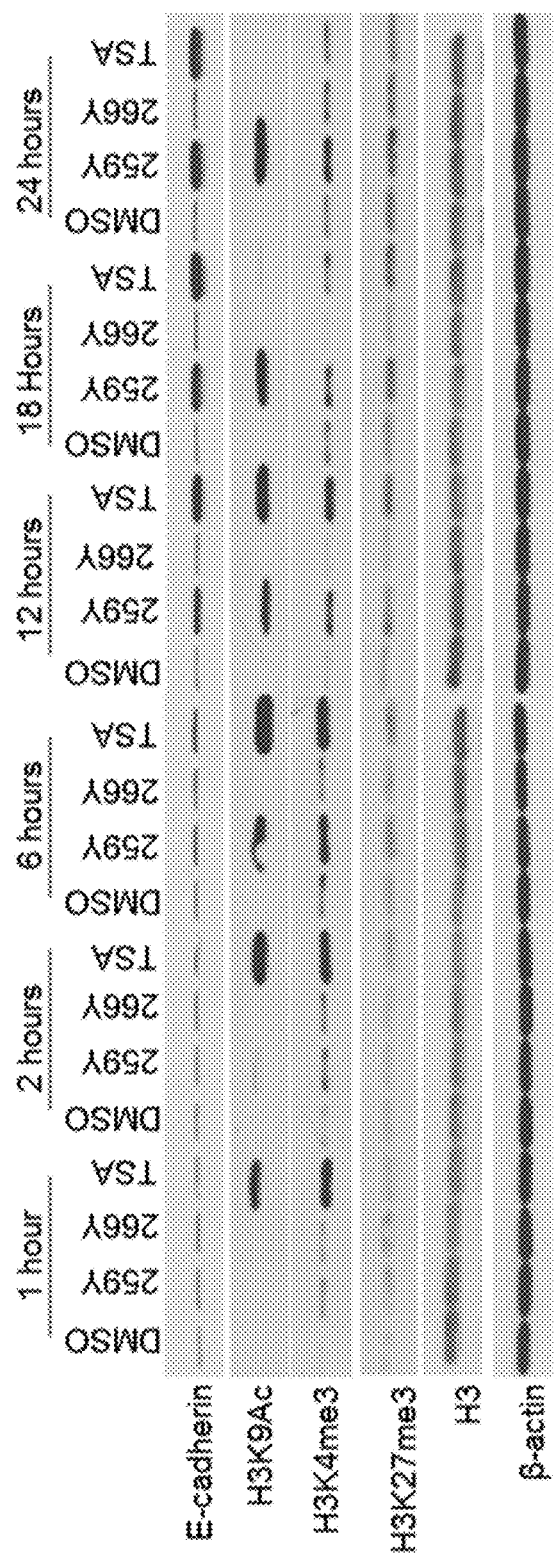
FIG. 7A-C shows representative data demonstrating that Compound 13 (259Y) activity alters histone acetylation and methylation status (7A) and is associated with a proximal region of the E-cadherin promoter in H520 lung carcinoma cells (7B) and SW620inv cells (7C).
Figure 7B:
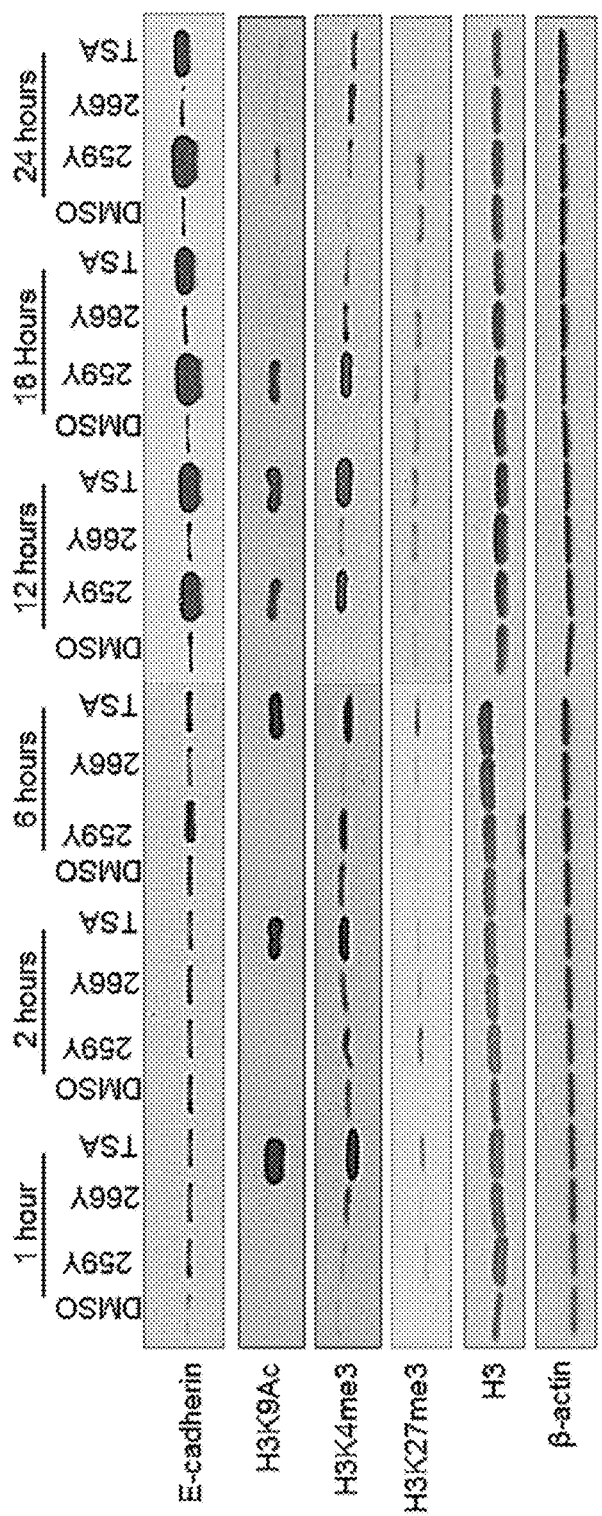

E-cadherin expression may be induced by HDAC inhibitors (Kakihana, M., et al. (2009) *Journal of Thoracic Oncology: Official Publication of the International Association for the Study of Lung Cancer* 4, 1455-1465). Trichostatin A (TSA) is a compound exhibiting well-known histone deacetylase (HDAC) inhibitory activity. The time-course of E-cadherin, acetylation and methylation of Histone 3 (H3) was monitored following treatment with DMSO, Compound 13, Compound 124, or TSA. It was discovered that Compound 13 increases E-cadherin expression with similar kinetics as does TSA in SW620inv cells. However, global H3 modifications marking active chromatin, namely H3K9Ac and H3K4me3, occur and are maintained later relative to the effect observed following TSA treatment. Thus, while TSA causes an increase in H3K9Ac and H3K4me3 levels as early as 1 hour and peaks by 6 hours post-treatment, similar changes are not observed with Compound 13 treatment until 6 hours. Further, these changes are maintained through 24 hours post-treatment, indicating a distinct and potentially indirect mode of action. Less overall modification of the repressive marker H3K27me3 was noted for both Compound 13 and TSA and the kinetic profile of these modifications were similar (FIG. 7A). Similar results were seen in H520 cells (FIG. 7B). It was previously reported that similar compounds did not show activity against any of HDACs 1-11(HDAC class I, II, and IV) on analysis by Reactive Biology Corporation or sirtuins (HDAC class III) as determined by MDS Pharma Services (Liu, Y. N., et al. (2005) *Oncogene* 24, 8277-8290). Therefore, without wishing to be bound by theory, these data suggest that Compound 13 does not act as a HDAC inhibitor, but that its effect on histone acetylation is indirect. These results do not exclude other mechanisms of histone modification that are linked with increased E-cadherin expression.

Referring to FIG. 7A, the relative abundance of E-cadherin, H3K9Ac, H3K4me3, H3K27me3, H3 and beta actin proteins are shown following treatment with DMSO, 10 µM Compound 13 (259Y), 10 µM Compound 124 (266Y), or 0.33 µM TSA at intervals over a 24 hour time course as measured by Western blot.

Referring to FIG. 7B, the results of a ChIP assay demonstrating Polymerase II (Pol2), H3K4me3, H3K9Ac and H3K27me3 association with the proximal region of the E-cadherin promoter are shown following 3 hour treatment in H520 lung carcinoma cells with either DMSO or 10 µM Compound 13 (259Y).

Figure 7C:
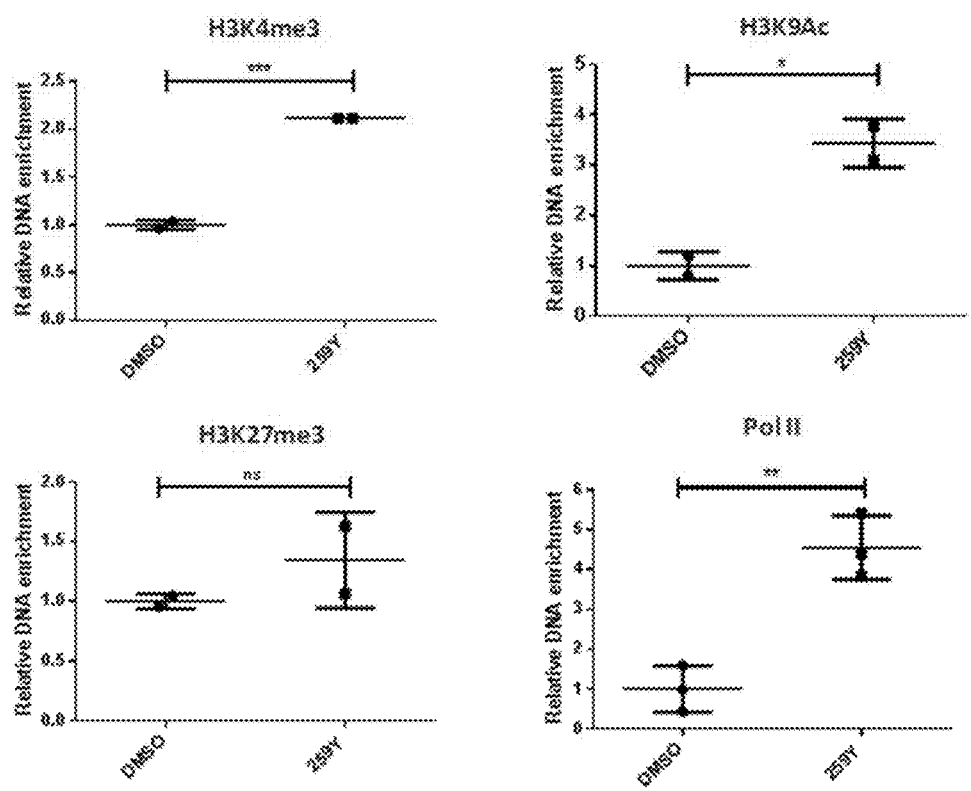
Figure 8:
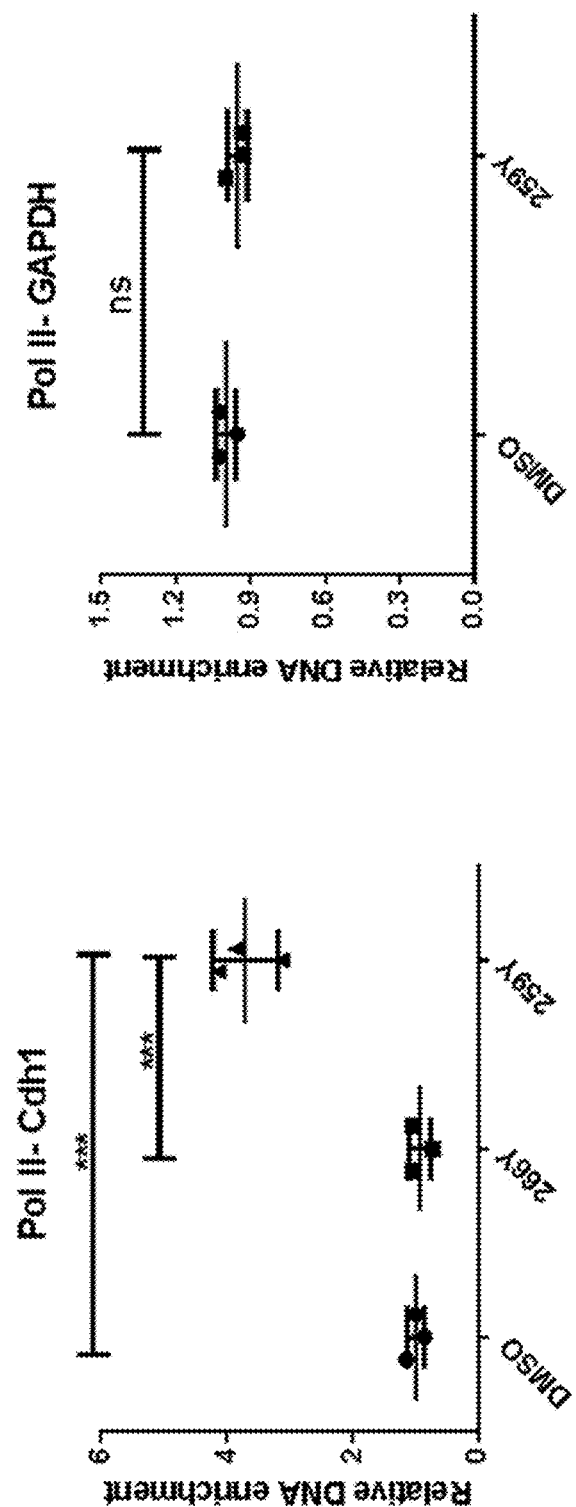
FIG. 8 shows representative data demonstrating that Polymerase II (Pol II) is associated with the proximal region of the E-cadherin promoter.

ChIP assays were performed using antibodies against H3K4me3, H3K9Ac, H3K27me3 and polymerase II (Pol II) in SW620inv cells treated with DMSO and Compound 13 for 4 hours, and the proximal promoter of E-cadherin was detected in the precipitates. As shown in FIG. 7C, significantly enriched binding of H3K4me3 (2.1-fold), H3K9Ac (3.4-fold) and Pol II (4.6-fold) was associated with the E-cadherin promoter following treatment of SW620inv cells with Compound 13. Compound 13 also increased Pol II association with the E-cadherin proximal promoter (3.7-fold), but did not alter Pol II association with GAPDH promoter, which was used as the internal control for all ChIP analysis in this study (FIG. 8). Compound 124 did not show any effect on Pol II occupancy on E-cadherin proximal promoter (FIG. 8). Without wishing to be bound by theory, these data suggest that Compound 13 may activate transcription at the E-cadherin promoter and act through a mechanism that alters chromatin structure by modification of transcriptionally relevant histone status in this region. In contrast, there was no significant difference in H3K27me3 binding, a marker of repressed chromatin, after treatment of cells with Compound 13.

Referring to FIG. 7C, the results of a ChIP assay demonstrating Polymerase II (Pol2), H3K4me3, H3K9Ac and H3K27me3 association with the proximal region of the E-cadherin promoter are shown following 3 hour treatment in SW620inv cells with either DMSO or 10 µM Compound 13 (259Y) (results from a representative experiment (n=2 or 3 technical replicates) are shown).

Figure 7D:
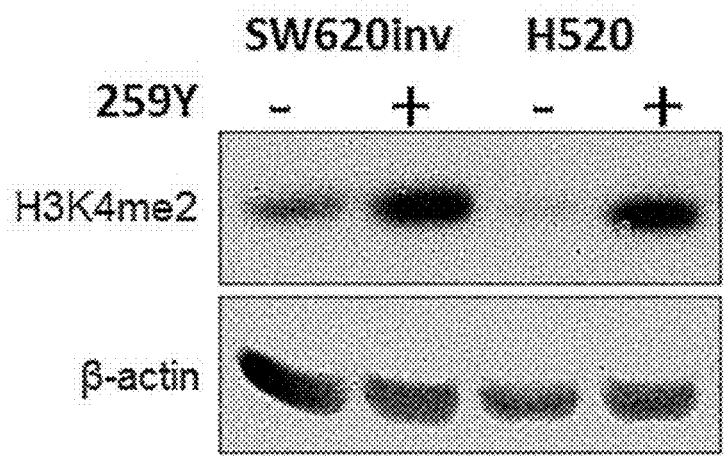
FIGS. 7D and 7E show representative data demonstrating an increase in H3K4me2 levels in response to Compound 13 (259Y) (7D) and a lack of increase in binding of H3K27me3 to the Cdh1 promoter (7E).

Referring to FIG. 7D, increased levels of H3K4me2 were observed in response to Compound 13 (259Y) in both SW620inv cells and H520 cells.

Figure 7E:
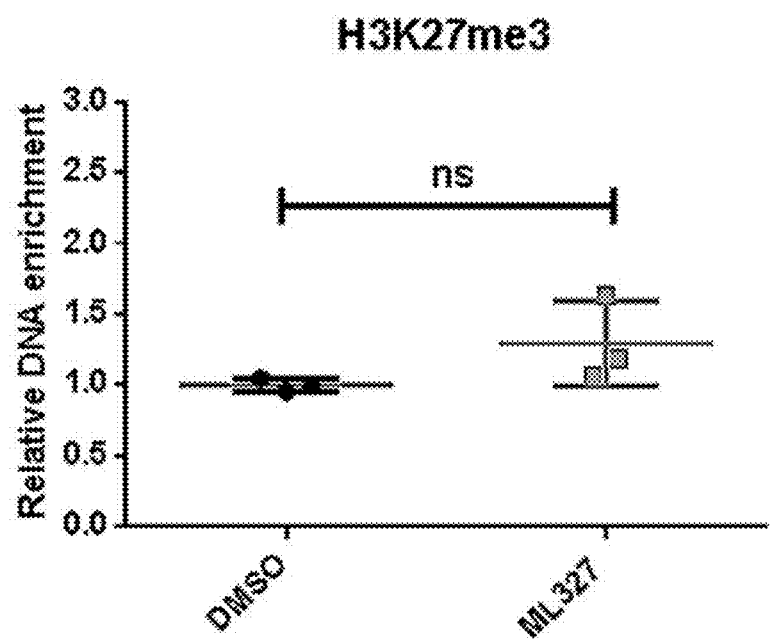

Referring to FIG. 7E, a lack of increase in binding of H3K27me3 to the Cdh1 promoter was observed in H520 cells.

Referring to FIG. 8, the results of a ChIP assay analyzing Pol2 binding to the E-cadherin promoter (Cdh1) after treatment with either DMSO vehicle, Compound 124 (266Y), or Compound 13 (259Y) are shown (left panel). The right panel shows a negative control demonstrating a lack of increase in Pol2 engagement with the GADPH promoter in response to Compound 13 (259Y).

7. Compound 13 Inhibits TGF-b-Induced EMT

Tumor cell dissemination is critical in cancer progression and involves multiple processes, leading to the generation of metastases at remote loci. Cancer dissemination is initiated by the process of EMT, which results in decreased cell-cell adhesion, increased motility and invasive properties that allow carcinoma cells to detach from the primary tumor and invade surrounding tissue, through collective or individual cell migration (Katsuno, Y., et al. (2013) *Current Opinion in Oncology* 25, 76-84). Overcoming cellular mechanisms of de novo and acquired resistance to drug therapy remains a central challenge in the clinical management of many cancers, and much work has linked the EMT in cancer cells to the emergence of drug resistance. Transforming growth factor-β (TGF-β), a secreted cytokine, regulates a variety of processes in development and cancer. Specifically, TGF-β can induce EMT of carcinoma cells. At the heart of TGF-β regulation of EMT is a nuclear reprogramming involving a set of transcription factors, i.e., the basic helix loop helix proteins Twist and E47, the zinc finger proteins Snail and Slug, the zinc finger and homeodomain proteins ZEB1 and ZEB2, and FOXC2. Together, these factors repress the expression of E-cadherin, which is a crucial step of EMT, as well as other epithelial markers, but also enhance the expression of mesenchymal genes (Heldin, C. H., et al. (2012) *FEBS Lett.* 586, 1959-1970). Murine mammary epithelial NMuMG cells are known to undergo an EMT that is readily apparent at 36 hours after TGF-β treatment (Miettinen, P. J., et al. (1994) *J. Cell Biol.* 127, 2021-2036).

To examine the ability of compounds of the present invention to push cells from the mesenchymal phenotype to a more epithelial phenotype, reversing the EMT, Compound 13 was examined in a well-studied and reproducible experimental system. For these experiments, cells were treated with TGF-β for 48 hours to induce EMT and then allowed to continue to grow under those conditions in the presence or absence of Compound 13 added to the culture media. It was found that Compound 13 restored E-cadherin expression at the plasma membrane in NMuMG cells treated with TGF-β (FIG. 9A) and also demonstrated that treatment with Compound 13 increased expression of both E-cadherin and occludin mRNA species in NMuMG cells, relative to cells treated with TGF-β alone. In addition, Compound 13 similarly decreased expression of Vimentin mRNA species in the same experimental system (FIG. 9B), indicating that Compound 13 reverses typical phenotypic features of EMT.

Figure 9A:
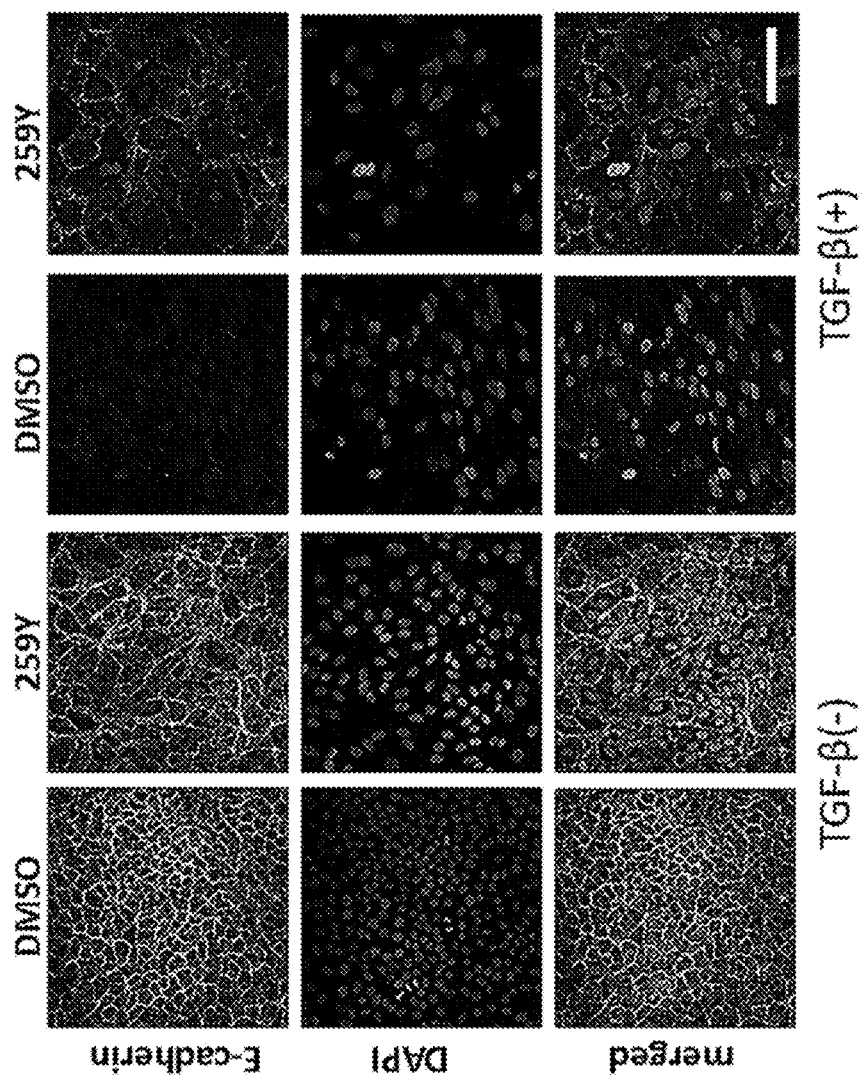
FIGS. 9A and 9B show representative data demonstrating that Compound 13 (259Y) partially reverses EMT in NMuMg cells.

Referring to FIG. 9A, immunofluorescence images showing E-cadherin (top panels) expression and localization in NMuMg cells following treatment with or without 5 ng/mL TGF-β for 72 hours, then adding either DMSO, 10 μM Compound 13 (259Y), or 10 μM Compound 124 (266Y) for another 48 hours are shown. The nuclear stain was labeled with DAPI. Bottom panels indicate merged E-cadherin and nuclear stain. The images were taken with Olympus Fluoview FV1000 confocal microscope. Bar=100 μM.

Figure 9B:
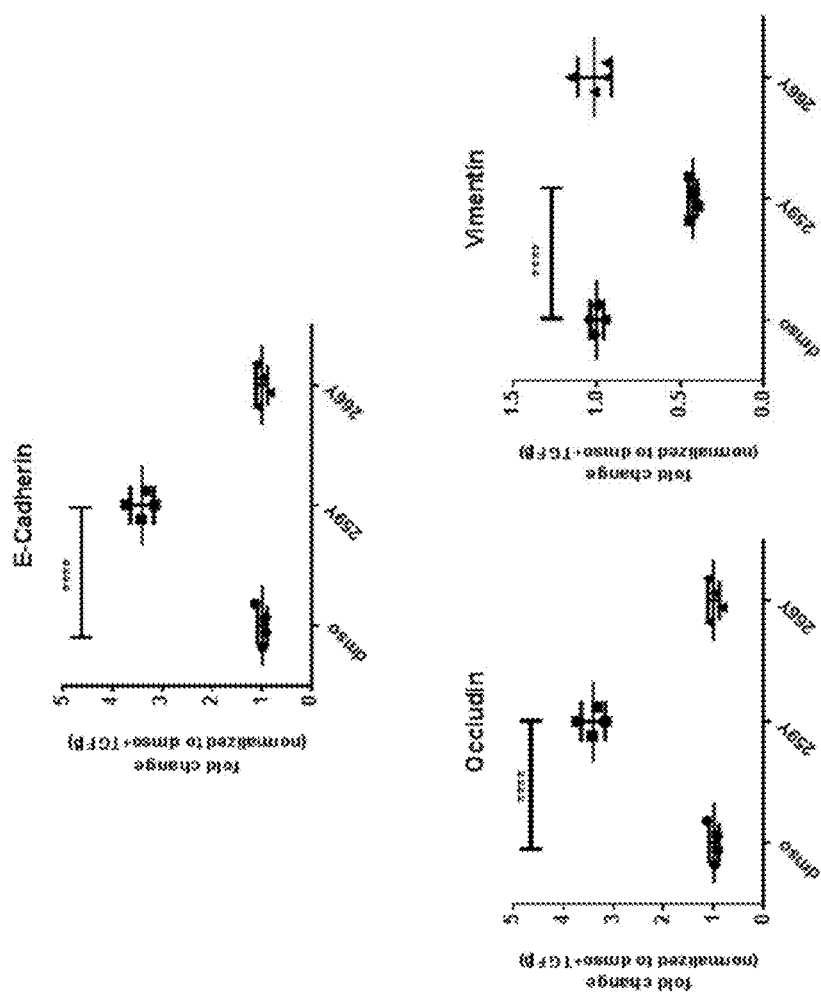

Referring to FIG. 9B, relative levels of E-cadherin, Occludin and Vimentin specific mRNA species in TGF-beta1 treated (48 hours) NMuMg cells followed by Compound 13 (259Y) treatment for 6 hours.

8. Compound 13 Alters E-Cadherin Expression and Global Markers of Histone Activation in Endothelial Cells Endothelial cells form a continuous cell layer along the walls of blood vessels and control the movement of solutes and fluid from the vascular space to the tissues (Stevens, T., et al. (2000) *American Journal of Physiology Lung Cellular and Molecular Physiology* 279, L419-422). Vascular endothelial (VE)-cadherin is a strictly endothelial specific adhesion molecule located at junctions between endothelial cells. In analogy to the role of E-cadherin as major determinant for epithelial cell contact integrity, VE-cadherin is of vital importance for the maintenance and control of endothelial cell contacts, and is essential for controlling endothelial monolayer permeability and angiogenesis (Vestweber, D. (2008) *Arteriosclerosis, Thrombosis, and Vascular Biology* 28, 223-232; Suzuki, H., et al. (2002) *Nat. Genet.* 31, 141-149).

Figure 10A:
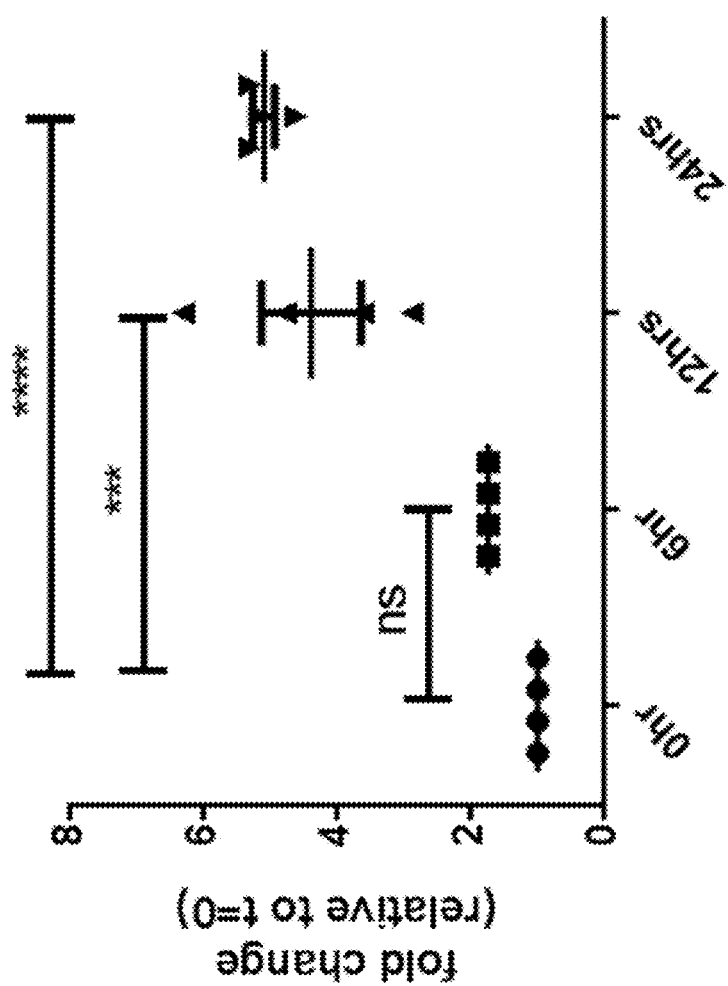
FIG. 10A-D shows representative data (10B) and quantitation (10A) pertaining to the changes in E-cadherin expression as well as changes in histone markers (10C) compared with effects induced by an HDAC inhibitor (10D) at extended time points upon dosing with Compound 13 (259Y).
Figure 10B:
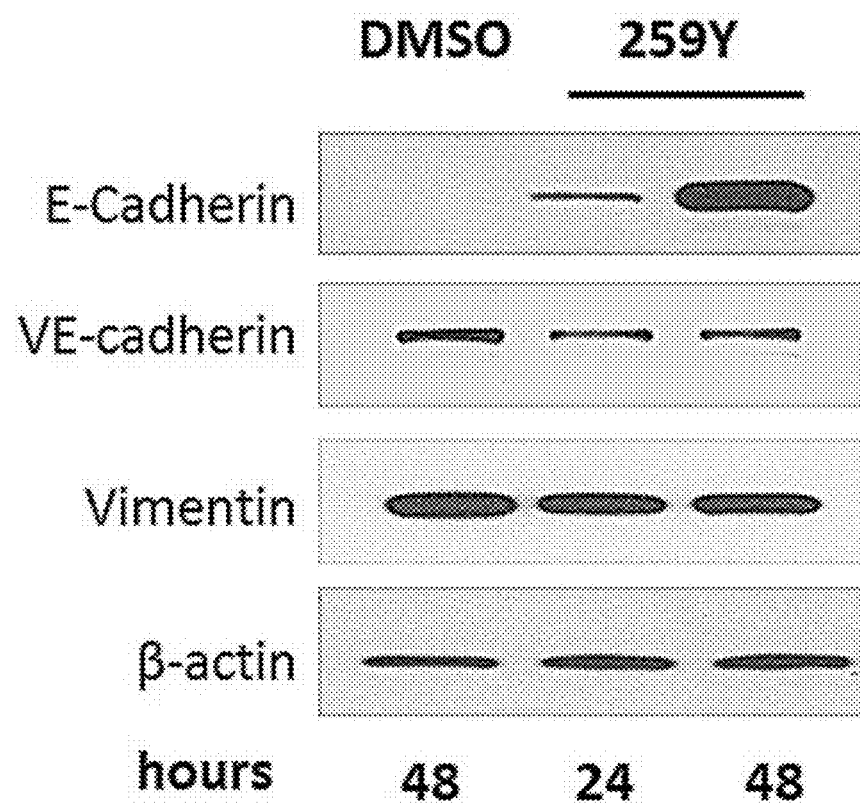
Figure 10C:
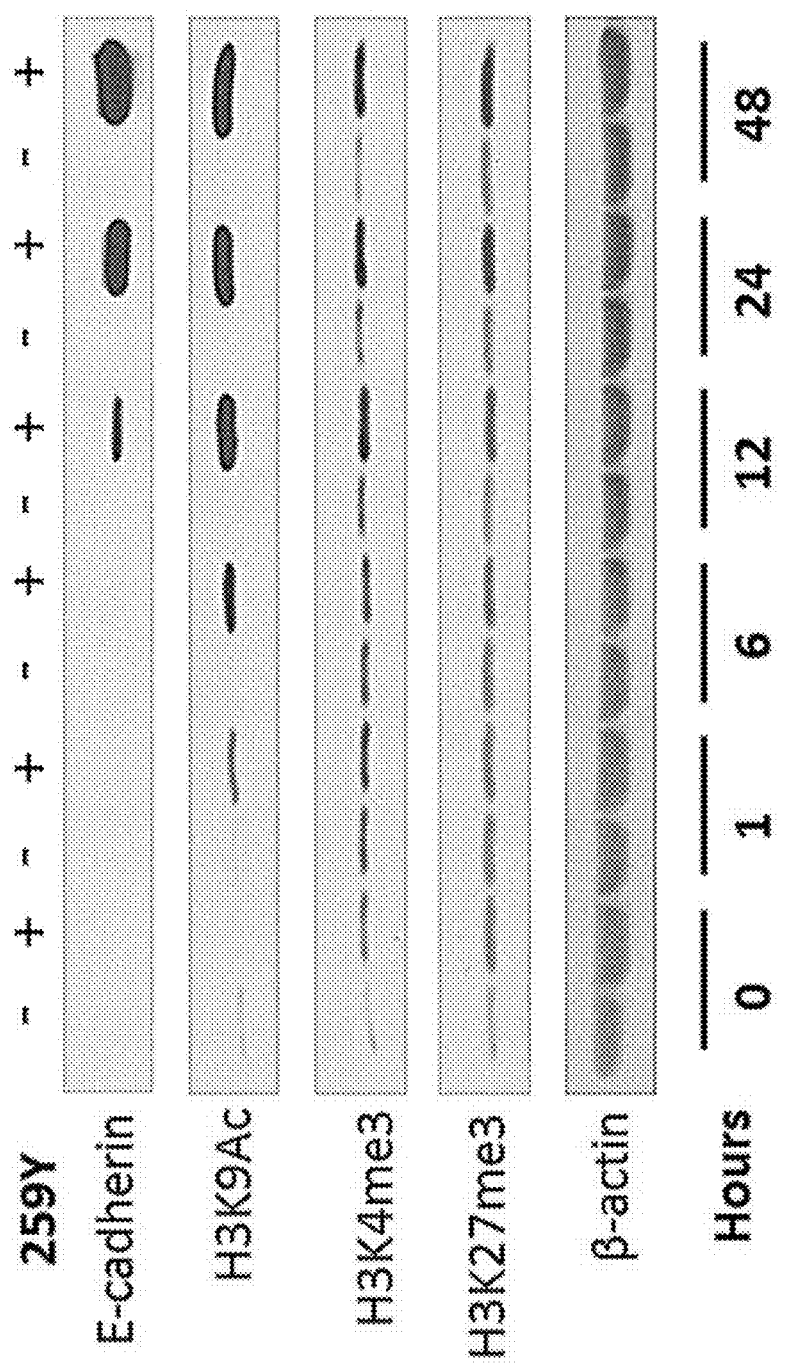

The human microvascular endothelial cell line, HMEC-1, is an immortalized human microvascular endothelial cell line that retains the morphologic, phenotypic, and functional characteristics of normal human microvascular endothelial cells, and does not express E-cadherin, but expresses abundant VE-cadherin. It was found that Compound 13 induced expression of E-cadherin mRNA species (>5x) in HMEC-1 cells by 12 and 24 hours after treatment (FIG. 10A). Compound 13 also induced E-cadherin protein levels from undetectable levels to abundant levels easily detectable by Western blot analysis by 24 hour after treatment of HMEC-1 cells. This effect was associated with decreased levels of VE-cadherin and Vimentin (FIG. 10B). The effects of Compound 13 on E-cadherin in HMEC-1 cells were associated with increased levels of H3K9Ac detectable by 1 hour after treatment and that preceded modest increases in both H3K4me3 and H3K27me3 at 12 hours (FIG. 10C). Without wishing to be bound by theory, these data may indicate a similar mechanism for the activity of Compound 13 and similar isoxazole-based analogs in the non-epithelial HMEC-1 cells as in the epithelial cell lines, but with different kinetics.

Figure 10D:
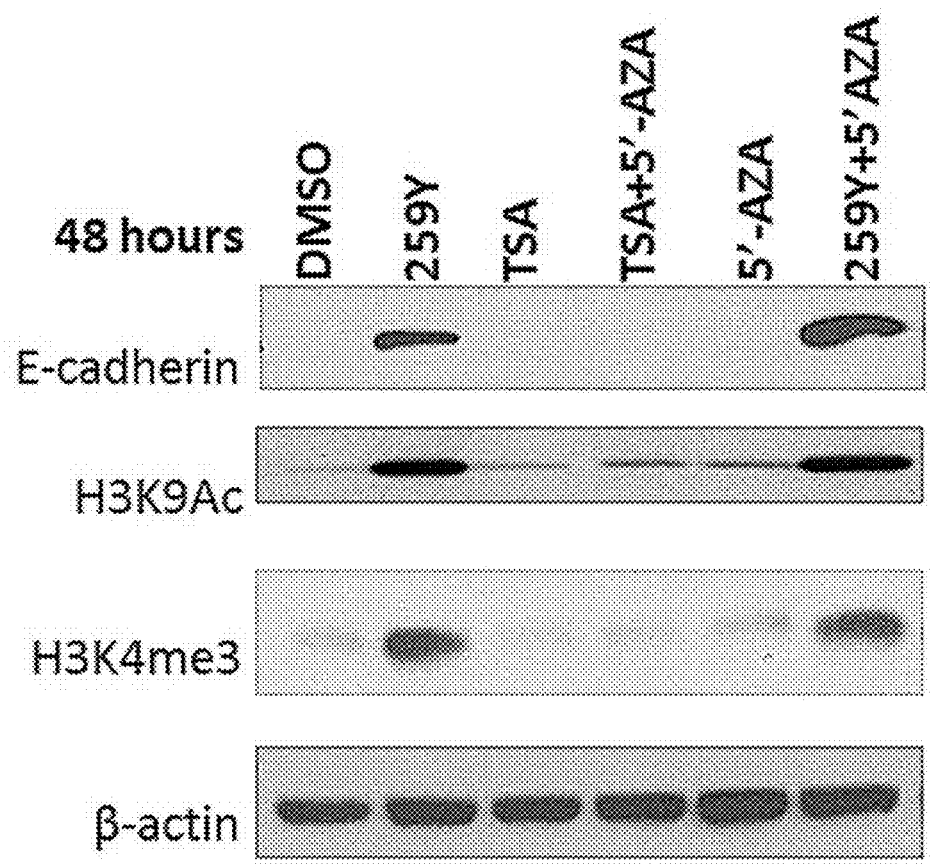

Promoter hypermethylation is an important epigenetic event associated with loss of E-cadherin gene expression. It has been reported that TSGs (tumor suppressor genes) that are only partially DNA methylated and not fully silenced, but expressed at low levels, are induced by TSA treatment alone. However, more fully DNA methylated and silenced genes cannot be reactivated by TSA alone, but may be activated by the DNA methyltransferase inhibitor 5-azacytidine (5-Aza) (Suzuki, H., et al. (2002) *Nat. Genet,* 31, 141-149). HMEC-1 cells were treated with the HDAC inhibitor TSA, or the DNA methyltransferase inhibitor 5-Aza, or both TSA and 5-Aza in combination. It was found that neither TSA nor 5-Aza, nor the combination of these two agents, was effective in restoring E-cadherin in HMEC-1 cells after 48 hours of treatment (FIG. 10D). Further, neither compound replicates the effects of Compound 13 on the histone modification that was observed in either the endothelial or epithelial cells (FIGS. 7A and 10D). Without wishing to be bound by theory, these data suggest that cytidine methylation or de-methylation is not responsible for the E-cadherin restoring activity of Compound 13.

Figure 11:
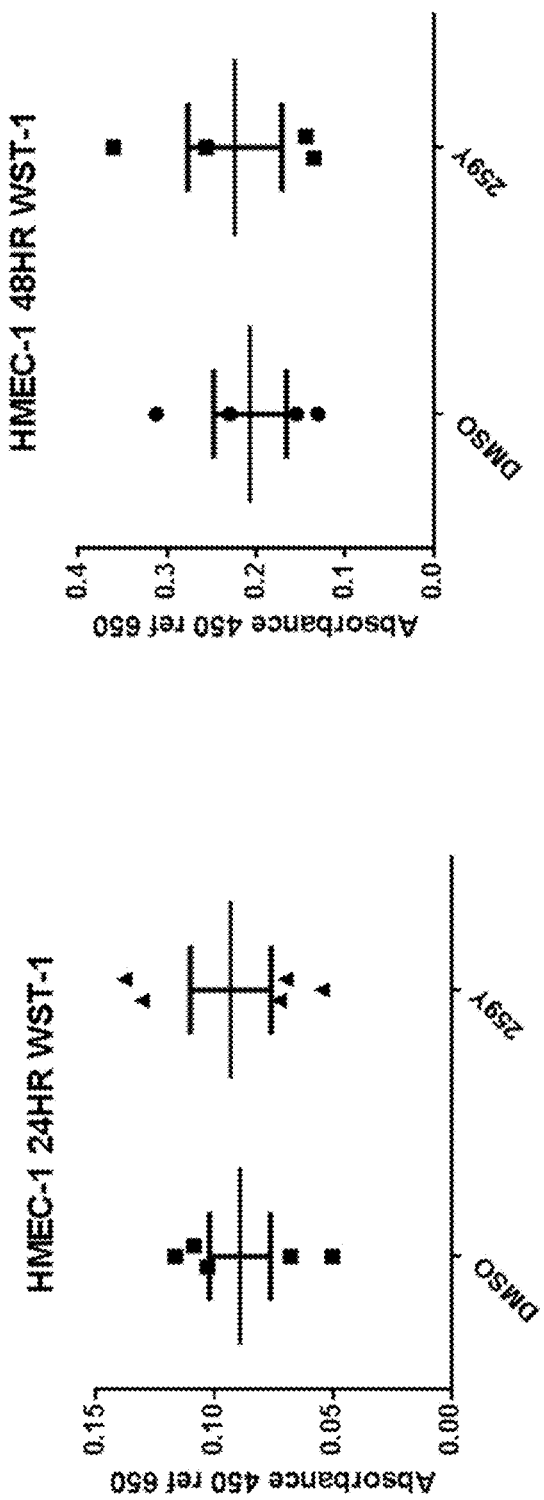
FIG. 11 shows representative data demonstrating that Compound 13 (259Y) has no significant effect on HMEC-1 cell proliferation.
Figure 12:
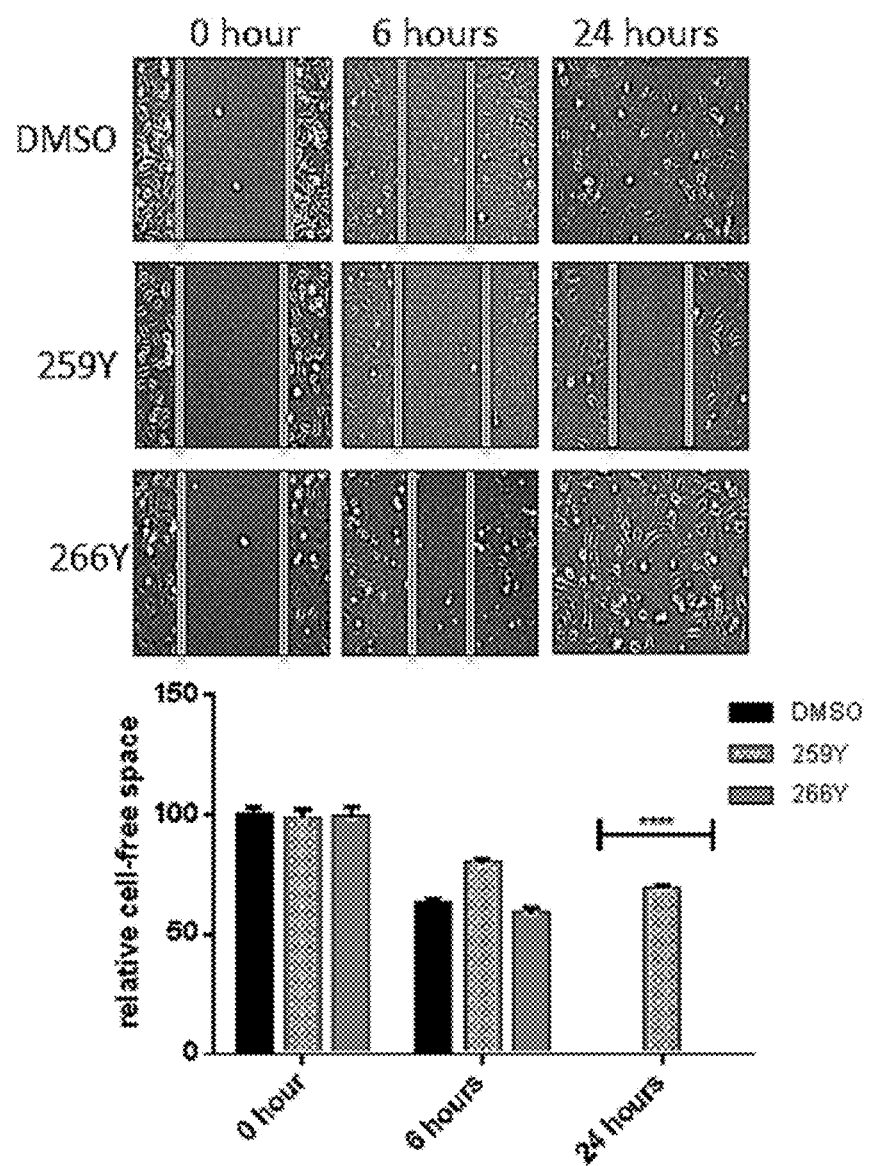
FIG. 12 shows representative data demonstrating that Compound 13 (259Y) provoked HMEC-1 wound healing.

Proliferation, migration, and tubular formation are essential characteristics of endothelial cells for the generation of new blood vessels. Compound 13 had no significant effect on HMEC-1 cell proliferation as determined by the WST-1 metabolism assay (FIG. 11). The lack of effect on cell proliferation is consistent with the lack of effect of compounds of similar class on the proliferation of SW620 and H520 cells (Stoops, S. L., et al. (2011) *ACS Chemical Biology* 6, 452-465). A scratch wound healing assay was performed on cultured HMEC-1 cells. Confluent monolayers of HMEC-1 cells were disrupted mechanically by scraping them with a sterile pipette tip. Within the observation period of 24 hours, Compound 13 treatment antagonized HMEC-1 monolayer wound healing (FIG. 12).

Referring to FIG. 11, HMEC-1 cells were treated with DMSO or 10 μM Compound 13 (259Y) using 96 wells plate, WST-1 was added (10 μL per well, incubate 37° C. for one hour, read at 450 nm reference 562 nm) at 24 h and 48 h. The blank control was a well with media but NO CELLS+wst-1. Each data point is a biological replicate that is the average of three technical replicates minus the average of three blank wells.

Figure 13A:
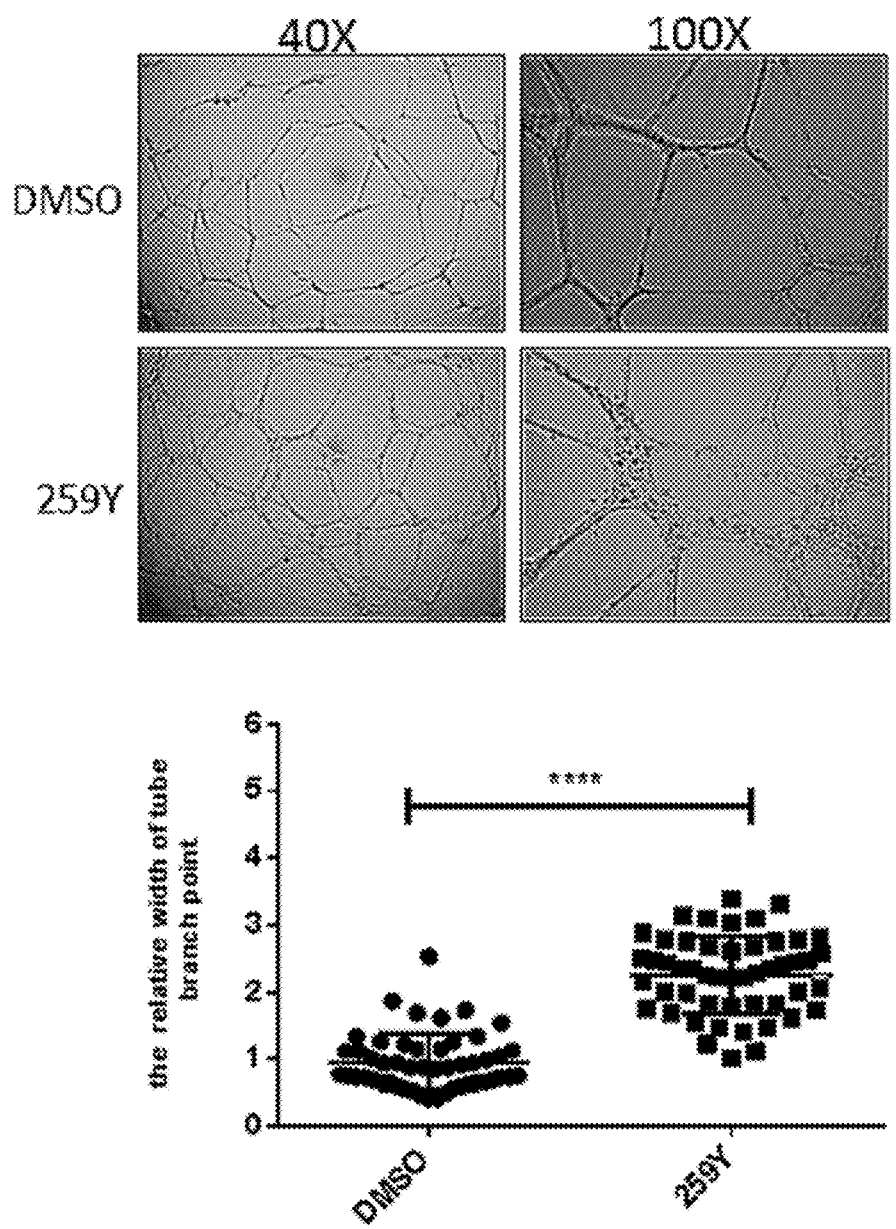
FIGS. 13A and 13B show representative data pertaining to the effect of Compound 13 (259Y) on motility and differentiation-related biological consequences for endothelial cells.

Similar to primary microvascular endothelial cells, HMEC-1 cells have been shown to form cord-like structures when cultured on Matrigel (Unger, R. E., et al. (2002) *Microvascular Research* 64, 384-397). Cells treated with DMSO vehicle arranged in a complex network of compact capillary-like tubes after a 6-hour incubation period (FIG. 13A). At a 10 μmol/L concentration, cells treated with Compound 13 also arranged in a complex of tubes, but the tube morphology was strikingly influenced by Compound 13 treatment, with tubes that were less condensed and tended to assemble and form larger cellular aggregates at the branch points (FIGS. 13A and 13B), a phenotype not observed in control vehicle treated cells. Without wishing to be bound by theory, these data taken together suggest that the activity of isoxazole-based analogs typified by Compound 13 may also have important motility and differentiation-related biological consequences for endothelial cells.

Figure 13B:
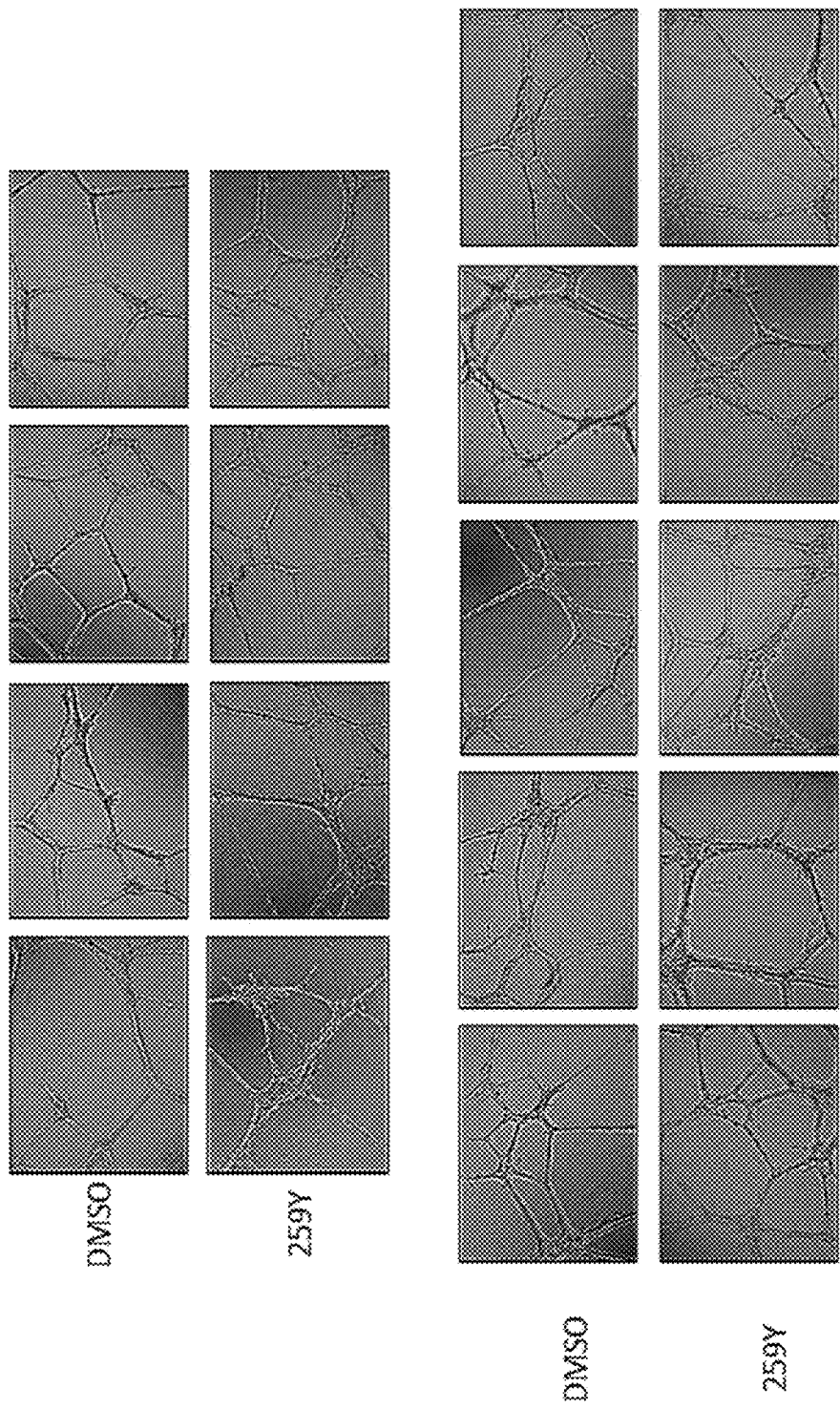

Referring to FIG. 13B, HMEC-1 cells treated with DMSO or 10 μM Compound 13 (259Y) for 48 h were plated on top of the matrigel. Tubes were imaged 18-20 hours later (magnification:100λ).

9. Compound 13 Restores E-Cadherin Expression In Vivo

Figure 14:
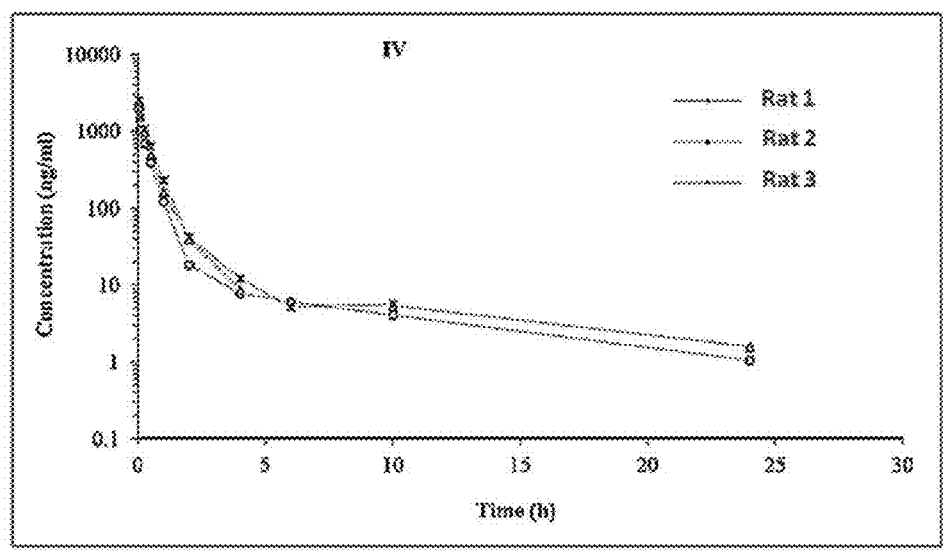
FIG. 14 shows representative data demonstrating that Compound 13 (259Y) alters global markers of histone activation and E-cadherin expression in endothelial cells.

The potency and efficacy of Compound 13 was evaluated in vivo. For these studies, the pharmacokinetics of Compound 13 were first evaluated in vitro and in vivo (FIG. 14). In these studies, the protein binding of Compound 13 varied across species, with relatively high protein binding noted only in human samples. While Compound 13 displayed high intrinsic clearance in mouse, it showed very moderate clearance in rat. Notably, minimal clearance was noted in human microsomes. The compound was also examined in IV dosing in Sprague-Dawley rats, where it displayed moderate clearance, a moderate volume of distribution, and a long elimination half-life.

Referring to FIG. 14, relative E-cadherin mRNA expression in HMEC-1 cells are shown following treatment with 10 μM Compound 13 (259Y), relative to treatment with DMSO, over a 24 hour time course as determined by qPCR. One-sample t-test 1.0; * $p<0.05$, *** $p<0.0001$.

Cell migration and metastasis are key features of aggressive tumors. These processes are difficult to study, as they often occur deep within the body of a cancer patient or an experimental animal. In vitro studies such as invasion assays and migration assays can model some aspects of these processes, but have inherent limitations that may miss important aspects of these processes as they occur in vivo. The Chick Chorioallantoic Membrane (CAM) assay is a quantifiable in vivo model to study metastases that overcomes many limitations of the in vitro studies (Kain, K. H., et al. (2014) *Dev. Dyn.* 243(2): 216-228).

Figure 15A:
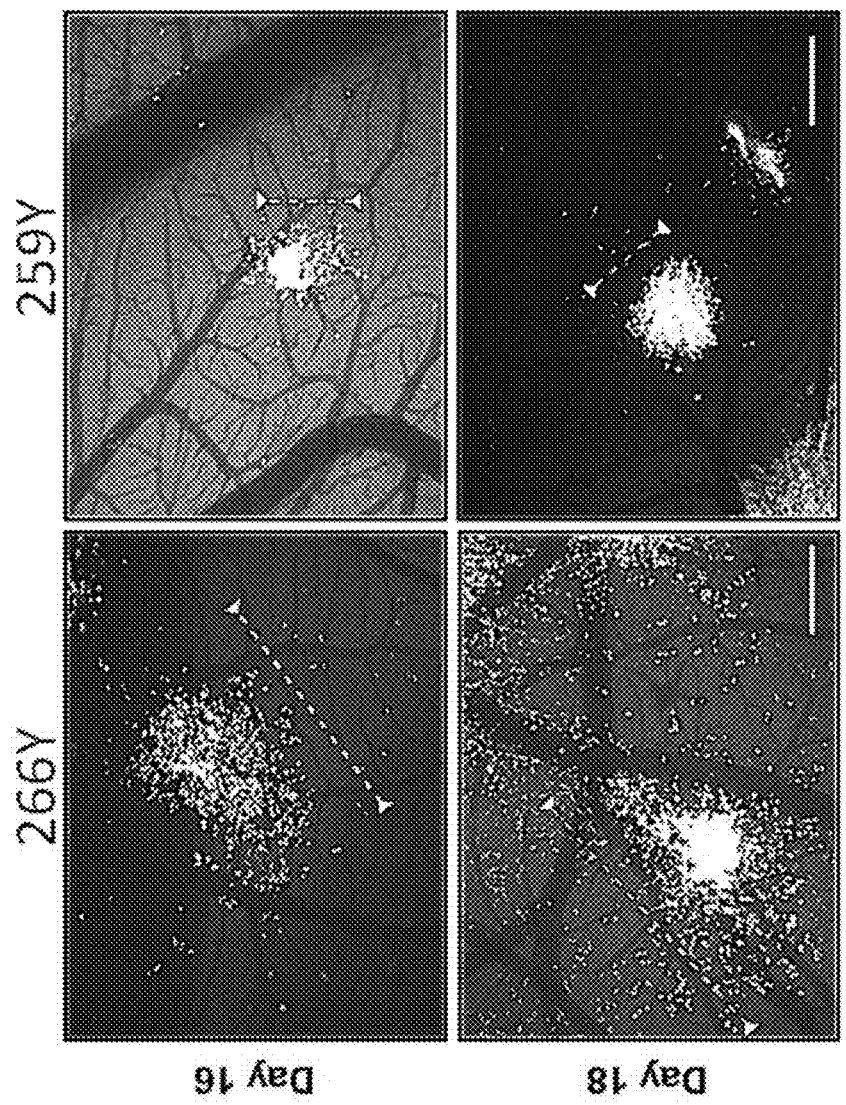
FIG. 15A-E shows representative data demonstrating the inhibition of tumor cell migration in vivo.
Figure 15B:
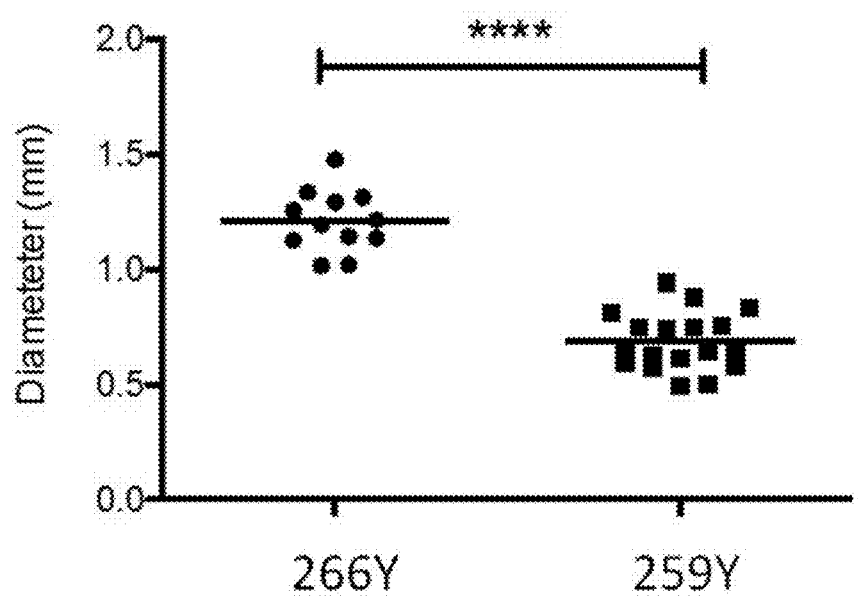

To monitor the migratory behavior of cells within the primary tumor affected by ML327 in vivo, an intravital imaging system was used as previously described (Zijlstra, A., et al. (2008) *Cancer Cell* 13(3): 221-234). Briefly, fluorescent (GFP) HEp3(Human Epidermoid Carcinoma) cells ($1\times10^5$) were intravascularly injected into the CAM of avian embryos and allowed to form a primary tumor colony. Embryos were treated with Compound 13 or Compound 124 at 24 hours post-implantation and colony formation was imaged at 4, 6, and 8 days postinjection (FIG. 15A). Quantitative comparison of colony size was performed at 6 days post injection by measuring the diameter of the colony (FIG. 15B). Clear, reproducible inhibition of motility was observed as reflected in the limited number of single cells emanating from the colonies when the embryos are treated with Compound 13.

Figure 15C:
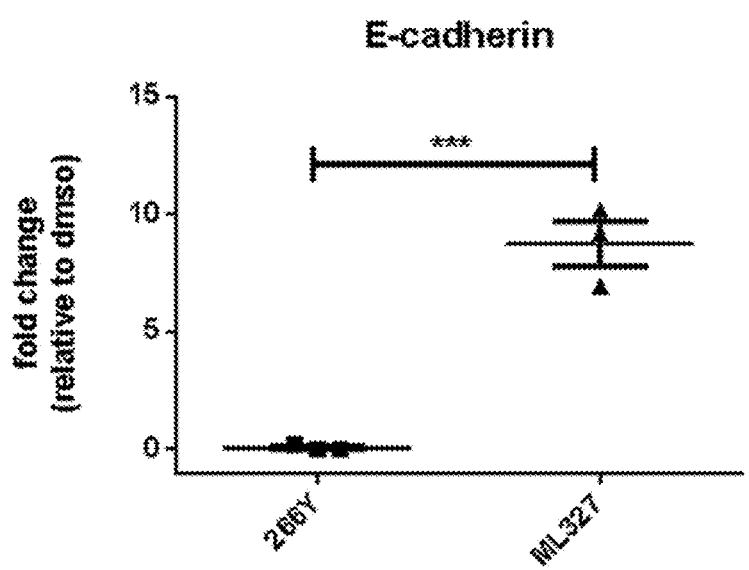
Figure 15D:
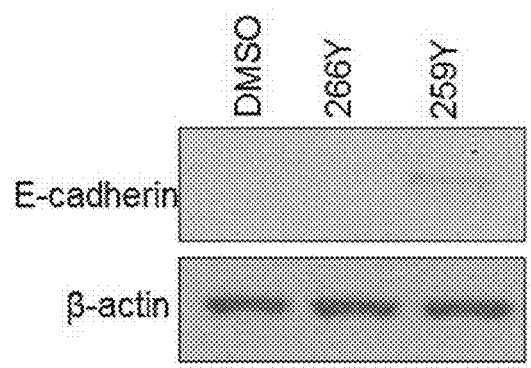
Figure 15E:
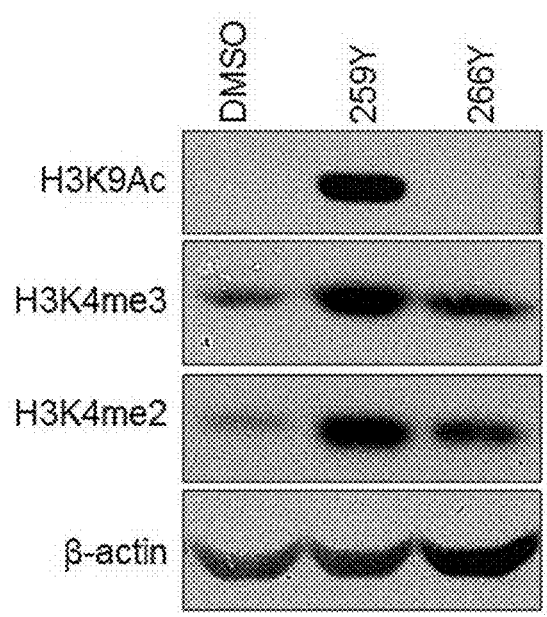

To determine if Compound 13 restores E-cadherin in HEp3 cells, the effect of Compound 13 treatment on E-cadherin mRNA expression was tested. Compound 13 induced an 8-fold increase in E-cadherin mRNA by 6 hours after treatment in the SW620inv cells compared with Compound 124 treatment (FIG. 15C). Not only E-cadherin specific mRNA, but also E-cadherin protein, was induced by Compound 13 treatment (FIG. 15D). As was seen in SW620inv and H520 cells, Compound 13 increased the global histone active marks (H3K9Ac, H3K4me3, or H3K4me2) in HEp3 cells (FIG. 15E).

Referring to FIG. 15, representative data demonstrating the inhibition of tumor cell migration in vivo is shown. Avian embryos were treated with Compound 124 (266Y) or Compound 13 (259Y) 24 hours after intravenous injection of GFP-expressing HEp3 cells. The formation of metastatic colonies was monitored visually by a fluorescent stereoscope at 50× magnification. Representative images are shown, scale bar=500 μm (15A). Colony diameter was quantified at 6 days post injection. The data represent a total of 30 embryos from two independent experiments: 12 treated with Compound 124 (266Y) and 18 treated with Compound 13 (259Y). The graph displays data from both experiments. Each data point on the scatterplot represents the geometric mean diameter of 6-10 colonies analyzed per embryo (15B). Relative E-cadherin mRNA expression in HEp3 cells following 6 hours treatment with either Compound 124 (266Y) or Compound 13 (259Y) is shown (15C). Western blot showing E-cadherin protein re-expression in HEp3 cells following treatment with DMSO, Compound 124 (266Y), or Compound 13 (259Y) for 24 hours is shown (15D). Western blot showing H3K9Ac, H3K4me3, H3K4me2, and β-actin proteins in HEp3 cells following treatment with DMSO, 10 μM Compound 13 (259Y), or 10 μM Compound 124 (266Y) for 24 hours is shown (15E).

What is claimed is:

1. A compound having a structure represented by a formula:

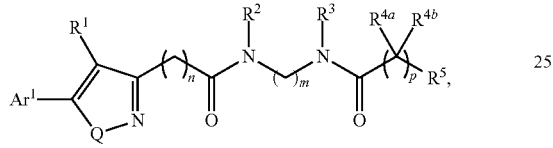

wherein m is an integer selected from 2, 3, and 4 and $Ar^1$ is aryl substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, or wherein m is 3 and $Ar^1$ is heteroaryl substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino;

wherein n is an integer selected from 0 and 1;

wherein p is an integer selected from 0, 1, 2, 3, and 4;

wherein Q is selected from $NR^6$, O, and S;

wherein $R^6$ is selected from hydrogen and C1-C4 alkyl;

wherein $R^1$ is selected from hydrogen and C1-C4 alkyl;

wherein each of $R^2$ and $R^3$ is independently selected from hydrogen and C1-C4 alkyl;

wherein each occurrence of $R^{4a}$ and $R^{4b}$ is independently selected from hydrogen, halogen, —OH, —CN, —$N_3$, —$NH_2$, and C1-C4 alkyl, or wherein each of $R^{4a}$ and $R^{4b}$ are optionally covalently bonded and, together with the intermediate atoms, comprise a 3- to 5-membered cycle;

wherein $R^5$ is selected from $Cy^2$ and $Ar^2$ wherein $Cy^2$, when present, is selected from cycloalkyl and heterocycloalkyl, and $Cy^2$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, provided that when m is 2 then $Cy^2$ is not cycloalkyl;

wherein $Ar^2$, when present, is selected from aryl and heteroaryl, and $Ar^2$ is substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, C1-C4 dialkylamino, $Cy^3$, $Ar^3$, and —NH(C=O)(C1-C4 alkyl)$Cy^3$, provided that when m is 2 then $Ar^2$ is not substituted or unsubstituted phenyl, substituted or unsubstituted furanyl, or substituted or unsubstituted pyridinyl;

wherein $Cy^3$, when present, is selected from cycloalkyl and heterocycloalkyl, and $Cy^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino;

wherein $Ar^3$, when present, is phenyl substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino;

provided that when m is 3, n is 0, and p is 0, that $Ar^2$, when present, is not a structure represented by a formula:

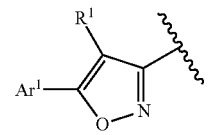

or a pharmaceutically acceptable salt thereof.

2. The compound of claim 1, wherein $Ar^2$ is aryl, and $Ar^2$ is substituted with 0, 1, 2, or 3 substituents independently selected from halogen, —OH, —CN, —$N_3$, —$NH_2$, C1-C3 alkyl, C1-C4 alkyl, C1-C4 alkoxy, C1-C4 monohaloalkyl, C1-C4 polyhaloalkyl, C1-C4 alkylamino, C1-C4 dialkylamino, $Cy^3$, and $Ar^3$.

3. The compound of claim 1, wherein $Ar^2$ is heteroaryl, and $Ar^2$ is substituted with 0, 1, 2, or 3 substituents independently selected from halogen, —OH, —CN, —$N_3$, —$NH_2$, C1-C3 alkyl, C1-C4 alkyl, C1-C4 alkoxy, C1-C4 monohaloalkyl, C1-C4 polyhaloalkyl, C1-C4 alkylamino, C1-C4 dialkylamino, $Cy^3$, and $Ar^3$.

4. The compound of claim 1, wherein $Ar^1$ is aryl, and $Ar^1$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino.

5. The compound of claim 1, wherein $Ar^1$ is phenyl, and $Ar^1$ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino.

6. The compound of claim 1, wherein $Ar^1$ is heteroaryl, and $Ar^1$ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino.

7. The compound of claim 1, wherein $Ar^1$ is thiophenyl, and $Ar^1$ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino.

8. The compound of claim 1, wherein the compound has a structure represented by a formula:

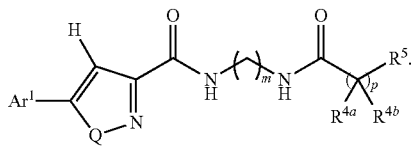

9. The compound of claim 1, wherein the compound has a structure represented by a formula:

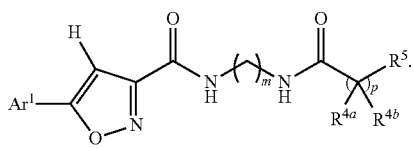

10. The compound of claim 1, wherein the compound has a structure represented by a formula:

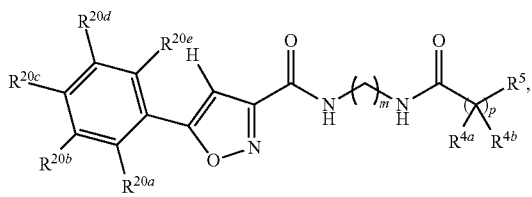

wherein each of $R^{20a}$, $R^{20b}$, $R^{20c}$, $R^{20d}$, and $R^{20e}$ are independently selected from hydrogen, halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, provided that at least two of $R^{20a}$, $R^{20b}$, $R^{20c}$, $R^{20d}$, and $R^{20e}$ are hydrogen.

11. The compound of claim 1, wherein the compound has a structure represented by a formula:

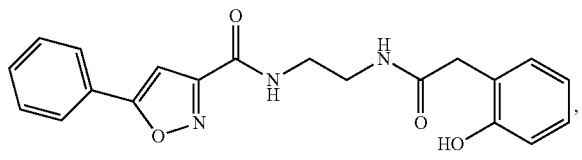

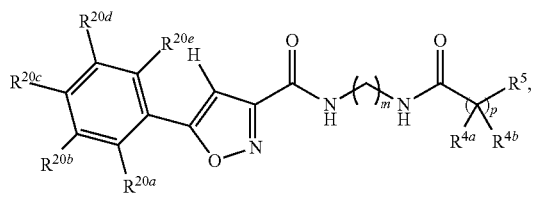

wherein each of $R^{20b}$, $R^{20c}$, and $R^{20d}$ are hydrogen and each of $R^{20a}$ and $R^{20e}$ are independently selected from hydrogen, halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino.

12. The compound of claim 1, wherein the compound has a structure represented by a formula:

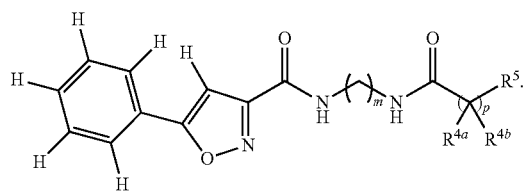

13. The compound of claim 1, wherein the compound has a structure represented by a formula:

wherein each of $R^{30a}$, $R^{30b}$, and $R^{30c}$ are independently selected from hydrogen, halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino.

14. The compound of claim 1, wherein the compound has a structure represented by a formula:

15. A compound having a structure selected from:

-continued

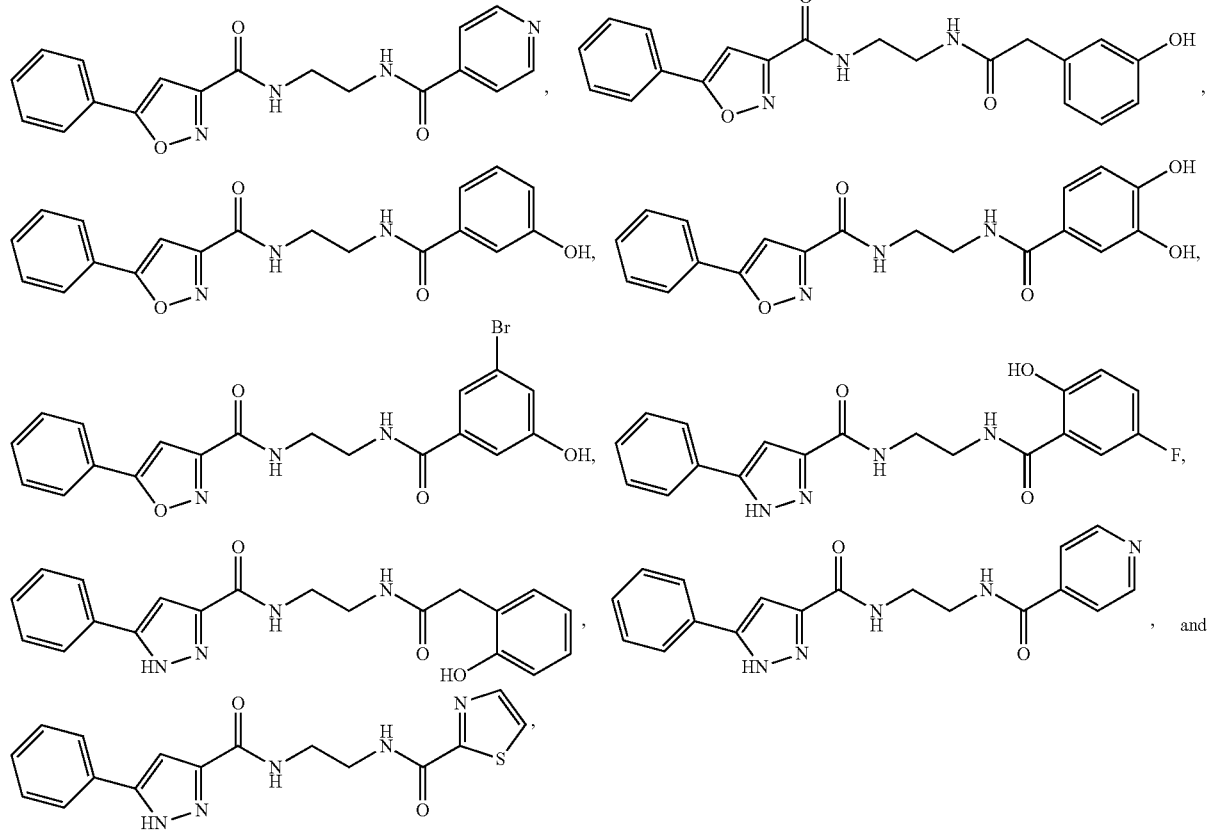

or a pharmaceutically acceptable salt thereof.

16. The compound of claim 1, wherein m is 3.

17. The compound of claim 1, wherein the compound has a structure represented by a formula:

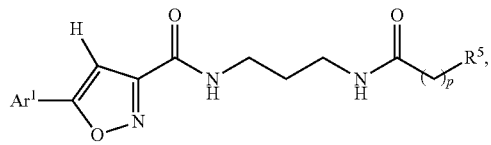

wherein p is an integer selected 0 and 1.

18. The compound of claim 1, wherein Ar² is selected from aryl and heteroaryl, and Xrush Ar² is substituted with 0, 1, 2, or 3 substituents independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, C1-C4 dialkylamino, and —NH(C=O)(C1-C4 alkyl)Cy³.

19. The compound of claim 1, wherein the compound has a structure represented by a formula:

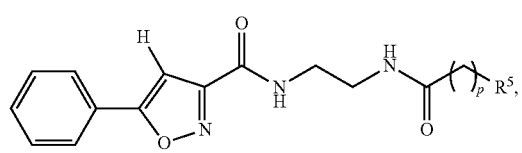

wherein p is an integer selected 0 and 1.

20. The compound of claim 1, wherein the compound is selected from:

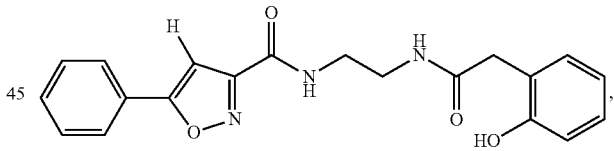

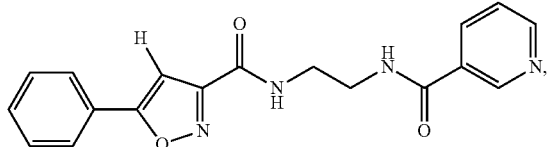

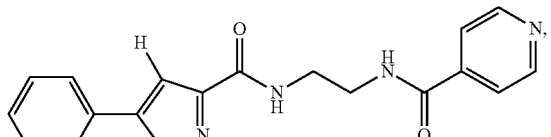

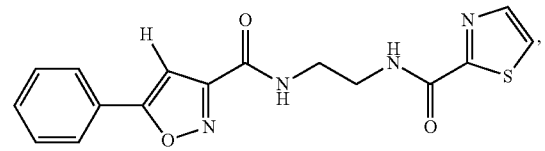

307
-continued
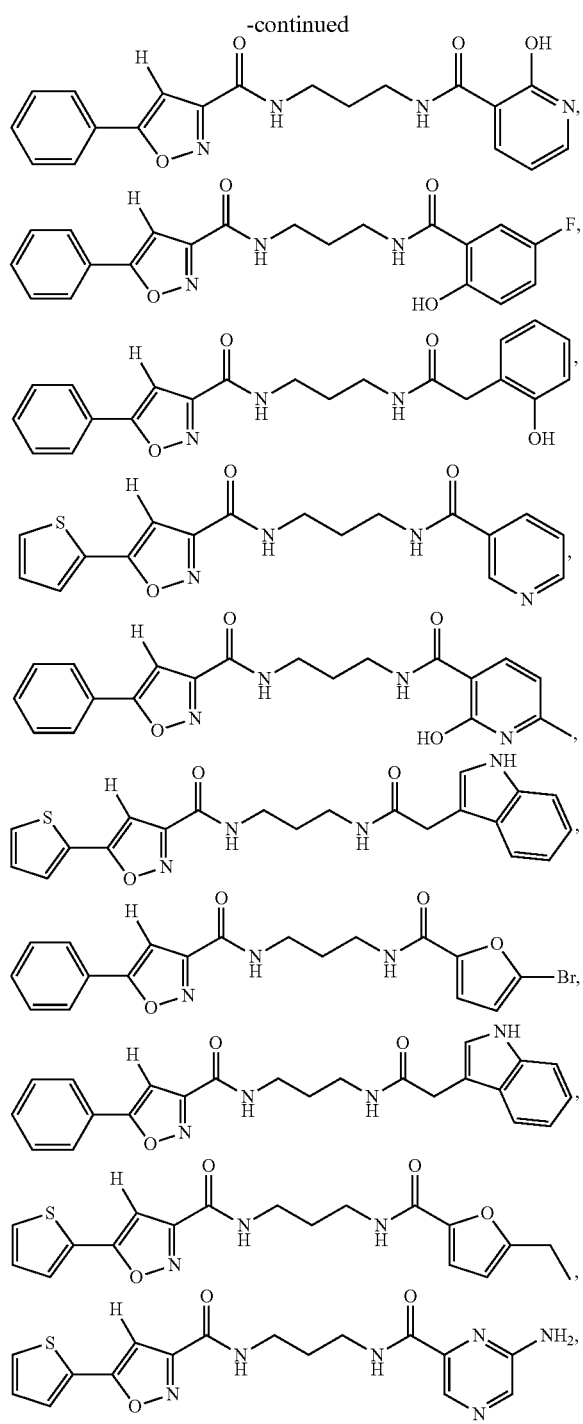
308
-continued
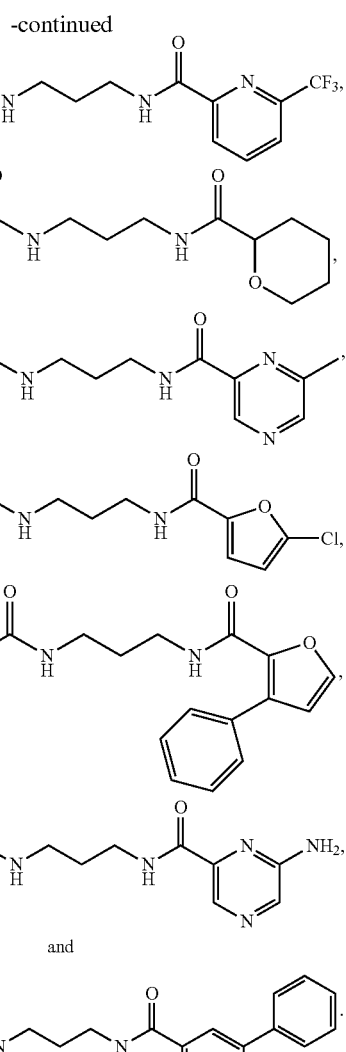
21. The compound of claim 1, wherein the compound is:
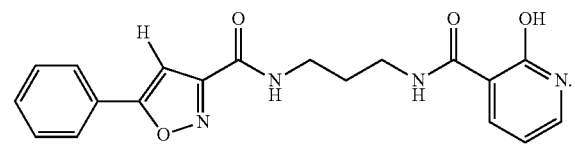 [SMILES: O=C(NCCCNC(=O)c1cccnc1O)c1cc(-c2ccccc2)on1]
* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: synthetic construct; forward primer

<400> SEQUENCE: 1
ttgacgccga gagctacac                                                 19

<210> SEQ ID NO 2
<211> LENGTH: 18
<212> TYPE: DNA
<213> ORGANISM: Artificial Sequence
<220> FEATURE:
<223> OTHER INFORMATION: synthetic construct; reverse primer

<400> SEQUENCE: 2
gtcgaccggt gcaatctt                                                  18
```

```
<210> SEQ ID NO 3
<211> LENGTH: 21
<212> TYPE: DNA
<213> ORGANISM: Artificial Sequence
<220> FEATURE:
<223> OTHER INFORMATION: synthetic construct; forward primer

<400> SEQUENCE: 3
ttctccgaac tggacaagaa a                                                21

<210> SEQ ID NO 4
<211> LENGTH: 20
<212> TYPE: DNA
<213> ORGANISM: Artificial Sequence
<220> FEATURE:
<223> OTHER INFORMATION: synthetic construct; reverse primer

<400> SEQUENCE: 4
ctctgttttc agggcttcca                                                  20

<210> SEQ ID NO 5
<211> LENGTH: 18
<212> TYPE: DNA
<213> ORGANISM: Artificial Sequence
<220> FEATURE:
<223> OTHER INFORMATION: synthetic construct; forward primer

<400> SEQUENCE: 5
aggaaccgag agccaggt                                                    18

<210> SEQ ID NO 6
<211> LENGTH: 20
<212> TYPE: DNA
<213> ORGANISM: Artificial Sequence
<220> FEATURE:
<223> OTHER INFORMATION: synthetic construct; reverse primer

<400> SEQUENCE: 6
ggatgagcaa tgccctttag                                                  20

<210> SEQ ID NO 7
<211> LENGTH: 21
<212> TYPE: DNA
<213> ORGANISM: Artificial Sequence
<220> FEATURE:
<223> OTHER INFORMATION: synthetic construct; forward primer

<400> SEQUENCE: 7
gaccagctaa ccaacgacaa a                                                21

<210> SEQ ID NO 8
<211> LENGTH: 18
<212> TYPE: DNA
<213> ORGANISM: Artificial Sequence
<220> FEATURE:
<223> OTHER INFORMATION: synthetic construct; reverse primer

<400> SEQUENCE: 8
gtcgaccggt gcaatctt                                                    18

<210> SEQ ID NO 9
<211> LENGTH: 24
<212> TYPE: DNA
<213> ORGANISM: Artificial Sequence
<220> FEATURE:
<223> OTHER INFORMATION: synthetic construct; forward primer
```

```
<400> SEQUENCE: 9
gtgaaccctc agccaatcag cggt                                          24

<210> SEQ ID NO 10
<211> LENGTH: 23
<212> TYPE: DNA
<213> ORGANISM: Artificial Sequence
<220> FEATURE:
<223> OTHER INFORMATION: synthetic construct; reverse primer

<400> SEQUENCE: 10
ggagcgggct ggagtctgaa ctg                                           23
```

UNITED STATES PATENT AND TRADEMARK OFFICE
CERTIFICATE OF CORRECTION

PATENT NO. : 9,783,510 B2
APPLICATION NO. : 14/828230
DATED : October 10, 2017
INVENTOR(S) : Craig W. Lindsley, Alex G. Waterson and R. Daniel Beauchamp Page 1 of 1

It is certified that error appears in the above-identified patent and that said Letters Patent is hereby corrected as shown below:

In Column 305, Line 49 - 56 Claim 18:
Replace: "The compound of claim 1, wherein $Ar^2$ is selected from aryl and heteroaryl, and Xrush $Ar^2$ is substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, C1-C4 dialkylamino, and —NH(C=O)(C1-C4 alkyl)$Cy^3$."

With -- The compound of claim 1, wherein $Ar^2$ is selected from aryl and heteroaryl, and $Ar^2$ is substituted with 0, 1, 2, or 3 substituents independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, C1-C4 dialkylamino, and —NH(C=O)(C1-C4 alkyl)$Cy^3$. --

Signed and Sealed this
Twenty-first Day of August, 2018

Andrei Iancu
*Director of the United States Patent and Trademark Office*